United States Patent
Irlapati et al.

(10) Patent No.: US 9,169,242 B2
(45) Date of Patent: Oct. 27, 2015

(54) OXAZOLINE AND ISOXAZOLINE DERIVATIVES AS CRAC MODULATORS

(75) Inventors: Nageswara Rao Irlapati, Maharashtra (IN); Gokul Keruji Deshmukh, Maharashtra (IN); Vijay Pandurang Karche, Maharashtra (IN); Santosh Madhukar Jachak, Maharashtra (IN); Neelima Sinha, Maharashtra (IN); Venkata P. Palle, Maharashtra (IN); Rajender Kumar Kamboj, Maharashtra (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 0 days.

(21) Appl. No.: 13/882,567

(22) PCT Filed: Oct. 31, 2011

(86) PCT No.: PCT/IN2011/000749
§ 371 (c)(1),
(2), (4) Date: Apr. 30, 2013

(87) PCT Pub. No.: WO2012/056478
PCT Pub. Date: May 3, 2012

(65) Prior Publication Data
US 2013/0225600 A1      Aug. 29, 2013

(30) Foreign Application Priority Data

Oct. 30, 2010 (IN) .......................... 1215/KOL/2010
Apr. 1, 2011 (IN) ............................. 473/KOL/2011

(51) Int. Cl.
| C07D 271/113 | (2006.01) |
| A61K 31/4245 | (2006.01) |
| A61P 17/06 | (2006.01) |
| A61P 19/02 | (2006.01) |
| A61P 35/00 | (2006.01) |
| C07D 261/12 | (2006.01) |
| C07D 413/10 | (2006.01) |
| C07D 413/14 | (2006.01) |
| C07D 417/14 | (2006.01) |
| A61K 31/497 | (2006.01) |

(52) U.S. Cl.
CPC ............ *C07D 417/14* (2013.01); *C07D 261/12* (2013.01); *C07D 413/10* (2013.01); *C07D 413/14* (2013.01)

(58) Field of Classification Search
CPC ........................ C07D 271/113; A61K 31/4245
USPC .......................................... 514/364; 548/144
See application file for complete search history.

(56) References Cited

U.S. PATENT DOCUMENTS

2010/0152241 A1    6/2010    Whitten

FOREIGN PATENT DOCUMENTS

| WO | WO 2005/009539 | 2/2005 |
| WO | WO 2005/009954 | 2/2005 |
| WO | WO 2006/034402 | 3/2006 |
| WO | WO 2006/081389 | 8/2006 |
| WO | WO 2006/081391 | 8/2006 |
| WO | WO 2006/083477 | 8/2006 |
| WO | WO 2007/087429 | 8/2007 |
| WO | WO 2007/087441 | 8/2007 |
| WO | WO 2007/087442 | 8/2007 |
| WO | WO 2007/089904 | 8/2007 |
| WO | WO 2009/017819 | 2/2009 |
| WO | WO 2009/035818 | 3/2009 |
| WO | WO 2009/076454 | 6/2009 |
| WO | WO 2010/025295 | 3/2010 |
| WO | WO 2010/027875 | 3/2010 |
| WO | WO 2010/039238 | 4/2010 |
| WO | WO 2011/034962 | 3/2011 |

OTHER PUBLICATIONS

Abeele et al., "Bcl-2-dependent modulation of $Ca^{2+}$ homeostasis and store-operated channels in prostate cancer cells", *Cancer Cell*, vol. 1, 2002, pp. 169-179.
Braun et al., "Orai 1 (CRACM1) is the platelet SOC channel and essential for pathological thrombus formation", *Blood*, vol. 113, No. 9, 2009, pp. 2056-2063.
Di Sabatino et al., "Targeting Gut T Cell $Ca^{2+}$ Release-Activated $Ca^{2+}$ Channels Inhibits T Cell Cytokine Production and T-Box Transcription Factor T-Bet in Inflammatory Bowel Disease", *The Journal of Immunology*, vol. 183, 2009, pp. 3454-3462.
Fahrner et al., "Mechanistic view on domains mediating STIM1-Orai coupling", *Immunological Reviews*, vol. 231, 2009, pp. 99-112.
Gilio et al., "Roles of Platelet STIM1 and Orai1 in Glycoprotein VI- and Thrombin-dependent Procoagulant Activity and Thrombus Formation", *Journal of Biological Chemistry*, vol. 285, No. 31, 2010, 23629-23638.
International Search Report and Written Opinion from International Application No. PCT/IN2011/000749 mailed Feb. 15, 2012.
Motiani et al., "A Novel Native Store-operated Calcium Channel Enclosed by Orai3 Selective Requirement of Orai3 Versus Orai1 in Estrogen Receptor-Positive Versus Estrogen Receptor-Negative Breast Cancer Cells", *The Journal of Biological Chemistry*, vol. 285, No. 25, 2010, pp. 19173-19183.
Parekh et al., "Store-Operated Calcium Channels", *Physiol. Rev*, vol. 85, 2005, pp. 757-810.
Anant B. Parekh, "Store-operated CRAC channels: function in health and disease", *Nature Reviews*, vol. 9, 2010, pp. 399-410.
Varga-Szabo et al., "The calcium sensor STIM1 is an essential mediator of arterial thrombosis and ischemic brain infarction", *The Journal of Experimental Medicine*, vol. 205, No. 7, 2008, pp. 1583-1591.
Yang et al., "Orai1 and STIM1 Are Critical for Breast Tumor Cell Migration and Metastasis", *Cancer Cell*, vol. 15, 2009, pp. 124-134.
Wuts et al., *Greene's Protective Groups in Organic Synthesis*, Fourth Edition, John Wiley & Sons, Inc., 2007. (reference in 4 parts).

*Primary Examiner* — Sreeni Padmanabhan
*Assistant Examiner* — Irina Neagu
(74) *Attorney, Agent, or Firm* — Merchant & Gould P.C.

(57) ABSTRACT

The present invention relates to compounds that are useful for treating, preventing and/or managing the diseases, disorders, syndromes or conditions associated with the modulation of CRAC and to processes for preparing these compounds. The invention further relates to methods of treating, preventing managing and/or lessening the diseases, disorders, syndromes or conditions associated with the modulation of CRAC by these compounds.

4 Claims, No Drawings

OXAZOLINE AND ISOXAZOLINE DERIVATIVES AS CRAC MODULATORS

RELATED APPLICATIONS

The present application is a National Stage Application of PCT/IN2011/000749, filed 31 Oct. 2011, which claims benefit of Indian Provisional Patent Application Nos. 1215/KOL/2010, filed on Oct. 30, 2010 and 0473/KOL/2011, filed on Apr. 1, 2011. and which applications are incorporated herein by reference. To the extent appropriate, a claim of priority is made to each of the above disclosed applications.

TECHNICAL FIELD OF THE INVENTION

The invention relates to heterocyclic compounds, pharmaceutically acceptable salts thereof and pharmaceutical compositions for the treatment, prevention, management, and/or lessening of severity of diseases, disorders, syndromes or conditions associated with the modulation of calcium release-activated calcium (CRAC) channel. The invention also relates to methods of treating, preventing, managing and/or lessening the severity of the diseases disorders, syndromes or conditions associated with the modulation of CRAC. The invention also relates to processes for the preparation of the compounds of the invention.

BACKGROUND OF THE INVENTION

Inflammation is the response by the body to infection, irritation or injury; wherein the immune cells of the body are activated in response to any of these stimuli. Inflammation plays a key role in many diseases not only of the immune cells such as allergy, asthma, arthritis, dermatitis, multiple sclerosis, systemic lupus but also organ transplant, diabetes, cardiovascular disease, Alzheimer's disease, Parkinson's disease, inflammatory and/or irritable bowel syndrome (Di Sabatino et. al., J. Immunol., 183, 3454-3462, 2009), psoriasis, and cancer. An initial inflammatory response to pathogens or injury is necessary and required to fight infection or heal the wound, but sustained or persistent inflammation can lead to any of the chronic disorders; characterized by the production of inflammatory cytokines as, specified above.

Inflammation is characterized by the production of different cytokines such as IL-2, IL-4, IL-10. IL-13, IL-17, IL-21, IL-23, IL-28, IFN-γ, TNF-α, etc., that have been implicated in playing a role in different diseases. Any drug which can modulate the production of these cytokines would help alleviate the disease symptoms and may also cure it.

$Ca^{+2}$ signals have been shown to be essential for diverse cellular functions in different cell types including differentiation, effector functions, and gene transcription in cells of the immune system as well as regulating the cytokine signaling pathway through calcineurin and nuclear factor of activated T cells (NFAT).

In immune cells, sustained $Ca^{+2}$ influx has been shown to be necessary for complete and long-lasting activation of calcineurin-NFAT pathways, essential for cytokine production. Engagement of receptors such as T-cell antigen receptor (TCR), the B-cell antigen receptor (BCR), and the Fc receptors (FcR) on mast cells, macrophages, and NK cells, leads to the tyrosine phosphorylation and activation of phospholipase C-γ (PLC-γ). PLC-γ hydrolyzes phosphatidylinositol-3,4-biphosphate ($PIP_2$) to the second messengers, inositol-1,4,5-triphosphate ($IP_3$) and diacylglycerol (DAG). $IP_3$ binds to $IP_3$ receptors ($IP_3R$) in the membrane of the endoplasmic reticulum (ER) and induces the release of ER $Ca^{+2}$ stores into the cytoplasma. The decrease in the $Ca^{+2}$ concentration in the ER induces store-operated $Ca^{+2}$ entry (SOCE) through plasma membrane $Ca^{+2}$ channels. SOCE through highly $Ca^{+2}$-selective $Ca^{+2}$ release-activated $Ca^{+2}$ (hereinafter, CRAC) channels constitutes the major pathway of intracellular $Ca^{+2}$ entry in T cells, B cells, macrophages, mast cells, and other cell types (Parekh and Putney, Physiol. Rev., 85, 757-810, 2005).

The CRAC channel is comprised of two family proteins, one which functions in sensing $Ca^{+2}$ levels in the ER—the stromal interacting molecules (STIM)-1 and -2 and the other which is a pore-forming protein—Orai1, 2 and 3. The STIM proteins are single transmembrane proteins localized on the ER membrane with their N-termini oriented toward the lumen and containing an EF-hand $Ca^{+2}$ binding motif. Depletion of $Ca^{+2}$ from the ER causes $Ca^{+2}$ to dissociate from STIM, which causes a conformational change that promotes oligomerization and migration of STIM molecules to closely apposed ER-plasma membrane junctions. At the junctions, the STIM oligomers interact with the Orai proteins. In resting cells, Orai channels are dispersed across the plasma membrane and on depletion of $Ca^{+2}$ from the stores, they aggregate in the vicinity of the STIM punctae. The eventual increase in intracellular $Ca^{+2}$ concentration activates the calcineurin-NFAT pathway. NFAT activates transcription of several genes including cytokine genes such as IL-2, etc along with other transcription factors such as AP-1, NFκB and Foxp3 (Fahmer et. al., Immuno. Rev., 231, 99-112, 2009).

The role of CRAC channel in different diseases such as allergy, inflammatory bowel disease, thrombosis and breast cancer has been reported in literature (Parekh, Nat. Rev., 9, 399-410, 2010). It has been reported in the art that STIM1 and Orai1 are essential in in vitro tumor cell migration and in vivo tumor metastasis. Thus the involvement of store operated $Ca^{2+}$ entry in tumor metastasis renders STIM 1 and Orai1 proteins potential targets for cancer therapy (Yang et. al., Cancer Cell, 15, 124-134, 2009). Additional literature available on the involvement of CRAC channel in cancer are Abeele et. al., Cancer Cell, 1, 169-179, 2002, Motiani et al., J. Biol. Chem., 285; 25, 19173-19183, 2010.

Recent literature reports the role of STIM1 and Orai1 in collagen dependent arterial thrombosis in mice in vivo and that deficiency in either protects against collagen dependent arterial thrombus formation as well as brain infarction (Varga-Szabo et. al., J. Exp. Med., 205, 1583-1591, 2008; Braun et. al., Blood, 113, 2056-2063, 2009). The role of STIM1-Orai1 mediated SOCE in thrombus formation makes Orai1 a potential target for treatment of thrombosis and related conditions (Gillo et. al., JBC, 285; 31, 23629-23638, 2010).

As the Orai pore channel proteins have been shown to be essential for transmitting the signal induced by the binding of antigens to the cellular receptors on the immune cells, a potential Orai channel interacting drug would be able to modulate the signaling thereby impacting the secretion of the cytokines involved in, as mentioned hereinbefore, inflammatory conditions, cancer, allergic disorders, immune disorders, rheumatoid arthritis, cardiovascular diseases, thrombocytopathies, arterial and/or venous thrombosis and associated or related conditions which can be benefitted by the CRAC channel modulatory properties of the compounds described herein.

Several compounds have been reported in the art as CRAC channel modulators. For example, patent application publications WO2005009954, WO2006081391, WO2006083477, WO2007089904, WO2009017819, WO2010039238, WO2007087429, WO2007087441 and WO2007087442 disclose substituted biaryl compounds for modulating CRAC channels.

Patent application publications WO2009076454, WO2010027875 and WO2006081389 WO2005009539, WO2005009954, WO2006034402, WO2009035818, US20100152241, WO2010025295, WO2011034962 disclose thiophene derivatives for modulating CRAC channels.

SUMMARY OF THE INVENTION

In accordance with one aspect, the invention provides the compounds of Formula (I):

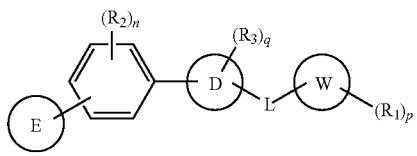

wherein,
ring E is a 5-membered non aromatic heterocyclic ring selected from

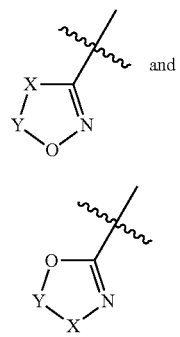

X, at each occurrence, is independently selected from —C(O)—, —CR$_4$R$_5$— and —NR—;
Y, at each occurrence, is independently selected from —C(O)— and —CR$_4$R$_5$—;
R is selected from alkyl, haloalkyl, cycloalkyl, cycloalkenyl, aryl, heteroaryl, heterocyclyl, —C(O)NR$_6$R$_7$, —C(O)OR$_6$ and —C(O)R$_6$;
ring W is selected from aryl, heteroaryl, cycloalkyl and heterocyclyl;
R$_1$, which may be same or different at each occurrence, is independently selected from halo, cyano, nitro, hydroxyl, alkyl, haloalkyl, alkoxy, haloalkoxy, cycloalkyl, aryl, heteroaryl, heterocyclyl, —S(O)$_n$R$_6$, —NR$_6$S(O)$_2$R$_7$, —NR$_6$(CR$_8$R$_4$C(O)OR$_6$, —NR$_6$(CR$_8$R$_4$C(O)R$_6$, —NR$_6$(CR$_8$R$_9$)$_n$C(O)NR$_6$R$_7$, —C(O)NR$_6$R$_7$, —C(O)(O)R$_6$, —C(O)R$_6$, —OC(O)R$_6$, and —OC(O)NR$_6$R$_7$;
R$_2$, which may be same or different at each occurrence, is independently selected from hydrogen, halo, hydroxyl, cyano, nitro, alkyl, haloalkyl, alkenyl, alkynyl, alkoxy, haloalkoxy, alkenyloxy, alkynyloxy, cycloalkyl, cycloalkoxy, —C(O)OR$_6$, —NR$_6$R$_7$, —C(O)R$_6$, —NHS(O)$_2$R$_7$ and —NHC(O)R$_6$;
R$_3$, which may be same or different at each occurrence, is independently selected from hydrogen, halo, hydroxyl, alkyl, alkoxy, haloalkyl, haloalkoxy, —NR$_6$R$_7$, —NR$_6$S(O)$_2$R$_7$, —C(O)NR$_6$R$_7$ and —C(O)OR$_6$;
R$_4$ and R$_5$, which may be same or different at each occurrence, are independently selected from hydrogen, halo, —OR$_{10}$, alkyl, haloalkyl, hydroxyalkyl, cycloalkyl, aryl, heteroaryl, heterocyclyl, —(CR$_8$R$_9$)$_n$C(O)NR$_6$R$_7$, —C(O)R$_6$, and —(CR$_8$R$_9$)$_n$C(O)OR$_6$;
provided that, when any of R$_4$ or R$_5$ in Y is —OR$_{10}$ then R$_{10}$ is not hydrogen; or
R$_4$ and R$_5$, taken together with the carbon atom to which they are attached to, may form a substituted or unsubstituted 3- to 7-membered carbocyclic or heterocyclic ring; or
any one of R$_4$ and R$_5$ in X and any one of R$_4$ and R$_5$ in Y combined together, when they are attached to carbon atoms, may form a 4- to 7-membered substituted or unsubstituted heterocyclic ring;
provided that
both of X and Y are not simultaneously —C(O)—;
ring D is selected from

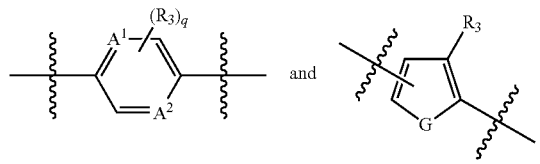

wherein A$^1$ and A$^2$ are independently selected from C and N;
L is —C(O)NR$_{11}$— or —NR$_{11}$C(O)—;
G is selected from S, NR$_{12}$ and O;
R$_{11}$, at each occurrence, is independently selected from hydrogen, alkyl and aryl;
R$_{12}$ is selected from hydrogen, alkyl, cycloalkyl, aryl, heteroaryl, and heterocyclyl;
R$_{10}$ is selected from hydrogen, alkyl, cycloalkyl, aryl, heteroaryl, and heterocyclyl;
R$_6$ and R$_7$, which may be same or different at each occurrence, are independently selected from hydrogen, alkyl, cycloalkyl, aryl, heteroaryl, and heterocyclyl; or R$_6$ and R$_7$, taken together with the nitrogen atom to which they are attached to, may form a substituted or unsubstituted 3- to 14-membered heterocyclic ring;
R$_8$ and R$_9$, which may be same or different at each occurrence, are independently selected from hydrogen, halo, alkyl and alkoxy; or R$_8$ and R$_9$, taken together with the carbon atom they are attached to, may form a 3- to 6-membered cyclic ring wherein the cyclic ring may be carbocyclic or heterocyclic;
n is an integer ranging from 0 to 2, both inclusive;
p is an integer ranging from 0 to 5, both inclusive;
q is an integer ranging from 1 to 4, both inclusive; and
wherein alkyl, haloalkyl, hydroxyalkyl, alkenyl, alkynyl, alkoxy, haloalkoxy, alkenyloxy, alkynyloxy, cycloalkyl, cycloalkoxy, aryl, heteroaryl, heterocyclyl, wherever they occur may optionally be substituted with one or more substituents independently selected from hydroxy, halo, cyano, nitro, oxo (=O), thio (=S), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, —C(O)OR$^x$, —C(O)R$^x$, —C(S)R$^x$, —C(O)NR$^x$R$^y$, —NR$^x$C(O) NR$^y$R$^z$, —N(R$^x$)S(O)R$^y$, —N(R$^x$)S(O)$_2$R$^y$, —NR$^x$R$^y$, —NR$^x$C(O)R$^y$, —NR$^x$C(S)R$^y$, —NR$^x$C(S)NR$^y$R$^z$, —S(O)$_2$NR$^x$R$^y$, —OR$^x$, —OC(O)R$^x$, —OC(O)NR$^x$R$^y$, —R$^x$C(O)OR$^y$, —R$^x$C(O)NR$^y$R$^z$, —R$^x$C(O)R$^y$, —SR$^x$, and —S(O)$_2$R$^x$; wherein each occurrence of R$^x$, R$^y$ and R$^z$ are independently selected from hydrogen, alkyl, haloalkyl, alkenyl, alkynyl, aryl, arylalkyl, cycloalkyl, cycloalkenyl, heteroaryl, heterocyclic ring, heterocyclylalkyl ring and heteroarylalkyl;

or a pharmaceutically acceptable salt thereof.

The below embodiments, which are illustrative in nature only and are not intended to limit the scope of the invention.

According to one embodiment are provided compounds of Formula (Ia):

(Ia)

or a pharmaceutically acceptable salt thereof;
wherein
ring is selected from Formula (i) to (iv)

(i)

(ii)

(iii)

(iv)

ring W, ring D, R, R$_1$, R$_2$, R$_3$, R$_4$, R$_5$, R$_{10}$, 'p' and 'q' are as defined herein above.

According to another embodiment are provided compounds of Formula (Ib):

(Ib)

or a pharmaceutically acceptable salt thereof;
wherein
ring is selected from Formula (i) to (iv) as defined in Formula (Ia);

ring W, ring D, R, R$_1$, R$_2$, R$_3$, R$_4$, R$_5$, R$_{10}$, 'p' and 'q' are as defined herein above.

According to another embodiment are provided compounds of Formula (Ic):

(Ic)

or a pharmaceutically acceptable salt thereof;
wherein ring is selected from Formula (v) to (vii)

(v)

(vi)

, and

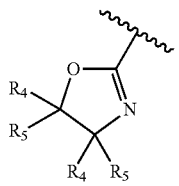

(vii)

ring W, ring D, R, $R_1$, $R_2$, $R_3$, $R_4$, $R_5$, 'p' and 'q' are as defined herein above.

According to another embodiment are provided compounds of Formula (Id):

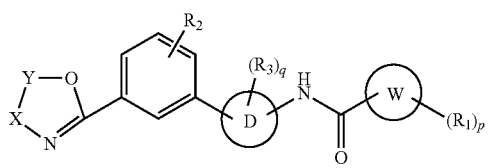

(Id)

or a pharmaceutically acceptable salt thereof; wherein ring

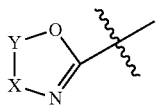

is selected from Formula (v) to (vii) as defined in Formula (Ic);

ring W, ring D, R, $R_1$, $R_2$, $R_3$, $R_4$, $R_5$, 'p' and 'q' are as defined herein above.

It should be understood that Formula (I), (Ia), (Ib), (Ic), and (Id) structurally encompass all N-oxides, tautomers, stereoisomers and pharmaceutically acceptable salts that may be contemplated from the chemical structures described herein.

According to sub embodiment are provided compounds of Formula (Ia), (Ib), (Ic) and/or (Id) in which ring D is

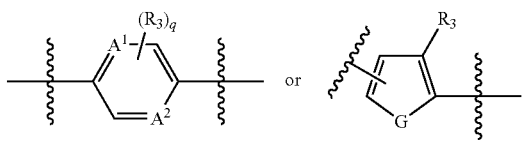

wherein $A^1$ and $A^2$ are independently selected from C and N; G is S or $NR_{12}$; 'q' is 1; $R_3$ and $R_{12}$ are as defined herein above.

According to one sub embodiment are provided compounds of Formula (Ia), (Ib), (Ic) and/or (Id) in which ring W is aryl, heteroaryl or cycloalkyl.

According to another sub embodiment are provided compounds of Formula (Ia), (Ib), (Ic) and/or (Id) in which $R_1$ is halo, hydroxyl, alkyl or alkoxy.

According to another sub embodiment are provided compounds of Formula (Ia), (Ib), (Ic) and/or (Id) in which $R_2$ is hydrogen, halo, hydroxyl, alkyl, alkenyl, haloalkyl, alkoxy, haloalkoxy, alkenyloxy, alkynyloxy, cycloalkyl, cycloalkoxy, —C(O)$OR_6$, —$NR_6R_7$ or —C(O)$R_6$; $R_6$ and $R_7$ are as defined herein above.

According to another sub embodiment are provided compounds of Formula (Ia), (Ib), (Ic) and/or (Id) in which $R_3$ is hydrogen, halo, hydroxy, alkyl, alkoxy, —C(O)$NR_6R_7$ or —C(O)$OR_6$; $R_6$ and $R_7$ are as defined herein above.

In another aspect, the invention provides a pharmaceutical composition comprising at least one compound of Formula (I) and at least one pharmaceutically acceptable excipient.

In another aspect of the invention, there is provided a compound of Formula (I) useful in treating, preventing, managing and/or lessening the severity of the diseases, disorders, syndromes or conditions associated with the modulation of CRAC channel.

In another aspect, the invention provides a pharmaceutical composition of a compound of Formula (I) useful in treating, preventing, managing and/or lessening the severity of the diseases disorders, syndromes or conditions associated with the modulation of CRAC channel in a subject in need thereof by administering to the subject, one or more compounds described herein in an amount.

In another aspect, the invention provides a method of modulating ion channel activity, for example, CRAC channel, by administering effective amount of a compound of Formula (I) and/or pharmaceutically acceptable salts.

In another aspect, the invention provides a method of modulating the secretion of cytokines, for example IL-2, IL-4, IL-10, IL-13, IL-17, IL-21, IL-23, IL-28, IFN-γ and TNF-α and the like, by regulating the cytokine signalling pathway through calcineurin and NFAT cells.

In another aspect of the invention are processes for the preparation of the compounds described herein.

According to another embodiment are provided a process for the preparation compounds of Formula (I):

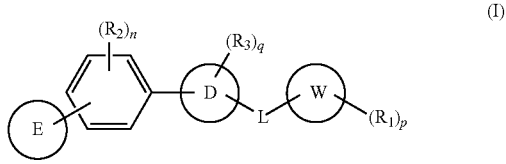

(I)

comprising reacting a compound of Formula (1) with a compound of Formula (2)

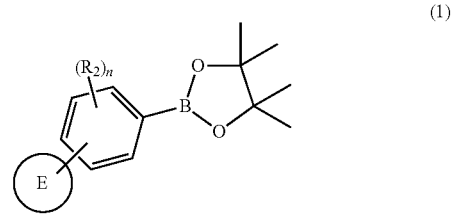

(1)

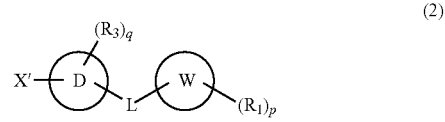

(2)

wherein X' is halo; ring E, ring D, ring W, L, $R_1$, $R_2$, $R_3$, p, q and n are as defined herein above;

in presence of a catalyst selected from Pd(PPh$_3$)$_2$Cl$_2$, Pd$_2$dba$_3$, Pd(PPh$_3$)$_4$ or Pd(OAc)$_2$ or a mixture thereof; a ligand selected from BINAP, xanthophos or triphenylphosphine or a mixture thereof and a base.

DETAILED DESCRIPTION OF THE INVENTION

Definitions and Abbreviations

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

Unless otherwise stated, in the present application "oxo" means C(=O) group. Such an oxo group may be a part of either a cycle or a chain in the compounds of the present invention.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched, substituted or unsubstituted.

The term "alkylene" refers to a saturated divalent hydrocarbon radical that includes solely carbon and hydrogen atoms in the backbone. In particular, "$C_1$-$C_5$ alkylene" means a saturated divalent hydrocarbon radical with one to six carbon atoms e.g. methylene (—$CH_2$—), ethylene (—$CH_2$—$CH_2$—), 2,2-dimethylethylene, n-propylene, 2-methylpropylene, and the like. Unless set forth or recited to the contrary, all alkylene groups described or claimed herein may be straight chain or branched, substituted or unsubstituted.

The term "alkenyl" refers to a hydrocarbon radical containing from 2 to 10 carbon atoms and including at least one carbon-carbon double bond. Non-limiting examples of alkenyl groups include ethenyl, 1-propenyl, 2-propenyl (allyl), iso-propenyl, 2-methyl-1-propenyl, 1-butenyl, 2-butenyl and the like. Unless set forth or recited to the contrary, all alkenyl groups described or claimed herein may be straight chain or branched, substituted or unsubstituted.

The term "alkynyl" refers to a hydrocarbon radical containing 2 to 10 carbon atoms and including at least one carbon-carbon triple bond. Non-limiting examples of alkynyl groups include ethynyl, propynyl, butynyl and the like. Unless set forth or recited to the contrary, all alkynyl groups described or claimed herein may be straight chain or branched, substituted or unsubstituted.

The term "alkoxy" refers to an alkyl group attached via an oxygen linkage. Non-limiting examples of such groups are methoxy, ethoxy and propoxy and the like. Unless set forth or recited to the contrary, all alkoxy groups described or claimed herein may be straight chain or branched, substituted or unsubstituted.

The term "alkenyloxy" refers to an alkenyl group attached via an oxygen linkage. Non-limiting examples of such groups are vinyloxy, allyloxy, 1-butenyloxy, 2-butenyloxy, isobutenyloxy, 1-pentenyloxy, 2-pentenyloxy, 3-methyl-1-butenyloxy, 1-methyl-2-butenyloxy, 2,3-dimethylbutenyloxy, 1-hexenyloxy and the like. Unless set forth or recited to the contrary, all alkenyloxy groups described or claimed herein may be straight chain or branched, substituted or unsubstituted.

The term "alkynyloxy" refers to an alkynyl group attached via an oxygen linkage. Non-limiting examples of such groups are acetylenyloxy, propynyloxy, 1-butynyloxy, 2-butynyloxy, 1-pentynyloxy, 2-pentynyloxy, 3-methyl-1-butynyloxy, 1-hexynyloxy, 2-hexynyloxy, and the like.

The term "cycloalkyl" refers to a non-aromatic mono or multicyclic ring system having 3 to 12 carbon atoms, such as cyclopropyl, cyclobutyl, cyclopentyl, cyclohexyl and the like. Examples of multicyclic cycloalkyl groups include, but are not limited to, perhydronapthyl, adamantyl and norbornyl groups, bridged cyclic groups or spirobicyclic groups, e.g., spiro(4,4)non-2-yl and the like. Unless set forth or recited to the contrary, all cycloalkyl groups described or claimed herein may be substituted or unsubstituted.

The term "cycloalkoxy" refers to an cycloalkyl, defined herein, group attached via an oxygen linkage. Non-limiting examples of such groups are cyclopropoxy, cyclobutoxy, cyclopentoxy, cyclohexyloxy and the like. Unless set forth or recited to the contrary, all alkoxy groups described or claimed herein may be straight chain or branched, substituted or unsubstituted.

The term "cycloalkenyl" refers to a non-aromatic mono or multicyclic ring system having 3 to 12 carbon atoms and including at least one carbon-carbon double bond, such as cyclopentenyl, cyclohexenyl, cycloheptenyl and the like. Unless set forth or recited to the contrary, all cycloalkenyl groups described or claimed herein may be substituted or unsubstituted.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl, etc. Unless set forth or recited to the contrary, all cycloalkylalkyl groups described or claimed herein may be substituted or unsubstituted.

The term "haloalkyl" refers to an alkyl group as defined above that is substituted by one or more halogen atoms as defined above. Preferably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Preferably, a polyhaloalkyl is substituted with up to 12 halogen atoms. Non-limiting examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms.

The term "haloalkoxy" refers to an haloalkyl, defined herein, group attached via an oxygen linkage. Non-limiting examples of such groups are monohaloalkoxy, dihaloalkoxy or polyhaloalkoxy including perhaloalkoxy. Unless set forth or recited to the contrary, all haloalkoxy groups described or claimed herein may be straight chain or branched, substituted or unsubstituted.

The term "hydroxyalkyl" refers to an alkyl group, as defined above that is substituted by one or more hydroxy groups. Preferably, the hydroxyalkyl is monohydroxyalkyl or dihydroxyalkyl. Non-limiting examples of a hydroxyalkyl include 2-hydroxyethyl, 3-hydroxypropyl, 2-hydroxypropyl, and the like.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like. Unless set forth or recited to the contrary, all aryl groups described or claimed herein may be substituted or unsubstituted.

The term "arylalkyl" refers to an aryl group as defined above directly bonded to an alkyl group as defined above, e.g., —CH₂C₆H₅ and —C₂H₄C₆H₅. Unless set forth or recited to the contrary, all arylalkyl groups described or claimed herein may be substituted or unsubstituted.

A "carbocyclic ring" or "carbocycle" as used herein refers to a 3- to 10-membered saturated or unsaturated, monocyclic, fused bicyclic, spirocyclic or bridged polycyclic ring containing carbon atoms, which may optionally be substituted, for example, carbocyclic rings include but are not limited to cyclopropyl, cyclobutyl, cyclopentyl, cyclohexyl, cyclopropylene, cyclohexanone, aryl, naphthyl, adamentyl etc. Unless set forth or recited to the contrary, all carbocyclic groups or rings described or claimed herein may be aromatic or non aromatic.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s), and one or two carbon atoms(s) in the heterocyclic ring or heterocyclyl may be interrupted with —C(O)—, —C(=N-alkyl)-, or —C(=N-cycloalkyl), etc. Non-limiting examples of heterocyclic rings include azepinyl, azetidinyl, benzodioxolyl, benzodioxanyl, benzopyranyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl, tetrahydropyranyl, thiazolinyl, thiazolidinyl, thiamorpholinyl, thiamorpholinyl sulfoxide, thiamorpholinyl sulfone and the like. The heterocyclic ring may be attached to the main structure at any heteroatom or carbon atom that results in the creation of a stable structure. Unless set forth or recited to the contrary, all heterocyclyl groups described or claimed herein may be substituted or unsubstituted.

The term "heteroaryl" unless otherwise specified, refers to a substituted or unsubstituted 5- to 14-membered aromatic heterocyclic ring with one or more heteroatom(s) independently selected from N, O or S. The heteroaryl may be a mono-, bi- or tricyclic ring system. The heteroaryl ring may be attached to the main structure at any heteroatom or carbon atom that results in the creation of a stable structure. Non-limiting examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like. Unless set forth or recited to the contrary, all heteroaryl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more substituents attached to the structural skeleton of the group or moiety. Such substituents include, but are not limited to hydroxy, halo, carboxyl, cyano, nitro, oxo (=O), thio (=S), alkyl, haloalkyl, alkenyl, alkynyl, aryl, arylalkyl, cycloalkyl, cycloalkylalkyl, cycloalkenyl, amino, heteroaryl, heterocyclic ring, heterocyclylalkyl, heteroarylalkyl, —C(O)OR$^x$, —C(O)R$^x$, —C(S)R$^x$, —C(O)NR$^x$R$^y$, —NR$^x$C(O)NR$^y$R$^z$, —N(R$^x$)S(O)R$^y$, —N(R$^x$)S(O)₂R$^y$, —NR$^x$R$^y$, —NR$^x$C(O) R$^y$, —NR$^x$C(S)R$^y$, —NR$^x$C(S)NR$^y$R$^z$, —S(O)₂NR$^x$R$^y$, —OR$^x$, —OC(O)R$^x$, —OC(O)NR$^x$R$^y$, —R$^x$C(O)OR$^y$, —R$^x$C(O)NR$^y$R$^z$, —R$^x$C(O)R$^y$, —SR$^x$, and —S(O)₂R$^x$; wherein each occurrence of R$^x$, R$^y$ and R$^z$ are independently selected from hydrogen, alkyl, haloalkyl, alkenyl, alkynyl, aryl, arylalkyl, cycloalkyl, cycloalkenyl, heteroaryl, heterocyclic ring, heterocyclylalkyl ring and heteroarylalkyl.

The phrase "may optionally be substituted" refers to a moiety or group that may or may not be substituted. For example, "optionally substituted aryl" means that the aryl radical may or may not be substituted and that the description includes both substituted and unsubstituted aryl radicals.

A "stereoisomer" refers to a compound having the same atoms bonded through the same bonds but having different three-dimensional orientations, which are not interchangeable. The invention contemplates various stereoisomers and mixtures thereof and includes enantiomers and diastereomers. The invention also includes geometric isomers "E" or "Z" or cis or trans configuration in a compound having either a double bond or having substituted cycloalkyl ring system.

A "Tautomer" refers to a compound that undergo rapid proton shifts from one atom of the compound to another atom of the compound. Some of the compounds described herein may exist as tautomers with different points of attachment of hydrogen. The individual tautomers as well as mixture thereof are encompassed with compounds of formula (I).

The term "treating" or "treatment" of a state, disease, disorder, condition or syndrome includes: (a) preventing or delaying the appearance of clinical symptoms of the state, disease, disorder, condition or syndrome developing in a subject that may be afflicted with or predisposed to the state, disease, disorder, condition or syndrome but does not yet experience or display clinical or subclinical symptoms of the state, disease, disorder, condition or syndrome; (b) inhibiting the state, disease, disorder, condition or syndrome, i.e., arresting or reducing the development of the disease or at least one clinical or subclinical symptom thereof; c) lessening the severity of a disease disorder or condition or at least one of its clinical or subclinical symptoms thereof; and/or (d) relieving the disease, i.e., causing regression of the state, disorder or condition or at least one of its clinical or subclinical symptoms.

The term "modulate" or "modulating" or "modulation" refers to a decrease or inhibition in the amount, quality, or effect of a particular activity, function or molecule; by way of illustration that block or inhibit calcium release-activated calcium (CRAC) channel. Any such modulation, whether it be partial or complete inhibition is sometimes referred to herein as "blocking" and corresponding compounds as "blockers". For example, the compounds of the invention are useful as modulators of the CRAC channel.

The term "subject" includes mammals, preferably humans and other animals, such as domestic animals; e.g., household pets including cats and dogs.

A "therapeutically effective amount" refers to the amount of a compound that, when administered to a subject in need thereof, is sufficient to cause a desired effect. The "therapeutically effective amount" will vary depending on the compound, the disease and its severity, age, weight, physical condition and responsiveness of the subject to be treated.

Pharmaceutically Acceptable Salts:

The compounds of the invention may form salts. In cases where compounds are sufficiently basic or acidic to form stable nontoxic acid or base salts, administration of the compound as a pharmaceutically acceptable salt may be appropriate. Non-limiting examples of pharmaceutically acceptable salts are organic acid addition salts formed by addition of acids, which form a physiological acceptable anion, for example, tosylate, methanesulfonate, acetate, citrate, malonate, tartarate, succinate, benzoate, ascorate, α-ketoglutarate, α-glycerophosphate, formate, fumarate, propionate, glycolate, lactate, pyruvate, oxalate, maleate, and salicylate. Suitable inorganic salts may also be formed, including, sulfate, nitrate, bicarbonate, carbonate salts, hydrobromate and phosphoric acid.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

With respect to the overall compounds described by the Formula (I) the invention extends to stereoisomeric forms and to mixtures thereof. The different stereoisomeric forms of the invention may be separated from one another by the method known in the art, or a given isomer may be obtained by stereospecific or asymmetric synthesis. Tautomeric forms and mixtures of compounds described herein are also contemplated.

Unless otherwise stated, in the present application "protecting group" refers to the groups intended to protect an otherwise labile group, e.g., an amino group, a carboxy group and the like, under specific reaction conditions. Various protecting groups along with the methods of protection and deprotection are generally known to a person of ordinary skilled in the art. Incorporated herein in this regard as reference is *Greene's Protective Groups in Organic Synthesis*, 4th Edition, John Wiley & Sons, New York. In the present invention, preferred amino protecting groups are t-butoxycarbonyl, benzyloxycarbonyl, acetyl and the like; while preferred carboxy protecting groups are esters, amides and the like.

Pharmaceutical Compositions

The invention relates to pharmaceutical compositions containing the compound of Formula (I). In particular, the pharmaceutical compositions contain a therapeutically effective amount of at least one compound of Formula (I) and at least one pharmaceutically acceptable excipient (such as a carrier or diluent). Preferably, the pharmaceutical compositions include the compound(s) described herein in an amount sufficient to modulate the calcium release-activated calcium (CRAC) channel to treat CRAC channel mediated diseases such as inflammatory diseases, autoimmune diseases, allergic disorders, organ transplant, cancer and cardiovascular disorders when administered to a subject.

The compound of the invention may be incorporated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes a pharmaceutical agent that does not itself induce the production of antibodies harmful to the individual receiving the composition, and which may be administered without undue toxicity.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be administered in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, capsules (soft or hard gelatin), dragees (containing the active ingredient in powder or pellet form), troches and lozenges.

Tablets, dragees, or capsules having talc and/or a carbohydrate carrier or binder or the like are particularly suitable for oral application. Liquid formulations include, but are not limited to, syrups, emulsions, soft gelatin and sterile injectable liquids, such as aqueous or non-aqueous liquid suspensions or solutions. For parenteral application, particularly suitable are injectable solutions or suspensions formulation.

Liquid formulations include, but are not limited to, syrups, emulsions, suspensions, solutions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

For administration to human patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 10000 mg, more typically 1.0 mg to 1000 mg, and most typically 10 mg to 500 mg, according to the potency of the active component or mode of administration.

Suitable doses of the compounds for use in treating the diseases disorders, syndromes and conditions described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects for the patient. For example, the daily dosage of the CRAC channel modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Method of Treatment

In a further embodiment, the invention is directed to the treatment or prophylaxis of inflammatory conditions by administering an effective amount of a compound of the present invention.

Inflammation is part of the normal host response to infection and injury or exposure to certain substances prone to cause it. Inflammation begins with the immunologic process of elimination of invading pathogens and toxins to repair damaged tissue. Hence, these responses are extremely ordered and controlled. However, excessive or inappropriate inflammation contributes to a range of acute and chronic human diseases and is characterized by the production of inflammatory cytokines, arachidonic acid-derived eicosanoids (prostaglandins, thromboxanes, leukotrienes, and other oxidized derivatives), other inflammatory agents (e.g., reactive oxygen species), and adhesion molecules. As used herein, the term "inflammatory conditions" is defined as a disease or disorder or abnormality characterized by involvement of inflammatory pathways leading to inflammation, and which may result from, or be triggered by, a dysregulation of the normal immune response.

The compound(s) of the present invention are useful in treatment of inflammatory conditions including, but not limited to, diseases of many body systems such as (musculoskeletal) arthritis, myositis, rheumatoid arthritis, osteoarthritis, gout, gouty arthritis, acute pseudogout, Reiter's syndrome, ankylosing spondylitis, psoriatic arthritis, dermatomyositis; (pulmonary) pleuritis, pulmonary fibrosis or nodules, restrictive lung disease, chronic obstructive pulmonary disease (COPD), acute respiratory distress syndrome (ARDS), (cardiovascular) aortic valve stenosis, restenosis, arrhythmias, coronary arteritis, myocarditis, pericarditis, Raynaud's phenomenon, systemic vasculitis, angiogenesis, atherosclerosis, ischaemic heart disease, thrombosis, myocardial infarction; (gastrointestinal) dysmotility, dysphagia, inflammatory bowel diseases, pancreatitis, (genitourinary) interstitial cystitis, renal tubular acidosis, urosepsis, (skin) purpura, vasculitis scleroderma, eczema, psoriasis, (neurologic) central nervous system disorders, cranial and peripheral neuropathies, peripheral neuropathy, radiculopathy, spinal cord or cauda equina compression with sensory and motor loss, multiple sclerosis (MS) (mental) cognitive dysfunction, Alzheimer's disease, (neoplastic) lymphoma, inflammation associated with cancer, (ophthalmologic) iridocyclitis, keratoconjunctivitis sicca, uveitis, (hematologic) chronic anemia, thrombocytopenia, (renal) amyloidosis of the kidney, glomerulonephritis, kidney failure and other diseases such as tuberculosis, leprosy, sarcoidosis, syphilis, Sjögren's syndrome, cystitis, fibromyalgia, fibrosis, septic shock, endotoxic shock, surgical complications, systemic lupus erthymotosus (SLE), transplantation associated arteriopathy, graft vs. host reaction, allograft rejection, chronic transplant rejection.

The inflammatory bowel diseases also include Crohn's disease, ulcerative colitis, indeterminate colitis, necrotizing enterocolitis, and infectious colitis.

"Allergic disorders" is defined as disorders/diseases that are caused by a combination of genetic and environmental factors resulting in a hypersensitivity disorder of the immune system. Allergic diseases are characterized by excessive immunoglobulin E (IgE) production, mast cell degranulation, tissue eosinophilia and mucus hypersecretion, resulting in an extreme inflammatory response. These responses also take place during infection with multicellular parasites, and are linked to the production of a characteristic set of cytokines by T helper (Th) 2 cells. For example asthma is a chronic inflammatory condition of the lungs, characterized by excessive responsiveness of the lungs to stimuli, in the form of infections, allergens, and environmental irritants. Allergic reactions can also result from food, insect stings, and reactions to medications like aspirin and antibiotics such as penicillin. Symptoms of food allergy include abdominal pain, bloating, vomiting, diarrhea, itchy skin, and swelling of the skin during hives. Food allergies rarely cause respiratory (asthmatic) reactions, or rhinitis. Insect stings, antibiotics, and certain medicines produce a systemic allergic response that is also called anaphylaxis. The main therapeutic interest around CRAC in allergic disorders, originates from its role in lymphocytes and mast cells, CRAC activation being a requirement for lymphocyte activation.

The compound(s) of the present invention are useful in treatment of allergic disorders including, but not limited to, atopic dermatitis, atopic eczema, Hay fever, asthma, urticaria (including chronic idiopathic urticaria), vernal conjunctivitis, allergic rhinoconjunctivitis, allergic rhinitis (seasonal and perennial), sinusitis, otitis media, allergic bronchitis, allergic cough, allergic bronchopulmonary aspergillosis, anaphylaxis, drug reaction, food allergies and reactions to the venom of stinging insects.

In yet another embodiment, the invention is directed to the treatment or prevention of "immune disorders" by administering an effective amount of a compound of the present invention.

The compounds of this invention can be used to treat subjects with immune disorders. As used herein, the term "immune disorder" and like terms mean a disease, disorder or condition caused by dysfunction or malfunction of the immune system as a whole or any of its components including autoimmune disorders. Such disorders can be congenital or acquired and may be characterized by the component(s) of the immune system getting affected or by the immune system or its components getting overactive. Immune disorders include those diseases, disorders or conditions seen in animals (including humans) that have an immune component and those that arise substantially or entirely due to immune system-mediated mechanisms. In addition, other immune system mediated diseases, such as graft-versus-host disease and allergic disorders, will be included in the definition of immune disorders herein. Because a number of immune disorders are caused by inflammation or lead to inflammation, there is some overlap between disorders that are considered immune disorders and inflammatory disorders. For the purpose of this invention, in the case of such an overlapping disorder, it may be considered either an immune disorder or an inflammatory disorder. An autoimmune disorder is a condition that occurs when the immune system mistakenly attacks and destroys its own body cells, tissues and/or organs. This may result in temporary or permanent destruction of one or more types of body tissue, abnormal growth of an organ, changes in organ function, etc. For example, there is destruction of insulin producing cells of the pancreas in Type 1 diabetes mellitus. Different autoimmune disorders can target different tissues, organs or systems in an animal while some autoimmune disorders target different tissues, organs or systems in different animals. For example, the autoimmune reaction is directed against the gastrointestinal tract in Ulcerative colitis and the nervous system in multiple sclerosis whereas in systemic lupus erythematosus (lupus), affected tissues and organs may vary among individuals with the same disease. For example, one person with lupus may have affected skin and joints whereas another may have affected kidney, skin and lungs.

Specific autoimmune disorders that may be ameliorated using the compounds and methods of this invention include without limitation, autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland), autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome), autoimmune disorders of the nervous system (e.g., multiple sclerosis, myasthenia gravis, autoimmune neuropathies such as Guillain-Barre, and autoimmune uveitis), autoimmune disorders of the blood (e.g., autoimmune hemolytic anemia, pernicious anemia, and autoimmune thrombocytopenia) and autoimmune disorders of the blood vessels (e.g., temporal arteritis, anti-phospholipid syndrome, vasculitides such as Wegener's granulomatosis, and Behcet's disease).

"Treatment of an immune disorder" herein refers to administering a compound or a composition of the invention alone or in combination with other agents to a subject, who has an immune disorder, a sign or symptom of such a disease or a risk factor towards such a disease, with a purpose to cure, relieve, alter, affect, or prevent such disorder or sign or symptom of such a disease, or the predisposition towards it.

In another embodiment, the invention is directed to the treatment or prevention of cancer by administering an effective amount of a compound of the present invention.

It has been reported in the art that STIM1 and Orai1 are essential in in vitro tumor cell migration and in vivo tumor metastasis. Thus the involvement of store operated $Ca^{2+}$ entry in tumor metastasis renders STIM1 and Orai1 proteins potential targets for cancer therapy (Yang et. al., Cancer Cell, 15, 124-134, 2009). Additional literature available on the involvement of CRAC channel in cancer are Abeele et. al., Cancer Cell, 1, 169-179, 2002, Motiani et al., J. Biol. Chem., 285; 25, 19173-19183, 2010.

The compound(s) of the present invention may be useful in treatment of cancers and/or its metastasis including, but not limited to, breast cancer, lung cancer, pancreatic cancer, ovarian cancer, colon cancer, neck cancer, kidney cancer, bladder cancer, thyroid, blood cancer, skin cancer and the like. In yet another embodiment, the invention is directed to the treatment or prophylaxis of allergic disorders by administering an effective amount of a compound of the present invention.

In yet another embodiment, the invention is directed to the treatment or prophylaxis of cardiovascular diseases or disorders by administering an effective amount of a compound of the present invention.

The compounds of this invention can be used to treat subjects with cardiovascular disorders. "Cardiovascular disorder" refers to a structural and functional abnormality of the heart and blood vessels, comprised of diseases including but not limited to, atherosclerosis, coronary artery disease, arrhythmia, heart failure, hypertension, diseases of the aorta and its branches, disorders of the peripheral vascular system, aneurysm, endocarditis, pericarditis, heart valve disease. It may be congenital or acquired. One of the main pathological feature of all these diseases is clogged and hardened arteries, obstructing the blood flow to the heart. The effects differ depending upon which vessels are clogged with plaque. The arteries carrying oxygen rich blood, if clogged, result in coronary artery disease, chest pain or heart attack. If the arteries reaching the brain are affected, it leads to transient ischemic attack or stroke. If the vessels in arms or legs are affected, leads to peripheral vascular disease. Because a number of cardiovascular diseases may also be related to or arise as a consequence of thrombocytopathies, there is some overlap between disorders that are considered under heading cardiovascular disorders and thrmobocytopathies. For the purpose of this invention, in the case of such an overlapping disorder, it may be considered either a cardiovascular disorder or a thrombocytopathy.

STIM1 is located on the endoplasmic reticulum (ER) and functions as a calcium sensor. Orai1 is a pore forming subunit of calcium channel located on the plasma membrane, the depletion of calcium in the endoplasmic reticulum is sensed by STIM1, and calcium enters via Orai1 to refill the endoplasmic reticulum. This pathway of filling the calcium is called store operated calcium entry (SOCE), which plays an important role in calcium homeostasis, cellular dysfunction and has a significant importance in cardiovascular diseases. In cardiomyocytes, calcium is not only involved in excitation-contraction coupling but also acts as a signalling molecule promoting cardiac hypertrophy. Hypertrophic hearts are susceptible to abnormalities of cardiac rhythm and have impaired relaxation. Vascular smooth muscle cells (VSMCs) are responsible for the maintenance of vascular tone. VSMCs disorders, usually manifested as a phenotype change, are involved in the pathogenesis of major vascular diseases such as atherosclerosis, hypertension and restenosis. SOCE was also found increased in metabolic syndrome (MetS) swine coronary smooth muscle cells. The compound of this invention can be used to treat neointimal hyperplasia, occlusive vascular diseases, MetS—which is a combination of medical disorders including coronary artery disease, stroke and type 2 diabetes, abdominal aortic aneurysm, angina, transient ischemic attack, stroke, peripheral artery occlusive disease which includes inflammation, complement activation, fibrinolysis, angiogenesis and/or diseases related to FXII-induced kinin formation such as hereditary angioedema, bacterial infection of the lung, trypanosome infection, hypotensive shock, pancreatitis, chagas disease, thrombocytopenia or articular gout, myocardial infarction, portal vein thrombosis which leads to hypertension, pulmonary hypertension, deep vein thrombosis, jugular vein thrombosis, systemic sepsis, pulmonary embolism, and papilledema, Budd-Chiari syndrome, Paget-Schroetter disease, cerebral venous sinus thrombosis ischemic cardiomyopathy, hypertrophic cardiomyopathy, arrhythmogenic right ventricular cardiomyopathy, Prinzmetal angina, angina pectoris, chronic venous insufficiency, acute coronary syndrome, endocarditis, conceptual apraxia, pulmonary valve stenosis, thrombophlebitis, ventricular tachycardia, temporal arteritis, tachycardia, paroxysmal atrial fibrillation, persistent atrial fibrillation, permanent atrial fibrillation, respiratory sinus arrhythmia, carotid artery dissection, cerebrovascular diseases include, hemorrhagic stroke and ischemic stroke (where the thrombo-inflammatory cascade results in infarct growth), cardiomegaly, endocarditis, pericarditis, pericardial effusion. Valvular heart disease, vascular diseases or vascular inflammation is the result of ruptured atherosclerotic plaque which initiates thrombus formation. Platelet activation play an important role in vascular inflammation leading to myocardial infarction and ischaemic stroke, the compound of this invention will prevent platelet activation and plaque formation and would also be useful to treat all peripheral vascular diseases (PVD), pulmonary thromboembolism, and venous thrombosis.

"Treatment of cardiovascular disorders" herein refers to administering a compound or a composition of the invention alone or in combination with other agents to a subject, who has a cardiovascular disease, a sign or symptom of such a disease or a risk factor towards such a disease, with a purpose to cure, relieve, alter, affect, or prevent such disorder or sign or symptom of such a disease, or the predisposition towards it.

In yet another embodiment, the invention is directed to the treatment or prevention of "thrombocytopathies" by administering an effective amount of a compound of the present invention.

Thrombocytopathies: The compounds of this invention can be used to treat subjects with thrombocytopathies. Thrombocytopathy is an abnormality of platelets or its functions. It may be congenital or acquired. It may cause a thrombotic or a bleeding tendency or may be part of a wider disorder such as myelodysplasia. Thrombocytopathies include such vascular disorders that arise due to dysfunction of platelets or coagulation system or diseases or complications that arise as a result of partial or complete restriction of blood flow to different organs or systems due to such thrombocytopathies. Thrombocytopathies will thus include without limitation; diseases due to superficial vein thrombosis, diseases due to deep vein thrombosis, diseases due to arterial thrombosis, peripheral vascular diseases, thrombophilia, thrombophlebitis, embolisms, thromboembolism, ischemic cardiovascular diseases including but not limited to myocardial ischemia, angina, ischemic cerebrovascular diseases including but not limited to stroke, transient ischemia attack, cerebral venous sinus thrombosis (CVST) and complications arising due to thrmobocytopathies. Besides this, the disorder related to venous or arterial thrombus formation can be inflammation, complement activation, fibrinolysis, angiogenesis and/or diseases related to FXII-induced kinin formation such as hereditary angioedema, bacterial infection of the lung, trypanosome infection, hypotensive shock, pancreatitis, chagas disease, thrombocytopenia or articular gout.

Under normal circumstances, when the endothelial cells lining blood vessels are breached, platelets interact with von Willebrand factor (vWF) via the membrane glycoprotein 1b complex to help seal the breach. Glycoprotein IIb/Ia complex attracts other platelets, which combine to form aggregates. The platelets contain granules which break down to release fibrinogen, vWF, platelet-derived growth factor adenosine 5'-diphosphate (ADP), calcium and 5-hydroxytryptamine (5-HT)-serotonin. All this helps to promote the formation of a haemostatic plug (primary haemostasis). Activated platelets also synthesise thromboxane A2 from arachidonic acid as well as presenting negatively charged phospholipids on the outer leaflet of the platelet membrane bilayer. This negative surface provides binding sites for enzymes and cofactors of the coagulation system. The total effect is therefore to stimulate the coagulation system to form a clot (secondary haemostasis).

Thus physiological platelet activation and thrombus formation are essential to stop bleeding in case of vascular injury, whereas under pathological conditions this may lead to vessel occlusion due to inadequate triggering of the same process in diseased vessels leading to thrombosis, thromboembolism or tissue ischemia of vital organs. A central step in platelet activation is agonist-induced elevation of the intracellular Ca(2+) concentration. This happens on the one hand through the release of Ca(2+) from intracellular stores and on the other hand through Ca(2+) influx from the extracellular space. In platelets, the major Ca(2+) influx pathway is through store operated Ca(2+) entry (SOCE), induced by store depletion. STIM1 is the Ca(2+) sensor in the endoplasmic reticulum (ER) membrane, whereas Orai1 is the major store operated Ca(2+) (SOC) channel in the plasma membrane, which play a key role in platelet SOCE.

"Treatment of thrombocytopathy" herein refers to administering a compound or a composition of the invention alone or in combination with other agents to a subject, who has a thrombocytopathy, a sign or symptom or complication of such a disease or a risk factor towards such a disease, with the purpose to cure, relieve, alter, affect, or prevent such a disorder or sign or symptom, or the predisposition towards it.

General Methods of Preparation

The compounds of the present invention, including compounds of general formula (I) and specific examples are prepared through the reaction sequences illustrated in synthetic Schemes 1 to 5 wherein ring E, ring W, ring D, L, $R_1$, $R_2$, $R_3$, 'n' 'p' and 'q' are as defined herein above. Starting materials are commercially available or may be prepared by the procedures described herein or by the procedures known in the art. Furthermore, in the following synthetic schemes, where specific acids, bases, reagents, coupling agents, solvents, etc., are mentioned, it is understood that other bases, acids, reagents, coupling agents, solvents etc., known in the art may also be used and are therefore included within the scope of the present invention. Variations in reaction conditions and parameters like temperature, pressure, duration of reaction, etc., which may be used as known in the art are also within the scope of the present invention. All the isomers of the compounds described in these schemes, unless otherwise specified, are also encompassed within the scope of this invention.

The compounds obtained by using the general reaction sequences may be of insufficient purity. These compounds can be purified by using any of the methods for purification of organic compounds known in the art, for example, crystallization or silica gel or alumina column chromatography using different solvents in suitable ratios. Unless mentioned otherwise, room temperature refers to a temperature in the range of 22 to 27° C.

$^1$H-NMR spectra of the compounds of the present invention were recorded using a BRUCKNER instrument (model: Avance-III), 400 MHz. Liquid chromatography-mass spectra (LCMS) of the compounds of the present invention were recorded using Agilent ion trap model 6320 and Thermo Scientific Single Quad model MSQ plus instruments. IUPAC nomencleature for the compounds of the present invention were used according to ChemBioDraw Ultra 12.0 software.

thereof; in the presence of a suitable base, preferably inorganic bases such as alkalimetal carbonates like sodium carbonate, cesium carbonate and phosphates like potassium phosphate or mixture(s) thereof. As also known from the art, such reactions are effected in the solvents like ethers such as tetrahydrofuran, dioxane, and the like; hydrocarbons like toluene; amides such as DMA, DMF and the like; sulfoxides like dimethylsulfoxide; halogenated hydrocarbons like DCM or mixture(s) thereof to afford the compounds of the formula (I).

Scheme 2

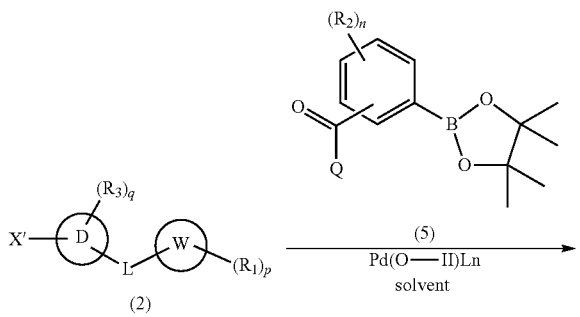

Scheme 1

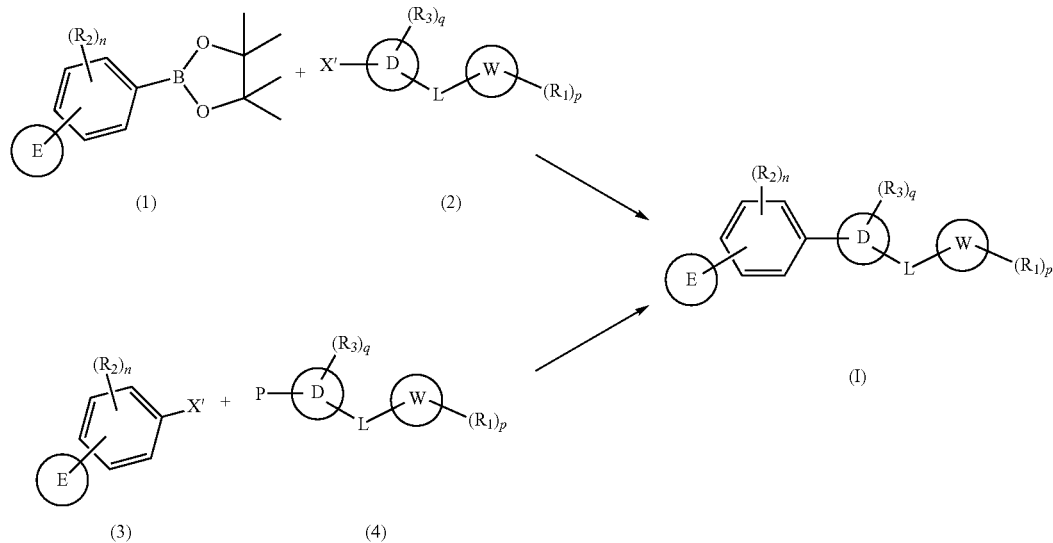

X' is halogen; P is pinacolatoboronate or stannane;

The compounds of formula (I) can be prepared by the reaction of borate derivative of formula (1) with various halobenzamides of formula (2) as depicted in Scheme 1.

Alternatively, the compounds of the formula (I) can also be prepared by the reaction of the halo derivatives of the formula (3) with borate/stannane derivatives of the formula (4) as shown in Scheme 1. The same transformation may also be carried out by other suitable coupling methods known in the art.

The said reaction can be mediated by a suitable catalyst known in the art such as Pd(PPh$_3$)$_2$Cl$_2$, Pd$_2$dba$_3$, Pd(PPh$_3$)$_4$, Pd(OAc)$_2$ or mixture(s) thereof; a suitable ligand known in the art such as 2,2'-bis(diphenylphosphino)-1,1'-binaphthyl (BINAP), xanthophos, triphenylphosphine or mixture(s)

-continued

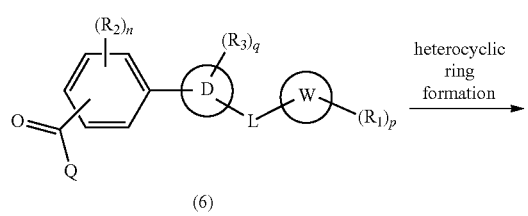

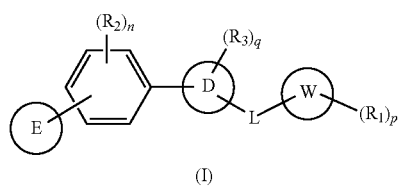

Q is H, OH or alkyl;

In an alternative approach, the compounds of the present invention can also be prepared as depicted in Scheme 2. Thus, the borate complex of formula (5) are prepared from the corresponding halo derivatives via a metal catalysed boration reaction. As also known in the art, such reactions are carried out in presence of a metal catalyst for example Pd(PPh$_3$)$_2$Cl$_2$, Pd$_2$dba$_3$, PdCl$_2$.dppf, Pd(PPh$_3$)$_4$, Pd(OAc)$_2$ in suitable solvent(s) for example ethers like THF, dioxane and the like; hydrocarbons like toluene; amides such as DMF, DMA and the like; sulfoxides like dimethylsulfoxide. The coupling reaction of halobenzamide derivatives of the formula (2) with borate derivatives of the formula (5) are carried out by following the methods known in the art or as described in the Scheme 1 to afford the compounds of the formula (6). This compounds of the formula (6) can be converted to compounds of formula (I) by following the procedure known in the art.

Another alternative approach is shown in Scheme 3, where the compound of formula (I) can be prepared by the reaction of the borate derivative of the formula (1) with the various halide derivatives of the formula (7) followed by amide coupling reaction.

Alternatively, the compounds of the present invention are also prepared by the reaction of the halo derivatives of the formula (3) with stannane derivatives of the formula (8) followed by amide coupling reaction as shown in Scheme 3. The same transformation may also be carried out by other suitable coupling methods known in the art. The coupling reaction of the halide derivatives of the formula (7) with borate derivatives of the formula (1), or halo derivatives of the formula (3) with stannane derivatives of the formula (8) are carried out as per the methods known in the art or as described in the Scheme 1 to afford compounds of the formula (9). This compounds of the formula (9) are transformed to compound of formula (I) using the techniques known in the art.

For example, compounds of the formula (9) are transformed to the compounds of the present invention by coupling with the other intermediate (9a) by amide coupling reaction, i.e., formation of an amide linkage. Such amide coupling reaction is carried out by condensing an amino group or a protected amino group with a carboxylate group like carboxylic acid or an activated carboxylic acid or an ester present on either intermediate (9) or (9a). Such groups are represented by Y' and Y'' on intermediate (9) and (9a). Condensation of an amino group or a protected amino group with a carboxylate group—like carboxylic acid or an activated carboxylic acid or an ester—present as either Y' or Y'' group is carried out using techniques known in the art. However, in Scheme 3

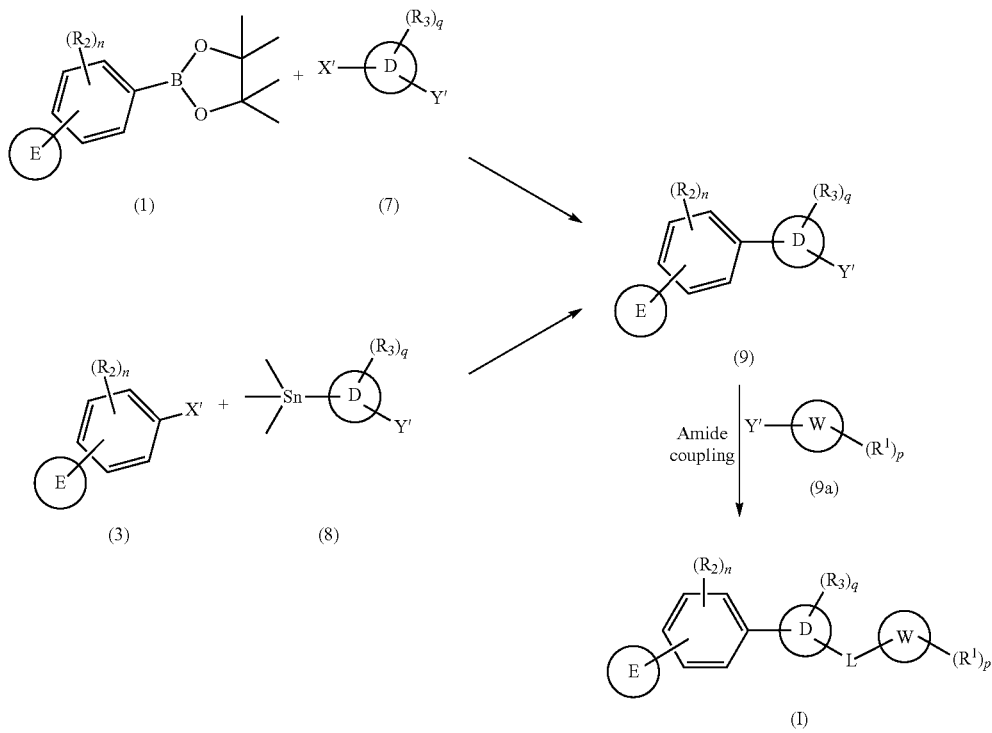

X' is halogen;
Y' is either NHR$_{11}$; or COOH, COOalkyl or COCl
Y' is either COOH, COOalkyl, COCo; or NHR$_{11}$ a few preferred aspects of the present invention, such amide coupling reactions are accomplished in either of the following ways—when Y' is an amino group or a protected amino group and Y" is a carboxylate group like carboxylic acid or an activated carboxylic acid or an ester group—or when Y' is an carboxylate group like carboxylic acid or an activated carboxylic acid or an ester group and Y" amino group or a protected amino group:

(a) condensation of Y' and Y" groups in the presence of a suitable activating reagent used in peptide linkage syntheses, e.g., hydroxybenzotriazole, 2-hydroxypyridine, acetoneoxime and a coupling reagent like carbodiimides such as EDC, DCC or mixture(s) thereof; or (e) amide coupling of the amine derivatives at Y' or Y" of the compounds of the formula (9) or (9a), with the corresponding acid chloride derivatives at Y" or Y' of the compounds of formula (9a) or (9), respectively.

Such reactions are carried out in one or more solvents known in the art for example, chlorinated solvents; DCM, chloroform and the like; ethers such as diethyl ether, THF and the like; amides such as DMF, DMA and the like; or a mixture thereof; in the presence of a suitable base like triethylamine, N-ethyldiisopropylamine; 4-dialkylaminopyridines like 4-dimethylaminopyridine, pyridine or mixture(s) thereof.

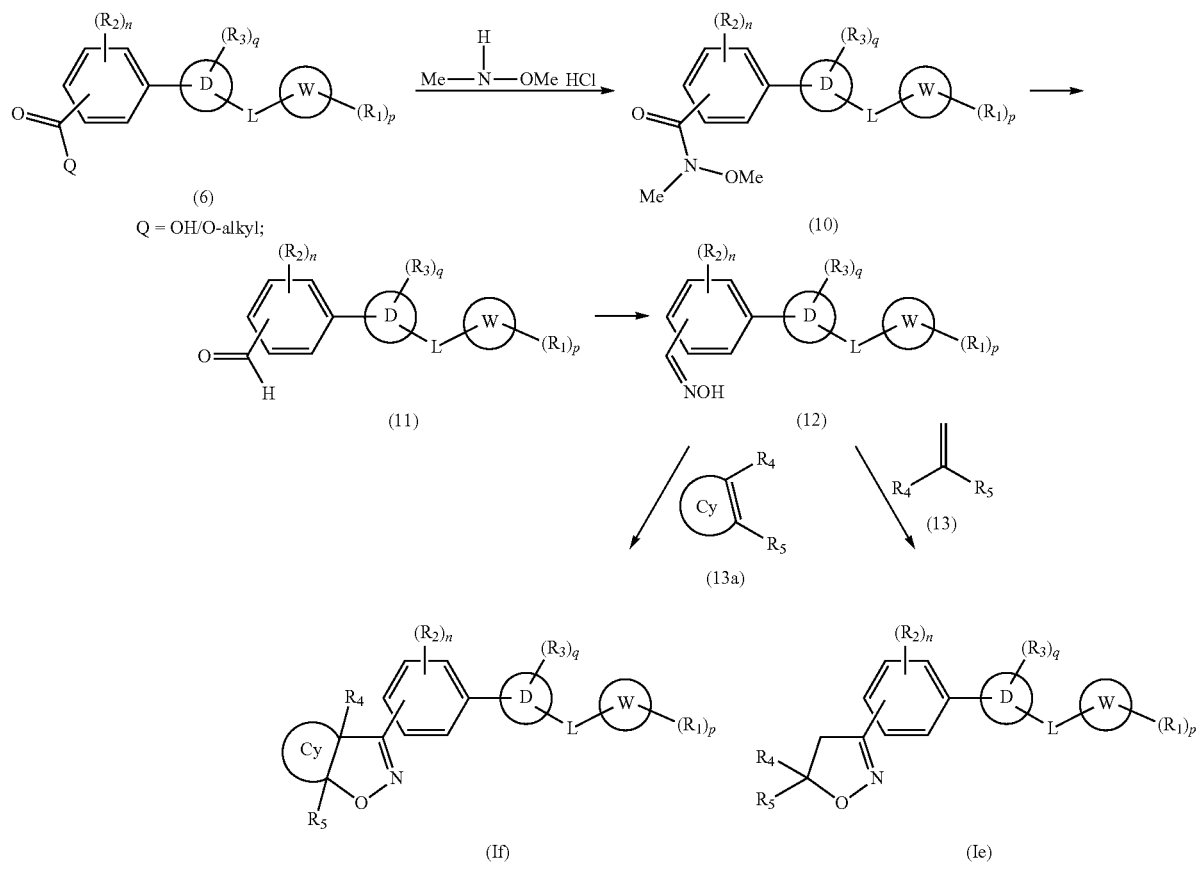

Cy = carbocycle or heterocycle (b) halogenation of the acid derivatives at Y' or Y" of the compounds of formula (9) or (9a) with thionyl chloride, oxalyl chloride and the like followed by condensation with the amino or protected amino group at Y" or Y', respectively; or (c) mixed anhydride formation of the acid derivatives at Y' or Y" of the compounds of the formula (9) or (9a) with isobutylchloroformate, ethylchloroformate and the like or mixture(s) thereof followed by condensation with the amino or protected amino group at Y" or Y' of the compounds of formula (9a) or (9), respectively; or (d) reaction at Y' or Y" of the compounds of formula (9) or (9a) with corresponding amine derivatives at Y' or Y" of the compounds of formula (9a) or (9) respectively, in presence of trimethyl aluminium; or In another embodiment, the compounds of the present invention, wherein ring E is dihydroisoxazols, can be prepared as described in synthetic Scheme 4. The compounds of formula (6), wherein Q=Oalkyl/OH, are then converted to the Weinreb amide of formula (10) by the reaction with N,O-dimethylhydroxylamine hydrochloride in presence of an activating reagent like hydroxybenzotriazole, 2-hydroxypyridine, acetoneoxime or mixture(s) thereof; and a coupling reagent like carbodiimides such as EDC, DCC or mixture(s) thereof. Such reactions are carried out in one or more solvents known in the art for example, chlorinated solvents; DCM, chloroform and the like; ethers such as diethyl ether, THF and the like; amides such as DMF, DMA and the like; or a mixture thereof; and in the presence of a suitable base like triethylamine, N-ethyldiisopropylamine; 4-dialkylaminopyridines like 4-dimethylaminopyridine or a mixture thereof.

The compounds of Formula (10) are reduced to the corresponding aldehydes of the formula (11) with a reducing agent known in the art. Although not limited, such reducing agents include alkyl- and alkoxy-metal hydrides like sodium bis(2-methoxyethoxy)aluminium hydride, lithium aluminium hydride, diisobutylaluminium hydride or mixture(s) thereof. Such reduction of the compounds of formula (10) are carried out in one or more solvents like ethers such as diethyl ether, THF and the like; alcohols such as methanol, ethanol, isopropanol and the like; amides such as DMF, DMA and the like; chlorinated solvents such as DCM, chloroform and the like; or mixture(s) thereof.

pound of formulae (Ie) or (1f) respectively. This reaction can be carried out as per the processes known in the art in presence of one or more halogenating reagents or oxidizing agents. Although not limited, halogenating reagents like N-halosuccinimide such as N-bromosuccinimide or N-chlorosuccinimide, sodium hypochlorite. Oxidizing agents like magtrieve are used as known from the art. Such reactions are effected in one or more solvents like nitriles such as acetonitrile; ketones such as acetone; alcohols such as methanol, ethanol, propanol, butanol and the like; ethers such as diethyl ether, THF and the like; amides: DMF, DMA and the like; sulfoxides like dimethylsulfoxide; hydrocarbons such as hexane, toluene and the like; halogenated hydrocarbons such as DCM, chloroform and the like or mixture(s) thereof.

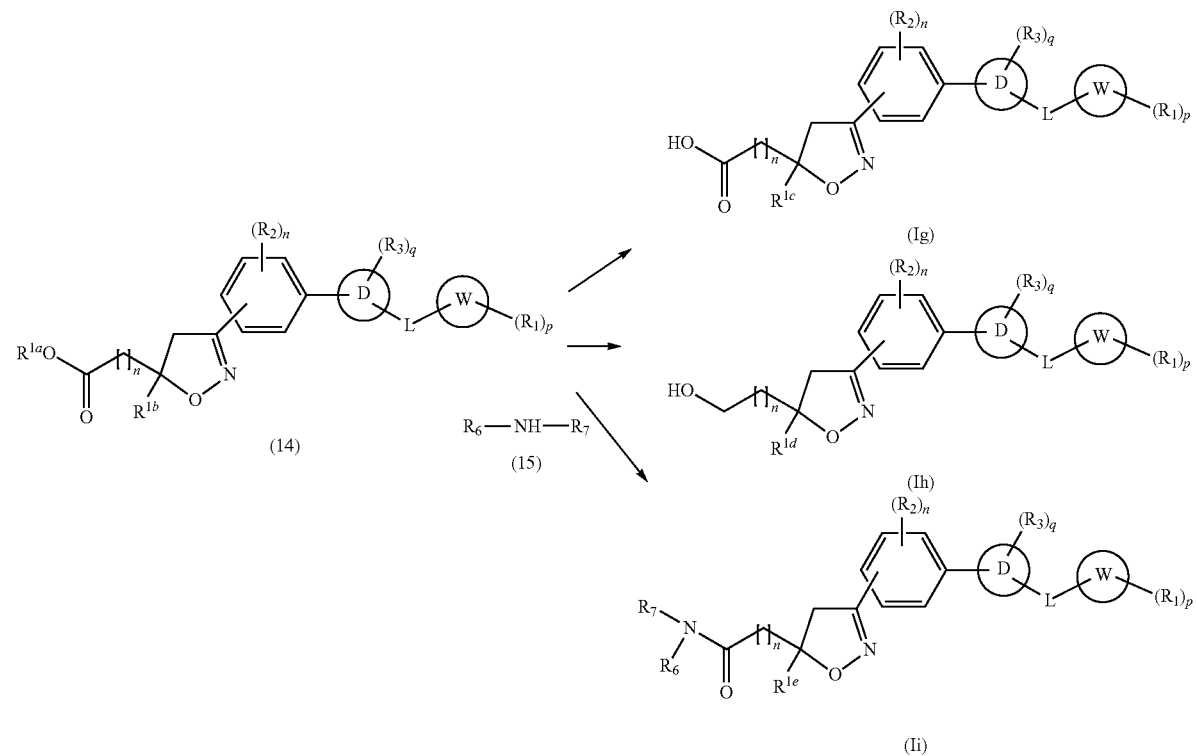

Scheme 5

$R^{1b}$ = alkyl or ester
$R^{1c}$ = alkyl or ——$(CH_2)_n$COOH
$R^{1d}$ = alkyl or ——$(CH_2)_n$CH$_2$OH
$R^{1e}$ = alkyl, ——$(CH_2)_n$CONR$_6$R$_7$ The compounds of formula (11) are converted to the corresponding oximes of the formula (12) by the processes known in the art. Preferably, compounds of the formula (11) are treated with hydroxylamine hydrochloride in the presence of bases. Any base known in the art can be used for the said reaction, for example, alkalimetal acetates such as sodium acetate; alkali metal hydroxides like potassium hydroxide, sodium hydroxide or mixture(s) thereof. Such a reaction can be effected; in one or more solvent generally used in the art like alcohols such as methanol, ethanol, isopropanol, butanol or mixture(s) thereof under the conditions generally used in the art.

The reaction of the oximes of formula (12) with substituted alkenes of formula (13) or cyclic alkene (13a) to afford com- Compound of formulae (Ig) can be prepared by following the procedure as depicted in Scheme 5. The ester derivatives of the formula (14) are converted to the compounds of the formula (Ig) by the hydrolysis processes known in the art. Thus, the hydrolysis can be carried out in presence of acids such as trifluoroacetic acid, hydrochloric acid and the like; or mixtures thereof or bases such as alkali metal hydroxides like sodium hydroxide, potassium hydroxide, lithium hydroxide and the like; or alkalineearth metal hydroxides such as barium hydroxide and the like; or mixtures thereof. Such hydrolysis reactions can be carried out in a suitable solvent like ethers such as diethyl ether, tetrahydrofuran and the like; protic solvents like water, methanol, ethanol, propanol, isobutanol; or mixtures thereof.

Accordingly, compound of formulae (Ih) can be prepared by following the procedure as depicted in Scheme 5. Ester derivatives of the formula (14) are converted to the compounds of the formula (Ih) by reduction processes known in the art by using suitable reducing agent such as lithium aluminium hydride, diisobutylaluminium hydride, sodium borohydride and in suitable solvent like ethers such as diethyl ether, THF, and the like; alcohols such as methanol, ethanol, propanol and the like; amides such as dimethylformamide, dimethylacetamide and the like; sulfoxides like dimethylsulfoxide; hydrocarbons such as hexane, toluene and the like; chlorinated solvents like DCM or mixture(s) thereof.

Accordingly, compound of formulae (Ii) can be prepared by following the procedure as depicted in Scheme 5. Compounds of the formula (14) are treated with a compound of the formula (15) where $R_4$ and $R_5$ are as defined herein above, in an appropriate solvent like alcohols such as methanol, ethanol, isopropanol and the like; ethers such as diethyl ether, tetrahydrofuran and the like; hydrocarbons such as benzene, toluene and the like; or mixture(s) thereof.

The present invention is further illustrated by the following intermediates and examples with detailed procedure to prepare them, which are not to be construed in any way as imposing limitations upon the scope of this disclosure, but rather are intended to be illustrative only.

INTERMEDIATES

All intermediates used for the preparation of the compounds of the present invention, were prepared by approaches reported in the literature or by methods known in the art of organic chemistry. Detailed experimental procedures for synthesis of the corresponding intermediates are given below:

Intermediate 1a & 1b 5,5-Dimethyl-3-(4,4,5,5-tetramethyl-1,3,2-dioxaborolan-2-yl)phenyl)isoxazol-4-(5H)-one (1a) and 3-(3-(5-Aminopyrazin-2-yl)-4-methylphenyl)-5,5-dimethylisoxazol-4-(5H)-one (1b)

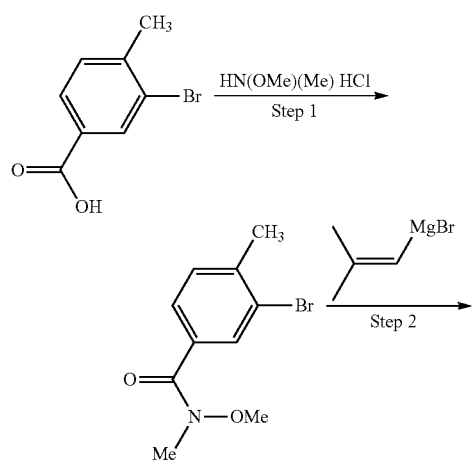

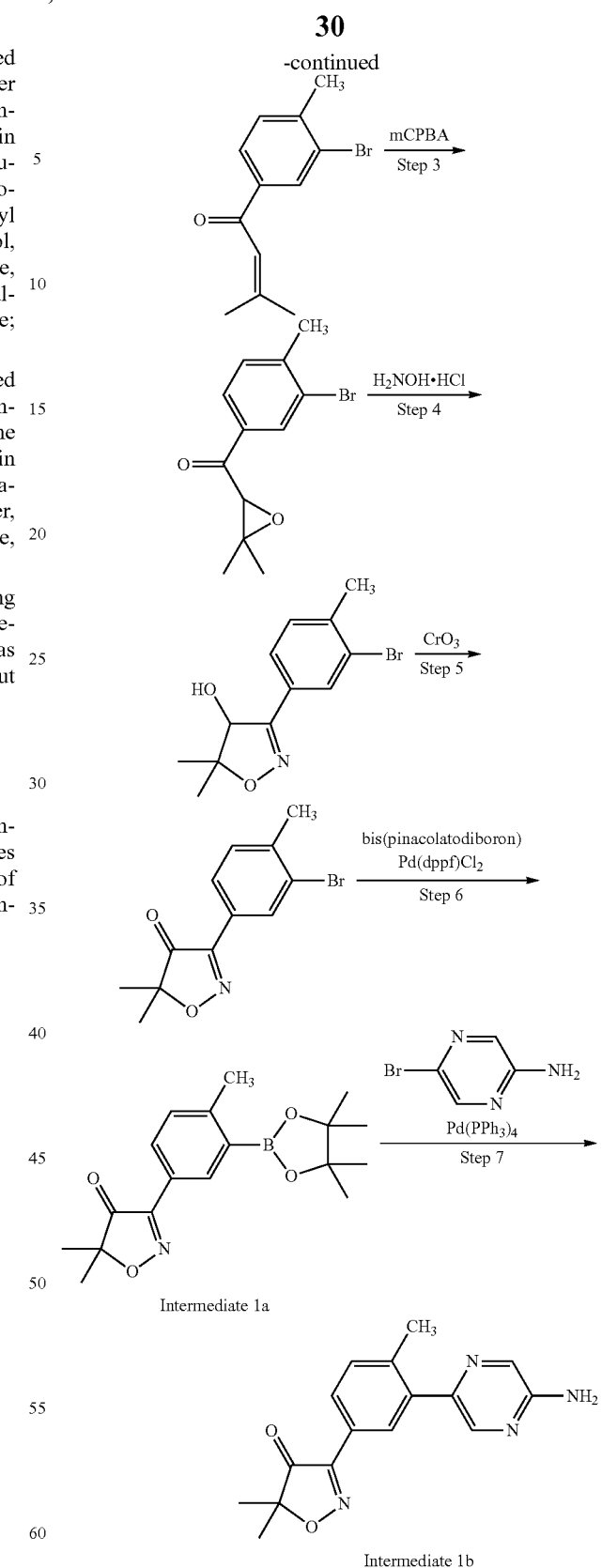

Step 1: 3-Bromo-4-methyl-[N-(methoxy)-N'-(methyl)] benzamide: To a solution of 3-bromo-4-methylbenzoic acid (10 g, 46.5 mmol) in DCM, N-methyl-N'-methoxyamine hydrochloride (4.5 g, 46.5 mmol, 1.0 eq), EDC. HCl (9.80 g, 51.1 mmol, 1.1 eq), HOBT (6.91 g, 51.15 mmol, 1.1 eq) and triethylamine (13 mL, 93 mmol, 2 eq) were added successively. The resulting mixture was stirred at room temperature for 3 h. The reaction mixture was diluted with ethyl acetate (50 mL) and water (50 mL). The layers were separated and the aqueous layer was extracted with ethyl acetate (2×50 mL). The combined organic layers were washed with brine (50 mL), dried (Na$_2$SO$_4$) and filtered. The filtrate was concentrated under reduced pressure to afford 6.80 g of the desired 3-bromo-4-methyl-[N-(methoxy)-N'-(methyl)]benzamide. $^1$HNMR (400 MHz, CDCl$_3$) δ 7.88 (s, 1H), 7.55 (d, J=8.0 Hz, 1H), 7.26 (d, J=8.0 Hz, 1H), 3.55 (s, 3H), 3.35 (s, 3H), 2.42 (s, 3H); ESI-MS (m/z) 258, 260 [(MH)$^+$, Br$^{79,81}$].

Step 2: 1-(3-Bromo-4-methylphenyl)-3-methylbut-2-en-1-one: To a stirred and cooled (at −20° C.) solution of 3-bromo-4-methyl-[N-(methoxy)-N'-(methyl)]benzamide (600 mg, 2.32 mmol, 1.0 eq) in THF (5 mL) a solution of isopropenylmagnesium bromide in THF (0.5 M, 5.6 mL, 2.79 mmol, 1.2 eq) was added. The resulting reaction mixture was allowed to warm to room temperature over a period of 15-20 minutes and then stirred at room temperature for 2 h. The reaction mixture was cooled to 0° C. before being quenched with saturated ammonium chloride solution (3 mL). The resulting mixture was extracted with ethyl acetate (3×10 mL). The combined organic layers were washed with brine (10 mL), dried (Na$_2$SO$_4$) and filtered. The filtrate was concentrated under vacuum to afford 0.58 g of the desired product as a white solid. $^1$HNMR (400 MHz, CDCl$_3$) δ 8.07 (d, J=1.0 Hz, 1H), 7.75 (dd, J=1.0, 8.0 Hz, 1H), 7.29 (d, J=8.0 Hz, 1H), 6.68 (s, 1H), 2.43 (s, 3H), 2.20 (s, 3H), 2.01 (s, 3H); ESI-MS (m/z) 253, 255 [(MH)$^+$, Br$^{79,81}$].

Step 3: (3-Bromo-4-methylphenyl)(3,3-dimethyloxiran-2-yl)methanone: To a cooled solution (at 0° C.) of 1-(3-bromo-4-methylphenyl)-3-methylbut-2-en-1-one (1.50 g, 5.92 mmol, 1.0 eq) in DCM (100 mL), m-chloroperbenzoic acid (77%, 4.30 g, 17.78 mmol, 3.0 eq) was added portion wise and then allowed to warm to room temperature. After stirring for 12 h at room temperature water was added to the reaction mixture and the layers were separated. The organic layer was washed with saturated aqueous solution of sodium bicarbonate (3×50 mL) followed by brine (50 mL) and then dried (Na$_2$SO$_4$) and filtered. The filtrate was concentrated under vacuum. The crude product was purified by flash column chromatography (silica gel, 5% ethyl acetate in hexane) to afford 1.60 g of the desired product, as a white solid. $^1$HNMR (400 MHz, CDCl$_3$) δ 8.13 (d, J=1.5 Hz, 1H), 7.81 (dd, J=1.5, 8.0 Hz, 1H), 7.36 (d, J=8.0 Hz, 1H), 3.99 (s, 1H), 2.47 (s, 3H), 1.58 (s, 3H), 1.23 (s, 3H); ESI-MS (m/z) 269, 271 [(MH)$^+$, Br$^{79,81}$].

Step 4: 3-(3-bromo-4-methylphenyl)-5,5-dimethyl-4,5-dihydroisoxazol-4-ol: A mixture of (3-bromo-4-methylphenyl)(3,3-dimethyloxiran-2-yl)methanone (500 mg, 1.85 mmol, 1.0 eq) and hydroxylamine hydrochloride (500 mg, 7.19 mmol, 3.9 eq) in a 5:3 volumetric mixture of methanol and pyridine was heated at gentle reflux for 12 h. The resulting mixture was cooled to room temperature and the solvent was evaporated under vacuum. The residue was taken in water (10 mL) acidified with glacial acetic acid and stirred for 10 min. Ethyl acetate (50 mL) was added to the above mixture and the layers were separated. The aqueous layer was extracted with ethyl acetate (3×20 mL). The combined organic layers were washed with water (20 mL), brine (20 mL), dried (Na$_2$SO$_4$) and filtered. The filtrate was evaporated under vacuum to afford 320 mg of the desired product as a white solid. $^1$HNMR (400 MHz, CDCl$_3$) δ 7.97 (d, J=1.0 Hz, 1H), 7.65 (dd, J=1.0, 8.0 Hz, 1H), 7.26 (d, J=8.0 Hz, 1H), 4.78 (s, 1H), 2.42 (s, 3H), 1.51 (s, 3H), 1.31 (s, 3H); ESI-MS (m/z) 284, 286 [(MH)$^+$, Br$^{79,81}$].

Step 5: 3-(3-Bromo-4-methylphenyl)-5,5-dimethylisoxazol-4(5H)-one: To a solution 3-(3-bromo-4-methylphenyl)-5,5-dimethyl-4,5-dihydroisoxazol-4-ol (1.80 g, 6.42 mmol) in glacial acetic acid (70 mL), chromium trioxide (640 mg, 6.42 mmol, 1.0 eq), water (4 mL) and concentrated sulfuric acid (0.8 mL) were successively added and the resulting mixture was stirred at 100° C. for 30 min. The reaction was cooled to room temperature and poured into water (10 mL) and extracted with ethyl acetate (3×20 mL). The combined organic layers were washed with water (10 mL), brine (10 mL) dried (Na$_2$SO$_4$) and filtered. The filtrate was concentrated under vacuum. The crude product was purified by flash column chromatography (silica gel, 2% ethyl acetate in hexane) to afford the 800 mg of the desired product as a white solid. $^1$HNMR (400 MHz, CDCl$_3$) δ 8.29 (d, J=1.0 Hz, 1H), 7.94 (dd, J=1.0, 8.0 Hz, 1H), 7.31 (d, J=8.0 Hz, 1H), 2.44 (s, 3H), 1.46 (s. 3H), 1.24 (s, 3H); ESI-MS (m/z) 282, 284 [(MH)$^+$, Br$^{79,81}$].

Step 6: 5,5-Dimethyl-3-(4-methyl-3-(4,4,5,5-tetramethyl-1,3,2-dioxaborolan-2-yl)phenyl) isoxazol-4(5H)-one:

General Procedure for Pinacolatodiboralane Formation: To a solution of 3-(3-bromo-4-methylphenyl)-5,5-dimethyl-isoxazol-4(5H)-one (180 mg, 0.64 mmol, 1.0 eq) in dioxane (10 mL), successively bis(pinacolato)diboron (243 mg, 0.95 mmol, 1.5 eq), potassium acetate (187 mg, 1.91 mmol, 3 eq) and Pd(dppf)Cl$_2$ (26 mg, 0.031 mmol, 0.05 eq) were added. The resulting solution was thoroughly deoxygenated by subjecting to vacuum/nitrogen cycle three times and the reaction mixture was then heated at 100° C. overnight under nitrogen atmosphere. The resulting mixture was cooled to room temperature and filtered through celite. The filtrate was concentrated under vacuum and the crude product was purified by flash column chromatography (silica gel, 6% ethyl acetate in hexane) to afford 140 mg of the intermediate 1a as a white solid. $^1$HNMR (400 MHz, CDCl$_3$) δ 8.44 (d, J=2.0 Hz, 1H), 7.99 (dd, J=2.0, 8.0 Hz, 1H), 7.23 (d, J=8.0 Hz, 1H), 2.55 (s, 3H), 1.44 (s, 6H), 1.33 (s, 12H); ESI-MS (m/z) 330 (MH)$^+$.

Step 7: 3-(3-(5-Aminopyrazin-2-yl)-4-methylphenyl)-5,5-dimethylisoxazol-4(5H)-one: To a solution of 5,5-dimethyl-3-(4,4,5,5-tetramethyl-1,3,2-dioxaborolan-2-yl)phenyl) isoxazol-4(5H)-one (5.4 g, 16.4 mmol, 1.0 eq) and 2-amino-5-bromopyrazine (2.8 g, 16.4 mmol, 1.0 eq), in THF:H$_2$O (4:1, 100 mL) was added sodium bicarbonate (4.5 g, 54.1 mmol, 3.3 eq) followed by Pd(PPh$_3$)$_4$ (0.95 g, 0.82 mmol, 0.05 eq). The resulting mixture was thoroughly deoxygenated by subjecting to vacuum/nitrogen cycle three times and the reaction mixture was heated at 75° C. for 15 h under nitrogen atmosphere. The resulting mixture was cooled to room temperature and filtered through celite. The filtrate was concentrated under vacuum and the crude product was purified by flash column chromatography (silica gel, ethyl acetate in hexane) to afford 1.5 g of the intermediate 1b as a white solid. $^1$HNMR (400 MHz, CDCl$_3$) δ 8.14 (s, 1H), 8.12 (s, 1H), 8.08 (d, J=1.5 Hz, 1H), 8.01 (dd, J=7.5, 1.5 Hz, 1H), 7.37 (d, J=8.0 Hz, 1H), 4.73 (s, 2H, D$_2$O exchangeable), 2.41 (s, 3H), 1.46 (s, 6H); ESI-MS (m/z) 297 (MH)$^+$.

The below intermediates 2 to 12b were prepared by following a procedure similar to that described in intermediate 1a or intermediate 1b:

| Intermediates/IUPAC name | Structure | $^1$HNMR/ESI-MS (MH)$^+$ |
|---|---|---|
| Intermediate 2: 3-(4-Ethyl-3-(4,4,5,5-tetramethyl-1,3,2-dioxaborolan-2-yl)phenyl)-5,5-dimethylisoxazol-4(5H)-one | 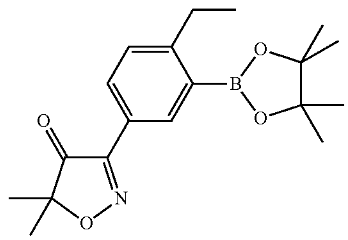 | $^1$HNMR (400 MHz, CDCl$_3$) δ 8.46 (d, J = 2.0 Hz, 1H), 8.04 (dd, J = 8.0, 2.0 Hz, 1H), 7.29 (d, J = 8.0 Hz, 1H), 2.94 (q, J = 7.5 Hz, 1H), 1.45 (s, 6H), 1.35 (s, 12H), 1.20 (t, J = 7.5 Hz, 3H); ESI-MS (m/z) 344 (MH)$^+$. |
| Intermediate 3: 3-(4-Isopropyl-3-(4,4,5,5-tetramethyl-1,3,2-dioxaborolan-2-yl)phenyl)-5,5-dimethylisoxazol-4(5H)-one | 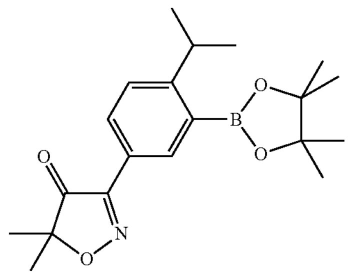 | $^1$HNMR (400 MHz, CDCl$_3$) δ 8.43 (s, 1H), 8.08 (dd, J = 8.5, 2.0 Hz, 1H), 7.41 (d, J = 8.5 Hz, 1H), 3.15-3.08 (m, 1H), 1.45 (s, 6H), 1.35 (s, 12H), 1.23 (d, J = 7.0 Hz, 6H); ESI-MS (m/z) 358 (MH)$^+$. |
| Intermediate 4a: 3-(3-Bromo-4-(tert-butyl)phenyl)-5,5-dimethylisoxazol-4(5H)-one | 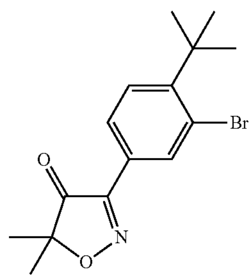 [SMILES: CC1(C)ON=C(c2ccc(C(C)(C)C)c(Br)c2)C1=O] | $^1$HNMR (400 MHz, CDCl$_3$) δ 8.36 (d, J = 2.0 Hz, 1H), 7.99 (dd, J = 8.5, 2.0 Hz, 1H), 7.55 (d, J = 8.5 Hz, 1H), 1.55 (s, 9H), 1.49 (s, 6H); ESI-MS (m/z) 324, 326 [(MH)$^+$, Br$^{79,81}$] |
| Example 4b: 3-(3-(5-Aminopyrazin-2-yl)-4-(tert-butyl)phenyl)-5,5-dimethylisoxazol-4(5H)-one | 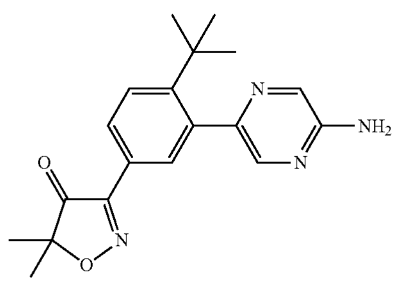 [SMILES: CC1(C)ON=C(c2ccc(C(C)(C)C)c(-c3cnc(N)cn3)c2)C1=O] | $^1$HNMR (400 MHz, CDCl$_3$) δ 8.08 (dd, J = 8.5, 2.0 Hz, 1H), 8.03-8.01 (m, 2H), 7.85 (s, 1H), 7.65 (d, J = 8.5 Hz, 1H), 4.63 (s, 2H, D$_2$O exchangeable), 1.44 (s, 6H), 1.24 (s, 9H); ESI-MS (m/z) 339 (MH)$^+$. |
| Intermediate 5: 3-(3-(5-Aminopyrazin-2-yl)-4-chlorophenyl)-5,5-dimethylisoxazol-4(5H)-one | 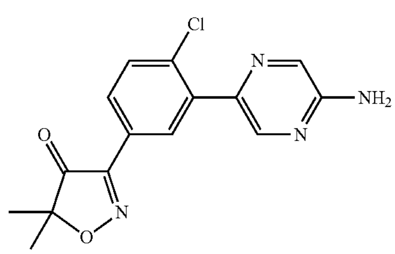 [SMILES: CC1(C)ON=C(c2ccc(Cl)c(-c3cnc(N)cn3)c2)C1=O] | ESI-MS (m/z) 317, 319 [(MH)$^+$, Cl$^{35,37}$] |
| Intermediate 6: 3-(4-Fluoro-3-(4,4,5,5-tetramethyl-1,3,2-dioxaborolan-2-yl)phenyl)-5,5-dimethyl-isoxazol-4(5H)-one | | $^1$HNMR (400 MHz, CDCl$_3$) δ 8.49 (dd, J = 5.5, 2.5 Hz, 1H), 8.20-8.15 (m, 1H), 7.13 (t, J = 8.5 Hz, 1H), 1.47 (s, 6H), 1.37 (s, 12H); ESI-MS (m/z) 334 (MH)$^+$. |

-continued

| Intermediates/IUPAC name | Structure | $^1$HNMR/ESI-MS (MH)$^+$ |
|---|---|---|
| Intermediate 7a: 3-(4-Methoxy-3-(4,4,5,5-tetramethyl-1,3,2-dioxaborolan-2-yl)phenyl)-5,5-dimethylisoxazol-4(5H)-one | 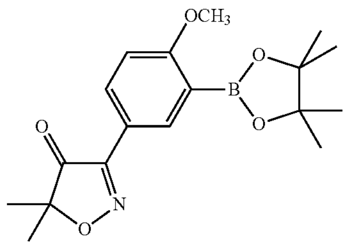 | $^1$HNMR (400 MHz, CDCl$_3$) δ 8.41 (d, J = 2.5 Hz, 1H), 8.15 (dd, J = 8.5, 2.5 Hz, 1H), 6.93 (d, J = 8.5 Hz, 1H), 3.88 (s, 3H), 1.45 (s, 6H), 1.36 (s, 12H); ESI-MS (m/z) 346 (MH)$^+$. |
| Intermediate 7b: 3-(3-(5-Aminopyrazin-2-yl)-4-methoxyphenyl)-5,5-dimethylisoxazol-4(5H)-one | 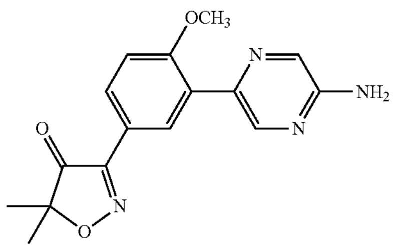 [SMILES: COc1ccc(C2=NOC(C)(C)C2=O)cc1-c1cnc(N)cn1] | $^1$HNMR (400 MHz, CDCl$_3$) δ 8.59 (s, 1H), 8.52 (s, 1H), 8.11-8.09 (m, 1H), 8.07 (d, J = 2.5 Hz, 1H), 7.06 (d, J = 8.5 Hz, 1H), 4.65 (s, 2H, D$_2$O exchangeable), 3.93 (s, 3H), 1.46 (s, 6H); ESI-MS (m/z) 313 (MH)$^+$ |
| Intermediate 8: N-(4-(5,5-dimethyl-4-oxo-4,5-dihydroisoxazol-3-yl)-2-(4,4,5,5-tetramethyl-1,3,2-dioxaborolan-2-yl)phenyl)acetamide | 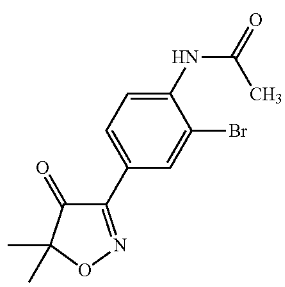 [SMILES: CC(=O)Nc1ccc(C2=NOC(C)(C)C2=O)cc1Br] | $^1$HNMR (400 MHz, CDCl$_3$) δ 8.52 (d, J = 8.5 Hz, 1H), 8.34 (d, J = 2.0 Hz, 1H), 8.08 (dd, J = 8.5, 2.0 Hz, 1H), 7.75 (s, 1H, D$_2$O exchangeable), 2.27 (s, 3H), 1.47 (s, 6H); ESI-MS (m/z) 325, 327 [(MH)$^+$, Br$^{79, 81}$] |
| Intermediate 9: 5,5-Dimethyl-3-(3-(4,4,5,5-tetramethyl-1,3,2-dioxaborolan-2-yl)phenyl)isoxazol-4(5H)-one | 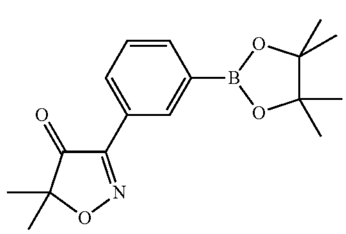 | $^1$HNMR (400 MHz, CDCl$_3$) δ 8.51 (s, 1H), 8.15 (td, J = 7.5, 1.0 Hz, 1H), 7.90 (td, J = 7.5, 1.0 Hz, 1H), 7.47 (t, J = 8.0 Hz, 1H), 1.47 (s, 6H), 1.35 (s, 12H); ESI-MS (m/z) 316 (MH)$^+$. |
| Intermediate 10: 5,5-Dimethyl-3-(3-methyl-4-(4,4,5,5-tetramethyl-1,3,2-dioxaborolan-2-yl)phenyl)isoxazol-4(5H)-one | 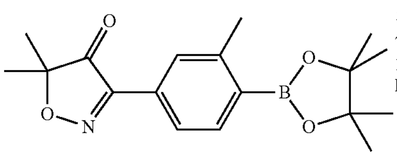 | $^1$HNMR (400 MHz, CDCl$_3$) δ 7.87-7.79 (m, 3H), 2.56 (s, 3H), 1.45 (s, 6H), 1.35 (s, 12H); ESI-MS (m/z) 330 (MH)$^+$. |
| Intermediate 11: 5,5-Dimethyl-3-(2-methyl-3-(4,4,5,5-tetramethyl-1,3,2-dioxaborolan-2-yl)phenyl)isoxazol-4(5H)-one | 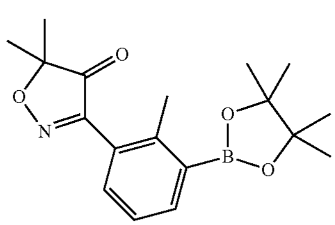 | $^1$HNMR (400 MHz, CDCl$_3$) δ 7.87 (dd, J = 8.0, 1.5 Hz, 1H), 7.48 (dd, J = 8.0, 1.5 Hz, 1H), 7.26 (t, J = 8.0 Hz, 1H), 2.53 (s, 3H), 1.48 (s, 6H), 1.35 (s, 12H); ESI-MS (m/z) 330 (MH)$^+$. |
| Intermediate 12a: 3-(3-Bromo-2-methoxyphenyl)-5,5-dimethylisoxazol-4(5H)-one | 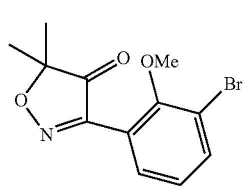 [SMILES: COc1c(Br)cccc1C1=NOC(C)(C)C1=O] | $^1$HNMR (400 MHz, CDCl$_3$) δ 7.68 (dd, J = 8.0, 1.5 Hz, 1H), 7.57 (dd, J = 8.0, 1.5 Hz, 1H), 7.09 (t, J = 8.0 Hz, 1H), 3.88 (s, 3H), 1.49 (s, 6H); ESI-MS (m/z) 298, 300 [(MH)$^+$, Br$^{79, 81}$] |

| Intermediates/IUPAC name | Structure | $^1$HNMR/ESI-MS (MH)$^+$ |
|---|---|---|
| Intermediate 12b: 3-(3-(5-aminopyrazin-2-yl)-2-methoxyphenyl)-5,5-dimethylisoxazol-4(5H)-one | 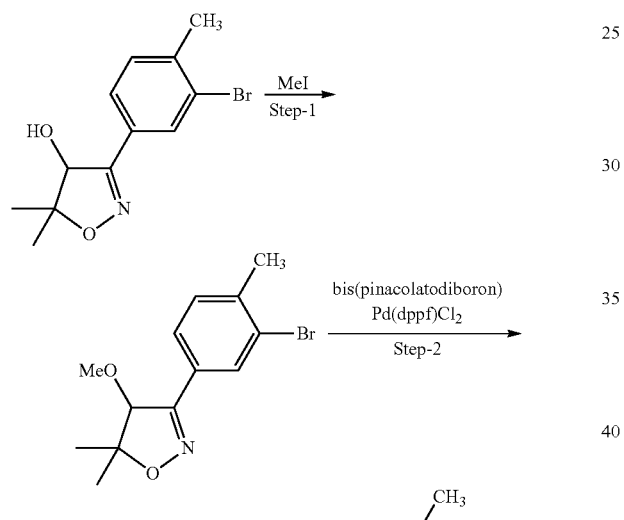 | $^1$HNMR (400 MHz, CDCl$_3$) δ 8.65 (s, 1H), 8.12 (s, 1H), 7.86 (dd, J = 8.0, 1.5 Hz, 1H), 7.61 (dd, J = 8.0, 1.5 Hz, 1H), 7.33 (t, J = 8.0 Hz, 1H), 3.55 (s, 3H), 1.52 (s, 6H); ESI-MS (m/z) 313 (MH)$^+$ |

Intermediate 13

4-Methoxy-5,5-dimethyl-3-(4-methyl-3-(4,4,5,5-tetramethyl-1,3,2-dioxaborolan-2-yl)phenyl)-4,5-dihydroisoxazole

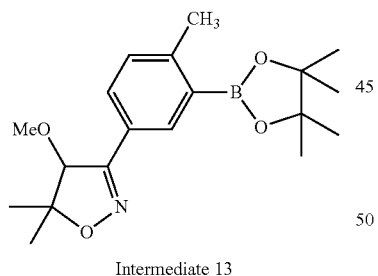

Intermediate 13

Step-1: 3-(3-Bromo-4-methylphenyl)-4-methoxy-5,5-dimethyl-4,5-dihydroisoxazole: To a 0° C. cooled solution of 3-(3-bromo-4-methylphenyl)-5,5-dimethyl-4,5-dihydroisoxazol-4-ol (240 mg, 0.84 mmol, 1.0 eq, prepared hereinbefore in step-4 of intermediate 1) in DMF (3 mL) was added sodium hydride (60% dispersion in oil, 43 mg, 1.09 mmol, 1.3 eq) in one portion. After stirring at the same temperature for 20 min, methyl iodide (70 μL, 1.09 mmol, 1.09 eq) was added to the above mixture and then continued stirring at room temperature for 1 h. Water (5 mL) was added to the reaction mixture followed by ethyl acetate (10 mL). The layers were separated and the aqueous layer was extracted with ethyl acetate (2×10 mL) and the combined organic layers were washed with water (2×10 mL), brine (10 mL), dried (Na$_2$SO$_4$) and filtered. The filtrate was concentrated under vacuum to afford 200 mg of the title product as syrupy oil. $^1$HNMR (400 MHz, CDCl$_3$) δ 7.93 (d, J=2.0 Hz, 1H), 7.62 (dd, J=8.0, 2.0 Hz, 1H), 7.29 (d, J=8.0 Hz, 1H), 4.52 (s, 1H), 3.46 (s, 3H), 2.44 (s, 3H), 1.54 (s, 3H), 1.35 (s, 3H); ESI-MS (m/z) 298, 300 [(MH)$^+$, Br$^{79,81}$]

Step-2: 4-Methoxy-5,5-dimethyl-3-(4-methyl-3-(4,4,5,5-tetramethyl-1,3,2-dioxaborolan-2-yl)phenyl)-4,5-dihydroisoxazole: The title compound was prepared by following the general procedure described hereinbefore for step-6 of intermediate 1. $^1$HNMR (400 MHz, CDCl$_3$) δ 8.09 (d, J=2.0 Hz, 1H), 7.73 (dd, J=8.0, 2.0 Hz, 1H), 7.21 (d, J=8.0 Hz, 1H), 4.58 (s, 1H), 3.42 (s, 3H), 2.55 (s, 3H), 1.54 (s, 3H) 1.34 (s, 12H), 1.31 (s, 3 H); ESI-MS (m/z) 346 (MH)$^+$ Intermediate 14

1-(2,2-Dimethyl-5-(4-methyl-3-(4,4,5,5-tetramethyl-1,3,2-dioxaborolan-2-yl)phenyl)-1,3,4-oxadiazol-3(2H)-yl)ethanone

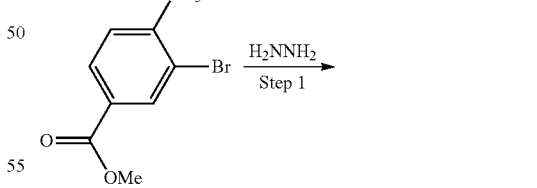

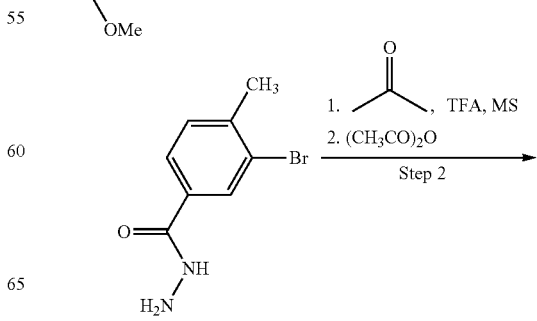

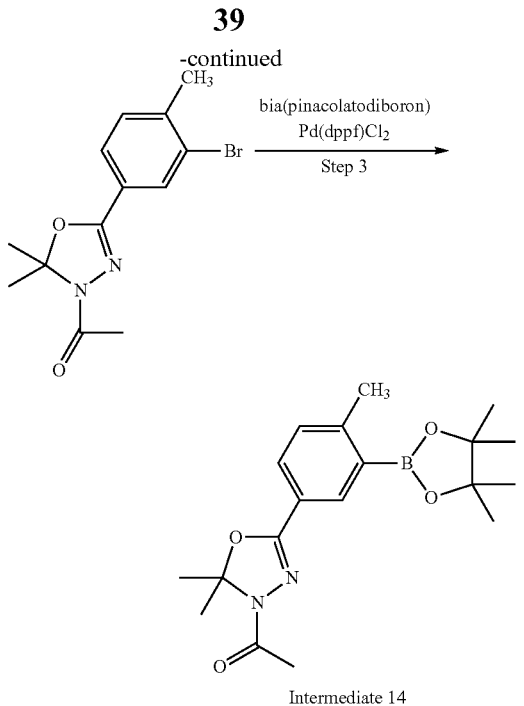

Intermediate 14 afford 800 mg of the desired product as an oil. $^1$HNMR (400 MHz, CDCl$_3$) δ 7.97 (s, 1H), 7.65 (d, J=8.0 Hz, 1H), 7.28 (d, J=8.0 Hz, 1H), 2.44 (s, 3H), 2.29 (s, 3H), 1.85 (s, 6H); ESI-MS (m/z) 311, 313 [(MH)$^+$, Br$^{79,81}$].

Step 3: 1-(2,2-Dimethyl-5-(4-methyl-3-(4,4,5,5-tetramethyl-1,3,2-dioxaborolan-2-yl)phenyl)-1,3,4-oxadiazol-3 (2H)-yl)ethanone: 1-(5-(3-bromo-4-methylphenyl)-2,2-dimethyl-1,3,4-oxadiazol-3(2H)-yl)ethanone (400 mg, 1.28 mmol, 1.0 eq) was reacted with bis(pinacolato)diboron (480 mg, 1.92 mmol, 1.5 eq) and Pd(dppf)Cl$_2$ (52 mg, 0.064 mmol, 0.05 eq) by following the procedure described hereinbefore in step 6 of intermediate 1 to afford 120 mg of the intermediate 2 as a white solid. $^1$HNMR (400 MHz, CDCl$_3$) δ 8.12 (s, 1H), 7.77 (d, J=8.0 Hz, 1H), 7.21 (d, J=8.0 Hz, 1H), 2.57 (s, 3H), 2.31 (s, 3H), 1.86 (s, 6H), 1.36 (s, 6H), 1.26 (s, 6H); ESI-MS (m/z) 359 (MH)$^+$.

Intermediate 15a & 15b 5-(3-Bromo-4-methylphenyl)-3-methyl-1,3,4-oxadiazol-2(3H)-one (15a) and 5-(3-(5-Aminopyrazine-2-yl)-4-methylphenyl)-3-methyl-1,3,4-oxadiazol-2(3H)-one (15b)

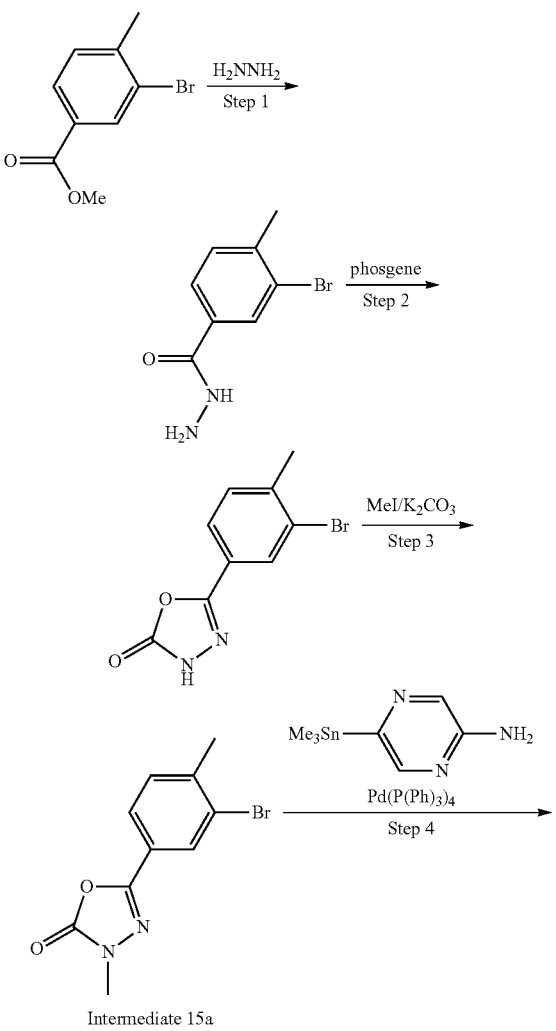

Intermediate 15a

Step 1: 3-Bromo-4-methylbenzohydrazide: A mixture of methyl-3-bromo-4-methylbenzoate (5.0 g, 21.8 mmol, 1.0 eq) and hydrazine hydrate (5 mL, 99 mmol, 4.5 eq) in methanol (50 mL) was heated to 80° C. overnight. The reaction mixture was cooled to room temperature and filtered. The filtrate was evaporated under vacuum. The residue was taken in ethyl acetate (100 mL) and washed with water (2×50 mL), brine (50 mL), dried (Na$_2$SO$_4$) and filtered. The filtrate was evaporated under reduced pressure to afford 2.5 g (50%) of the desired product as a white solid. $^1$HNMR (400 MHz, DMSO-d$_6$) δ 9.84 (s, 1H, D$_2$O exchangeable), 8.02 (d, J=1.0 Hz, 1H), 7.74 (dd, J=1.0, 8.0 Hz, 1H), 7.44 (d, J=8.0 Hz, 1H), 3.35 (s, 2H, D$_2$O exchangeable), 2.38 (s, 3H); ESI-MS (m/z) 229, 231 [(MH)$^+$, Br$^{79,81}$].

Step 2: 1-(5-(3-Bromo-4-methylphenyl)-2,2-dimethyl-1,3,4-oxadiazol-3(2H)-yl)ethanone: To a mixture of 3-bromo-4-methylbenzohydrazide (2.0 g, 8.72 mmol, 1.0 eq) and acetone (10 mL, 172 mmol, 21 eq) in hexane (10 mL), was added molecular sieves (500 mg) followed by trifluoroacetic acid (2 mL) and the resulting mixture was refluxed for 3 h. The reaction mixture was cooled to room temperature and filtered. The filtrate was concentrated under vacuum and the residue was taken in ethyl acetae (100 mL), washed with water (50 mL), aqueous saturated sodium bicarbonate solution (50 mL), brine (50 mL), dried (Na$_2$SO$_4$) and filtered. The filtrate was concentrated under reduced pressure to afford the 2.10 g of the 3-bromo-4-methyl-N'-(propan-2-ylidene)benzohydrazide. $^1$HNMR (400 MHz, DMSO-d$_6$) δ 10.51 (s, 1H, D$_2$O exchangeable), 8.02 (s, 1H), 7.75 (dd, J=1.0, 8.0 Hz, 1H), 7.44 (d, J=8.0 Hz, 1H), 2.40 (s, 3H), 2.01 (s, 3H), 1.94 (s, 3H); ESI-MS (m/z) 269, 271 [(MH)$^+$, Br$^{79,81}$].

A mixture of 3-bromo-4-methyl-N'-(propan-2-ylidene) benzohydrazide (2.0 g, 7.46 mmol), as obtained hereinbefore, and acetic anhydride (30 mL) was refluxed for one hour. The excess of acetic anhydride was removed under vacuum after cooling the reaction mixture to room temperature and the crude residue obtained was triturated with hexane to remove traces of acetic anhydride present in the reaction mixture. The crude product was purified by flash column chromatography (silica gel, 100-200 mesh, 13% ethyl acetate in hexane) to

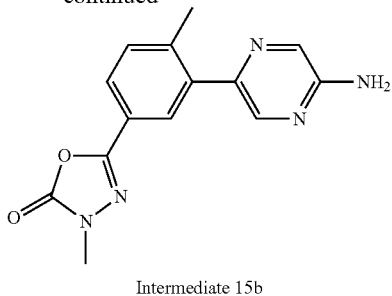

Intermediate 15b

Step 1: 3-Bromo-4-methylbenzohydrazide: A mixture of methyl-3-bromo-4-methylbenzoate (5.0 g, 21.8 mmol, 1.0 eq) and hydrazine hydrate (5 mL, 99 mmol, 4.5 eq) in methanol (50 mL) was heated to 80° C. overnight. The reaction mixture was cooled to room temperature and filtered. The filtrate was evaporated under vacuum. The residue was taken in ethyl acetate (100 mL) and washed with water (2×50 mL), brine (50 mL), dried ($Na_2SO_4$) and filtered. The filtrate was evaporated under reduced pressure to afford 2.5 g (50%) of the desired product as a white solid. $^1$HNMR (400 MHz, DMSO-d6) δ 9.83 (s, 1H, $D_2O$ exchangeable), 8.01 (d, J=2.0 Hz, 1H), 7.74 (dd, J=8.0, 2.0 Hz, 1H), 7.43 (d, J=8.0 Hz, 1H), 4.50 (s, 2H, $D_2O$ exchangeable), 2.37 (s, 3H); ESI-MS (m/z) 229, 231 [(MH)$^+$, Br$^{79,81}$].

Step-2: 5-(3-Bromo-4-methylphenyl)-1,3,4-oxadiazol-2 (3H)-one: To a stirred and cooled (0° C.) solution of 3-bromo-4-methylbenzohydrazide (3.0 g, 13.1 mmol, 1.0 eq) and diisopropylethyl amine (4.6 mL, 26.8 mmol, 2.0 eq) in DCM (20 mL) was added a solution of triphosgene (1.55 g, 5.2 mmol, 0.4 eq) in DCM (10 mL) over a period of 10 min. The resulting mixture was stirred for 1 h at the same temperature. The reaction mixture was diluted with DCM (50 mL) and washed with water (50 mL), aqueous sodium bicarbonate (10%, 50 mL), brine (50 mL), dried ($Na_2SO_4$) and filtered. The filtrated was evaporated under vacuum to afford 3.0 g of the desired product as a white solid. $^1$HNMR (400 MHz, DMSO-d6) δ 12.66 (s, 1H, $D_2O$ exchangeable), 7.90 (d, J=2.0 Hz, 1H), 7.69 (dd, J=8.0, 2.0 Hz, 1H), 7.52 (d, J=8.0 Hz, 1H), 2.40 (s, 3H); ESI-MS (m/z) 255, 257 [(MH)$^+$, Br$^{79,81}$].

Step-3: 5-(3-Bromo-4-methylphenyl)-3-methyl-1,3,4-oxadiazol-2(3H)-one: A mixture of 5-(3-bromo-4-methylphenyl)-1,3,4-oxadiazol-2(3H)-one (400 mg, 1.57 mmol, 1.0 eq), methyl iodide (0.2 mL, 3.15 mmol, 2.0 eq) and potassium carbonate (210 mg, 3.15 mmol, 2.0 eq) in DMF (10 mL) was stirred at room temperature for 24 h. Water (50 mL) was added to the reaction mixture followed by ethyl acetate (30 mL). The layers were separated and the aqueous layer was extracted with ethyl acetate (2×20 mL). The combined organic layers were washed with water (2×25 mL), brine (20 mL), dried ($Na_2SO_4$) and filtered. The filtrate was concentrated under vacuum to afford 400 mg of the desired product as a white solid. $^1$HNMR (400 MHz, DMSO-d6) δ 7.90 (d, J=2.0 Hz, 1H), 7.70 (dd, J=8.0, 2.0 Hz, 1H), 7.54 (d, J=8.0 Hz, 1H), 3.40 (s, 3H), 2.41 (s, 3H); ESI-MS (m/z) 269, 271 [(MH)$^+$, Br$^{79,81}$].

Step 4: 5-(3-(5-Aminopyrazin-2-yl)-4-methylphenyl)-3-methyl-1,3,4-oxadiazol-2(3H)-one: To a solution of 5-(3-bromo-4-methylphenyl)-3-methyl-1,3,4-oxadiazol-2(3H)-one (500 mg, 1.76 mmol) and 5-(trimethyl stannyl)-pyrazine-2-amine (683 mg, 2.65 mmol, prepared from 2-amino-5-bromopyrazine by following the procedure described in Chem. Eur. J. 2000, 6, 4132) in THF (10 mL) was added Pd(PPh$_3$)$_4$ (100 mg, 0.088 mmol). The resulting mixture was thoroughly deoxygenated by subjecting to vacuum/nitrogen cycle three times and the reaction mixture was heated at 75° C. for 15 h under nitrogen atmosphere. The resulting mixture was cooled to room temperature and filtered through celite. The filtrate was concentrated under vacuum and the crude product was purified by flash column chromatography over silica gel using ethyl acetate-hexane mixture as eluent to afford 250 mg of the intermediate 15b as a white solid. $^1$HNMR (400 MHz, DMSO-d6) δ 8.07 (s, 1H), 7.99 (s, 1H), 7.69 (d, J=2.0 Hz, 1H), 7.64 (dd, J=8.0, 2.0 Hz, 1H), 7.44 (d, J=8.0 Hz, 1H), 6.62 (s, 2H, $D_2O$ exchangeable), 3.36 (s, 3H), 2.35 (s, 3H); ESI-MS (m/z) 284 (MH)$^+$.

The following intermediates were prepared by following the above procedure from the corresponding starting materials.

The below intermediates 16a to 24b were prepared by following a procedure similar to that described in intermediate 15a or intermediate 15b:

| Intermediates/IUPAC name | Structure | $^1$HNMR/ESI-MS(MH)$^+$ |
| --- | --- | --- |
| Intermediate 16a: 5-(3-Bromo-4-methylphenyl)-3-ethyl-1,3,4-oxadiazol-2(3H)-one | | $^1$HNMR (400 MHz, DMSO-d6) δ 7.89 (d, J = 1.5 Hz, 1H), 7.69 (dd, J = 8.0, 1.5 Hz, 1H), 7.52 (d, J = 8.0 Hz, 1H), 3.76 (q, J = 7.0 Hz, 2H), 2.40 (s, 3H), 1.29 (t, J = 7.0 Hz, 3H); ESI-MS (m/z) 283, 285 [(MH)$^+$, Br$^{79,81}$]. |
| Intermediate 16b: 5-(3-(5-Aminopyrazin-2-yl)-4-methylphenyl)-3-ethyl-1,3,4-oxadiazol-2(3H)-one | 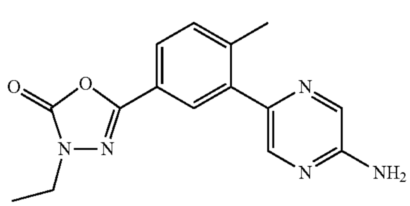 [SMILES: CCn1nc(-c2ccc(C)c(-c3cnc(N)cn3)c2)oc1=O] | $^1$HNMR (400 MHz, DMSO-d6) δ 8.13 (s, 1H), 7.98 (s, 1H), 7.77 (d, J = 1.0 Hz, 1H), 7.67 (d, J = 8.0 Hz, 1H), 7.45 (d, J = 8.0 Hz, 1H), 6.62 (s, 2H, $D_2O$ exchangeable), 3.76 (q, J = 7.0 Hz, 2H), 2.41 (s, 3H), 1.29 (t, J = 7.0 Hz, 3H); ESI-MS (m/z) 298 (MH)$^+$ |

| Intermediates/IUPAC name | Structure | ¹HNMR/ESI-MS(MH)⁺ |
|---|---|---|
| Intermediate 17a: 5-(3-Bromo-4-methylphenyl)-3-propyl-1,3,4-oxadiazol-2(3H)-one | 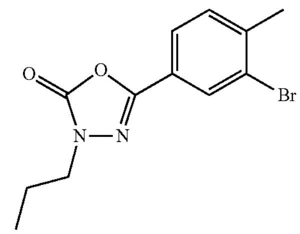 [SMILES: CCCn1nc(-c2ccc(C)c(Br)c2)oc1=O] | ¹HNMR (400 MHz, DMSO-d6) δ 7.91 (d, J = 1.5 Hz, 1H), 7.69 (dd, J = 8.0, 1.5 Hz, 1H), 7.54 (d, J = 8.0 Hz, 1H), 3.69 (t, J = 7.0 Hz, 2H), 2.41 (s, 3H), 1.75-1.70 (m, 2H), 0.90 (t, J = 7.0 Hz, 3H); ESI-MS (m/z) 296, 298 [(MH)⁺, Br⁷⁹, ⁸¹]. |
| Intermediate 17b: 5-(3-(5-Aminopyrazin-2-yl)-4-methylphenyl)-3-propyl-1,3,4-oxadiazol-2(3H)-one | 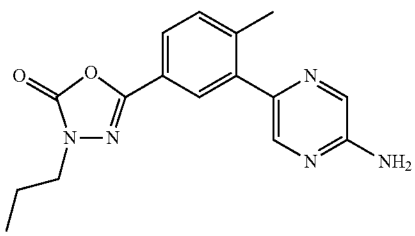 [SMILES: CCCn1nc(-c2ccc(C)c(-c3cnc(N)cn3)c2)oc1=O] | ¹HNMR (400 MHz, CDCl₃) δ 8.14 (s, 1H), 8.09 (s, 1H), 7.86 (d, J = 1.5 Hz, 1H), 7.73 (dd, J = 8.0, 1.5 Hz, 1H), 7.37 (d, J = 8.0 Hz, 1H), 3.74 (t, J = 7.0 Hz, 2H), 2.43 (s, 3H), 1.87-1.78 (m, 2H), 0.98 (t, J = 7.0 Hz, 3H); ESI-MS (m/z) 312 (MH)⁺. |
| Intermediate 18a: 5-(3-Bromo-4-ethylphenyl)-3-methyl-1,3,4-oxadiazol-2(3H)-one | 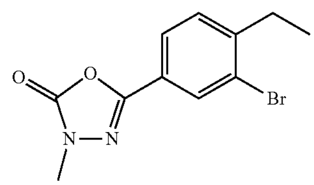 [SMILES: CCc1ccc(-c2nn(C)c(=O)o2)cc1Br] | ¹HNMR (400 MHz, DMSO) δ 7.89 (s, 1H), 7.73 (dd, J = 8.0, 2.0 Hz, 1H), 7.53 (d, J = 8.0 Hz, 1H), 3.40 (s, 3H), 2.75 (q, J = 7.5 Hz, 2H), 1.19 (t, J = 7.5 Hz, 3H); ESI-MS (m/z) 283, 285 [(MH)⁺, Br⁷⁹,⁸¹]. |
| Intermediate 18b: 5-(3-(5-Aminopyrazin-2-yl)-4-ethylphenyl)-3-methyl-1,3,4-oxadiazol-2(3H)-one | 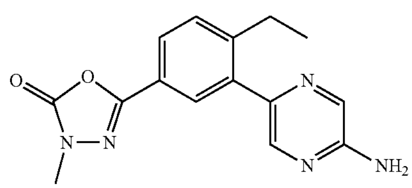 [SMILES: CCc1ccc(-c2nn(C)c(=O)o2)cc1-c1cnc(N)cn1] | ¹HNMR (400 MHz, DMSO-d6) δ 8.07 (s, 1H), 7.97 (s, 1H), 7.72 (dd, J = 8.0, 2.0 Hz, 1H), 7.67 (d, J = 2.0 Hz, 1H), 7.54 (d, J = 8.0 Hz, 1H), 6.61 (s, 2H, D₂O exchangeable), 3.40 (s, 3H), 2.75 (q, J = 7.5 Hz, 2H), 1.08 (t, J = 7.5 Hz, 3H); ESI-MS (m/z) 298 (MH)⁺. |
| Intermediate 19a: 5-(3-Bromo-4-methoxyphenyl)-3-methyl-1,3,4-oxadiazol-2(3H)-one | 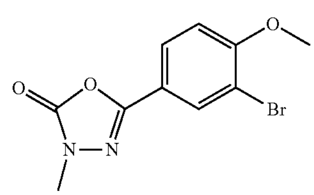 [SMILES: COc1ccc(-c2nn(C)c(=O)o2)cc1Br] | ¹HNMR (400 MHz, DMSO) δ 7.91 (d, J = 2.5 Hz, 1H), 7.79 (dd, J = 8.5, 2.0 Hz, 1H), 7.28 (d, J = 8.5 Hz, 1H), 3.93 (s, 3H); ESI-MS (m/z) 285, 287 [(MH)⁺, Br⁷⁹,⁸¹]. |
| Intermediate 19b: 5-(3-(5-Aminopyrazin-2-yl)-4-methoxyphenyl)-3-methyl-1,3,4-oxadiazol-2(3H)-one | 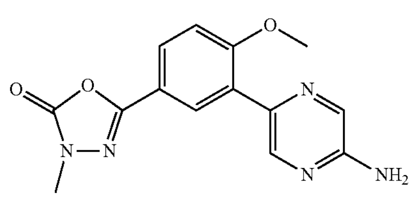 [SMILES: COc1ccc(-c2nn(C)c(=O)o2)cc1-c1cnc(N)cn1] | ¹HNMR (400 MHz, DMSO-d6) δ 8.55 (s, 1H), 8.21 (d, J = 2.0 Hz, 1H), 8.01 (s, 1H), 7.73 (dd, J = 8.0, 2.0 Hz, 1H), 7.28 (d, J = 8.0 Hz, 1H), 6.63 (s, 2H, D₂O exchangeable), 3.94 (s, 3H), 3.39 (s, 3H); ESI-MS (m/z) 300 (MH)⁺. |
| Intermediate 20a: 5-(3-Bromo-4-(difluoromethoxy)phenyl)-3-methyl-1,3,4-oxadiazol-2(3H)-one | 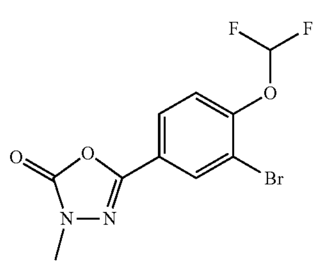 [SMILES: Cn1nc(-c2ccc(OC(F)F)c(Br)c2)oc1=O] | ¹HNMR (400 MHz, CDCl₃) δ 8.09 (d, J = 2.5 Hz, 1H), 7.76 (dd, J = 8.5, 2.0 Hz, 1H), 7.30 (d, J = 8.5 Hz, 1H), 6.60 (t, J = 72.5 Hz, 1H), 3.45 (s, 3H); ESI-MS (m/z) 321, 323 [(MH)⁺, Br⁷⁹,⁸¹]. |

| Intermediates/IUPAC name | Structure | ¹HNMR/ESI-MS(MH)⁺ |
|---|---|---|
| Intermediate 20b: 5-(3-(5-Aminopyrazin-2-yl)-4-(difluoromethoxy)phenyl)-3-methyl-1,3,4-oxadiazol-2(3H)-one | 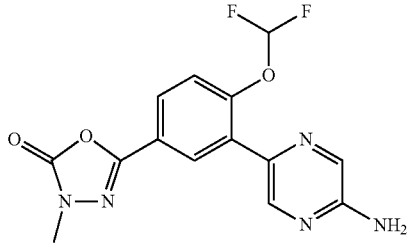 [SMILES: Cn1nc(-c2ccc(OC(F)F)c(-c3cnc(N)cn3)c2)oc1=O] | ¹HNMR (400 MHz, DMSO-d6) δ 8.42 (s, 1H), 8.22 (d, J = 2.0 Hz, 1H), 8.03 (s, 1H), 7.80 (dd, J = 8.0, 2.0 Hz, 1H), 7.53 (d, J = 8.0 Hz, 1H), 7.45 (t, J = 72.5 Hz, 1H), 6.78 (s, 2H, D₂O exchangeable), 3.41 (s, 3H); ESI-MS (m/z) 336 (MH)⁺. |
| Intermediate 21a: 5-(3-Bromo-4-chlorophenyl)-3-methyl-1,3,4-oxadiazol-2(3H)-one | 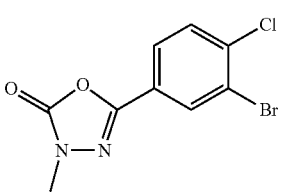 | ¹HNMR (400 MHz, CDCl₃) δ 8.09 (d, J = 2.0 Hz, 1H), 7.69 (dd, J = 8.0, 2.0 Hz, 1H), 7.55 (d, J = 8.0 Hz, 1H), 3.50 (s, 3H); ESI-MS (m/z) 289, 291 [(MH)⁺, Cl³⁵, ³⁷] |
| Intermediate 21b: 5-(3-(5-Aminopyrazin-2-yl)-4-chlorophenyl)-3-methyl-1,3,4-oxadiazol-2(3H)-one | 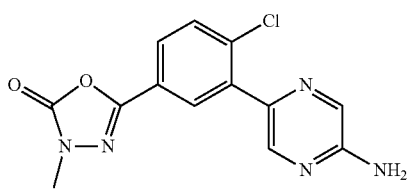 | ESI-MS (m/z) 304, 306 [(MH)⁺, Cl³⁵, ³⁷] |
| Intermediate 22a: 5-(3-Bromo-4-fluorophenyl)-3-methyl-1,3,4-oxadiazol-2(3H)-one | 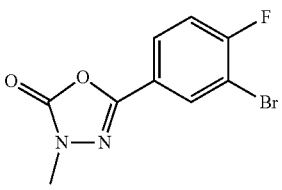 | ¹HNMR (400 MHz, CDCl₃) δ 8.05 (dd, J = 6.5, 2.5 Hz, 1H), 7.77-7.73 (m, 1H), 7.21 (t, J = 8.5 Hz, 1H), 3.50 (s, 3H); ESI-MS (m/z) 273, 275 [(MH)⁺, Br⁷⁹,⁸¹] |
| Intermediate 22b: 5-(3-(5-Aminopyrazin-2-yl)-4-fluorophenyl)-3-methyl-1,3,4-oxadiazol-2(3H)-one | 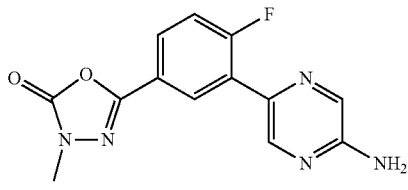 [SMILES: Cn1nc(-c2ccc(F)c(-c3cnc(N)cn3)c2)oc1=O] | ¹HNMR (400 MHz, DMSO-d6) δ 8.42 (s, 1H), 8.32 (dd, J = 7.0, 2.5 Hz, 1H), 8.04 (s, 1H), 7.77-7.73 (m, 1H), 7.48 (dd, J = 8.5, 11.5 Hz, 1H), 6.86 (s, 2H, D₂O exchangeable), 3.41 (s, 3H); ESI-MS (m/z) 288 (MH)⁺ |
| Intermediate 23a: 5-(3-Bromo-2-methylphenyl)-3-methyl-1,3,4-oxadiazol-2(3H)-one | 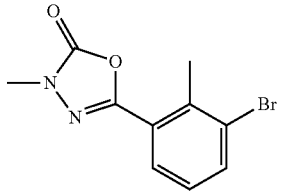 | ¹HNMR (400 MHz, DMSO-d6) δ 7.84 (d, J = 8.0 Hz, 1H), 7.71 (d, J = 8.0 Hz, 1H), 7.32 (d, J = 8.0 Hz, 1H), 3.42 (s, 3H), 2.62 (s, 3H); ESI-MS (m/z) 269, 271 [(MH)⁺, Br⁷⁹, ⁸¹] |
| Intermediate 23b: 5-(3-(5-Aminopyrazin-2-yl)-2-methylphenyl)-3-methyl-1,3,4-oxadiazol-2(3H)-one | 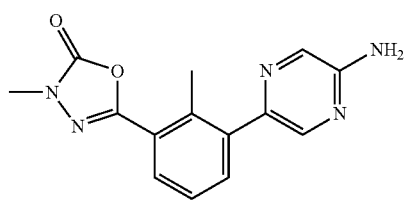 [SMILES: Cc1c(-c2cnc(N)cn2)cccc1-c1nn(C)c(=O)o1] | ESI-MS (m/z) 284 (MH)⁺ |

| Intermediates/IUPAC name | Structure | ¹HNMR/ESI-MS(MH)⁺ |
|---|---|---|
| Intermediate 24a: 5-(3-Bromo-2-ethylphenyl)-3-methyl-1,3,4-oxadiazol-2(3H)-one | 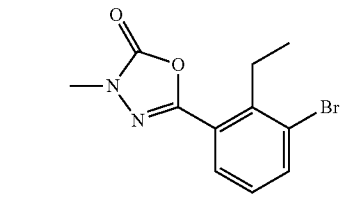 [SMILES: CCc1c(Br)cccc1-c1nn(C)c(=O)o1] | ¹HNMR (400 MHz, CdCl₃) δ 7.71 (d, J = 8.0 Hz, 2H), 7.16 (t, J = 8.0 Hz, 1H), 3.53 (s, 3H), 3.16 (q, J = 7.5 Hz, 2H), 1.22 (t, J = 7.5 Hz, 3H) |
| Intermediate 24b: 5-(3-(5-Aminopyrazin-2-yl)-2-ethylphenyl)-3-methyl-1,3,4-oxadiazol-2(3H)-one | 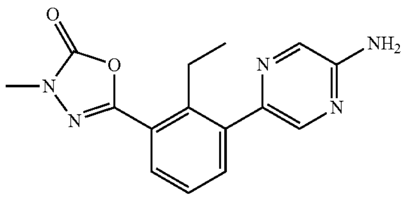 [SMILES: CCc1c(-c2cnc(N)cn2)cccc1-c1nn(C)c(=O)o1] | ESI-MS (m/z) 298 (MH)⁺ |

Intermediate 25

5,5-Dimethyl-3-(4-methyl-3-(4,4,5,5-tetramethyl-1,3,2-dioxaborolan-2-yl)phenyl)-4,5-dihydroisoxazole

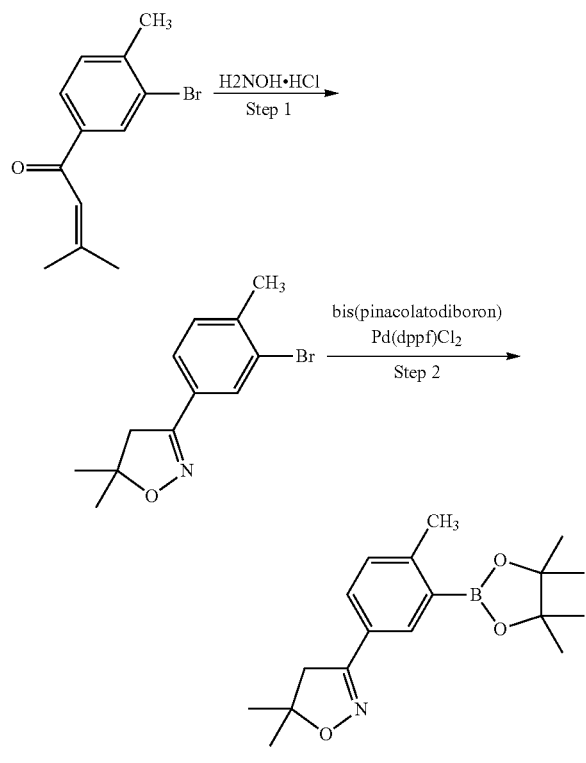

Intermediate 25

Step 1: 3-(3-Bromo-4-methylphenyl)-5,5-dimethyl-4,5-dihydroisoxazole: To a mixture of 1-(3-bromo-4-methylphenyl)-3-methylbut-2-en-1-one, (prepared herein before in step 2 of intermediate 1; 1.0 g, 3.95 mmol, 1.0 eq), and hydroxylamine hydrochloride (330 mg, 4.74 mmol, 1.2 eq) in ethanol (10 mL) at 0° C., was added an aqueous solution of potassium hydroxide (1N, 4 mL) until the pH of the reaction was basic. The resulting mixture was stirred at room temperature for 4 h. The reaction mixture was diluted with ethyl acetate (20 mL) followed by water (20 mL). The layers were separated and the organic layer was extracted with ethyl acetate (2×20 mL). The combined organic layers were washed with brine (20 mL), dried (Na₂SO₄) and filtered. The filtrate was concentrated under vacuum. The crude product was purified by flash column chromatography (silica gel, 5% EtOAc in hexane) to afford 250 mg of the desired product as a white solid. ¹HNMR (400 MHz, CDCl₃) δ 7.79 (s, 1H), 7.53 (d, J=8.0 Hz, 1H), 7.27 (d, J=8.0 Hz, 1H), 3.08 (s, 2H), 2.43 (s, 3H), 1.50 (s, 6H); ESI-MS (m/z) 268, 270 [(MH)⁺, Br⁷⁹,⁸¹].

Step 2: 5,5-Dimethyl-3-(4-methyl-3-(4,4,5,5-tetramethyl-1,3,2-dioxaborolan-2-yl)phenyl)-4,5-dihydroisoxazole: 3-(3-bromo-4-methylphenyl)-5,5-dimethyl-4,5-dihydroisoxazole (250 mg, 0.93 mmol, 1.0 eq) was reacted with bis(pinacolato)diboron by following the procedure described hereinbefore in step 6 of intermediate I to afford 200 mg of the desired product as a white solid. ¹HNMR (400 MHz, CDCl₃) δ 7.91 (s, 1H), 7.73 (d, J=8.0 Hz, 1H), 7.21 (d, J=8.0 Hz, 1H), 3.16 (s, 2H), 2.57 (s, 3H), 1.49 (s, 6H), 1.36 (s, 12H); ESI-MS (m/z) 316 (MH)⁺.

Intermediate 26

4,4-Dimethyl-2-(4-methyl-3-(4,4,5,5-tetramethyl-1,3,2-dioxaborolan-2-yl)phenyl)-4,5-dihydrooxazole

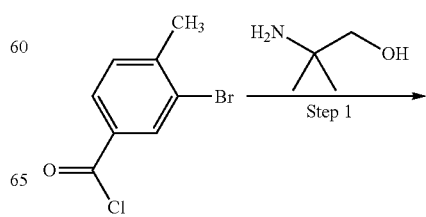

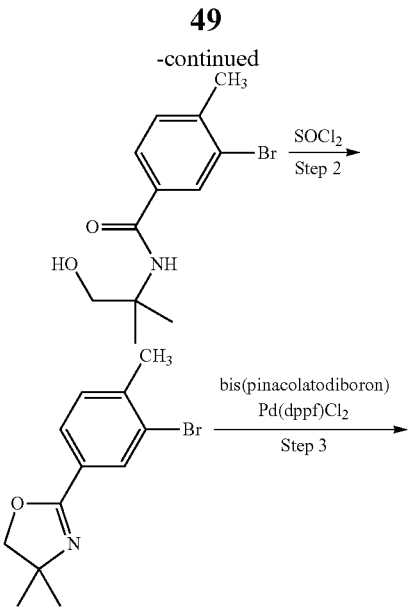

Intermediate 26

Step 1: 3-Bromo-N-(1-hydroxy-2-methylpropan-2-yl)-4-methylbenzamide: To a stirred 0° C. cooled solution of 3-bromo-4-methylbenzoyl chloride (prepared from the corresponding carboxylic acid; 1.40 g, 6.04 mmol, 1.0 eq) in DCM (10 mL), was added a solution of 2-amino-2-methylpropanol (1.44 mL, 15.11 mmol, 2.5 eq) in DCM (10 mL) drop wise for 15 min and then warmed to room temperature. After stirring for 24 h at room temperature, the reaction mixture was diluted with DCM (50 mL) and the organic layer was washed with water (20 mL) followed by brine (20 mL), dried ($Na_2SO_4$) and filtered. The filtrate was concentrated under vacuum to afford the 1.7 g of the desired product as a white solid. $^1$HNMR (400 MHz, DMSO-$d_6$) δ 8.00 (d, J=1.0 Hz, 1H), 7.70 (dd, J=1.0, 8.0 Hz, 1H), 7.62 (s, 1H, $D_2O$ exchangeable), 7.40 (d, J=8.0 Hz, 1H), 4.85 (t, J=6.0 Hz, 1H, $D_2O$ exchangeable), 3.49 (d, J=6.0 Hz, 2H), 2.37 (s, 3H), 1.28 (s, 6H); ESI-MS (m/z) 286, 288 [(MH)$^+$, Br$^{79,81}$].

Step 2: 2-(3-Bromo-4-methylphenyl)-4,4-dimethyl-4,5-dihydrooxazole: 3-bromo-N-(1-hydroxy-2-methylpropan-2-yl)-4-methylbenzamide (1.7 g, 6.04 mmol, 1.0 eq) was treated with thionyl chloride (0.9 mL, 12.08 mmol, 2.0 eq) and the neat reaction mixture was stirred at room temperature for 12 h. The mixture is diluted with diethyl ether (50 mL) and the precipitated solid was filtered and washed with diethyl ether (20 mL). The solid collected was dissolved in sodium hydroxide solution (1N, 15 mL) and extracted with diethyl ether (2×20 mL). The combined organic layers were washed with brine (20 mL), dried ($Na_2SO_4$) and filtered. The filtrate was concentrated under vacuum to afford the 1.0 g of the desired title product as a white solid. $^1$HNMR (400 MHz, CDCl$_3$) δ 8.12 (d, J=1.0 Hz, 1H), 7.75 (dd, J=1.0, 8.0 Hz, 1H), 7.25 (d, J=8.0 Hz, 1H), 4.09 (s, 2H), 2.42 (s, 3H), 1.37 (s, 6H); ESI-MS (m/z) 268, 270 [(MH)$^+$, Br$^{79,81}$].

Step 3: 2-(3-bromo-4-methylphenyl)-4,4-dimethyl-4,5-dihydrooxazole (600 mg, 2.23 mmol, 1.0 eq) was reacted with bis(pinacolato)diboron (850 mg, 3.35 mmol, 1.5 eq) and Pd(dppf)Cl$_2$ (90 mg, 0.11 mmol, 0.05 eq) by following the procedure described hereinbefore in step 6 of intermediate I to afford 700 mg of the desired product as a white solid. $^1$HNMR (400 MHz, CDCl$_3$) δ 8.28 (d, J=1.0 Hz, 1H), 7.87 (dd, J=1.0, 8.0 Hz, 1H), 7.18 (d, J=8.0 Hz, 1H), 4.07 (s, 2H), 2.55 (s, 3H), 1.36 (s, 6H), 1.33 (s, 12H); ESI-MS (m/z) 316 (MH)$^+$.

Intermediate 27

3-(4-Methyl-3-(4,4,5,5-tetramethyl-1,3,2-dioxazorolan-2-yl)phenyl)-1-oxa-2-azaspiro[4,4]non-2-ene

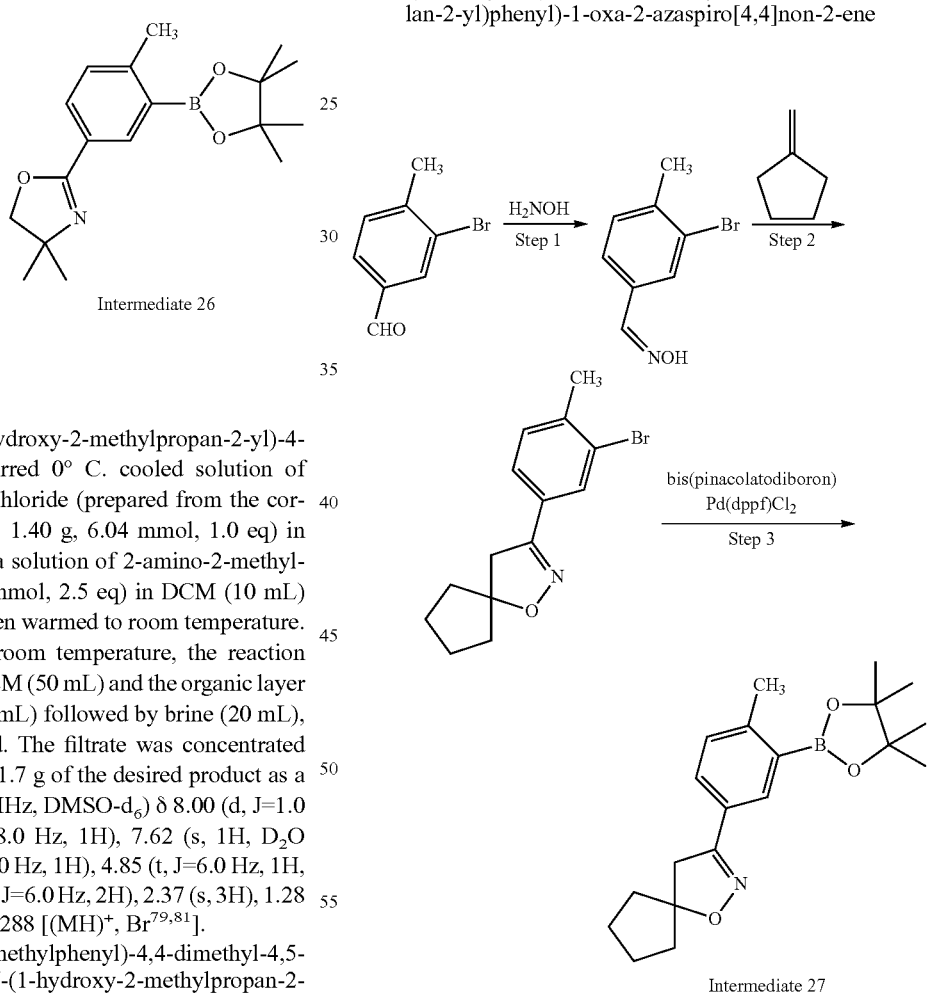

Intermediate 27

Step 1: 3-Bromo-4-methylbenzaldehyde oxime: To a stirred suspension of 3-bromo-4-methylbenzaldehyde (1.0 g, 5 mmol, 1.0 eq) in methanol (50 mL) was added a solution hydroxylamine hydrochloride (434 mg, 6.3 mmol, 1.2 eq) in water (2 mL) at room temperature. The resulting solution was cooled to 0° C. and then treated with an aqueous solution of sodium carbonate (2M, 2 mL). After stirring for 1 h at room temperature, the solvent was removed under vacuum. The residue was taken into ethyl acetate (20 mL) and water (10 mL). The layers were separated and the aqueous layer was extracted with ethyl acetate (2×20 mL). The combined organic layers were washed with brine (15 mL), dried (Na$_2$SO$_4$) and filtered. The filtrate was evaporated under vacuum to afford 0.85 g of the title product as a white solid. $^1$HNMR (400 MHz, CDCl$_3$) δ 8.08 (s, 1H), 7.87 (s, 1H, D$_2$O exchangeable) 7.76 (d, J=1.5 Hz, 1H), 7.43 (dd, J=8.0 Hz, 1H), 7.27 (d, J=8.0 Hz, 1H), 2.44 (s, 3H); ESI-MS (m/z) 214, 216 [(MH)$^+$, Br$^{79,81}$].

Step 2: 3-(3-Bromo-4-methylphenyl)-1-oxa-2-azaspiro[4,4]non-2-ene: To a solution of 3-bromo-4-methylbenzaldehyde oxime (0.85 g, 4 mmol, 1.0 eq) in THF (50 mL) was added pyridine (0.2 mL, 2.4 mmol, 0.6 eq) followed by N-chlorosuccinimide (530 mg, 4 mmol, 1.0 eq) and the resulting mixture was refluxed for 1 h. The reaction was cooled to room temperature before the addition of a solution of methylenecyclopentane (0.42 mL, 4 mmol, 1.0 eq) in THF (5 mL) followed by triethyl amine (0.94 mL, 7 mmol, 1.7 eq). The resulting solution was refluxed for 1 h. The solvent was evaporated under vacuum and usual work up afforded 690 mg of the title product as a white solid. $^1$HNMR (400 MHz, CDCl$_3$) δ 8.09 (s, 1H), 7.52 (d, J=8.0 Hz, 1H), 7.24 (d, J=8.0 Hz, 1H), 3.22 (s, 2H), 2.41 (s, 3H), 2.14-2.11 (m, 2H), 1.88-1.84 (m, 2H), 1.77-1.72 (m, 4H); ESI-MS (m/z) 294, 296 [(MH)$^+$, Br$^{79,81}$].

Step 3: 3-(4-Methyl-3-(4,4,5,5-tetramethyl-1,3,2-dioxazorolan-2-yl)phenyl)-1-oxa-2-azaspiro[4,4]non-2-ene: 3-(3-Bromo-4-methylphenyl)-1-oxa-2-azaspiro[4,4]non-2-ene (690 mg, 2 mmol, 1.0 eq) was reacted with bis(pinacolatodiboron) (720 mg, 3 mmol, 1.2 eq) and Pd(dppf)Cl$_2$ (96 mg, 0.11 mmol, 0.05 eq) by following the procedure described hereinbefore in step 6 of intermediate 1 to afford 640 mg of the desired product as a white solid. $^1$HNMR (400 MHz, CDCl$_3$) δ 7.88 (d, J=1.5 Hz, 1H), 7.72 (dd, J=8.0, 1.5 Hz, 1H), 7.18 (d, J=8.0 Hz, 1H), 3.29 (s, 2H), 2.54 (s, 3H), 2.11-2.09 (m, 2H), 1.88-1.84 (m, 2H), 1.74-1.70 (m, 4H); ESI-MS (m/z) 342 (MH)$^+$ The below intermediates 28 to 29 were prepared by following a procedure similar to that described in intermediate 27:

Intermediate 30

3-(3-Bromo-4-methylphenyl)-1-oxa-2-azaspiro[4.5]dec-2-en-4-one

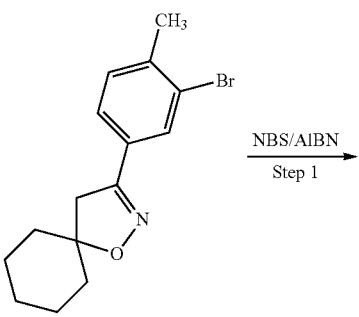

NBS/AIBN
Step 1

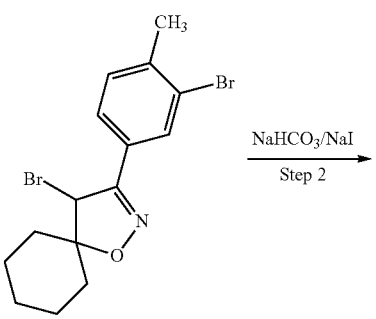

NaHCO$_3$/NaI
Step 2

| Intermediates/IUPAC name | Structure | $^1$HNMR/ESI-MS(MH)$^+$ |
|---|---|---|
| Intermediate 28: Methyl 5-methyl-3-(4-methyl-3-(4,4,5,5-tetramethyl-1,3,2-dioxaborolan-2-yl)phenyl)-4,5-dihydroisoxazole-5-carboxylate | 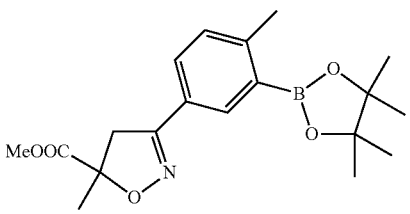 | $^1$HNMR (400 MHz, CDCl$_3$) δ 7.87 (d, J = 1.5 Hz, 1H), 7.59 (dd, J = 8.0, 1.5 Hz, 1H), 7.33 (d, J = 8.0 Hz, 1H), 3.92 (d, J = 17.0 Hz, 1H), 3.88 (s', 3H), 3.26 (d, J = 17.0 Hz, 1H), 2.50 (s, 3H), 1.79 (s, 3H); ESI-MS (m/z) 312, 314 [(MH)$^+$, Br$^{79,81}$] |
| Intermediate 29: (±)-Ethyl 3-(3-bromo-4-methylphenyl)-4,4-dimethyl-4,5-dihydroisoxazole-5-carboxylate | 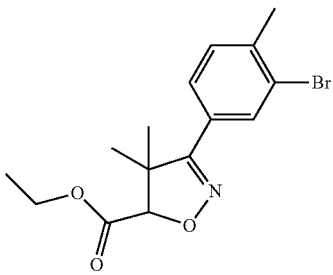 [SMILES: CCOC(=O)C1ON=C(c2ccc(C)c(Br)c2)C1(C)C] | $^1$HNMR (400 MHz, DMSO-d$_6$) δ 7.75 (d, 1.5 Hz, 1H), 7.52 (dd, J = 8.0, 1.5 Hz, 1H), 7.43 (d, J = 8.0 Hz, 1H), 4.53 (s, 1H), 4.10 (q, J = 7.0 Hz, 2H), 2.34 (s, 3H), 1.44 (s, 3H), 1.40 (s, 3H), 1.15 (t, J = 7.0 Hz, 3H); ESI-MS (m/z) 340, 342 [(MH$^+$, Br$^{79,81}$] |

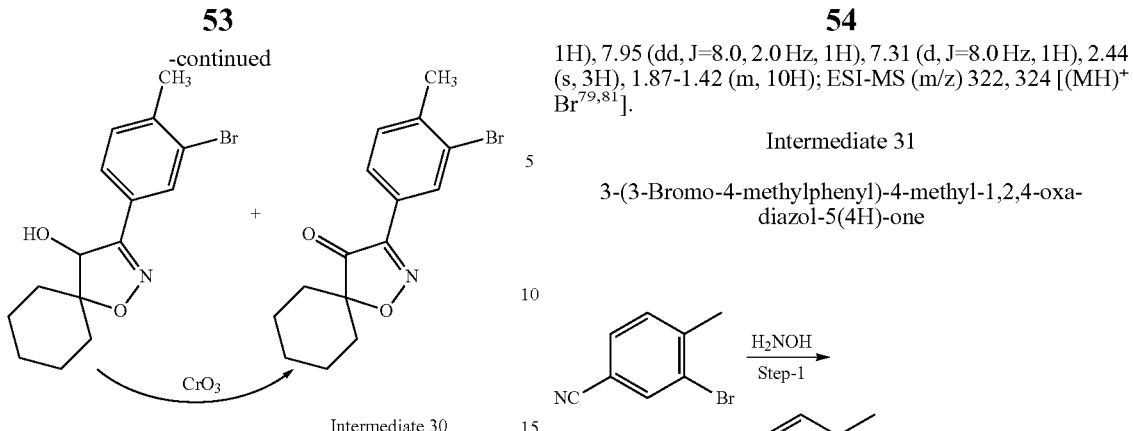

Intermediate 30

Step 1: 4-Bromo-3-(3-bromo-4-methylphenyl)-1-oxa-2-azaspiro[4.5]dec-2-ene: To a solution of 3-(3-bromo-4-methylphenyl)-1-oxa-2-azaspiro[4.5]dec-2-ene (2.0 g, 6.49 mmol, 1.0 eq) (prepared by following the procedure described for step-2 of the intermediate 27 by the reaction of 3-methyl-4-methylbenzaldehyde oxime with methylenecyclohexane) in chloroform (20 mL) was added NBS (1.15 g, 6.49 mmol, 1.0 eq) followed by catalytic amount of AIBN (21 mg, 0.13 mmol, 0.02 eq). The resulting mixture was stirred at room temperature overnight. The reaction was diluted with chloroform (50 mL) and washed with water (50 mL) and brine (50 mL). The organic layer was dried ($Na_2SO_4$) and filtered. The filtrate was concentrated under vacuum. The crude product was purified by flash column chromatography (silica gel, ethyl acetate and hexane) to afford 600 mg of the title product as a white solid. $^1$HNMR (400 MHz, $CDCl_3$) δ 7.97 (d, J=2.0 Hz, 1H), 7.65 (dd, J=8.0, 2.0 Hz, 1H), 7.29 (d, J=8.0 Hz, 1H), 5.14 (s, 1H), 2.43 (s, 3H), 2.13-2.10 (m, 1H), 2.01-1.99 (m, 1H), 1.82-1.76 (m, 4H), 1.65-1.62 (m, 1H), 1.52-1.45 (m, 3H); ESI-MS (m/z) 386, 388, 390 [(MH)$^+$ Br$^{79,81}$].

Step 2: 3-(3-Bromo-4-methylphenyl)-1-oxa-2-azaspiro[4.5]dec-2-en-4-one: To a solution of 4-bromo-3-(3-bromo-4-methylphenyl)-1-oxa-2-azaspiro[4.5]dec-2-ene (500 mg, 1.29 mmol, 1.0 eq) in DMSO (8 mL) was added sodium bicarbonate (218 mg, 2.59 mmol, 2.0 eq) followed by sodium iodide (289 mg, 1.93 mmol, 1.5 eq). The resulting mixture was stirred at 100° C. for 5 h. The reaction was cooled to room temperature and water (15 mL) was added to the above reaction mixture followed by ethyl acetate (15 mL). The layers were separated and the aqueous layer was extracted with ethyl acetate (2×10 mL). The combined organic layers were washed with water (2×10 mL), brine (15 mL), dried ($Na_2SO_4$) and filtered. The filtrate was evaporated under vacuum.

The crude product was purified with column chromatography (silica gel, ethyl acetate and hexane) to afford the desired product 170 mg of the title product along with 100 mg of the 3-(3-bromo-4-methylphenyl)-1-oxa-2-azaspiro[4.5]dec-2-en-4-ol. The 3-(3-bromo-4-methylphenyl)-1-oxa-2-azaspiro[4.5]dec-2-en-4-ol was again converted to the title product by the oxidation with chromium trioxide by following the procedure described for step-5 of the intermediate 1.

3-(3-bromo-4-methylphenyl)-1-oxa-2-azaspiro[4.5]dec-2-en-4-ol: $^1$HNMR (400 MHz, $CDCl_3$) δ 7.94 (d, J=2.0 Hz, 1H), 7.63 (dd, J=8.0, 2.0 Hz, 1H), 7.23 (d, J=8.0 Hz, 1H), 4.82 (d, J=10.0 Hz, 1H), 2.40 (s, 3H), 1.87-1.33 (m, 8H), 0.89-0.83 (m, 2H); ESI-MS (m/z) 324, 326 [(MH)$^+$ Br$^{79,81}$].

3-(3-Bromo-4-methylphenyl)-1-oxa-2-azaspiro[4.5]dec-2-en-4-one: $^1$HNMR (400 MHz, $CDCl_3$) δ 8.30 (d, J=2.0 Hz, 1H), 7.95 (dd, J=8.0, 2.0 Hz, 1H), 7.31 (d, J=8.0 Hz, 1H), 2.44 (s, 3H), 1.87-1.42 (m, 10H); ESI-MS (m/z) 322, 324 [(MH)$^+$ Br$^{79,81}$].

Intermediate 31

3-(3-Bromo-4-methylphenyl)-4-methyl-1,2,4-oxadiazol-5(4H)-one

Intermediate 31

Step-1: 3-Bromo-N-hydroxy-4-methylbenzimidamide: To a stirred solution of 3-bromo-4-methylbenzonitrile (2.0 g, 10.2 mmol, 1.0 eq) in ethanol (20 mL) was added hydroxylamine hydrochloride (1.77 g, 25.5 mmol, 2.5 eq) followed by a solution of sodium carbonate (2.70 g, 25.5 mmol, 2.5 eq) in water (2 mL). The resulting mixture was refluxed for 6 h. The reaction was cooled to room temperature and the solvent was removed under vacuum. The residue was taken in DCM (100 mL) and washed with water (30 mL), brine (30 mL), dried ($Na_2SO_4$) and filtered. The filtrate was rotary evaporated to afford 1.5 g of the title compound as a white solid. $^1$HNMR (400 MHz, $CDCl_3$) δ 9.70 (s, 1H), 7.86 (d, J=1.5 Hz, 1H), 7.59 (dd, J=7.5, 1.5 Hz, 1H), 7.34 (d, J=8.0 Hz, 1H), 5.86 (s, 2H), 2.34 (s, 3H); ESI-MS (m/z) 229, 231 [(MH)$^+$ Br$^{79,81}$].

Step-2: 3-(3-Bromo-4-methylphenyl)-1,2,4-oxadiazol-5(4H)-one: To a 0° C. cooled solution of 3-bromo-N-hydroxy-4-methylbenzimidamide (500 mg, 2.18 mmol, 1.0 eq) in DCM (10 mL) was added triphosgene (250 mg, 0.87 mmol, 0.4 eq) followed by diisopropylethylamine (0.76 mL, 4.46 mmol, 2 eq). The resulting mixture was stirred at room temperature for 3 h. The reaction was cooled back down to room temperature and quenched with water (5 mL) followed by dilution with DCM. The layers were separated and the organic layer was washed with brine (10 mL), dried ($Na_2SO_4$) and filtered. The filtrate was evaporated under vacuum to afford 250 mg of the title product as white solid. $^1$HNMR (400 MHz, DMSO-$d_6$) δ 13.10 (s, 1H, $D_2O$ exchangeable), 8.01 (d, J=1.5 Hz, 1H), 7.74 (dd, J=8.0, 1.5 Hz, 1H), 7.56 (d, J=8.0 Hz, 1H) 2.42 (s, 3H); ESI-MS (m/z) 255, 257 [(MH)$^+$, Br$^{79,81}$]

Step-3: 3-(3-Bromo-4-methylphenyl)-4-methyl-1,2,4-oxadiazol-5(4H)-one: To a stirred solution of 3-(3-bromo-4-methylphenyl)-1,2,4-oxadiazol-5(4H)-one (1.5 g, 5.92 mmol, 1.0 eq) in DMF (10 mL) was added methyl iodide (0.73 mL, 11.85 mmol, 2.0 eq) and potassium carbonate (1.6 g, 11.85 mmol, 2.0 eq) and the reaction was stirred at room temperature overnight. Water (20 mL) was added to the reaction mixture followed by ethyl acetate (20 mL). The layers were separated and the aqueous layer was extracted with ethyl acetate (2×20 mL) and the combined organic layers were washed with water (2×20 mL), brine (20 mL), dried ($Na_2SO_4$) and filtered. The filtrate was rotary evaporated and the crude product was purified by flash column chromatography (silica gel, 10% ethyl acetate in hexane system as eluent) to afford 1.35 g of the title product as a white solid. $^1$HNMR (400 MHz, DMSO-$d_6$) δ 7.93 (d, J=2.0 Hz, 1H), 7.66 (dd, J=7.5, 2.0 Hz, 1H), 7.60 (d, J=7.5 Hz, 1H), 3.34 (s, 3H), 2.44 (s, 3H); ESI-MS (m/z) 269, 271 [(MH)$^+$, Br$^{79,81}$]

Intermediate 32

N-(5-Bromopyrazine-2-yl)-2,6-difluorobenzamide

Step 1: 2-Amino-5-bromopyrazine: To a 0° C. cooled and stirred solution of 2-aminopyrazine (10 g, 105 mmol, 1.0 eq) in DCM (1000 mL) was added N-bromosuccinimide (16.8 g, 94.6 mmol, 0.9 eq) portion wise and the resulting solution was stirred at the same temperature for 30 min. The reaction mixture was filtered while keeping the filtrate at 0° C. and cold water (500 mL) was added to the filtrate. The layers were separated and the organic layer was washed with brine (200 mL), dried ($Na_2SO_4$) and filtered. The filtrate was concentrated under vacuum. The crude product was purified by re-crystallization using DCM and hexane to afford 12 g of the desired product as a pale yellow solid. $^1$HNMR (400 MHz, $CDC_3$) δ 8.06 (s, 1H), 7.75 (s, 1H), 4.72 (brs, 2H, $D_2O$ exchangeable); ESI-MS (m/z) 174, 176 [(MH)$^+$ Br$^{79,81}$].

Step 2: N-(5-Bromopyrazine-2-yl)-2,6-difluorobenzamide: To a 0° C. cooled and stirred, solution of 2,6-difluorobenzoyl chloride (5.7 g, 36.2 mmol, 0.9 eq) in DCM (200 mL) was added drop wise a solution of 2-amino-5-bromopyrazine (7.0 g, 40.2 mmol, 1.0 eq) in DCM (50 mL) followed b pyridine (3.1 g, 36.2 mmol, 0.9 eq). The resulting mixture was stirred at room temperature for 15 h. The reaction was diluted with DCM (100 mL), and washed with 10% hydrochloric acid (100 mL), dried ($Na_2SO_4$) and filtered. The filtrate was concentrated under vacuum and the crude product was purified by flash column chromatography (silica gel, 10% ethyl acetate in hexane) to afford 6.0 g of the title product as a yellow solid. $^1$HNMR (400 MHz, $CDCl_3$) δ 9.47 (s, 1H), 8.62 (s, 1H, $D_2O$ exchangeable), 8.24 (s, 1H), 7.53-7.45 (m, 1H), 7.03 (t, J=8.0 Hz, 2H); ESI-MS (m/z) 314, 316 [(MH)$^+$ Br$^{79,81}$].

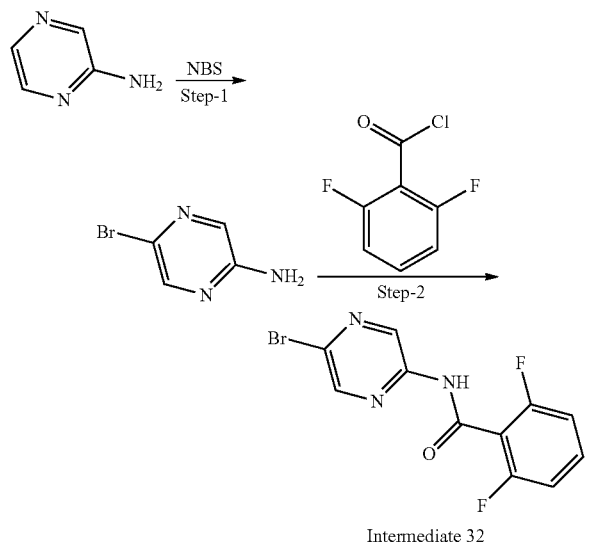

Intermediate 32

The below intermediates 33 to 44 were prepared by following a procedure similar to that described in intermediate 32:

| Intermediates/IUPAC name | Structure | $^1$HNMR/ESI-MS MH$^+$ |
|---|---|---|
| Intermediate 33: N-(5-Bromopyrazin-2-yl)-2-fluorobenzamide | 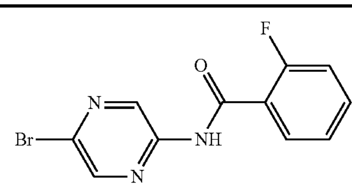 | $^1$HNMR (400 MHz, $CDCl_3$) δ 9.51 (s, 1H), 9.08 (d, J = 15 Hz, 1H, $D_2O$ exchangeable), 8.40 (s, 1H), 8.17 (dt, J = 1.5, 8.0 Hz, 1H), 7.62-7.56 (m, 1H), 7.35 (t, J = 7.5 Hz, 1H), 7.23 (dd, J = 9.0, 12.5 Hz, 1H); ESI-MS (m/z) 296, 298 [(MH)$^+$ Br$^{79, 81}$]. |
| Intermediate 34: N-(5-Bromopyrazine-2-yl)-2,4-difluorobenzamide | 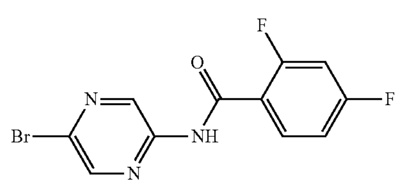 [SMILES: O=C(Nc1cnc(Br)cn1)c1ccc(F)cc1F] | $^1$HNMR (400 MHz, DMSO) δ 11.40 (s, 1H, $D_2O$ exchangeable), 9.23 (s, 1H), 8.67 (s, 1H), 7.80 (q, J = 8.0 Hz, 1H), 7.45-7.39 (m, 1H), 7.26-7.19 (m, 1H); ESI-MS (m/z) 314, 316 [(MH)$^+$ Br$^{79, 81}$]. |
| Intermediate 35: N-(5-Bromopyrazine-2-yl)-2,5-difluorobenzamide | 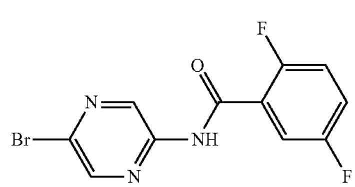 [SMILES: O=C(Nc1cnc(Br)cn1)c1cc(F)ccc1F] | $^1$HNMR (400 MHz, DMSO) δ 11.52 (s, 1H, $D_2O$ exchangeable), 9.23 (s, 1H), 8.69 (s, 1H), 7.61-7.56 (m, 1H), 7.51-7.41 (m, 2H); ESI-MS (m/z) 314, 316 [(MH)$^+$ Br$^{79, 81}$]. |

-continued

| Intermediates/IUPAC name | Structure | $^1$HNMR/ESI-MS MH$^+$ |
|---|---|---|
| Intermediate 36: N-(5-Bromopyrazine-2-yl)-2,3-difluorobenzamide | 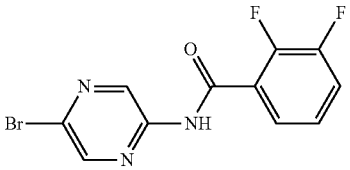 [SMILES: O=C(Nc1cnc(Br)cn1)c1cccc(F)c1F] | $^1$HNMR (400 MHz, DMSO-d6) δ 11.57 (s, 1H, D$_2$O exchangeable), 9.24 (s, 1H,), 8.69 (s, 1H), 7.69-7.62 (m, 1H), 7.54-7.50 (m, 1H), 7.38-7.33 (m, 1H); ESI-MS (m/z) 314, 316 [(MH)$^+$ Br$^{79, 81}$] |
| Intermediate 37: N-(5-bromopyrazin-2-yl)-3-fluorobenzamide | 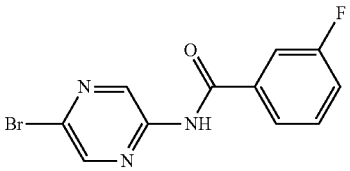 [SMILES: O=C(Nc1cnc(Br)cn1)c1cccc(F)c1] | $^1$HNMR (400 MHz, DMSO-d6) δ 11.43 (s, 1H, D$_2$O exchangeable), 9.25 (s, 1H,), 8.72 (s, 1H), 7.90-7.85 (m, 2H), 7.60-7.57 (m, 1H), 7.51-7.45 (m, 1H); ESI-MS (m/z) 296, 298 [(MH)$^+$ Br$^{79, 81}$] |
| Intermediate 38: N-(5-Bromopyrazine-2-yl)-4-fluorobenzamide | 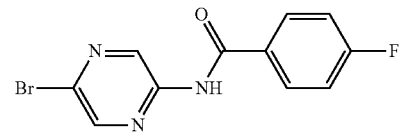 [SMILES: O=C(Nc1cnc(Br)cn1)c1ccc(F)cc1] | $^1$HNMR (400 MHz, DMSO-d6) δ 11.37 (s, 1H, D$_2$O exchangeable), 9.24 (s, 1H,), 8.70 (s, 1H), 8.14-8.10 (m, 2H), 7.37 (t, J = 8.5 Hz, 2H); ESI-MS (m/z) 296, 298 [(MH)$^+$ Br$^{79, 81}$] |
| Intermediate 39: N-(5-Bromopyrazine-2-yl)-2,4,5-trifluorobenzamide | 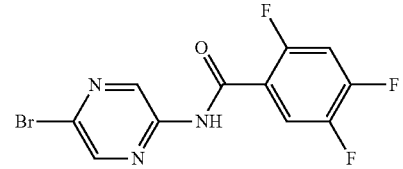 | $^1$HNMR (400 MHz, DMSO-d6) δ 11.52 (s, 1H, D$_2$O exchangeable), 9.22 (s, 1H,), 8.70 (s, 1H), 7.93-7.87 (m, 1H), 7.80-7.73 (m, 1H); ESI-MS (m/z) 332, 334 [(MH)$^+$ Br$^{79, 81}$] |
| Intermediate 40: N-(5-Bromopyrazine-2-yl)-2,3-dimthylbenzamide | 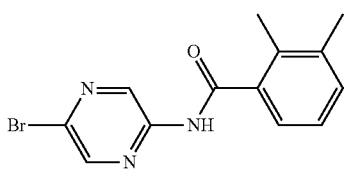 [SMILES: Cc1cccc(C(=O)Nc2cnc(Br)cn2)c1C] | $^1$HNMR (400 MHz, CDCl$_3$) δ 9.51 (s, 1H), 8.38 (s, 1H, D$_2$O exchangeable), 8.14 (s, 1H), 7.33 (t, J = 8.0 Hz, 2H), 7.19 (t, J = 8.0 Hz, 1H), 2.38 (s, 3H), 2.34 (s, 3H); ESI-MS (m/z) 306, 308 [(MH)$^+$ Br$^{79, 81}$]. |
| Intermediate 41: N-(5-Bromopyrazine-2-yl)-4-trifluoromethylbenzamide | 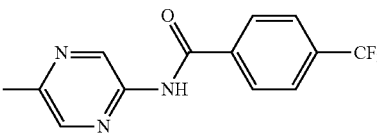 | $^1$HNMR (400 MHz, DMSO-d6) δ 11.59 (s, 1H, D$_2$O exchangeable), 9.26 (s, 1H,), 8.72 (s, 1H), 8.21 (d, J = 8.0 Hz, 2H), 7.92 (d, J = 8.0 Hz, 1H); ESI-MS (m/z) 346, 348 [(MH)$^+$ Br$^{79, 81}$] |
| Intermediate 42: N-(5-Bromopyrazine-2-yl)-4-fluoro-3-methylbenzamide | 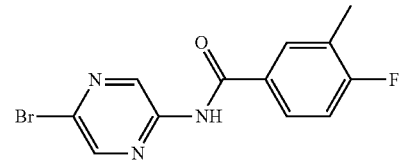 [SMILES: Cc1cc(C(=O)Nc2cnc(Br)cn2)ccc1F] | $^1$HNMR (400 MHz, CdCl$_3$) δ 9.48 (s, 1H), 8.40-8.37 (m, 2H), 7.80 (d, J = 7.0 Hz, 1H), 7.74-7.72 (m, 1H), 7.14 (t, J = 8.0 Hz, 1H), 2.36 (s, 3H); ESI-MS (m/z) 310, 312 [(MH)$^+$ Br$^{79, 81}$] |
| Intermediate 43: N-(5-Bromopyrazine-2-yl)-2-methylbenzamide | 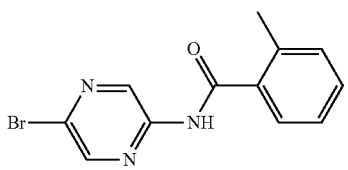 | $^1$HNMR (400 MHz, CDCl$_3$) δ 9.50 (s, 1H), 8.29 (s, 1H, D$_2$O exchangeable), 8.26 (s, 1H), 7.54 (d, J = 7.5 Hz, 1H), 7.43 (d, J = 8.0 Hz, 1H), 7.32-7.26 (m, 2H), 2.46 (s, 3H); ESI-MS (m/z) 292, 294 [(MH)$^+$ Br$^{79, 81}$]. |
| Intermediate 44: N-(5-Bromopyrazine-2-yl)-3-fluoro-5-trifluoromethylbenzamide | 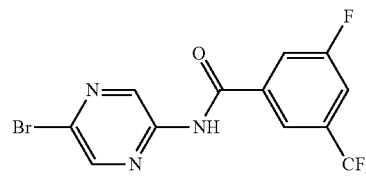 | $^1$HNMR (400 MHz, DMSO-d$_6$) δ 11.69 (s, 1H, D$_2$O exchangeable), 9.25 (s, 1H), 8.73 (s, 1H), 8.27 (s, 1H), 8.17 (d, J = 8.0 Hz, 1H), 8.01 (d, J = 8.0 Hz, 1H); ESI-MS (m/z) 364, 366 [(MH)$^+$ Br$^{79, 81}$] |

Intermediate 45

N-(5-Bromopyrazin-2-yl)-4-methyl-1,2,3-thiadiazole-5-carboxamide

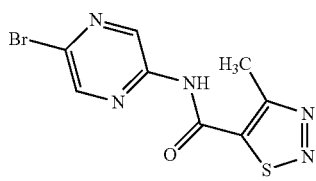 [SMILES: Cc1nnsc1C(=O)Nc1cnc(Br)cn1]

To a solution of 2-amino-5-bromopyrazine (1.0 g, 5.74 mmol, 1.2 eq) and 4-methyl-1,2,3-thiadiazole-5-carboxylic acid (690 mg, 4.79 mmol, 1.0 eq) in THF (20 mL) at room temperature was sequentially added EDC. HCl (970 mg, 7.18 mmol, 1.5 eq), HOBT (1.37 g, 7.18 mmol, 1.5 eq) and diisopropylethyl amine (1.23 mL, 9.58 mmol, 2.0 eq). The resulting solution was stirred at the same temperature for 24 h. Water (30 mL) was added to the reaction mixture followed by ethyl acetate (30 mL). The layers were separated and the aqueous layer was extracted with ethyl acetate (3×20 mL). The combined organic layers were washed with 1N hydrochloric acid (20 mL), saturated sodium bicarbonate solution (20 mL), brine (20 mL) dried ($Na_2SO_4$) and filtered. The filtrate was concentrated under vacuum and the crude product was purified by flash column chromatography (silica gel) to afford 321 mg of the desired product as a white solid. $^1$HNMR (400 MHz, DMSO-$d_6$) δ 11.91 (s, 1H, $D_2O$ exchangeable), 9.20 (s, 1H), 8.72 (s, 1H), 2.83 (s, 3H); ESI-MS (m/z) 300, 302 [(MH)$^+$, Br$^{79,81}$].

Intermediate 46a and 46b

N-(4-bromophenyl)-2,6-difluorobenzamide (46a) and

2,6-Difluoro-N-(4-(4,4,5,5,-tetramethyl-1,3,2-dioxaborolan-2-yl)phenyl)benzamide (46b)

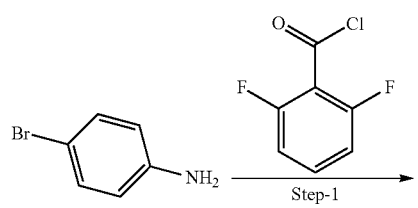

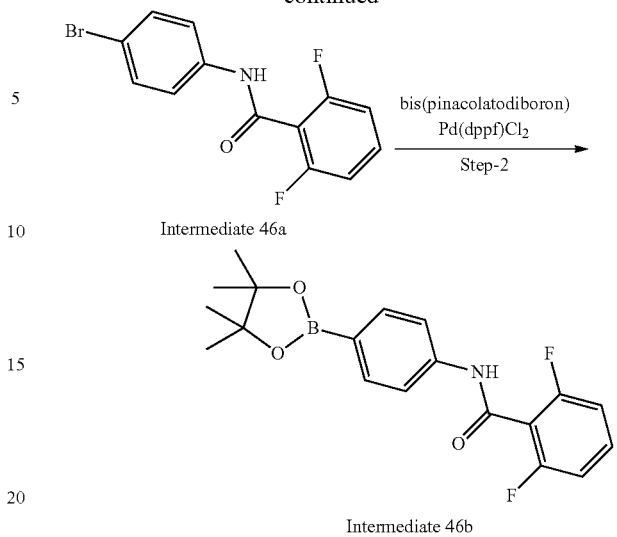

Intermediate 46a

Intermediate 46b

Step 1: N-(4-Bromophenyl)-2,6-difluorobenzamide: To a stirred and 0° C. cooled solution of 4-bromoaniline (1.0 g, 5.8 mmol, 1.0 eq) and pyridine (0.61 mL, 7 mmol, 1.2 eq) in DCM (20 mL) was added drop wise a solution of 2,6-difluorobenzoyl chloride (0.8 mL, 6.4 mmol, 1.1 eq) in DCM (5 mL). After stirring the resulting mixture at the same temperature for 1 h, the solvent was removed under vacuum. The residue was taken into ethyl acetate (20 mL) and water (20 mL). The layers were separated. The aqueous layer was extracted with ethyl acetate (2×20 mL) and the combined organic layers were washed with brine (20 mL), dried ($Na_2SO_4$) and filtered. The filtrate was concentrated under vacuum to afford 1.20 g of the desired product as a white solid. $^1$HNMR (400 MHz, DMSO-$d_6$) δ 7.78 (brs, 1H, $D_2O$ exchangeable), 7.53-7.37 (m, 5H), 7.02-6.95 (m, 2H); ESI-MS (m/z) 312, 314 [(MH)$^+$ Br$^{79,81}$].

Step 2: 2,6-Difluoro-N-(4-(4,4,5,5,-tetramethyl-1,3,2-dioxaborolan-2-yl)phenyl)benzamide: N-(4-Bromophenyl)-2,6-difluorobenzamide (5.0 g, 16.1 mmol, 1.0 eq) was reacted with bis(pinacolato)diboron (4.88 g, 19.2 mmol, 1.2 eq) by following the procedure described in step 6 of intermediate 1 to afford 4.20 g of the desired product as a white solid. $^1$HNMR (400 MHz, DMSO-$d_6$) δ 10.92 (brs, 1H, $D_2O$ exchangeable), 7.72-7.64 (m, 4H), 7.62-7.56 (m, 1H), 7.26 (t, J=8.0 Hz, 2H), 1.29 (s, 12H); ESI-MS (m/z) 360 (MH)$^+$.

The below intermediates 47a to 49 were prepared by following a procedure similar to that described in intermediate 46a or intermediate 46b:

| Intermediates/IUPAC name | Structure | $^1$HNMR/ESI-MS MH$^+$ |
|---|---|---|
| Intermediate 47a: N-(4-Bromophenyl)-2-chloro-6-fluorobenzamide | (structure: 4-bromophenyl-NH-C(=O)-2-chloro-6-fluorobenzene) | $^1$HNMR (400 MHz, DMSO-$d_6$) δ 10.95 (s, 1H, $D_2O$ exchangeable), 7.68 (d, J = 8.5 Hz, 2H) 7.59-7.53 (m, 3H), 7.46 (d, J = 8.0 Hz, 1H), 7.42-7.33 (m, 1H); ESI-MS (m/z) 327, 329 [(MH)$^+$, Br$^{79,81}$] |

| Intermediates/IUPAC name | Structure | ¹HNMR/ESI-MS MH⁺ |
|---|---|---|
| Intermediate 47b: 2-Chloro-6-fluoro-N-(4-(4,4,5,5-tetramethyl-1,3,2-dioxaborolan-2-yl)phenyl)benzamide | 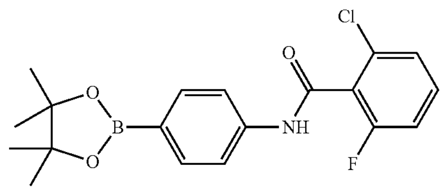 [SMILES: CC1(C)OB(c2ccc(NC(=O)c3c(F)cccc3Cl)cc2)OC1(C)C] | ¹HNMR (400 MHz, CDCl₃) δ 7.81 (d, J = 8.5 Hz, 2H), 7.63 (d, J = 8.5 Hz, 2H), 7.56 (s, 1H, D₂O exchangeable), 7.38-7.32 (m, 1H), 7.25 (d, 1H), 7.09 (t, J = 8.5 Hz, 1H), 1.35 (s, 12H); ESI-MS (m/z) 376 (MH)⁺ |
| Intermediate 48a: N-(4-Bromophenyl)-2-fluoro-6-methylbenzamide | 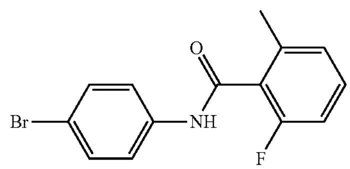 [SMILES: Cc1cccc(F)c1C(=O)Nc1ccc(Br)cc1] | ¹HNMR (400 MHz, CDCl₃) δ 7.63 (s, 1H, D₂O exchangeable), 7.51 (d, J = 8.5 Hz, 2H), 7.45 (d, J = 8.5 Hz, 2H), 7.31-7.26 (m, 1H), 7.03 (d, J = 8.0 Hz, 1H), 6.95 (t, J = 8.5 Hz, 1H), 2.43 (s, 3H); ESI-MS (m/z) 307, 309 [(MH)⁺, Br⁷⁹,⁸¹] |
| Intermediate 48b: 2-Fluoro-6-methyl-N-(4-(4,4,5,5-tetramethyl-1,3,2-dioxaborolan-2-yl)phenyl)benzamide | 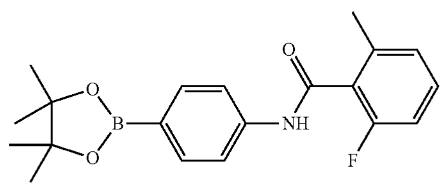 [SMILES: Cc1cccc(F)c1C(=O)Nc1ccc(B2OC(C)(C)C(C)(C)O2)cc1] | ¹HNMR (400 MHz, CDCl₃) δ 7.81 (d, J = 8.5 Hz, 2H), 7.64 (d, J = 8.5 Hz, 2H), 7.54 (s, 1H, D₂O exchangeable), 7.32-7.26 (m, 1H), 7.05 (d, J = 8.5 Hz, 1H), 6.97 (t, J = 8.0 Hz, 1H), 2.46 (s, 3H), 1.34 (s, 12H); ESI-MS (m/z) 356 (MH)⁺. |
| Intermediate 49: 4-Ethyl-N-(4-(4,4,5,5-tetramethyl-1,3,2-dioxaborolan-2-yl)phenyl)benzamide | 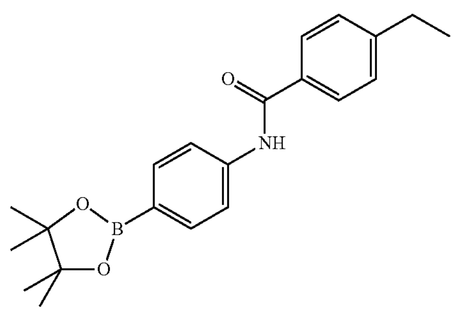 [SMILES: CCc1ccc(C(=O)Nc2ccc(B3OC(C)(C)C(C)(C)O3)cc2)cc1] | ESI-MS (m/z) 352 (MH)⁺. |

Intermediate 50

4-Methyl-N-(4-(4,4,5,5-tetramethyl-1,3,2-dioxaborolan-2-yl)phenyl)-1,2,3-thiadiazol-5-carboxamide

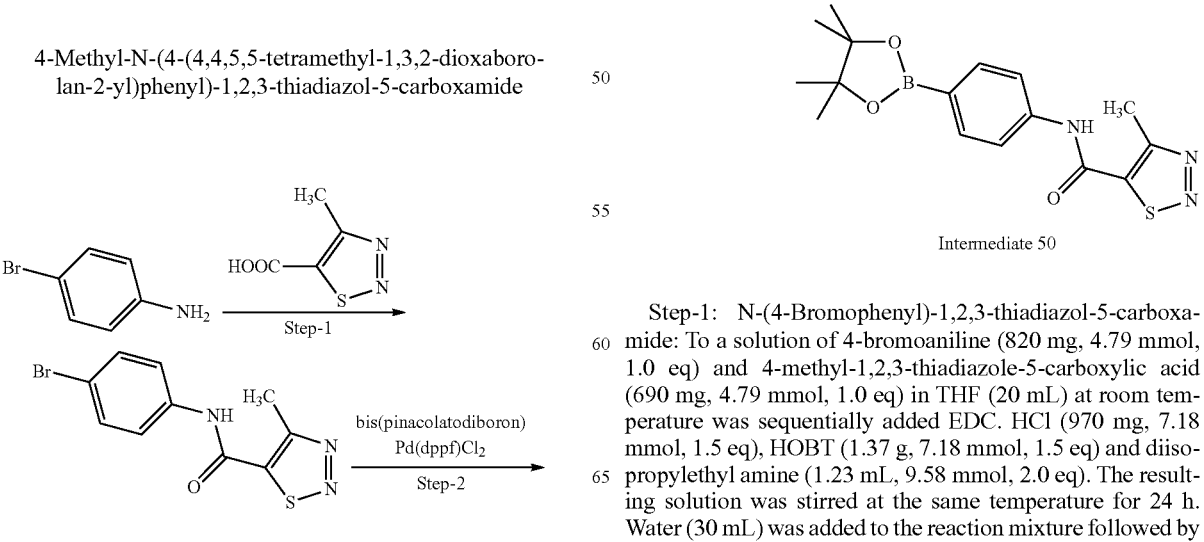

Intermediate 50

Step-1: N-(4-Bromophenyl)-1,2,3-thiadiazol-5-carboxamide: To a solution of 4-bromoaniline (820 mg, 4.79 mmol, 1.0 eq) and 4-methyl-1,2,3-thiadiazole-5-carboxylic acid (690 mg, 4.79 mmol, 1.0 eq) in THF (20 mL) at room temperature was sequentially added EDC. HCl (970 mg, 7.18 mmol, 1.5 eq), HOBT (1.37 g, 7.18 mmol, 1.5 eq) and diisopropylethyl amine (1.23 mL, 9.58 mmol, 2.0 eq). The resulting solution was stirred at the same temperature for 24 h. Water (30 mL) was added to the reaction mixture followed by ethyl acetate (30 mL). The layers were separated and the aqueous layer was extracted with ethyl acetate (3×20 mL). The combined organic layers were washed with 1N hydrochloric acid (20 mL), saturated sodium bicarbonate solution (20 mL), brine (20 mL) dried (Na$_2$SO$_4$) and filtered. The filtrate was concentrated under vacuum and the crude product was purified by flash column chromatography (silica gel) to afford 321 mg of the desired product as a white solid. $^1$HNMR (400 MHz, CDCl$_3$) δ 7.64 (brs, 1H, D$_2$O exchangeable), 7.51-7.45 (m, 4H), 2.94 (s, 3H); ESI-MS (m/z) 298, 300 [(MH)$^+$ Br$^{79,81}$].

Step-2: 4-Methyl-N-(4-(4,4,5,5-tetramethyl-1,3,2-dioxaborolan-2-yl)phenyl)-1,2,3-thiadiazol-5-carboxamide: The title compound was prepared by the reaction of N-(4-bromophenyl)-1,2,3-thiadiazol-5-carboxamide with bis(pinacolato)diboron by following the procedure described for step 6 of intermediate 1. $^1$HNMR (400 MHz, CDCl$_3$) δ 7.80 (d, J=8.5 Hz, 2H), 7.61 (s, 1H, D$_2$O exchangeable), 7.55 (d, J=8.5 Hz, 2H), 2.94 (s, 3H), 1.32 (s, 12H); ESI-MS (m/z) 346 (MH)$^+$.

Intermediate 51

N-(5-Bromopyridin-2-yl)-2,6-difluorobenzamide

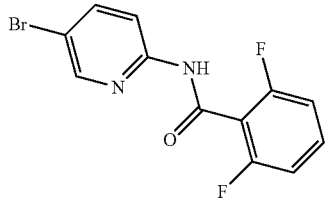 [SMILES: O=C(Nc1ccc(Br)cn1)c1c(F)cccc1F]

To a mixture of 2-chloro-5-bromopyridine (370 mg, 1.9 mmol, 1.2 eq) and 2,6-difluorobenzamide (250 mg, 1.5 mmol, 1.0 eq) in dioxane (10 mL), copper iodide (151 mg, 0.75 mmol, 0.5 eq), potassium phosphate (670 mg, 3.15 mmol, 2.1 eq) and N,N-dimethylethylene diamine (0.1 mL, 1.05 mmol, 0.7 eq) were added sequentially. The resulting mixture was stirred at reflux for 15 h. The reaction was cooled to room temperature, filtered to remove the solid components and the filtrate was concentrated under vacuum. The residue was dissolved in ethyl acetate (50 mL), washed with water (20 mL), brine (20 mL), dried (Na$_2$SO$_4$) and filtered. The filtrate was concentrated under vacuum and the crude product was purified by flash column chromatography (silica gel, ethyl acetate and hexane) to afford 300 mg of the solid product as a white solid. $^1$HNMR (400 MHz, DMSO-d$_6$) δ 11.22 (s, 1H, D$_2$O exchangeable), 8.70 (d, J=2.5 Hz, 1H), 8.18 (dd, J=8.0, 2.5 Hz, 1H), 7.67-7.59 (m, 1H), 7.55 (d, J=8.0 Hz, 1H), 7.29 (t, J=8.0 Hz, 2H); ESI-MS (m/z) 313, 315 [(MH)$^+$ Br$^{79,81}$].

Intermediate 52

N-(6-Bromopyridin-3-yl)-2,6-difluorobenzamide

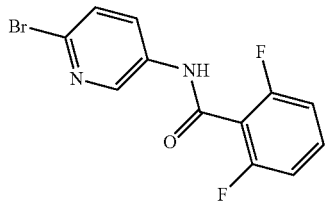 [SMILES: O=C(Nc1ccc(Br)nc1)c1c(F)cccc1F]

To a (0° C.) cooled and stirred solution of 2-bromo-5-aminopyridine (2.0 g, 11.56 mmol, 1.0 eq) in DCM (25 mL) was added sequentially 2,6-difluorobenzoyl chloride (1.44 mL, 11.56 mmol, 1.0 eq) and pyridine (1.19 mL, 13.87 mmol, 1.2 eq). The resulting mixture was allowed to warm to room temperature and then stirred at the same temperature for 30 min.

Reaction was diluted with DCM (30 mL) and washed with water (20 mL), saturated aqueous sodium bicarbonate solution (30 mL), brine (20 mL), dried (Na$_2$SO$_4$) and filtered. The filtrate was rotary evaporated and the residue was triturated with hexane to afford 3.4 g of the desired product as a white solid. $^1$HNMR (400 MHz, CDCl$_3$) δ 8.42 (d, J=2.5 Hz, 1H), 8.18 (dd, J=8.5, 2.5 Hz, 1H), 7.96 (brs, 1H, D$_2$O exchangeable), 7.49 (d, J=8.5 Hz, 1H), 7.46-7.41 (m, 1H), 7.00 (t, J=8.0 Hz, 2H); ESI-MS (m/z) 313, 315 [(MH)$^+$ Br$^{79,81}$].

Intermediate 53a: 5-bromo-N-(2,6-difluorophenyl)thiophene-2-carboxamide and

Intermediate 53b: N-(2,6-difluorophenyl)-5-(trimethylstannyl)thiophene-2-carboxamide

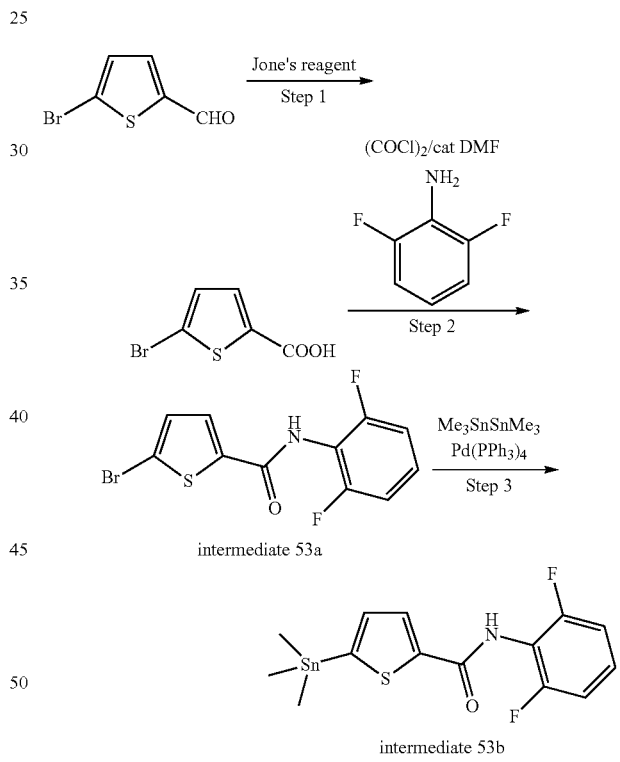

Step 1: 5-Bromothiophene-2-carboxylic acid: To a 0° C. solution of 5-bromothiophene-2-carboxaldehyde (5.0 g, 26.1 mmol) in acetone (50 mL) was added drop wise a freshly prepared jone's reagent (25 mL) (25 g of chromium trioxide dissolved in 25 mL of conc sulfuric acid, is added slowly to 75 mL of water that had been cooled to 0° C. and stirring) and the resulting mixture was stirred at room temperature for 4 h. Water (50 mL) was then added to the above mixture followed by ethyl acetate (50 mL). The layers were separated and the aqueous layer was extracted with ethyl acetate (2×50 mL). the combined extracts were washed with water (50 mL), brine (50 mL), dried (Na$_2$SO$_4$) and filtered. The filtrate was to evaporated under vacuum. to afford 5.2 g (95) of the desired product as a white solid. $^1$HNMR (400 MHz, CDCl$_3$) δ 10.87 (brs, 1H, D$_2$O Exchangeable), 7.63 (d, J=4.0 Hz, 1H), 7.11 (d, J=4.0 Hz, 1H).

Step 2: 5-Bromo-N-(2,6-difluorophenyl)thiophene-2-carboxamide To a 0° C. solution of 5-bromothiophene-2-carboxylic acid (5.20 g, 25 mmol, 1.0 eq) in DCM (60 mL) was added drop wise a solution of oxalyl chloride (16 g, 125 mmol, 5 eq) in DCM (20 mL) followed by a catalytic amount of DMF (0.5 mL). The resulting mixture was stirred for 2 h at room temperature and then the solvent, excess of oxalyl chloride were removed under vacuum. To the residue obtained above was taken into DCM (50 mL) cooled to 0° C., then added a solution of 2,6-difluoroaniline (4.0 g, 31 mmol, 1.2 eq) followed by pyridine (5 mL). The reaction was gradually allowed to warm to room temperature and then stirred overnight at the same temperature. The reaction was diluted with DCM (100 mL) and washed with water (2×50 mL), 10% HCl (50 mL), brine (50 mL), dried (Na$_2$SO$_4$) and filtered. The filtrate was evaporated under vacuum to afford the 5 g (65%) of desired product as a white solid. $^1$HNMR (400 MHz, CDCl$_3$) δ 7.52 (s, 1H, D$_2$O Exchangeable), 7.43 (d, J=4.0 Hz, 1H), 7.24-7.17 (m, 1H), 7.06 (d, J=4.0 Hz, 1H), 6.94 (t, J=8.0 Hz, 2H); ESI-MS (m/z) 320, 322 [(MH)$^+$, Br$^{79,81}$].

Step 3: N-(2,6-Difluorophenyl)-5-(trimethylstannyl)thiophene-2-carboxamide: To a solution of 5-bromo-N-(2,6-difluorophenyl)thiophene-2-carboxamide (2.50 g, 7.86 mmol, 1.0 eq) and hexamethylditin (1.63 mL, 7.86 mmol, 1.0 eq) in dioxane (40 mL) was added Pd(PPh$_3$)$_4$ (454 mg, 0.39 mmol, 0.05 eq). The resulting mixture was thoroughly deoxygenated by subjecting to vacuum/nitrogen cycle three times and the reaction mixture was heated at 75° C. for 15 h under nitrogen atmosphere. The resulting mixture was cooled to room temperature and filtered through celite. The filtrate was concentrated under vacuum and the crude product was purified by flash column chromatography (silica gel, ethyl acetate-hexane mixture as eluent) to afford 1.0 g (31%) of the desired product as a pale yellow solid. ESI-MS (m/z) 404 [(MH)$^+$].

Intermediate 54

5-Bromo-N-(3-methylpyridin-4-yl)thiophene-2-carboxamide

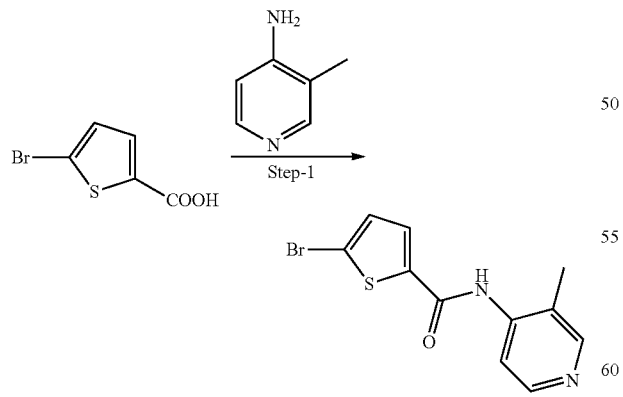

To a solution of 3-methylpyridine-4-amine (1.23 g, 11.37 mmol, 1.2 eq) in DMF (5 mL) at 0° C. was added solid sodium hydride (60% suspension in mineral oil, 0.44 g, 18.49 mmol, 2.0 eq) and stirred for 1 h at room temperature. In a separate flask, to a solution of 5-bromothiophene-2-carboxylic acid (1.91 g, 9.25 mmol, 1.0 eq) in DCM (10 mL) was added oxalyl chloride (4.0 mL, 46.2 mmol, 5.0 eq) at 0° C. and then stirred at the same temperature for 2 h. The solvent and excess of oxalyl chloride were removed by evaporation under vacuum. The residue was dissolved in DMF (2 mL) and added to the above mixture at 0° C. and the resulting mixture was stirred at room temperature overnight. Water (10 mL) was added to the reaction followed by ethyl acetate (10 mL). The layers were separated and the aqueous layer was extracted with ethyl acetate (2×20 mL). The combined organic layers were washed with water (2×20 mL), brine (20 mL), dried (Na$_2$SO$_4$) and filtered. The filtrate was concentrated under vacuum and purified by column chromatography (silica gel, DCM:MeOH system) to afford 1.0 g of the desired product as a white solid. $^1$HNMR (400 MHz, CDCl$_3$) δ 8.39 (d, J=5.5 Hz, 1H), 8.36 (s, 1H), 8.05 (d, J=5.5 Hz, 1H), 7.87 (s, 1H, D$_2$O exchangeable), 7.40 (d, J=4.0 Hz, 1H), 7.09 (d, J=4.0 Hz, 1H), 2.29 (s, 3H); ESI-MS (m/z) 297, 299 [(MH)$^+$ Br$^{79,81}$].

Intermediate-55a & 55b

5-Bromo-N-(2,6-difluorophenyl)-3-methylthiophene-2-carboxamide (55a) and

N-(2,6-Difluorophenyl)-3-methyl-5-(trimethylstannyl)thiophene-2-carboxamide (55b)

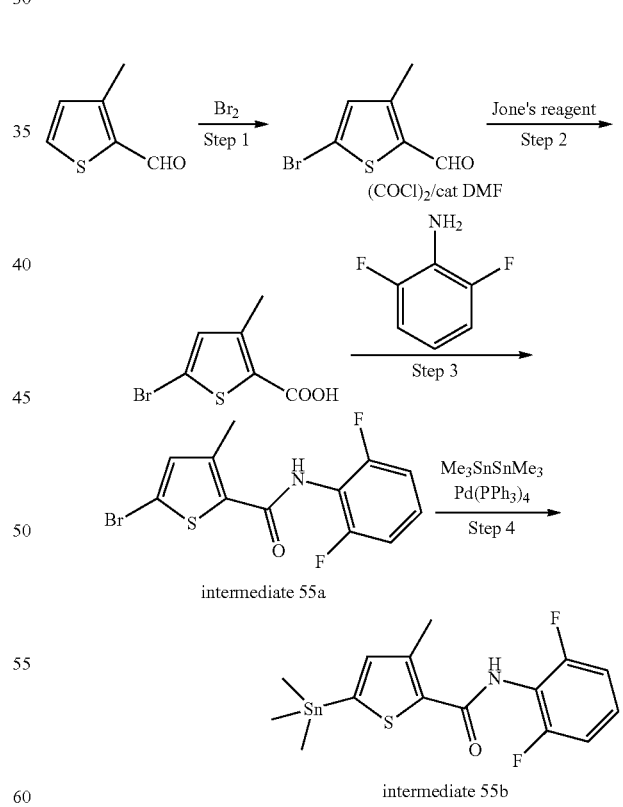

Step 1: 5-Bromo-3-methylthiophene-2-carbaldehyde: To 0° C. cooled solution of 3-methylthiophene-2-carbaldehyde (10.0 g, 79.3 mmol, 1.0 eq) in DCM (100 mL) was added drop wise a solution of bromine (12.6 g, 79.3 mmol, 1.0 eq) and the resulting mixture was stirred 70° C. for 4 h. The reaction was cooled to room temperature and diluted with DCM (100 mL). The resulting organic layer was washed with water (100 mL), saturated sodium bicarbonate solution (100 mL), brine (100 mL), dried ($Na_2SO_4$) and filtered. The filtrate was rotary evaporated to afford 11 g of the desired product as a brown solid. $^1$HNMR (400 MHz, $CDCl_3$) δ 9.87 (s, 1H), 6.93 (s, 1H), 2.51 (s, 3H); ESI-MS (m/z) 205, 207 [(MH)$^+$, $Br^{79,81}$].

Step 2: 5-Bromo-3-methylthiophene-2-carboxylic acid: The title compound was prepared from the 5-bromo-3-methylthiophene-2-carboxaldehyde by following the procedure described for step 1 of intermediate 53. $^1$HNMR (400 MHz, DMSO-$d_6$) δ 13.20 (s, 1H, $D_2O$ Exchangeable), 7.20 (s, 1H), 2.43 (s, 3H); SI-MS (m/z) 221, 223 [(MH)$^+$, $Br^{79,81}$].

Step 3: 5-Bromo-N-(2,6-difluorophenyl)-3-methylthiophene-2-carboxamide: The title compound was prepared by following the procedure described for step 2 of the intermediate 53. $^1$HNMR (400 MHz, DMSO-$d_6$) δ 9.78 (s, 1H, $D_2O$ Exchangeable), 7.41-7.34 (m, 1H), 7.20-7.15 (m, 3H), 2.43 (s, 3H); ESI-MS (m/z) 332, 334 [(MH)$^+$, $Br^{79,81}$].

Step-4: N-(2,6-Difluorophenyl)-3-methyl-5-(trimethylstannyl)thiophene-2-carboxamide: The title compound was prepared by following the procedure described hereinbefore for step 3 of intermediate 53. ESI-MS (m/z) 418 (MH)$^+$.

Intermediate 56

4-Bromo-N-(2,6-difluorophenyl)thiophene-2-carboxamide

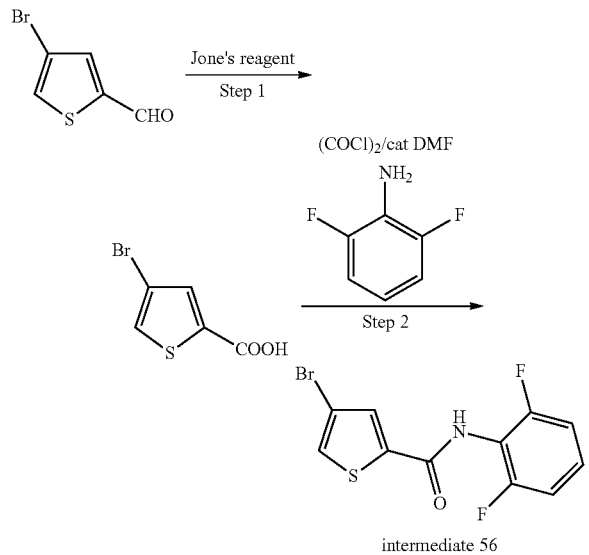

intermediate 56

The title compound was prepared by following the procedure described for intermediate 53 from the corresponding starting materials. $^1$HNMR (400 MHz, $CDCl_3$) δ 7.76 (s, 1H, $D_2O$ exchangeable), 7.60 (d, J=1.5 Hz, 1H), 7.46 (d, J=1.5 Hz, 1H), 7.24-7.16 (m, 1H), 6.93 (t, J=8.5 Hz, 2H); ESI-MS (m/z) 318, 320 [(MH)$^+$, $Br^{79,81}$].

Intermediate 57

4-Bromo-N-(2,6-difluorophenyl)-3-methylthiophene-2-carboxamide

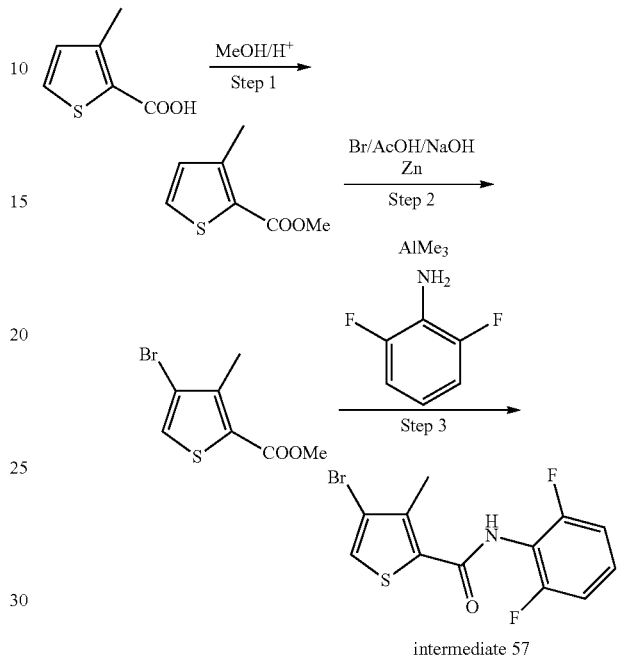

intermediate 57

Step 1: Methyl 3-methylthiophene-2-carboxylate: To a solution of 3-Methylthiophene-2-carboxylic acid (15 g, 105 mmol, 1.0 eq) in methanol (150 mL) was added conc sulfuric acid (7.5 mL) drop wise and refluxed for 12 h. The solvent was evaporated under vacuum and the residue was taken into ethyl acetate (200 mL), washed with water (2×50 mL), saturated aqueous sodium bicarbonate solution (2×50 mL), brine (50 mL), dried ($Na_2SO_4$) and filtered. The filtrate was evaporated under vacuum to afford 20 g (97%) of the desired product as a oil. $^1$HNMR (400 MHz, $CDCl_3$) δ 7.38 (d, J=5.0 Hz, 1H), 6.91 (d, J=5.0 Hz, 1H), 3.85 (s, 3H), 2.55 (s, 3H); ESI-MS [(m/z) 157 (MH)$^+$]

Step 2: Methyl 4-bromo-3-methylthiophene-2-carboxylate: A solution of methyl 3-methylthiophene-2-carboxylate (20 g, 103 mmol, 1.0 eq) and sodium hydroxide (12.3 g, 307 mmol, 3 eq) in acetic acid (75 mL) was heated to 60° C. Bromine (46.9 g, 294 mmol, 2.85 eq) was added drop wise at such a rate so as to maintain the temperature of the reaction mixture at <85° C. The resulting mixture was stirred at 85° C. for 6 h. The solution was then allowed to cool to 50° C. and zinc dust (15.4 g, 236 mmol, 2.3 eq) was added in 3 gram portions to the reaction such that the exotherm was controlled to remain below 85° C. The resulting mixture was stirred at 85° C. for 1 h, and then filtered hot through a small bed of celite. Water (300 mL) was added and the mixture was extracted with hexane (300 mL). The organic phase was washed with water, then concentrated to dryness to give 27 g (89%) an off white oil which slowly crystallized upon standing at room temperature. $^1$HNMR (400 MHz, $CDCl_3$) δ 7.43 (s, 1H), 3.87 (s, 3H), 2.56 (s, 3H)

Step 3: 4-Bromo-N-(2,6-difluorophenyl)-3-methylthiophene-2-carboxamide: To a 0° C. solution of 2,6-difluoroaniline (1.10 g, 8.58 mmol, 1.0 eq) in DCM (20 mL) was added drop wise trimethyl aluminium (2 M in toluene, 4.3 mL, 1.0 eq) followed by a solution of methyl-4-bromo-3-methylthiophene-2-carboxylate (2.0 g, 8.58 mmol, 1.0 eq). The reaction was allowed to come to room temperature and then stirred for 2 h at the same temperature. The reaction was quenched with water (10 mL) followed by the addition of DCM (20 mL). The layers were separated, and the organic layer was washed with brine (15 mL), dried (Na$_2$SO$_4$) and filtered. The filtrate was rotary evaporated and the residue was purified by flash column chromatography (silica gel, 30% ethyl acetate in hexane) to afford 1.0 g (35%) of the desired product as a brown solid. $^1$HNMR (400 MHz, CDCl$_3$) δ 7.42 (s, 1H), 7.28-7.21 (m, 1H), 7.15 (s, 1H, D$_2$O exchangeable), 7.03-6.94 (m, 2H), 2.56 (s, 3H); ESI-MS (m/z) 332, 334 [(MH)$^+$, Br$^{79,81}$].

Intermediate 58a & 58b

5-Bromo-N-(2,6-difluorophenyl)-1-methyl-1H-pyrrole-2-carboxamide (58a) and

N-(2,6-Difluorophenyl)-1-methyl-5-(trimethylstannyl)-1H-pyrrole-2-carboxamide (58b)

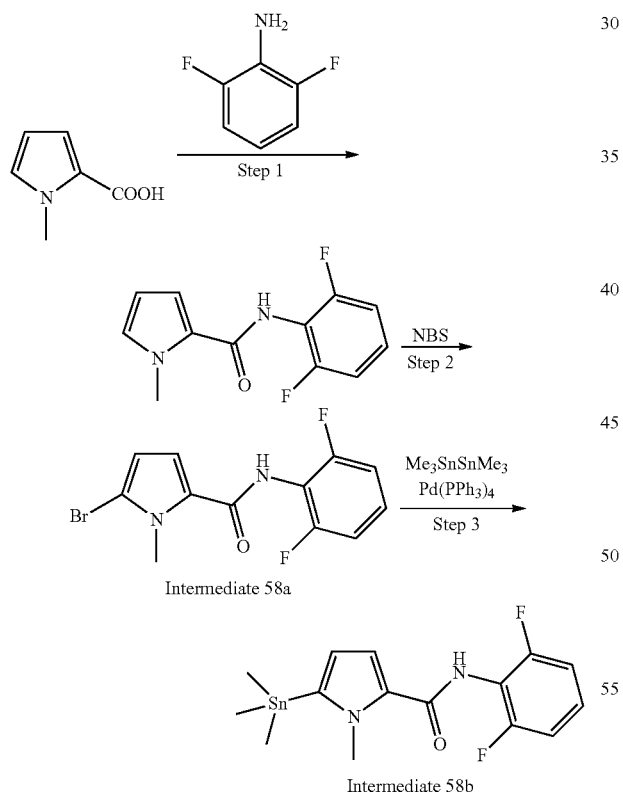

Step-1: N-(2,6-Difluorophenyl)-1-methyl-1H-pyrrole-2-carboxamide: A mixture of 1-methylpyrrol-2-carboxylic acid (1.0 g, 7.99 mmol, 1.0 eq) and thionyl chloride (9.5 g, 80 mmol, 10 eq) was refluxed for 3 h. The reaction was cooled to room temperature and excess of thionyl chloride was removed under vacuum. The resulting residue was co-distilled with benzene to remove the traces of thionyl chloride. The residue was dissolved in DCM (10 mL), cooled to 0° C. and a solution of 2,6-difluoroaniline (1.0 g, 7.99 mmol, 1.0 eq) in DCM (2 mL) was added drop wise followed by the addition of pyridine (1.0 g, 12.79 mmol, 1.5 eq). The reaction was warmed to room temperature and stirred for 12 h. The reaction was diluted with DCM (50 mL), and water (30 mL) was added to the reaction mixture. The layers were separated and the organic layer was washed with 1N HCl (20 mL), brine (20 mL), dried (Na$_2$SO$_4$) and filtered. The filtrate was concentrated under vacuum. The crude product was used for the next step. ESI-MS (m/z) 237 (MH)$^+$.

Step-2: 5-Bromo-N-(2,6-difluorophenyl)-1-methyl-1H-pyrrole-2-carboxamide: A mixture of N-(2,6-difluorophenyl)-1-methyl-1H-pyrrole-2-carboxamide (3.40 g, 14.39 mmol, 1.0 eq) and NBS (2.70 g, 15.11 mmol, 1.05 eq) in DCM (30 mL) was stirred at room temperature for 12 h. Water (50 mL) was added to the reaction followed by DCM (100 mL) and the layers were separated. The organic layer was washed with water (50 mL), brine (50 mL), dried (Na$_2$SO$_4$) and filtered. The filtrate was rotary evaporated and the crude product was purified by flash column chromatography (silica gel, ethyl acetate in hexane system as eluent) to afford 3.30 g of the title product as a white solid. $^1$HNMR (400 MHz, CDCl$_3$) δ 7.25-7.18 (m, 1H), 6.98 (t, J=8.0 Hz, 2H), 6.82 (d, J=4.0 Hz, 1H), 6.27 (d, J=4.0 Hz, 1H), 3.97 (s, 3H); ESI-MS (m/z) 315, 317 [(MH)$^+$, Br$^{79,81}$]

Step-3: N-(2,6-Difluorophenyl)-1-methyl-5-(trimethylstannyl)-1H-pyrrole-2-carboxamide: To a solution of 5-bromo-N-(2,6-difluorophenyl)-1-methyl-1H-pyrrole-2-carboxamide (1.20 g, 3.81 mmol, 1.0 eq) and hexamethylditin (1.25 g, 3.81 mmol, 1.0 eq) in dioxane (15 mL) was added Pd(PPh$_3$)$_4$ (220 mg, 0.19 mmol, 0.05 eq). The resulting mixture was thoroughly deoxygenated by subjecting to a vacuum/nitrogen cycle three times and the reaction mixture was heated at 75° C. for 15 h under nitrogen atmosphere. The resulting mixture was cooled to room temperature and filtered through celite. The filtrate was concentrated under vacuum and the crude product was used for next step without further purification. ESI-MS (m/z) 400 (MH)$^+$.

EXAMPLES

Example 1

N-(5-(5-(5,5-Dimethyl-4-oxo-4,5-dihydroisoxazol-3-yl)-2-methylphenyl)pyrazin-2-yl)-2,6-difluorobenzamide

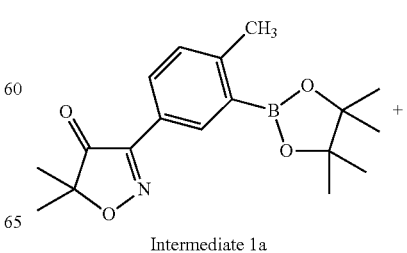

Intermediate 1a

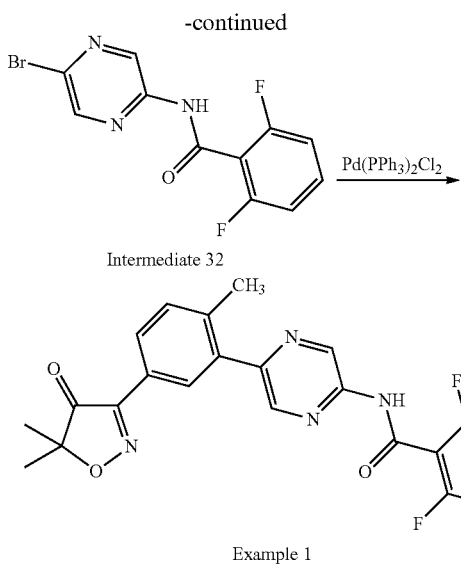

To a stirred solution of N-(5-Bromopyrazine-2-yl)-2,6-difluorobenzamide, Intermediate 32, (400 mg, 1.27 mmol, 1.0 eq) in dioxane (10 mL), 5,5-Dimethyl-3-(4,4,5,5-tetramethyl-1,3,2-dioxaborolan-2-yl)phenyl)isoxazol-4(5H)-one, Intermediate 1a (419 mg, 1.27 mmol, 1.0 eq), aq sodium carbonate solution (2N, 4 mL) and Pd(PPh$_3$)$_2$Cl$_2$ (44 mg, 0.063 mmol, 0.05 eq) were sequentially added. The resulting mixture was thoroughly deoxygenated by subjecting to a vacuum/nitrogen cycle three times and then heated at 100° C. for 24 h under nitrogen atmosphere. The reaction mixture was cooled to room temperature and filtered through celite. The filtrate was concentrated under vacuum and the crude product was purified by flash column chromatography (silica gel, 30% ethyl acetate in hexane) to afford 200 mg of the desired product as a white solid. $^1$HNMR (400 MHz, DMSO-d$_6$) δ 11.82 (s, 1H, D$_2$O exchangeable), 9.53 (s, 1H), 8.69 (s, 1H), 8.11 (d, J=1.0 Hz, 1H), 7.99 (dd, J=1.0, 8.0 Hz, 1H), 7.65-7.59 (m, 1H), 7.54 (d, J=8.0 Hz, 1H), 7.27 (t, J=8.0 Hz, 2H), 2.44 (s, 3H), 1.43 (s, 6H); ESI-MS (m/z) 437 (MH)$^+$.

The below Examples 2 to 75 were prepared from the corresponding intermediates by following a procedure similar to that described in Example 1:

| Example No: IUPAC name | Structure | $^1$H NMR/ESI-MS(MH)$^+$ |
|---|---|---|
| Example 2: N-(5-(5 (5,5-Dimethyl-4-oxo-4,5-dihydroisoxazol-3-yl)-2-methylphenyl)pyrazin-2-yl)-4-methyl-1,2,3-thiadiazole-5-carboxamide | 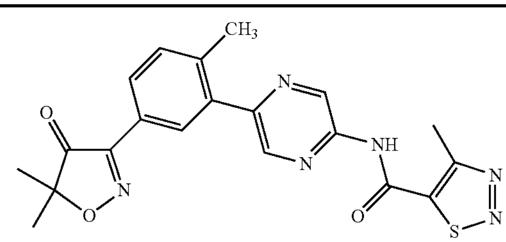 | $^1$HNMR (400 MHz, DMSO-d$_6$) δ 11.82 (s, 1H, D$_2$O exchangeable), 9.48 (s, 1H), 8.73 (s, 1H), 8.12 (s, 1H), 8.00 (d, J = 8.0 Hz, 1H), 7.55 (d, J = 8.0 Hz, 1H), 2.86 (s, 3H), 2.45 (s, 3H), 1.44 (s, 6H); ESI-MS (m/z) 423 (MH)$^+$. |
| Example 3: N-(5'-(5,5-Dimethyl-4-oxo-4,5-dihydroisoxazol-3-yl)-2'-methyl-[1,1'-biphenyl]-4-yl-2,6-difluorobenzamide | 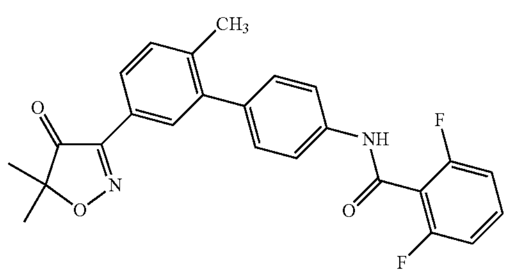 [SMILES: Cc1ccc(C2=NOC(C)(C)C2=O)cc1-c1ccc(NC(=O)c2c(F)cccc2F)cc1] | $^1$HNMR (400 MHz, CDCl$_3$) δ 8.00-7.98 (m, 2H), 7.70 (d, J = 8.0 Hz, 3H), 7.46-7.42 (m, 1H), 7.38-7.35 (m, 3H), 7.02 (t, J = 8.0 Hz, 2H), 2.33 (s, 3H), 1.46 (s, 6H); ESI-MS (m/z) 435 (MH)$^+$. |
| Example 4: N-(5-(5-(5,5-Dimethyl-4-oxo-4,5-dihydroisoxazol-3-yl)-2-methylphenyl)pyridin-2-yl)-2,6-difluorobenzamide | 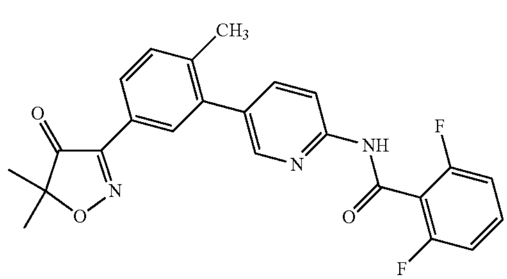 [SMILES: Cc1ccc(C2=NOC(C)(C)C2=O)cc1-c1ccc(NC(=O)c2c(F)cccc2F)nc1] | $^1$HNMR (400 MHz, DMSO-d$_6$) δ 11.2 (s, 1H, D$_2$O exchangeable), 8.94 (s, 1H), 8.28 (d, J = 8.0 Hz, 1H), 8.05 (s, 1H), 7.93 (d, J = 8.0 Hz, 1H), 7.63 (d, J = 8.0 Hz, 2H), 7.49 (d, J = 8.0 Hz, 1H), 7.30 (d, J = 8.0 Hz, 2H), 2.41 (s, 3H), 1.42 (s, 6H); ESI-MS (m/z) 436 (MH)$^+$. |

| Example No: IUPAC name | Structure | ¹H NMR/ESI-MS(MH)⁺ |
|---|---|---|
| Example 5: N-(5-(5-(5,5-dimethyl-4-oxo-4,5-dihydroisoxazol-3-yl)-2-ethylphenyl)pyrazin-2-yl)-2,6-difluorobenzamide | 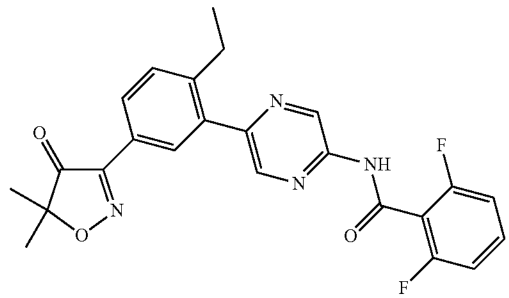 [SMILES: CCc1ccc(C2=NOC(C)(C)C2=O)cc1-c1cnc(NC(=O)c2c(F)cccc2F)cn1] | ¹HNMR (400 MHz, DMSO-$d_6$) δ 11.82 (s, 1H, $D_2O$ exchangeable), 9.51 (s, 1H), 8.63 (s, 1H), 8.03-8.01 (m, 3H), 7.64-7.60 (m, 1H), 7.56 (d, J = 8.0 Hz, 1H), 7.26 (t, J = 8.0 Hz, 2H), 2.76 (q, J = 7.5 Hz, 2H), 1.41 (s, 6H), 1.09 (t, J = 7.5 Hz, 3H); ESI-MS (m/z) 451 (MH)⁺. |
| Example 6: N-(5'-(5,5-dimethyl-4-oxo-4,5-dihydroisoxazol-3-yl)-2'-ethyl-[1,1'-biphenyl]-4-yl)-2,6-difluorobenzamide | 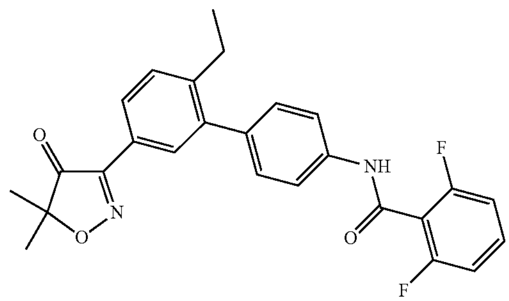 [SMILES: CCc1ccc(C2=NOC(C)(C)C2=O)cc1-c1ccc(NC(=O)c2c(F)cccc2F)cc1] | ¹HNMR (400 MHz, DMSO-d6) δ 10.94 (s, 1H, $D_2O$ exchangeable), 7.94 (dd, J = 8.0, 2.0 Hz, 1H), 7.81-7.78 (m, 3H), 7.63-7.59 (m, 1H), 7.51 (d, J = 8.0 Hz, 1H), 7.35 (d, J = 8.5 Hz, 2H), 7.28 (t, J = 8.0 Hz, 2H), 2.62 (q, J = 7.5 Hz, 2H), 1.41 (s, 6H), 1.06 (t, J = 7.5 Hz, 3H); ESI-MS (m/z) 449 (MH)⁺. |
| Example 7: N-(6-(5-(5,5-dimethyl-4-oxo-4,5-dihydroisoxazol-3-yl)-2-ethylphenyl)pyridin-3-yl)-2,6-difluorobenzamide | 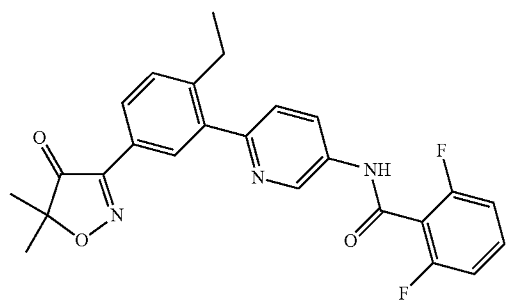 [SMILES: CCc1ccc(C2=NOC(C)(C)C2=O)cc1-c1ccc(NC(=O)c2c(F)cccc2F)cn1] | ¹HNMR (400 MHz, DMSO-$d_6$) δ 11.19 (s, 1H, $D_2O$ exchangeable), 8.93 (s, 1H), 8.27 (dd, J = 8.5, 2.5 Hz, 1H), 7.98 (d, J = 1.5 Hz, 1H), 7.96 (s, 1H), 7.66-7.62 (m, 1H), 7.58 (d, J = 8.5 Hz, 1H), 7.52 (d, J = 8.0 Hz, 1H), 7.30 (d, J = 8.0 Hz, 2H), 2.75 (q, J = 7.5 Hz, 2H), 1.42 (s, 6H), 1.07 (t, J = 7.5 Hz, 3H); ESI-MS (m/z) 450 (MH)⁺. |
| Example 8: N-(5-(5-(5,5-dimethyl-4-oxo-4,5-dihydroisoxazol-3-yl)-2-isopropylphenyl)pyrazin-2-yl)-2,6-difluorobenzamide | 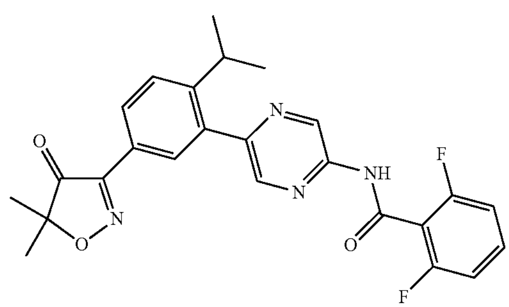 [SMILES: CC(C)c1ccc(C2=NOC(C)(C)C2=O)cc1-c1cnc(NC(=O)c2c(F)cccc2F)cn1] | ¹HNMR (400 MHz, CDCl₃) δ 9.76 (s, 1H), 8.54 (s, 1H, $D_2O$ exchangeable), 8.34 (s, 1H), 8.16 (dd, J = 8.0, 1.5 Hz, 1H), 8.07 (s, 1H), 7.55 (d, J = 8.0 Hz, 1H), 7.51-7.46 (m, 1H), 7.05 (t, J = 8.5 Hz, 2H), 3.25-3.18 (m, 1H), 1.43 (s, 6H), 1.22 (d, J = 7.0 Hz, 6H); ESI-MS (m/z) 465 (MH)⁺. |
| Example 9: N-(5'-(5,5-dimethyl-4-oxo-4,5-dihydroisoxazol-3-yl)-2'-isopropyl-[1,1'-biphenyl]-4-yl)-2,6-difluorobenzamide | 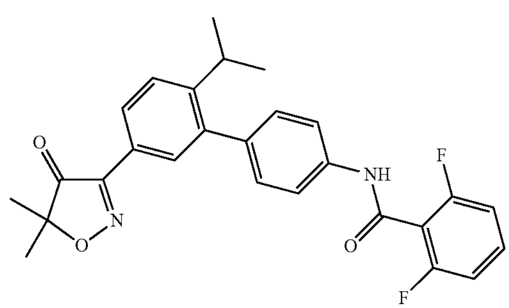 [SMILES: CC(C)c1ccc(C2=NOC(C)(C)C2=O)cc1-c1ccc(NC(=O)c2c(F)cccc2F)cc1] | ¹HNMR (40 MHz, CDCl₃) δ 8.07 (dd, J = 8.0, 1.5 Hz, 1H), 7.93 (s, 1H), 7.71 (d, J = 8.0 Hz, 2H+1H $D_2O$ exchangeable), 7.49 (d, J = 8.0 Hz, 1H), 7.46-7.42 (m, 1H), 7.33 (d, J = 8.0 Hz, 2H), 7.02 (t, J = 8.0 Hz, 2H), 3.15-3.08 (m, 1H), 1.46 (s, 6H), 1.18 (d, J = 7.0 Hz, 6H); ESI-MS (m/z) 463 (MH)⁺. |

-continued

| Example No: IUPAC name | Structure | $^1$H NMR/ESI-MS(MH)$^+$ |
|---|---|---|
| Example 10: N-(2'-(tert-butyl)-5'-(5,5-dimethyl-4-oxo-4,5-dihydroisoxazol-3-yl)-[1,1'-biphenyl]-4-yl)-2,6-difluorobenzamide | 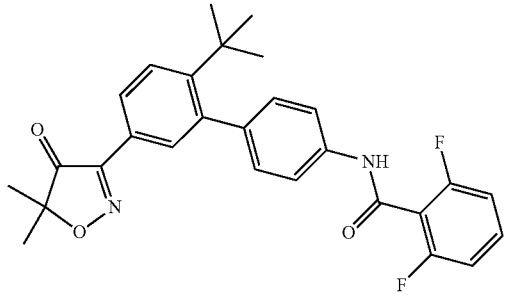 [SMILES: CC1(C)ON=C(c2ccc(C(C)(C)C)c(-c3ccc(NC(=O)c4c(F)cccc4F)cc3)c2)C1=O] | $^1$HNMR (400 MHz, CDCl$_3$) δ 8.01 (dd, J = 8.5, 2.0 Hz, 1H), 7.74 (d, J = 2.0 Hz, 1H), 7.68 (brs, D$_2$O exchangeable, 1H), 7.63 (d, J = 8.0 Hz, 2H), 7.62 (d, J = 8.5 Hz, 1H), 7.45-7.41 (m, 1H), 7.27 (d, J = 8.0 Hz, 2H), 7.02 (t, J = 8.0 Hz, 2H), 1.43 (s, 6H), 1.22 (s, 9H); ESI-MS (m/z) 477 (MH)$^+$. |
| Example 11: N-(2'-chloro-5'-(5,5-dimethyl-4-oxo-4,5-dihydroisoxazol-3-yl)-[1,1'-biphenyl]-4-yl)-2,6-difluorobenzamide | 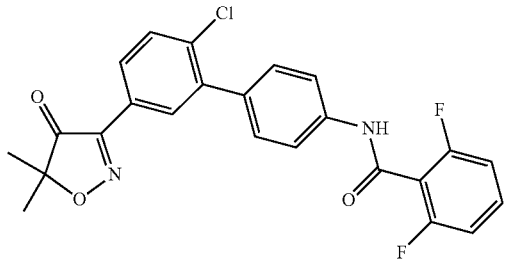 [SMILES: CC1(C)ON=C(c2ccc(Cl)c(-c3ccc(NC(=O)c4c(F)cccc4F)cc3)c2)C1=O] | $^1$HNMR (400 MHz, DMSO-d$_6$) δ 10.99 (s, 1H, D$_2$O Exchangeable), 8.03-7.97 (m, 2H), 7.83 (dd, J = 8.5, 1.5 Hz, 2H), 7.76 (d, J = 8.5 Hz, 1H), 7.64-7.59 (m, 1H), 7.52-7.47 (m, 2H), 7.28 (t, J = 8.0 Hz, 2H) 1.45 (s, 3H), 1.43 (s, 3H); ESI-MS [(m/z) 455, 457 [(MH)$^+$, Cl$^{35,37}$) |
| Example 12: N-(5-(5-(5,5-dimethyl-4-oxo-4,5-dihydroisoxazol-3-yl)-2-fluorophenyl)pyrazin-2-yl)-2,6-difluorobenzamide | 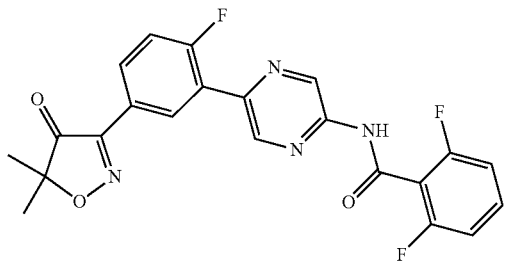 [SMILES: CC1(C)ON=C(c2ccc(F)c(-c3cnc(NC(=O)c4c(F)cccc4F)cn3)c2)C1=O] | $^1$HNMR (400 MHz, DMSO-d$_6$) δ 11.89 (s, 1H, D$_2$O exchangeable), 9.58 (s, 1H), 8.92 (s, 1H), 8.65 (dd, J = 7.5, 2.5 Hz, 1H), 8.15-8.11 (m, 1H), 7.66-7.57 (m, 2H), 7.27 (t, J = 8.0 Hz, 2H), 1.45 (s, 6H); ESI-MS (m/z) 441 (MH)$^+$. |
| Example 13: N-(5'-(5,5-dimethyl-4-oxo-4,5-dihydroisoxazol-3-yl)-2'-fluoro-[1,1'-biphenyl]-4-yl)-2,6-difluorobenzamide | 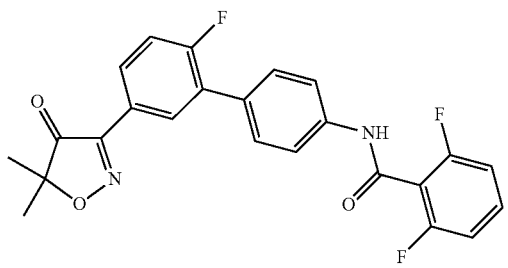 [SMILES: CC1(C)ON=C(c2ccc(F)c(-c3ccc(NC(=O)c4c(F)cccc4F)cc3)c2)C1=O] | $^1$HNMR (400 MHz, DMSO-d6) δ 10.98 (s, 1H, D$_2$O exchangeable), 8.12 (dd, J = 8.0, 2.0 Hz, 1H), 8.03-7.99 (m, 1H), 7.83 (d, J = 8.5 Hz, 2H), 7.63-7.59 (m, 3H), 7.51 (dd, J = 11.0, 8.5, Hz, 1H), 7.27 (t, J = 8.0 Hz, 2H), 1.43 (s, 6H); ESI-MS (m/z) 439 (MH)$^+$. |
| Example 14: N-(5-(5-(5,5-dimethyl-4-oxo-4,5-dihydroisoxazol-3-yl)-2-methoxyphenyl)pyrazin-2-yl)-2,6-difluorobenzamide | 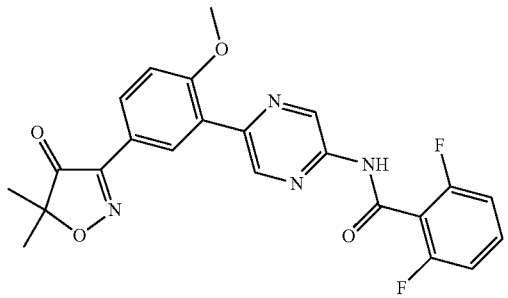 [SMILES: COc1ccc(C2=NOC(C)(C)C2=O)cc1-c1cnc(NC(=O)c2c(F)cccc2F)cn1] | $^1$HNMR (400 MHz, CDCl$_3$) δ 9.76 (s, 1H), 8.81 (s, 1H), 8.62 (d, J = 2.0 Hz, 1H), 8.60 (s, 1H, D$_2$O exchangeable), 8.17 (dd, J = 8.0, 2.0 Hz, 1H), 7.49-7.45 (m, 1H), 7.10 (d, J = 8.0 Hz, 1H), 7.04 (t, J = 8.0 Hz, 2H), 3.95 (s, 3H), 1.47 (s, 6H); ESI-MS (m/z) 453 (MH)$^+$. |

-continued

| Example No: IUPAC name | Structure | ¹H NMR/ESI-MS(MH)⁺ |
|---|---|---|
| Example 15: N-(5'-(5,5-dimethyl-4-oxo-4,5-dihydroisoxazol-3-yl)-2'-methoxy-[1,1'-biphenyl]-4-yl)-2,6-difluorobenzamide | 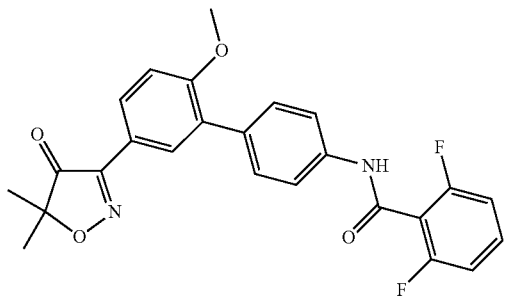 [SMILES: COc1ccc(C2=NOC(C)(C)C2=O)cc1-c1ccc(NC(=O)c2c(F)cccc2F)cc1] | ¹HNMR (400 MHz, CDCl₃) δ 8.14-8.11 (m, 3H), 7.77 (s, 1H, D₂O exchangeable), 7.72 (d, J = 8.5 Hz, 2H), 7.60 (d, J = 8.5 Hz, 2H), 7.46-7.42 (m, 1H), 7.07 (d, J = 8.0 Hz, 1H), 7.03 (t, J = 8.0 Hz, 2H), 3.90 (s, 3H), 1.49 (s, 6H); ESI-MS (m/z) 451 (MH)⁺. |
| Example 16: N-(5'-(5,5-Dimethyl-4-oxo-4,5-dihydroisoxazol-3-yl)-2'-methoxy-[1,1'-biphenyl]-4-yl)-4-methyl-1,2,3-thiadiazole-5-carboxamide | 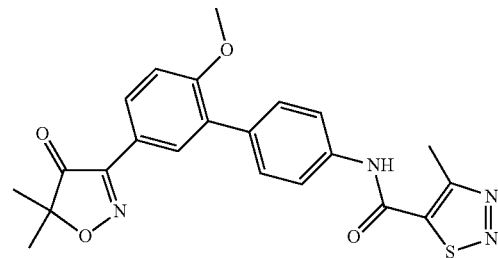 [SMILES: COc1ccc(C2=NOC(C)(C)C2=O)cc1-c1ccc(NC(=O)c2snnc2C)cc1] | ¹HNMR (400 MHz, DMSO-d₆) δ 10.84 (s, 1H, D₂O exchangeable), 7.99 (dd, J = 8.5, 2.0 Hz, 1H), 7.92 (d, J = 2.0 Hz, 1H), 7.75 (d, J = 8.5 Hz, 2H), 7.52 (d, J = 8.5 Hz, 2H), 7.29 (d, J = 8.5 Hz, 1H), 3.85 (s, 3H), 2.83 (s, 3H), 1.41 (s, 6H); ESI-MS (m/z) 437 (MH)⁺. |
| Example 17: N-(5-(5-(5,5-dimethyl-4-oxo-4,5-dihydroisoxazol-3-yl)-2-methoxyphenyl)pyridin-2-yl)-2,6-difluorobenzamide | 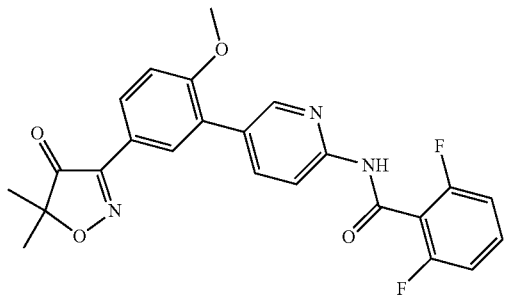 [SMILES: COc1ccc(C2=NOC(C)(C)C2=O)cc1-c1ccc(NC(=O)c2c(F)cccc2F)nc1] | ¹HNMR (400 MHz, CDCl₃) δ 8.68 (d, J = 2.5 Hz, 1H), 8.51 (d, J = 2.5 Hz, 1H), 8.42 (dd, J = 8.5, 2.5 Hz, 1H), 8.12 (dd, J = 8.5, 2.5 Hz, 1H), 7.95 (s, 1H, D₂O exchangeable), 7.88 (d, J = 8.5 Hz, 1H), 7.48-7.41 (m, 1H), 7.08 (d, J = 8.5 Hz, 1H), 7.02 (t, J = 8.0 Hz, 2H), 3.92 (s, 3H), 1.46 (s, 6H); ESI-MS (m/z) 452 (MH)⁺. |
| Example 18: N-(6-(5-(5,5-dimethyl-4-oxo-4,5-dihydroisoxazol-3-yl)-2-methoxyphenyl)pyridin-3-yl)2,6-difluorobenzamide | 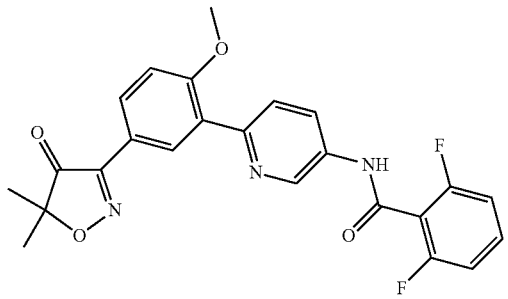 [SMILES: COc1ccc(C2=NOC(C)(C)C2=O)cc1-c1ccc(NC(=O)c2c(F)cccc2F)cn1] | ¹HNMR (400 MHz, CDCl₃) δ 8.67 (d, J = 2.5 Hz, 1H), 8.49 (d, J = 2.5 Hz, 1H), 8.39 (dd, J = 8.5, 2.5 Hz, 1H), 8.10 (dd, J = 8.5, 2.5 Hz, 1H), 7.97 (s, 1H, D₂O exchangeable), 7.84 (d, J = 8.5 Hz, 1H), 7.44-7.40 (m, 1H), 7.06 (d, J = 8.5 Hz, 1H), 7.70 (t, J = 8.0 Hz, 2H), 3.90 (s, 3H), 1.44 (s, 6H); ESI-MS (m/z) 452 (MH)⁺. |
| Example 19: N-(2'-acetamido-5'-(5,5-dimethyl-4-oxo-4,5-dihydroisoxazol-3-yl)-[1,1'-biphenyl]-4-yl)-2,6-difluorobenzamide | 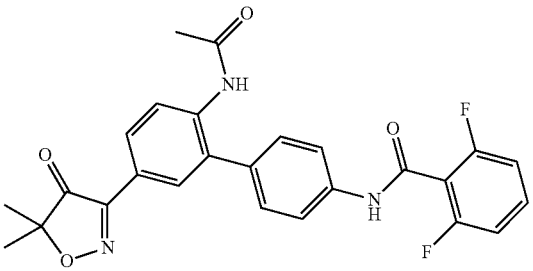 [SMILES: CC(=O)Nc1ccc(C2=NOC(C)(C)C2=O)cc1-c1ccc(NC(=O)c2c(F)cccc2F)cc1] | ¹HNMR (400 MHz, DMSO-d₆) δ 11.95 (s, 1H, D₂O exchangeable), 9.34 (s, 1H, D₂O exchangeable), 7.96-7.92 (m, 2H), 7.82-7.78 (m, 3H), 7.65-7.57 (m, 1H), 7.42 (d, J = 8.5 Hz, 2H), 7.26 (t, J = 8.0 Hz, 2H), 1.96 (s, 3H), 1.42 (s, 6H); ESI-MS (m/z) 478 (MH)⁺. |

-continued

| Example No: IUPAC name | Structure | ¹H NMR/ESI-MS(MH)⁺ |
|---|---|---|
| Example 20: N-(5-(3-(5,5-dimethyl-4-oxo-4,5-dihydroisoxazol-3-yl)phenyl)pyrazin-2-yl)-2,6-difluorobenzamide | 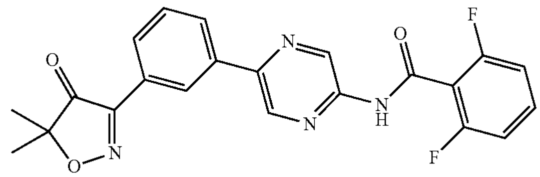 [SMILES: CC1(C)ON=C(c2cccc(-c3cnc(NC(=O)c4c(F)cccc4F)cn3)c2)C1=O] | ¹HNMR (400 MHz, CDCl₃) δ 9.75 (s, 1H), 8.76 (s, 1H), 8.73 (t, J = 1.5 Hz, 1H), 8.41 (s, 1H, D₂O exchangeable), 8.20-8.14 (m, 2H), 7.62 (t, J = 8.0 Hz, 1H), 7.51-7.47 (m, 1H), 7.06 (t, J = 8.5 Hz, 2H), 1.55 (s, 6H); ESI-MS (m/z) 423 (MH)⁺ |
| Example 21: N-(6-(3-(5,5-dimethyl-4-oxo-4,5-dihydroisoxazol-3-yl)phenyl)pyridin-3-yl)-2,6-difluorobenzamide | 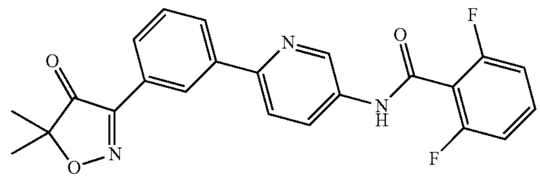 [SMILES: CC1(C)ON=C(c2cccc(-c3ccc(NC(=O)c4c(F)cccc4F)cn3)c2)C1=O] | ¹HNMR (400 MHz, CDCl₃) δ 8.71-8.69 (m, 2H), 8.45 (dd, J = 8.5, 2.5 Hz, 1H), 8.13 (dd, J = 8.0, 1.5 Hz, 2H), 7.84 (d, J = 8.0 Hz, 1H), 7.76 (s, 1H, D₂O exchangeable), 7.58 (t, J = 8.0 Hz, 1H), 7.48-7.44 (m, 1H), 7.03 (t, J = 8.5 Hz, 2H), 1.49 (s, 6H); ESI-MS (m/z) 422 (MH)⁺. |
| Example 22: N-(3'-(5,5-dimethyl-4-oxo-4,5-dihydroisoxazol-3-yl)-[1,1'-biphenyl]-4-yl)-2,6-difluorobenzamide | 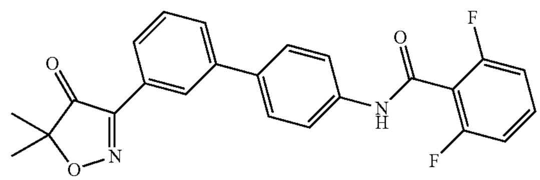 [SMILES: CC1(C)ON=C(c2cccc(-c3ccc(NC(=O)c4c(F)cccc4F)cc3)c2)C1=O] | ¹HNMR (400 MHz, CDCl₃) δ 8.33 (t, J = 1.5 Hz, 1H), 8.07 (td, J = 8.0, 1.5 Hz, 1H), 7.74-7.63 (m, 6H), 7.53 (t, J = 8.0 Hz, 1H), 7.48-7.39 (m, 1H), 7.01 (t, J = 8.5 Hz, 2H), 1.48 (s, 6H); ESI-MS (m/z) 421 (MH)⁺. |
| Example 23: 2,6-difluoro-N-(5-(5-(4-methoxy-5,5-dimethyl-4,5-dihydroisoxazol-3-yl)-2-methylphenyl)pyrazin-2-yl)benzamide | 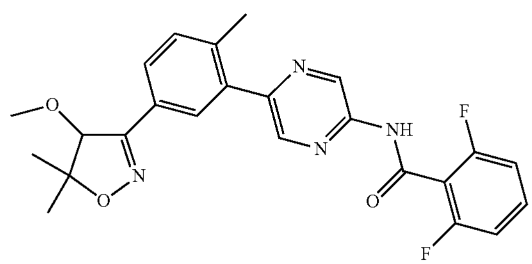 [SMILES: COC1C(c2ccc(C)c(-c3cnc(NC(=O)c4c(F)cccc4F)cn3)c2)=NOC1(C)C] | ¹HNMR (400 MHz, CDCl₃) δ 9.76 (s, 1H), 8.61 (s, 1H, D₂O exchangeable), 8.36 (s, 1H), 7.79 (s, 1H), 7.73 (dd, J = 8.0, 1.0 Hz, 1H), 7.52-7.45 (m, 1H), 7.37 (d, J = 8.0 Hz, 1H), 7.05 (t, J = 8.0 Hz, 2H), 4.57 (s, 1H), 3.43 (s, 3H), 2.43 (s, 3H), 1.53 (s, 3H), 1.34 (s, 3H); ESI-MS (m/z) 453 (MH)⁺. |
| Example 24: 2,6-Difluoro-N-(5'-(4-methoxy-5,5-dimethyl-4,5-dihydroisoxazol-3-yl)-2'-methyl-[1,1'-biphenyl]-4-yl)benzamide | 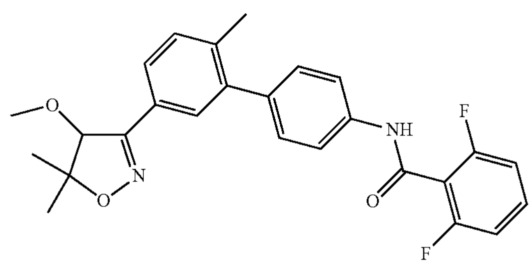 [SMILES: COC1C(c2ccc(C)c(-c3ccc(NC(=O)c4c(F)cccc4F)cc3)c2)=NOC1(C)C] | ¹HNMR (400 MHz, CDCl₃) δ 7.73 (s, 1H, D₂O exchangeable), 7.70 (d, J = 8.5 Hz, 2H), 7.65 (dd, J = 8.0, 1.5 Hz, 1H), 7.60 (d, J = 1.5 Hz, 1H), 7.46-7.42 (m, 1H), 7.36 (d, J = 8.5 Hz, 2H), 7.32 (d, J = 8.0 Hz, 1H), 7.02 (t, J = 8.0 Hz, 2H), 4.55 (s, 1H), 3.43 (s, 3H), 2.31 (s, 3H), 1.53 (s, 3H), 1.34 (s, 3H); ESI-MS (m/z) 451 (MH)⁺. |
| Example 25: N-(4'-(5,5-Dimethyl-4-oxo-4,5-dihydroisoxazol-3-yl)-2'-methyl-[1,1'-biphenyl]-4-yl)-2,6-difluorobenzamide | | ¹HNMR (400 MHz, CDCl₃) δ 8.04 (s, 1H), 8.00 (d, J = 8.0 Hz, 1H), 7.79 (s, 1H, D₂O exchangeable), 7.74 (d, J = 8.5 Hz, 2H), 7.48-7.42 (m, 1H), 7.37 (d, J = 8.5 Hz, 2H), 7.35 (d, J = 8.0 Hz, 1H), 7.04 (t, J = 8.5 Hz, 2H), 2.37 (s, 3H), 1.51 (s, 6H); ESI-MS (m/z) 435 (MH)⁺. |
| Example 26: N-(5-(4-(5,5-Dimethyl-4-oxo-4,5-dihydroisoxazol-3-yl)-2-methylphenyl)pyrazin-2-yl)-2,6-difluorobenzamide | 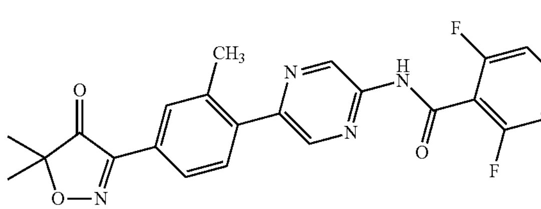 | ¹HNMR (400 MHz, CDCl₃) δ 9.78 (s, 1H), 8.56 (s, 1H, D₂O exchangeable), 8.38 (s, 1H), 8.08 (s, 1H), 8.06 (d, J = 8.0 Hz, 1H), 7.53 (d, J = 8.0 Hz, 1H), 7.51-7.46 (m, 1H), 7.05 (t, J = 8.5 Hz, 2H), 2.48 (s, 3H), 1.50 (s, 6H); ESI-MS (m/z) 437 (MH)⁺ |

-continued

| Example No: IUPAC name | Structure | ¹H NMR/ESI-MS(MH)⁺ |
|---|---|---|
| Example 27: N-(5-(4-(5,5-Dimethyl-4-oxo-4,5-dihydroisoxazol-3-yl)-2-methylphenyl)pyridin-2-yl)-2,6-difluorobenzamide | 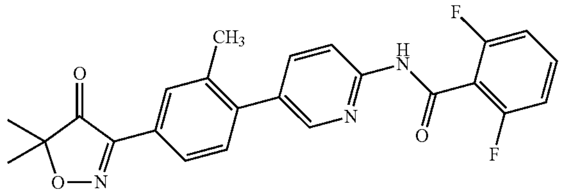 [SMILES: Cc1cc(C2=NOC(C)(C)C2=O)ccc1-c1ccc(NC(=O)c2c(F)cccc2F)nc1] | ¹HNMR (400 MHz, CDCl₃) δ 8.71 (d, J = 2.0 Hz, 1H), 8.44 (d, J = 8.0 Hz, 1H), 8.04 (s, 1H), 8.01 (d, J = 8.5 Hz, 1H), 7.51-7.42 (m, 3H), 7.04 (t, J = 8.5 Hz, 2H), 2.44 (s, 3H), 1.46 (s, 6H); ESI-MS (m/z) 436 (MH)⁺. |
| Example 28: N-(5-(3-(5,5-Dimethyl-4-oxo-4,5-dihydroisoxazol-3-yl)-2-methylphenyl)pyrazin-2-yl)-2,6-difluorobenzamide | 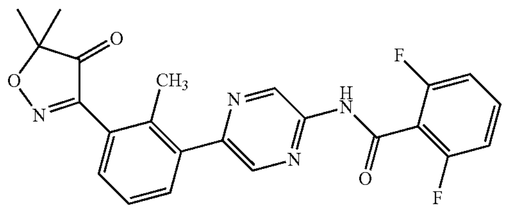 [SMILES: Cc1c(C2=NOC(C)(C)C2=O)cccc1-c1cnc(NC(=O)c2c(F)cccc2F)cn1] | ¹HNMR (400 MHz, DMSO-d₆) δ 11.82 (s, 1H, D₂O exchangeable), 9.48 (s, 1H), 8.62 (s, 1H), 7.64-7.56 (m, 3H), 7.49 (t, J = 7.5 Hz, 1H), 7.27 (t, J = 8.0 Hz, 2H), 2.26 (s, 3H), 1.47 (s, 6H); ESI-MS (m/z)437 (MH)⁺. |
| Example 29: N-(3'-(5,5-Dimethyl-4-oxo-4,5-dihydroisoxazol-3-yl)-2'-methyl-[1,1'-biphenyl]-4-yl)-2,6-difluorobenzamide | 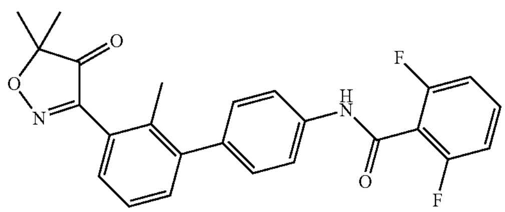 [SMILES: Cc1c(C2=NOC(C)(C)C2=O)cccc1-c1ccc(NC(=O)c2c(F)cccc2F)cc1] | ¹HNMR (400 MHz, CDCl₃) δ 7.73 (s, 1H, D₂O exchangeable), 7.70 (d, J = 8.5 Hz, 2H), 7.48-7.41 (m, 2H), 7.35-7.33 (m, 4H), 7.02 (t, J = 8.5 Hz, 2H), 2.25 (s, 3H), 1.50 (s, 6H); ESI-MS (m/z) 435 (MH)⁺. |
| Example 30: N-(5-(3-(5,5-Dimethyl-4-oxo-4,5-dihydroisoxazol-3-yl)-2-methylphenyl)pyridin-2-yl)-2,6-difluorobenzamide | 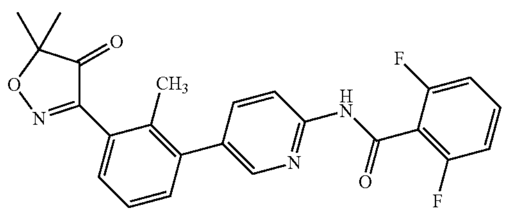 [SMILES: Cc1c(C2=NOC(C)(C)C2=O)cccc1-c1ccc(NC(=O)c2c(F)cccc2F)nc1] | ¹HNMR (400 MHz, DMSO-d₆) δ 11.18 (s, 1H, D₂O exchangeable), 8.93 (d, J = 2.5 Hz, 1H), 8.26 (dd, J = 9.5, 2.5 Hz, 1H), 7.67-7.42 (m, 5H), 7.30 (t, J = 8.0 Hz, 2H), 3.34 (s, 3H), 1.46 (s, 6H); ESI-MS (m/z) 436 (MH)⁺. |
| Example 31: N-(3'-(5,5-Dimethyl-4-oxo-4,5-dihydroisoxazol-3-yl)-2'-methoxy-[1,1'-biphenyl]-4-yl)-3,6-difluorobenzamide | 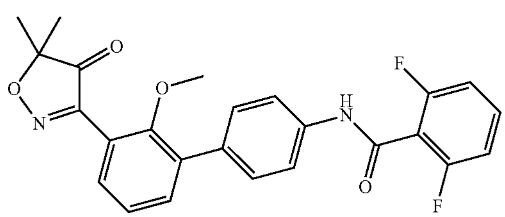 [SMILES: COc1c(C2=NOC(C)(C)C2=O)cccc1-c1ccc(NC(=O)c2c(F)cccc2F)cc1] | ¹HNMR (400 MHz, CDCl₃) δ 7.79 (s, 1H, D₂O exchangeable), 7.72 (d, J = 8.5 Hz, 2H), 7.62 (d, J = 8.5 Hz, 2H), 7.52 (dd, J = 7.5, 1.5 Hz, 1H), 7.48 (dd, J = 7.5, 1.5 Hz, 1H), 7.44-7.39 (m, 1H), 7.27 (t, J = 7.5 Hz, 1H), 7.01 (t, J = 8.5 Hz, 2H), 3.38 (s, 3H), 1.50 (s, 6H); ESI-MS (m/z) 451 (MH)⁺. |
| Example 32: N-(5-(5-(4-Acetyl-5,5-dimethyl-4,5-dihydro-1,3,4-oxadiazol-2-yl)-2-methylphenyl)pyrazin-2-yl)-2,6-difluorobenzamide | 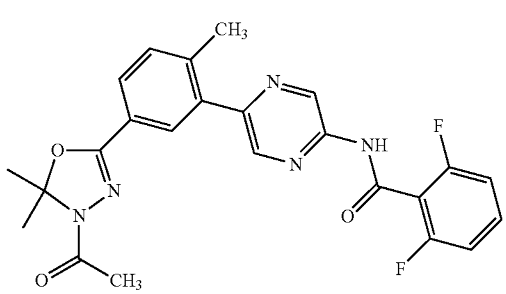 [SMILES: CC(=O)N1N=C(c2ccc(C)c(-c3cnc(NC(=O)c4c(F)cccc4F)cn3)c2)OC1(C)C] | ¹HNMR (400 MHz, CDCl₃) δ 9.78 (s, 1H), 8.53 (s, 1H, D₂O exchangeable), 8.41 (s, 1H), 7.87 (s, 1H), 7.80 (d, J = 8.0 Hz, 1H), 7.52-7.48 (m 1H), 7.38 (d, J = 8.0 Hz, 1H), 7.06 (t, J = 8.5 Hz, 2H), 2.46 (s, 3H), 2.30 (s, 3H), 1.86 (s, 6H); ESI-MS (m/z) 466 (MH)⁺. |

| Example No: IUPAC name | Structure | $^1$H NMR/ESI-MS(MH)$^+$ |
| --- | --- | --- |
| Example 33: 2,6-Difluoro-N-(2'-methyl-5'-(4-methyl-5-oxo-4,5-dihydro-1,3,4-oxadiazol-2-yl)-[1,1'-biphenyl]-4-yl)benzamide | 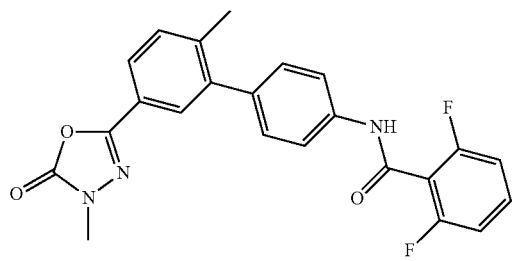 [SMILES: Cc1ccc(-c2nn(C)c(=O)o2)cc1-c1ccc(NC(=O)c2c(F)cccc2F)cc1] | $^1$HNMR (400 MHz, DMSO-d6) δ 10.95 (s, 1H, D$_2$O exchangeable), 7.81 (d, J = 8.5 Hz, 2H), 7.70 (dd, J = 8.0, 1.5 Hz, 1H), 7.66-7.61 (m, 1H), 7.59 (d, J = 1.5 Hz, 1H), 7.51 (d, J = 8.0 Hz, 1H), 7.42 (d, J = 8.5 Hz, 2H), 7.28 (t, J = 8.0 Hz, 2H), 3.41 (s, 3H), 2.33 (s, 3H); ESI-MS (m/z) 422 (MH)$^+$. |
| Example 34: N-(5'-(4-Ethyl-5-oxo-4,5-dihydro-1,3,4-oxadiazol-2-yl)-2'-methyl-[1,1'-biphenyl]-4-yl)-2,6-difluorobenzamide | 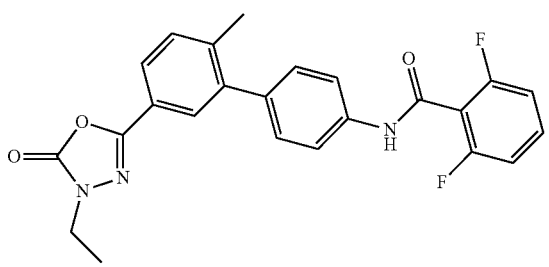 [SMILES: CCn1nc(-c2ccc(C)c(-c3ccc(NC(=O)c4c(F)cccc4F)cc3)c2)oc1=O] | $^1$HNMR (400 MHz, DMSO-d6) δ 10.95 (s, 1H, D$_2$O exchangeable), 7.80 (d, J = 8.5 Hz, 2H), 7.70 (dd, J = 8.0, 1.5 Hz, 1H), 7.65-7.59 (m, 1H), 7.58 (d, J = 1.5 Hz, 1H), 7.50 (d, J = 8.0 Hz, 1H), 7.41 (d, J = 8.5 Hz, 2H), 7.28 (t, J = 8.0 Hz, 2H), 3.77 (q, J = 7.0 Hz, 2H), 2.32 (s, 3H), 1.29 (t, J = 7.0 Hz, 3H); ESI-MS (m/z) 436 (MH)$^+$. |
| Example 35: 2,6-Difluoro-N-(2'-methyl-5'-(5-oxo-4-propyl-4,5-dihydro-1,3,4-oxadiazol-2-yl)-[1,1'-biphenyl]-4-yl)benzamide | 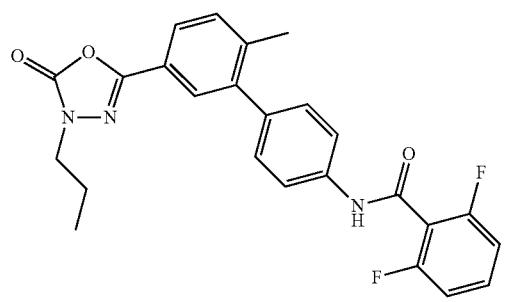 [SMILES: CCCn1nc(-c2ccc(C)c(-c3ccc(NC(=O)c4c(F)cccc4F)cc3)c2)oc1=O] | $^1$HNMR (400 MHz, DMSO-d6) δ 10.95 (s, 1H, D$_2$O exchangeable), 7.76 (d, J = 8.5 Hz, 2H), 7.65 (dd, J = 8.0, 1.5 Hz, 1H), 7.59-7.53 (m, 1H), 7.53 (d, J = 1.5 Hz, 1H), 7.46 (d, J = 8.0 Hz, 1H), 7.36 (d, J = 8.5 Hz, 2H), 7.22 (t, J = 8.0 Hz, 2H), 3.65 (t, J = 7.0 Hz, 2H), 2.27 (s, 3H), 1.68 (q, J = 7.0 Hz, 2H), 0.86 (t, J = 7.0 Hz, 3H); ESI-MS (m/z) 450 (MH)$^+$. |
| Example 36: N-(2'-Ethyl-5'-(4-methyl-5-oxo-4,5-dihydro-1,3,4-oxadiazol-2-yl)-[1,1'-biphenyl]-4-yl)-2,6-difluorobenzamide | 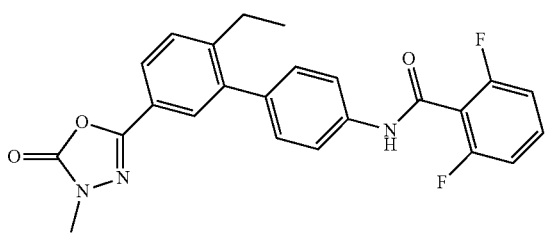 [SMILES: CCc1ccc(-c2nn(C)c(=O)o2)cc1-c1ccc(NC(=O)c2c(F)cccc2F)cc1] | $^1$HNMR (400 MHz, CDCl$_3$) δ 7.74 (dd, J = 8.5, 2.0 Hz, 1H), 7.71 (d, J = 8.0 Hz, 2H+1H D$_2$O exchangeable), 7.67 (s, 1H), 7.46-7.42 (m, 1H), 7.41 (d, J = 8.5 Hz, 1H), 7.32 (d, J = 8.0 Hz, 2H), 7.03 (t, J = 8.0 Hz, 2H), 3.49 (s, 3H), 2.65 (q, J = 7.5 Hz, 2H), 1.12 (t, J = 7.5 Hz, 3H); ESI-MS (m/z) 436 (MH)$^+$. |
| Example 37: 2-Chloro-N-(2'-ethyl-5'-(4-methyl-5-oxo-4,5-dihydro-1,3,4-oxadiazol-2-yl)-[1,1'-biphenyl]-4-yl)-6-fluorobenzamide | 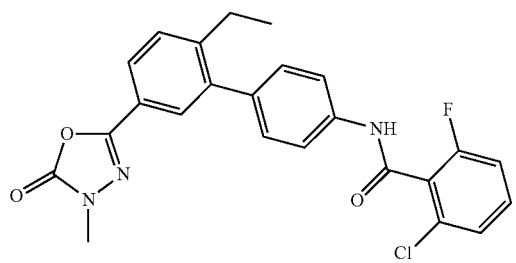 [SMILES: CCc1ccc(-c2nn(C)c(=O)o2)cc1-c1ccc(NC(=O)c2c(F)cccc2Cl)cc1] | $^1$HNMR (400 MHz, CDCl$_3$) δ 7.77 (dd, J = 8.0, 1.5 Hz, 1H), 7.73 (d, J = 8.5 Hz, 2H), 7.69 (d, J = 1.5 Hz, 1H), 7.62 (s, 1H, D$_2$O exchangeable), 7.42 (d, J = 8.0 Hz, 1H), 7.42-7.37 (m, 1H), 7.35 (d, J = 8.5 Hz, 2H), 7.30 (d, J = 8.0 Hz, 1H), 7.14 (m, 1H), 3.50 (s, 3H), 2.66 (q, J = 7.5 Hz, 2H), 1.15 (t, J = 7.5 Hz, 3H); ESI-MS [(m/z) 452, 454 [(MH)$^+$. Cl$^{35, 37}$) |

-continued

| Example No: IUPAC name | Structure | ¹H NMR/ESI-MS(MH)⁺ |
|---|---|---|
| Example 38: N-(2'-Ethyl-5'-(4-methyl-5-oxo-4,5-dihydro-1,3,4-oxadiazol-2-yl)-[1,1'-biphenyl]-4-yl)-2-fluoro-6-methylbenzamide | 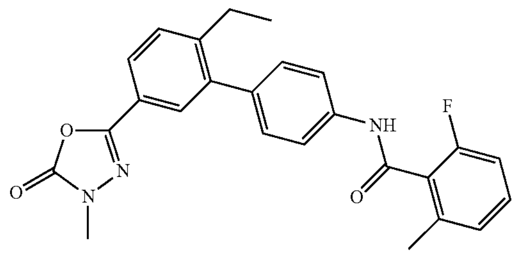 [SMILES: CCc1ccc(-c2nn(C)c(=O)o2)cc1-c1ccc(NC(=O)c2c(C)cccc2F)cc1] | ¹HNMR (400 MHz, CDCl₃) δ 7.76 (dd, J = 8.5, 2.0 Hz, 1H), 7.73 (d, J = 8.0 Hz, 2H), 7.61 (s, 1H, D₂O exchangeable), 7.42 (d, J = 8.5 Hz, 1H), 7.36-7.31 (m, 3H), 7.10 (d, J = 7.5 Hz, 1H), 7.02 (t, J = 8.0 Hz, 2H), 3.51 (s, 3H), 2.68 (q, J = 7.5 Hz, 2H), 2.52 (s, 3H), 1.15 (t, J = 7.5 Hz, 3H); ESI-MS (m/z) 432 (MH)⁺. |
| Example 39: N-(2'-Ethyl-5'-(4-methyl-5-oxo-4,5-dihydro-1,3,4-oxadiazol-2-yl)-[1,1'-biphenyl]-4-yl)-4-methyl-1,2,3-thiadiazole-5-carboxamide | 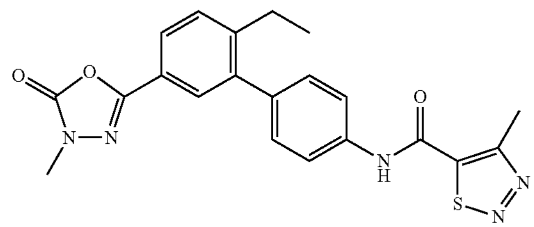 [SMILES: CCc1ccc(-c2nn(C)c(=O)o2)cc1-c1ccc(NC(=O)c2snnc2C)cc1] | ¹HNMR (400 MHz, CdCl₃) δ 7.78 (dd, J = 8.5, 2.0 Hz, 1H), 7.70-7.64 (m, 4H), 7.43 (d, J = 8.0 Hz, 1H), 7.36 (d, J = 7.5 Hz, 2H), 3.50 (s, 3H), 3.03 (s, 3H) 2.66 (q, J = 7.5 Hz, 2H), 1.14 (t, J = 7.5 Hz, 3H); ESI-MS (m/z) 422 (MH)⁺ |
| Example 40: 2,6-Difluoro-N-(2'-methoxy-5'-(4-methyl-5-oxo-4,5-dihydro-1,3,4-oxadiazol-2-yl)-[1,1'-biphenyl]-4-yl)benzamide | 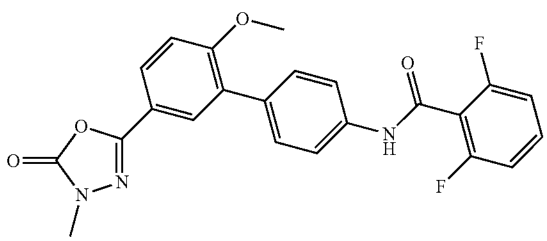 [SMILES: COc1ccc(-c2nn(C)c(=O)o2)cc1-c1ccc(NC(=O)c2c(F)cccc2F)cc1] | ¹HNMR (400 MHz, CDCl₃) δ 7.81-7.77 (m, 2H), 7.72 (d, J = 8.5 Hz, 2H), 7.67 (brs, 1H, D₂O exchangeable), 7.56 (d, J = 8.5 Hz, 2H), 7.47-7.42 (m, 1H), 7.05 (d, J = 8.5 Hz, 1H), 7.03 (t, J = 8.0 Hz, 2H), 3.89 (s, 3H), 3.49 (s, 3H); ESI-MS (m/z) 438 (MH)⁺ |
| Example 41: 2-Chloro-6-fluoro-N-(2'-methoxy-5'-(4-methyl-5-oxo-4,5-dihydro-1,3,4-oxadiazol-2-yl)-[1,1'-biphenyl]-4-yl)benzamide | 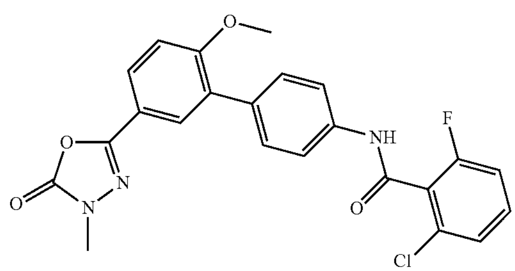 [SMILES: COc1ccc(-c2nn(C)c(=O)o2)cc1-c1ccc(NC(=O)c2c(F)cccc2Cl)cc1] | ¹HNMR (400 MHz, CDCl₃) δ 7.81-7.76 (m, 2H), 7.71 (d, J = 8.5 Hz, 2H), 7.55 (m, 3H), 7.40-7.35 (m, 1H), 7.28 (d, J = 8.5 Hz, 1H), 7.11 (dt, J = 8.5, 1.0 Hz, 1H), 7.05 (d, J = 8.5 Hz, 1H), 3.89 (s, 3H), 3.49 (s, 3H); ESI-MS (m/z) 454, 456 [(MH)⁺, (Cl³⁵, ³⁷)] |
| Example 42: 2-Fluoro-N-(2'-methoxy-5'-(4-methyl-5-oxo-4,5-dihydro-1,3,4-oxadiazol-2-yl)-[1,1'-biphenyl]-4-yl)-6-methylbenzamide | 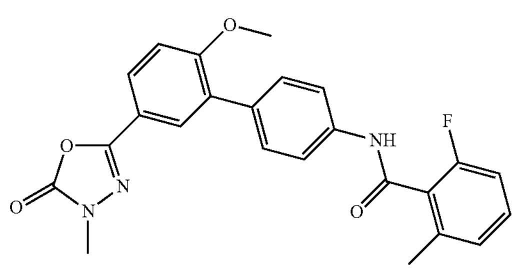 [SMILES: COc1ccc(-c2nn(C)c(=O)o2)cc1-c1ccc(NC(=O)c2c(C)cccc2F)cc1] | ¹HNMR (400 MHz, CDCl₃) δ 7.81-7.77 (m, 2H), 7.72 (d, J = 8.5 Hz, 2H), 7.56-7.54 (m, 3H), 7.34-7.28 (m, 1H), 7.08-6.97 (m, 3H), 3.89 (s, 3H), 3.49 (s, 3H), 2.49 (s, 3H); ESI-MS (m/z) 434 (MH)⁺. |
| Example 43: 4-Ethyl-N-(2'-methoxy-5'-(4-methyl-5-oxo-4,5-dihydro-1,3,4-oxadiazol-2-yl)-[1,1'-biphenyl]-4-yl)benzamide | 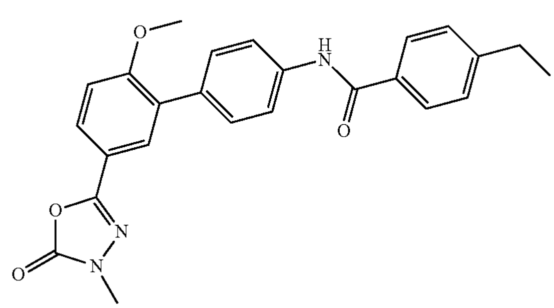 [SMILES: CCc1ccc(C(=O)Nc2ccc(-c3cc(-c4nn(C)c(=O)o4)ccc3OC)cc2)cc1] | ¹HNMR (400 MHz, CDCl₃) δ 7.85 (s, 1H, D₂O exchangeable), 7.83-7.81 (m, 3H), 7.77 (dd, J = 8.5, 2.0 Hz, 1H), 7.72 (d, J = 8.0 Hz, 2H), 7.55 (d, J = 8.5 Hz, 2H), 7.33 (d, J = 8.0 Hz, 2H), 7.04 (d, J = 8.0 Hz, 1H), 3.88 (s, 3H), 3.49 (s, 3H), 2.73 (q, J = 7.5 Hz, 1H), 1.28 (t, J = 7.5 Hz, 3H); ESI-MS (m/z) 430 (MH)⁺. |

| Example No: IUPAC name | Structure | $^1$H NMR/ESI-MS(MH)$^+$ |
| --- | --- | --- |
| Example 44: N-(2'-(Difluoromethoxy)-5'-(4-methyl-5-oxo-4,5-dihydro-1,3,4-oxadiazol-2-yl)-[1,1'-biphenyl]-4-yl)-2,6-difluorobenzamide | 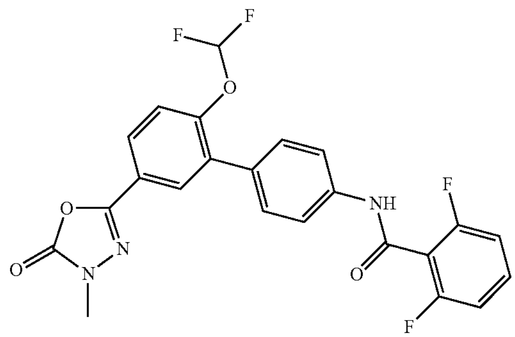 [SMILES: Cn1nc(-c2ccc(OC(F)F)c(-c3ccc(NC(=O)c4c(F)cccc4F)cc3)c2)oc1=O] | $^1$HNMR (400 MHz, CDCl$_3$) δ 7.89 (d, J = 1.5 Hz, 1H), 7.81-7.73 (m, 4H), 7.52 (d, J = 8.5 Hz, 2H), 7.48-7.40 (m, 1H), 7.33 (d, J = 8.5 Hz, 1H), 7.02 (t, J = 8.5 Hz, 2H), 6.44 (t, J = 73 Hz, 1H), 3.49 (s, 3H); ESI-MS (m/z) 474 (MH)$^+$ |
| Example 45: N-(2'-(Difluoromethoxy)-5'-(4-methyl-5-oxo-4,5-dihydro-1,3,4-oxadiazol-2-yl)-[1,1'-biphenyl]-4-yl)-4-methyl-1,2,3-thiadiazole-5-carboxamide | 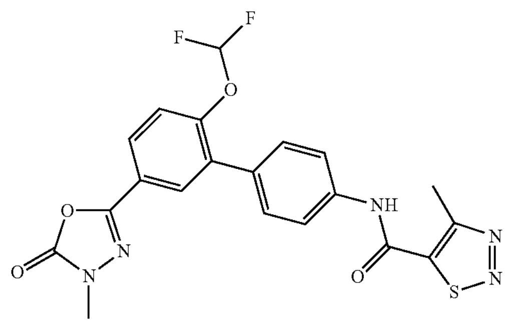 [SMILES: Cc1nnsc1C(=O)Nc1ccc(-c2cc(-c3nn(C)c(=O)o3)ccc2OC(F)F)cc1] | $^1$HNMR (400 MHz, CDCl$_3$) δ 7.91 (d, J = 2.0 Hz, 1H), 7.84 (dd, J = 8.5, 2.0 Hz, 1H), 7.77 (s, 1H, D$_2$O exchangeable), 7.71 (d, J = 8.5 Hz, 1H), 7.57 (d, J = 8.5 Hz, 2H), 7.36 (d, J = 8.5 Hz, 1H), 6.47 (t, J = 73 Hz, 1H), 3.52 (s, 3H), 3.02 (s, 3H); ESI-MS (m/z) 460 (MH)$^+$ |
| Example 46: N-(2'-Chloro-5'-(4-methyl-5-oxo-4,5-dihydro-1,3,4-oxadiazol-2-yl)-[1,1'-biphenyl]-4-yl)-2,6-difluorobenzamide | 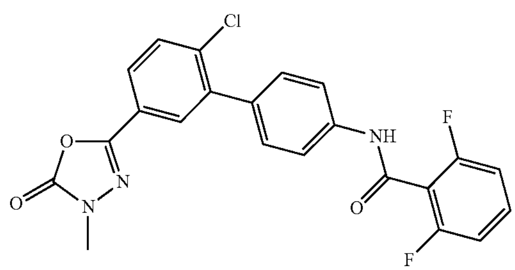 [SMILES: Cn1nc(-c2ccc(Cl)c(-c3ccc(NC(=O)c4c(F)cccc4F)cc3)c2)oc1=O] | $^1$HNMR (400 MHz, CDCl$_3$) δ 7.82 (d, J = 2.5 Hz, 1H), 7.76-7.71 (m, 4H), 7.58 (d, J = 8.0 Hz, 1H), 7.48 (d, J = 8.5 Hz, 2H), 7.45-7.42 (m, 1H), 7.03 (d, J = 8.0 Hz, 2H), 3.50 (s, 3H); ESI-MS (m/z) 442, 444 [(MH)$^+$, (Cl$^{35, 37}$)] |
| Example 47: N-(2'-Chloro-5'-(4-methyl-5-oxo-4,5-dihydro-1,3,4-oxadiazol-2-yl)-[1,1'-biphenyl]-4-yl)-4-methyl-1,2,3-thiadiazole-5-carboxamide | 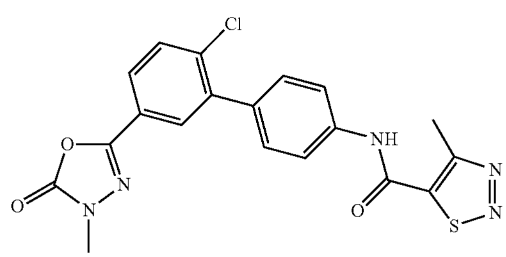 [SMILES: Cc1nnsc1C(=O)Nc1ccc(-c2cc(-c3nn(C)c(=O)o3)ccc2Cl)cc1] | $^1$HNMR (400 MHz, CDCl$_3$) δ 7.81 (d, J = 2.0 Hz, 1H), 7.41 (dd, J = 8.5, 2.0 Hz, 1H), 7.69 (d, J = 8.5 Hz, 2H), 7.63 (s, 1H, D$_2$O exchangeable), 7.59 (d, J = 8.5 Hz, 1H), 7.50 (d, J = 8.5 Hz, 2H), 3.50 (s, 3H), 3.00 (s, 3H); ESI-MS (m/z) 428, 430 [(MH)$^+$ (Cl$^{35, 37}$)] |
| Example 48: 2,6-Difluoro-N-(2'-methyl-3'-(4-methyl-5-oxo-4,5-dihydro-1,3,4-oxadiazol-2-yl)-[1,1'-biphenyl]-4-yl)benzamide | 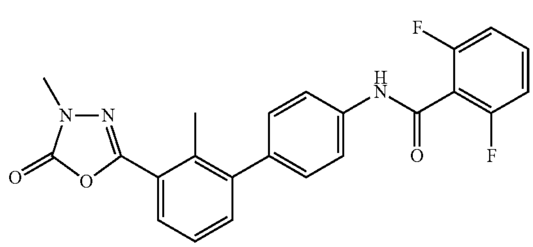 [SMILES: Cc1c(-c2ccc(NC(=O)c3c(F)cccc3F)cc2)cccc1-c1nn(C)c(=O)o1] | $^1$HNMR (400 MHz, DMSO-d6) δ 10.94 (s, 1H, D$_2$O exchangeable, 7.79 (d, J = 8.5 Hz, 2H), 7.72 (dd, J = 7.0, 2.0 Hz, 1H), 7.63-7.57 (m, 1H), 7.46-7.40 (m, 2H), 7.36 (d, J = 8.5 Hz, 2H), 7.26 (t, J = 8.0 Hz, 2H), 3.43 (s, 3H), 2.41 (s, 3H); ESI-MS (m/z) 422 (MH)$^+$. |

| Example No:<br>IUPAC name | Structure | ¹H NMR/ESI-MS(MH)⁺ |
|---|---|---|
| Example 49: 2-Chloro-6-fluoro-N-(2'-methyl-3'-(4-methyl-5-oxo-4,5-dihydro-1,3,4-oxadiazol-2-yl)-[1,1'-biphenyl]-4-yl)benzamide | 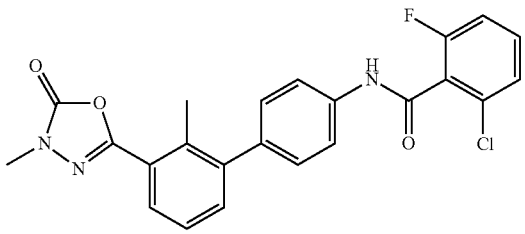 [SMILES: Cc1c(-c2ccc(NC(=O)c3c(F)cccc3Cl)cc2)cccc1-c1nn(C)c(=O)o1] | ¹HNMR (400 MHz, DMSO-d6) δ 10.93 (s, 1H, D₂O exchangeable, 7.79 (d, J = 8.5 Hz, 2H), 7.72 (dd, J = 7.0, 2.0 Hz, 1H), 7.60-7.54 (m, 1H), 7.48-7.37 (m, 4H), 7.36 (d, J = 8.5 Hz, 2H), 3.43 (s, 3H), 2.41 (s, 3H); ESI-MS (m/z) 438, 440 [(MH)⁺, Cl³⁵, ³⁷] |
| Example 50: 4-Methyl-N-(2'-methyl-3'-(4-methyl-5-oxo-4,5-dihydro-1,3,4-oxadiazol-2-yl)-[1,1'-biphenyl]-4-yl)-1,2,3-thiadiazol-5-carboxamide | 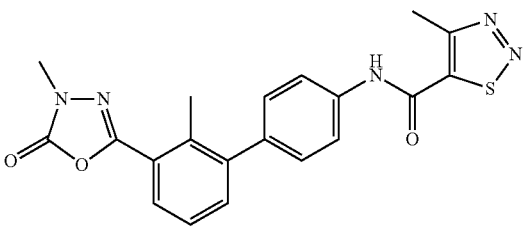 [SMILES: Cc1nnsc1C(=O)Nc1ccc(-c2cccc(-c3nn(C)c(=O)o3)c2C)cc1] | ¹HNMR (400 MHz, DMSO-d6) δ 10.87 (s, 1H, D₂O exchangeable, 7.78 (d, J = 8.5 Hz, 2H), 7.72 (dd, J = 7.0, 2.0 Hz, 1H), 7.48-7.49 (m, 1H), 7.43-7.42 (d, J = 7.0 Hz, 1H), 7.37 (d, J = 8.5 Hz, 2H), 3.43 (s, 3H), 2.83 (s, 3H), 2.41 (s, 3H); ESI-MS (m/z) 408 (MH)⁺ |
| Example 51: N-(2'-ethyl-3'-(4-methyl-5-oxo-4,5-dihydro-1,3,4-oxadiazol-2-yl)-[1,1'-biphenyl]-4-yl)-4-methyl-1,2,3-thiadiazole-5-carboxamide | 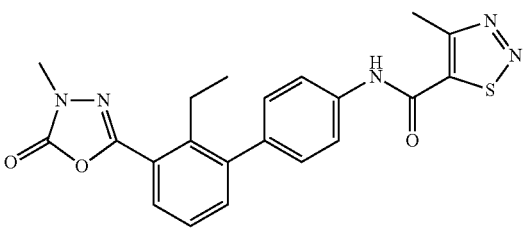 [SMILES: CCc1c(-c2ccc(NC(=O)c3snnc3C)cc2)cccc1-c1nn(C)c(=O)o1] | ¹HNMR (400 MHz, CDCl₃) δ 7.78 (dd, J = 7.0, 2.5 Hz, 1H), 7.73 (s, 1H, D₂O exchangeable), 7.67 (d, J = 8.0 Hz, 2H), 7.37-7.32 (m, 4H), 3.54 (s, 3H), 3.02 (s, 3H), 2.92 (q, J = 7.5 Hz, 2H), 1.01 (t, J = 7.5 Hz, 3H); ESI- MS (m/z) 422 (MH)⁺ |
| Example 52: N-(2'-ethyl-3'-(4-methyl-5-oxo-4,5-dihydro-1,3,4-oxadiazol-2-yl)-[1,1'-biphenyl]-4-yl)-2,6-difluorobenzamide | 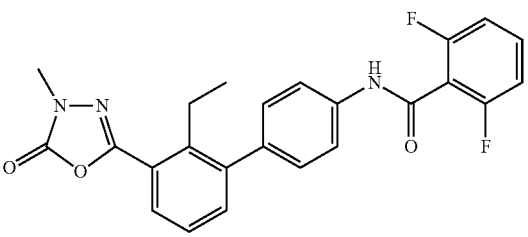 [SMILES: CCc1c(-c2ccc(NC(=O)c3c(F)cccc3F)cc2)cccc1-c1nn(C)c(=O)o1] | ¹HNMR (400 MHz, CDCl₃) δ 7.93-7.76 (m, 1H), 7.76-7.71 (m, 3H), 7.50-7.43 (m, 1H), 7.36-7.31 (m, 4H), 7.04 (t, J = 8.5 Hz, 2H), 3.54 (s, 3H), 2.94 (q, J = 7.5 Hz, 2H), 1.02 (t, J = 7.5 Hz, 3H); ESI-MS (m/z) 435 (MH)⁺ |
| Example 53: N-(5-(5,5-Dimethyl-4,5-dihydroisoxazol-3-yl)-2-methylphenyl)pyrazin-2-yl)-2,6-difluorobenzamide | 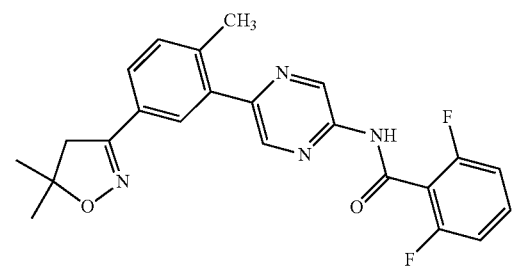 [SMILES: Cc1ccc(C2=NOC(C)(C)C2)cc1-c1cnc(NC(=O)c2c(F)cccc2F)cn1] | ¹HNMR (400 MHz, CDCl₃) δ 11.80 (brs, 1H, D₂O exchangeable), 9.50 (s, 1H), 8.69 (s, 1H), 7.71 (s, 1H), 7.67-7.60 (m, 2H), 7.42 (d, J = 8.0 Hz, 1H), 7.26 (t, J = 8.0 Hz, 2H), 3.21 (s, 2H), 2.40 (s, 3H), 1.38 (s, 6H); ESI-MS (m/z) 423 (MH)⁺. |
| Example 54: Methyl 3-(3-(5-(2,6-difluorobenzamido)pyrazin-2-yl)-4-methylphenyl)-5-methyl-4,5-dihydroisoxazole-5-carboxylate | 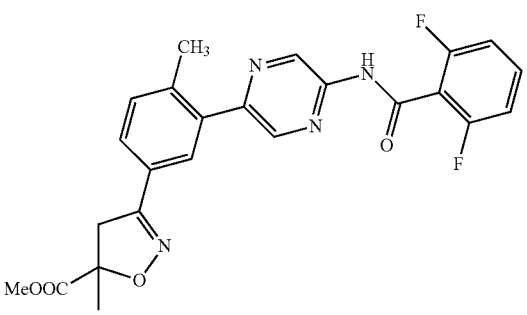 [SMILES: COC(=O)C1(C)CC(c2ccc(C)c(-c3cnc(NC(=O)c4c(F)cccc4F)cn3)c2)=NO1] | ¹HNMR (400 MHz, CDCl₃) δ 9.75 (s, 1H), 8.62 (s, 1H, D₂O exchangeable), 8.35 (s, 1H), 7.68 (d, J = 1.5 Hz, 1H), 7.65 (dd, J = 8.0, 1.5 Hz, 1H), 7.52-7.47 (m, 1H), 7.36 (d, J = 8.0 Hz, 1H), 7.02 (t, J = 8.0 Hz, 2H), 3.90 (d, J = 17.0 Hz, 1H), 3.81 (s, 3H), 3.25 (d, J = 17.0 Hz, 1H), 2.43 (s, 3H), 1.72 (s, 3H); ESI-MS (m/z) 467 (MH)⁺. |

-continued

| Example No: IUPAC name | Structure | ¹H NMR/ESI-MS(MH)⁺ |
|---|---|---|
| Example 55: Methyl-3-(4'-(2,6-difluorobenzamido)-6-methyl-[1,1'-biphenyl]-3-yl)-5-methyl-4,5-dihydroisoxazole-5-carboxylate | 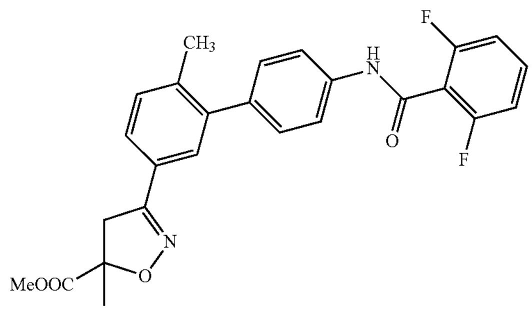 [SMILES: COC(=O)C1(C)CC(c2ccc(C)c(-c3ccc(NC(=O)c4c(F)cccc4F)cc3)c2)=NO1] | ¹HNMR (400 MHz, CDCl₃) δ 7.70 (d, J = 8.5 Hz, 2H), 7.58 (dd, J = 8.0, 1.5 Hz, 1H), 7.47 (d, J = 1.5 Hz, 1H), 7.49-7.40 (m, 1H), 7.33-7.29 (m, 3H), 7.03 (t, J = 8.0 Hz, 2H), 3.88 (d J = 17.0 Hz, 1H), 3.80 (s, 3H), 3.22 (d, J = 17.0 Hz, 1H), 2.30 (s, 3H), 1.72 (s, 3H); ESI-MS (m/z) 465 (MH)⁺ |
| Example 56: 2,6-Difluoro-N-(2'-methyl-5'-(1-oxa-2-azaspiro[4.4]non-2-en-3-yl)-[1,1'-biphenyl]-4-yl)benzamide | 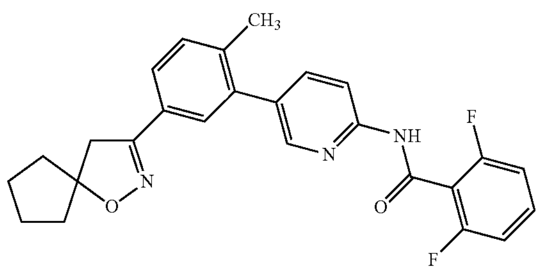 [SMILES: Cc1ccc(C2=NOC3(CCCC3)C2)cc1-c1ccc(NC(=O)c2c(F)cccc2F)nc1] | ¹HNMR (400 MHz, DMSO-d₆) δ 11.17 (s, 1H, D₂O exchangeable), 8.92 (d, J = 2.0 Hz, 1H), 8.26 (dd, J = 8.5, 2.5 Hz, 1H), 7.66-7.59 (m, 4H), 7.38 (d, J = 8.0 Hz, 1H), 7.30 (t, J = 8.5 Hz, 2H), 2.37 (s, 3H), 1.92-1.89 (m, 2H), 1.78-1.72 (m, 6H); ESI-MS (m/z) 448 (MH)⁺. |
| Example 57: 2,6-Difluoro-N-(5-(2-methyl-5-(1-oxa-2-azaspiro[4.4]non-2-en-3-yl)phenyl)pyrazin-2-yl)benzamide | 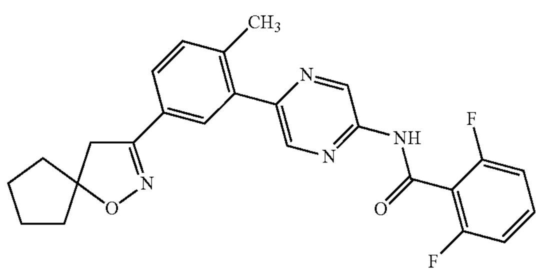 [SMILES: Cc1ccc(C2=NOC3(CCCC3)C2)cc1-c1cnc(NC(=O)c2c(F)cccc2F)cn1] | ¹HNMR (400 MHz, DMSO-d₆) δ 11.81 (s, 1H, D₂O exchangeable), 9.51 (s, 1H), 8.70 (s, 1H), 7.72 (s, 1H), 7.67 (dd, J = 8.0, 1.5 Hz, 1H), 7.65-7.60 (m, 1H), 7.43 (d, J = 8.0 Hz, 1H), 7.27 (t, J = 8.5 Hz, 2H), 2.41 (s, 3H), 1.95-1.91 (m, 2H), 1.80-1.67 (m, 6H); ESI-MS (m/z) 449 (MH)⁺. |
| Example 58: 2,6-Difluoro-N-(2'-methyl-5'-(4-oxo-1-oxa-2-azaspiro[4.5]dec-2-en-3-yl)-[1,1'-biphenyl]-4-yl)benzamide | 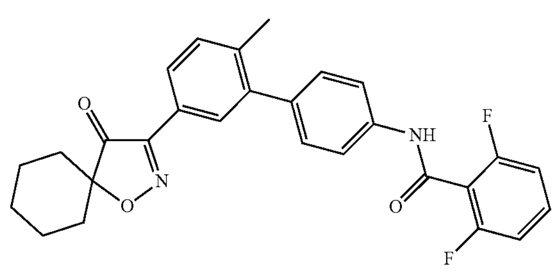 [SMILES: Cc1ccc(C2=NOC3(CCCCC3)C2=O)cc1-c1ccc(NC(=O)c2c(F)cccc2F)cc1] | ¹HNMR (400 MHz, CDCl₃) δ 7.99-7.97 (m, 2H), 7.70 (d, J = 8.5 Hz, 2H+1H D₂O exchangeable), 7.41-7.37 (m, 1H), 7.35 (d, J = 7.5 Hz, 3H), 7.01 (t, J = 8.0 Hz, 2H), 2.32 (s, 3H), 1.85-0.82 (m, 10H); ESI-MS (m/z) 475 (MH)⁺. |
| Example 59: N-(5-(5-(4,4-Dimethyl-4,5-dihydrooxazol-2-yl)-2-methylphenyl)pyrazine-2-yl)-2,6-difluorobenzamide | 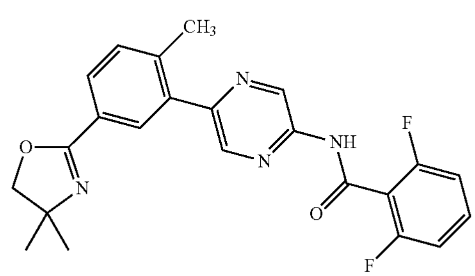 [SMILES: Cc1ccc(C2=NC(C)(C)CO2)cc1-c1cnc(NC(=O)c2c(F)cccc2F)cn1] | ¹HNMR (400 MHz, CDCl₃) δ 9.75 (s, 1H), 8.66 (s, 1H), 8.34 (s, 1H, D₂O exchangeable), 7.98 (s, 1H), 7.90 (d, J = 8.0 Hz, 1H), 7.51-7.47 (m, 1H), 7.36 (d, J = 8.0 Hz, 1H), 7.05 (t, J = 8.0 Hz, 2H), 4.11 (s, 2H), 2.44 (s, 3H), 1.39 (s, 6H); ESI-MS (m/z) 423 (MH)⁺. |

| Example No: IUPAC name | Structure | ¹H NMR/ESI-MS(MH)⁺ |
|---|---|---|
| Example 60: N-(5-(5-(4,4-dimethyl-4,5-dihydrooxazol-2-yl)-2-methylphenyl)pyridin-2-yl)-2,6-difluorobenzamide | 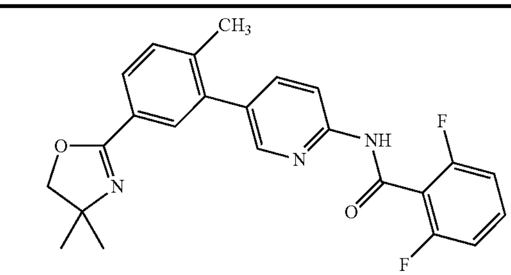 | ¹HNMR (400 MHz, CDCl₃) δ 8.70 (d, J = 1.5 Hz, 1H), 8.39 (dd, J = 2.0, 8.5 Hz, 1H), 8.23 (s, 1H, D₂O exchangeable), 7.94 (s, 1H), 7.83 (d, J = 8.0 Hz, 1H), 7.46-7.40 (m, 2H), 7.31 (d, J = 8.0 Hz, 1H), 7.02 (t, J = 8.0 Hz, 2H), 4.09 (s, 2H), 2.41 (s, 3H), 1.35 (s, 6H); ESI-MS (m/z) 422 (MH)⁺. |
| Example 61: N-(5'-(4,4-dimethyl-4,5-dihydrooxazol-2-yl)-2'-methyl-[1,1'-biphenyl]-4-yl)-2,6-difluorobenzamide | 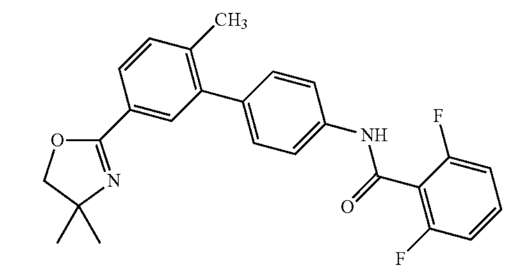 [SMILES: Cc1ccc(C2=NC(C)(C)CO2)cc1-c1ccc(NC(=O)c2c(F)cccc2F)cc1] | ¹HNMR (400 MHz, CDCl₃) δ 7.82-7.80 (m, 2H), 7.77 (brs, 1H, D₂O exchangeable), 7.68 (d, J = 8.0 Hz, 2H), 7.48-7.40 (m, 1H), 7.35-7.29 (m, 3H), 7.02 (t, J = 8.0 Hz, 2H), 4.09 (s, 2H), 2.31 (s, 3H), 1.37 (s, 6H); ESI-MS (m/z) 421 (MH)⁺. |
| Example 62: 2,6-Difluoro-N-(2'-methyl-5'-(4-methyl-5-oxo-4,5-dihydro-1,2,4-oxadiazol-3-yl)-[1,1'-biphenyl]-4-yl)benzamide | 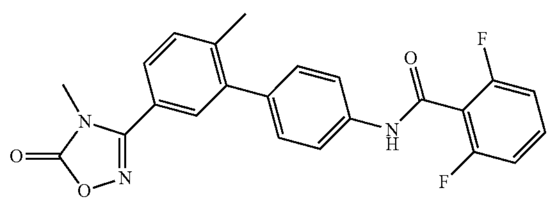 [SMILES: Cc1ccc(-c2noc(=O)n2C)cc1-c1ccc(NC(=O)c2c(F)cccc2F)cc1] | ¹HNMR (400 MHz, DMSO-d₆) δ 10.95 (s, 1H, D₂O exchangeable), 7.81 (d, J = 8.0 Hz, 2H), 7.66-7.60 (m, 1H), 7.55-7.41 (m, 3H), 7.43 (d, J = 8.0 Hz, 2H), 7.28 (d, J = 8.0 Hz, 2H), 3.24 (s, 3H), 2.35 (s, 3H); ESI-MS (m/z) 422 (MH)⁺ |
| Example 63: 4-Methyl-N-(2'-methyl-5'-(4-methyl-5-oxo-4,5-dihydro-1,2,4-oxadiazol-3-yl)-[1,1'-biphenyl]-4-yl)-1,2,3-thiadiazole-5-carboxamide | 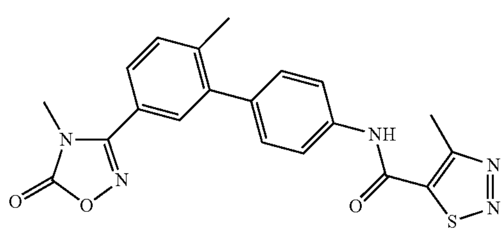 [SMILES: Cc1ccc(-c2noc(=O)n2C)cc1-c1ccc(NC(=O)c2snnc2C)cc1] | ¹HNMR (400 MHz, DMSO-d₆) δ 10.88 (s,1H, D₂O exchangeable), 7.8 (d, J = 8.5 Hz, 2H), 7.64 (dd, J = 8.5, 1.5 Hz, 1H), 7.55 (d, J = 8.0 Hz, 2H), 7.44 (d, J = 8.5 Hz, 2H), 3.24 (s, 3H), 2.83 (s, 3H), 2.35 (s, 3H); ESI-MS (m/z) 406 (M − H) |
| Example 64: Ethyl 3-(4'-(2,6-difluorobenzamido)-6-methyl-[1,1'-biphenyl]-3-yl)-4,4-dimethyl-4,5-dihydroisoxazole-5-carboxylate | 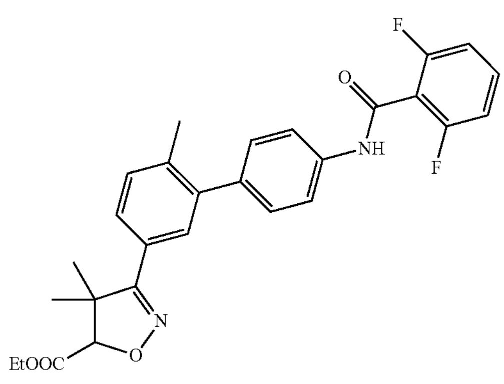 [SMILES: CCOC(=O)C1ON=C(c2ccc(C)c(-c3ccc(NC(=O)c4c(F)cccc4F)cc3)c2)C1(C)C] | ¹HNMR (400 MHz, CDCl₃) δ 7.71 (d, J = 8.5 Hz, 2H), 7.52 (dd, J = 8.0, 1.5 Hz, 1H), 7.48 (d, J = 1.5 Hz, 1H), 7.47-7.41 (m, 1H), 7.31 (d, J = 8.5 Hz, 2H), 7.28 (d, J = 8.0 Hz, 1H), 7.03 (t, J = 8.0 Hz, 2H), 4.22 (q, J = 7.5 Hz, 2H), 2.29 (s, 3H), 1.50 (s, 3H), 1.49 (s, 3H), 1.21 (t, J = 7.5 Hz, 3H); ESI-MS (m/z) 493 (MH)⁺ |
| Example 65: N-(5-(5-(5,5-Dimethyl-4-oxo-4,5-dihydroisoxazol-3-yl)-2-methylphenyl)pyrazine-2-yl)-2-fluorobenzamide | 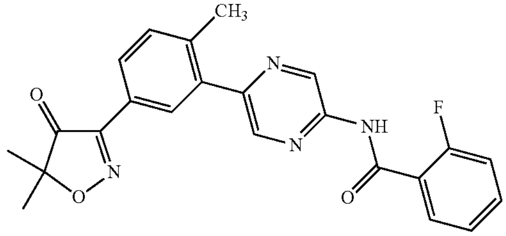 [SMILES: Cc1ccc(C2=NOC(C)(C)C2=O)cc1-c1cnc(NC(=O)c2ccccc2F)cn1] | ¹HNMR (400 MHz, CDCl₃) δ 9.79 (s, 1H), 9.13 (d, J = 15 Hz, 1H, D₂O exchangeable), 8.47 (s, 1H), 8.23-8.19 (m, 2H), 8.07 (d, J = 8.0 Hz, 1H), 7.62-7.56 (m, 1H), 7.42 (d, J = 8.0 Hz, 1H), 7.36 (t, J = 8.0 Hz, 1H), 7.25-7.21 (m, 1H), 2.46 (s, 3H), 1.47 (s, 6H); ESI-MS (m/z) 419 (MH)⁺. |

| Example No: IUPAC name | Structure | ¹H NMR/ESI-MS(MH)⁺ |
|---|---|---|
| Example 66: N-(5-(5-(5,5-Dimethyl-4-oxo-4,5-dihydroisoxazol-3-yl)-2-methylphenyl)pyrazine-2-yl)-2,4-difluorobenzamide | 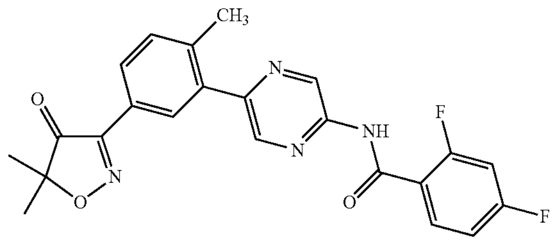 [SMILES: Cc1ccc(C2=NOC(C)(C)C2=O)cc1-c1cnc(NC(=O)c2ccc(F)cc2F)cn1] | ¹HNMR (400 MHz, DMSO-d6) δ 11.36 (s, 1H, D₂O exchangeable), 9.52 (s, 1H), 8.68 (s, 1H), 8.10 (s, 1H), 7.98 (d, J = 8.0 Hz, 1H), 7.83 (q, J = 8.0 Hz, 1H), 7.54 (d, J = 8.0 Hz, 1H), 7.48-7.42 (m, 1H), 7.26 (t, J = 8.0 Hz, 1H), 2.44 (s, 3H), 1.43 (s, 6H); ESI-MS (m/z) 437 (MH)⁺. |
| Example 67: N-(5-(5-(5,5-Dimethyl-4-oxo-4,5-dihydroisoxazol-3-yl)-2-methylphenyl)pyrazine-2-yl)-2,5-difluorobenzamide | 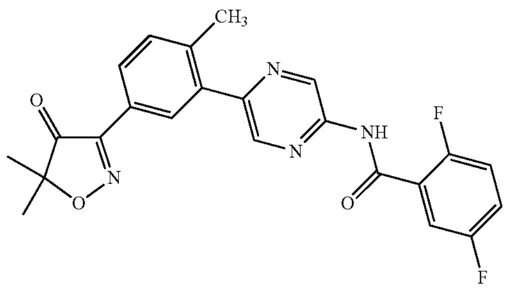 [SMILES: Cc1ccc(C2=NOC(C)(C)C2=O)cc1-c1cnc(NC(=O)c2cc(F)ccc2F)cn1] | ¹HNMR (400 MHz, DMSO-d6) δ 11.46 (s, 1H, D₂O exchangeable), 9.51 (s, 1H), 8.69 (s, 1H), 8.11 (d, J = 1.5 Hz, 1H), 7.99 (dd, J = 8.0, 1.5 Hz, 1H), 7.64-7.59 (m, 1H), 7.54 (d, J = 8.0 Hz, 1H), 7.50-7.44 (m, 1H), 7.26 (t, J = 8.0 Hz, 2H), 2.44 (s, 3H), 1.43 (s, 6H); ESI-MS (m/z) 437 (MH)⁺. |
| Example 68: N-(5-(5-(5,5-Dimethyl-4-oxo-4,5-dihydroisoxazol-3-yl)-2-methylphenyl)pyrazine-2-yl)-2,3-difluorobenzamide | 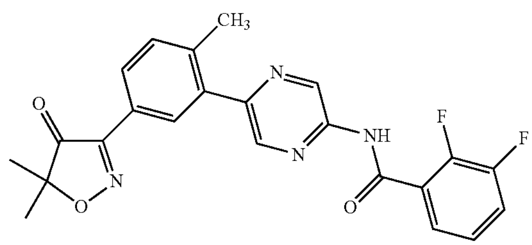 [SMILES: Cc1ccc(C2=NOC(C)(C)C2=O)cc1-c1cnc(NC(=O)c2cccc(F)c2F)cn1] | ¹HNMR (400 MHz, DMSO-d6) δ 11.52 (s, 1H, D₂O exchangeable), 9.52 (s, 1H), 8.69 (s, 1H), 8.11 (s, 1H), 7.99 (dd, J = 8.0, 1.6 Hz, 1H), 7.67 (q, J = 9.0 Hz, 1H), 7.57-7.53 (m, 2H), 7.40-7.34 (m, 1H), 2.44 (s, 3H), 1.43 (s, 6H); ESI-MS (m/z) 437 (MH)⁺. |
| Example 69: N-(5-(5-(5,5-Dimethyl-4-oxo-4,5-dihydroisoxazol-3-yl)-2-methylphenyl)pyrazine-2-yl)-4-fluorobenzamide | 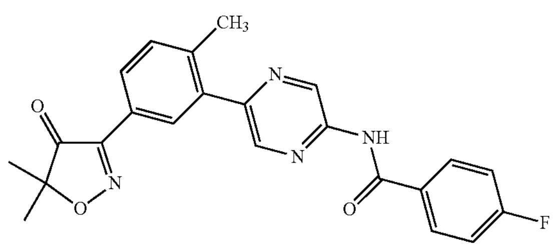 [SMILES: Cc1ccc(C2=NOC(C)(C)C2=O)cc1-c1cnc(NC(=O)c2ccc(F)cc2)cn1] | ¹HNMR (400 MHz, DMSO-d6) δ 11.33 (s, 1H, D₂O exchangeable), 9.52 (s, 1H), 8.70 (s, 1H), 8.16 (dd, J = 8.4, 11.0 Hz, 2H), 8.12 (s, 1H), 7.98 (d, J = 8.0 Hz, 1H), 7.53 (d, J = 8.0 Hz, 1H), 7.40 (t, J = 10.0 Hz, 2H), 2.45 (s, 3H), 1.43 (s, 6H); ESI-MS (m/z) 419 (MH)⁺. |
| Example 70: N-(5-(5-(5,5-Dimethyl-4-oxo-4,5-dihydroisoxazol-3-yl)-2-methylphenyl)pyrazine-2-yl)-2,4,5-trifluorobenzamide | 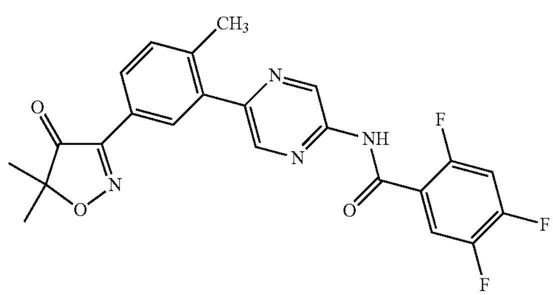 [SMILES: Cc1ccc(C2=NOC(C)(C)C2=O)cc1-c1cnc(NC(=O)c2cc(F)c(F)cc2F)cn1] | ¹HNMR (400 MHz, DMSO-d6) δ 11.47 (s, 1H, D₂O exchangeable), 9.50 (s, 1H), 8.70 (s, 1H), 8.11 (s, 1H), 7.98 (dd, J = 8.0, 1.5 Hz, 1H), 7.96-7.89 (m, 1H), 7.81-7.74 (m, 1H), 7.54 (d, J = 8.0 Hz, 1H), 2.44 (s, 3H), 1.43 (s, 6H); ESI-MS (m/z) 455 (MH)⁺. |
| Example 71: N-(5-(5-(5,5-Dimethyl-4-oxo-4,5-dihydroisoxazol-3-yl)-2-methylphenyl)pyrazine-2-yl)-2,3-dimethylbenzamide | 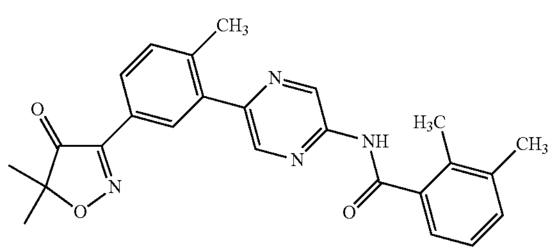 | ¹HNMR (400 MHz, DMSO-d6) δ 11.26 (s, 1H, D₂O exchangeable), 9.55 (s, 1H), 8.65 (s, 1H), 8.11 (s, 1H), 7.98 (dd, J = 8.0, 1.5 Hz, 1H), 7.54 (d, J = 8.0 Hz, 1H), 7.34-7.30 (m, 2H), 7.22-7.19 (m, 1H), 2.44 (s, 3H), 2.31 (s, 3H), 2.30 (s, 3H), 1.43 (s, 6H); ESI-MS (m/z) 429 (MH)⁺. |

| Example No: IUPAC name | Structure | ¹H NMR/ESI-MS(MH)+ |
|---|---|---|
| Example 72: N-(5-(5-(5,5-Dimethyl-4-oxo-4,5-dihydroisoxazol-3-yl)-2-methylphenyl)pyrazine-2-yl)-4-trifluoromethylbenzamide | 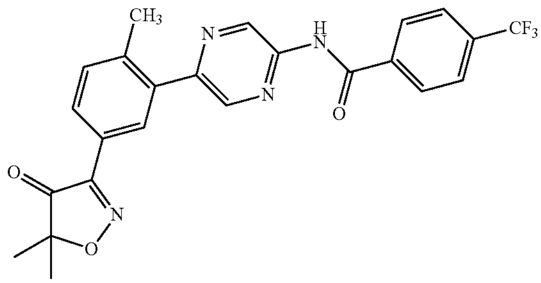 [SMILES: Cc1ccc(C2=NOC(C)(C)C2=O)cc1-c1cnc(NC(=O)c2ccc(C(F)(F)F)cc2)cn1] | ¹HNMR (400 MHz, DMSO-d6) δ 11.56 (s, 1H, D₂O exchangeable), 9.55 (s, 1H), 8.73 (s, 1H), 8.25 (d, J = 8.0 Hz, 2H), 8.13 (s, 1H), 7.99 (dd, J = 8.0, 2.0 Hz, 1H), 7.94 (d, J = 8.0 Hz, 2H), 7.54 (d, J = 8.0 Hz, 1H), 2.45 (s, 3H), 1.43 (s, 6H); ESI-MS (m/z) 469 (MH)+. |
| Example 73: N-(5-(5-(5,5-Dimethyl-4-oxo-4,5-dihydroisoxazol-3-yl)-2-methylphenyl)pyrazine-2-yl)-4-fluoro-3-methylbenzamide | 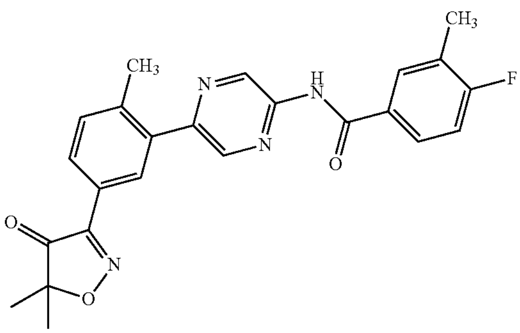 [SMILES: Cc1cc(C(=O)Nc2cnc(-c3cc(C4=NOC(C)(C)C4=O)ccc3C)cn2)ccc1F] | ¹HNMR (400 MHz, CDCl₃) δ 9.76 (s, 1H), 8.50 (s, 1H, D₂O exchangeable), 8.44 (s, 1H), 8.19 (d, J = 1.5 Hz, 1H), 8.08 (dd, J = 8.0, 1.5 Hz, 1H), 7.84 (d, J = 7.0 Hz, 1H), 7.80-7.76 (m, 1H), 7.42 (d, J = 8.0 Hz, 1H), 7.14 (t, J = 8.5 Hz, 1H), 2.46 (s, 3H), 2.37 (s, 3H), 1.47 (s, 6H); ESI-MS (m/z) 433 (MH)+ |
| Example 74: N-(5-(5-(5,5-Dimethyl-4-oxo-4,5-dihydroisoxazol-3-yl)-2-methylphenyl)pyrazine-2-yl)-2-methylbenzamide | 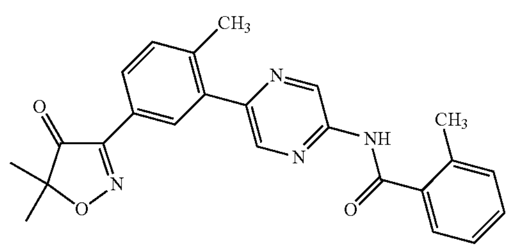 [SMILES: Cc1ccccc1C(=O)Nc1cnc(-c2cc(C3=NOC(C)(C)C3=O)ccc2C)cn1] | ¹HNMR (400 MHz, DMSO-d₆) δ 11.26 (s, 1H, D₂O exchangeable), 9.54 (s, 1H), 8.66 (s, 1H), 8.10 (d, J = 2.0 Hz, 1H), 7.98 (dd, J = 8.0, 1.5 Hz, 1H), 7.56-7.53 (m, 2H), 7.45-7.41 (m, 1H), 7.34-7.29 (m, 2H), 2.45 (s, 3H), 2.44 (s, 3H), 1.43 (s, 6H); ESI-MS (m/z) 415 (MH+) |
| Example 75: N-(5-(5-(5,5-Dimethyl-4-oxo-4,5-dihydroisoxazol-3-yl)-2-methylphenyl)pyrazine-2-yl)-3-fluoro-5-trifluoromethylbenzamide | 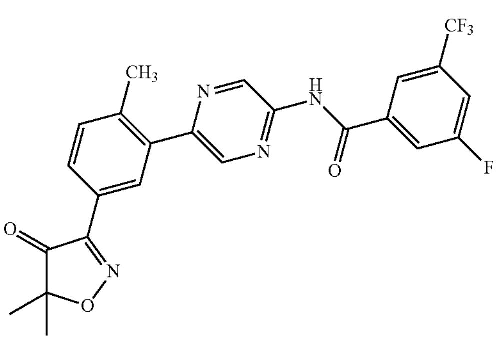 [SMILES: Cc1ccc(C2=NOC(C)(C)C2=O)cc1-c1cnc(NC(=O)c2cc(F)cc(C(F)(F)F)c2)cn1] | ¹HNMR (400 MHz, CdCl₃) δ 9.78 (s, 1H), 8.73 (s, 1H, D₂O exchangeable), 8.50 (s, 1H), 8.23 (d, J = 1.5 Hz, 1H), 8.12 (dd, J = 8.0, 1.5 Hz, 1H), 8.05 (s, 1H), 7.92 (d, J = 8.5 Hz, 1H), 7.61 (d, J = 7.5 Hz, 1H), 7.45 (d, J = 8.0 Hz, 1H), 2.49 (s, 3H), 1.5 (s, 6H); ESI-MS (m/z) 487 (MH)+ |

Example 76

Methyl-3-(4'-(2,6-difluorobenzmido)-6-methyl-[1,1'-biphenyl]-3-yl)-5-(2-methoxy-2-oxoethyl)-4,5-dihydroisoxazole-5-carboxylate

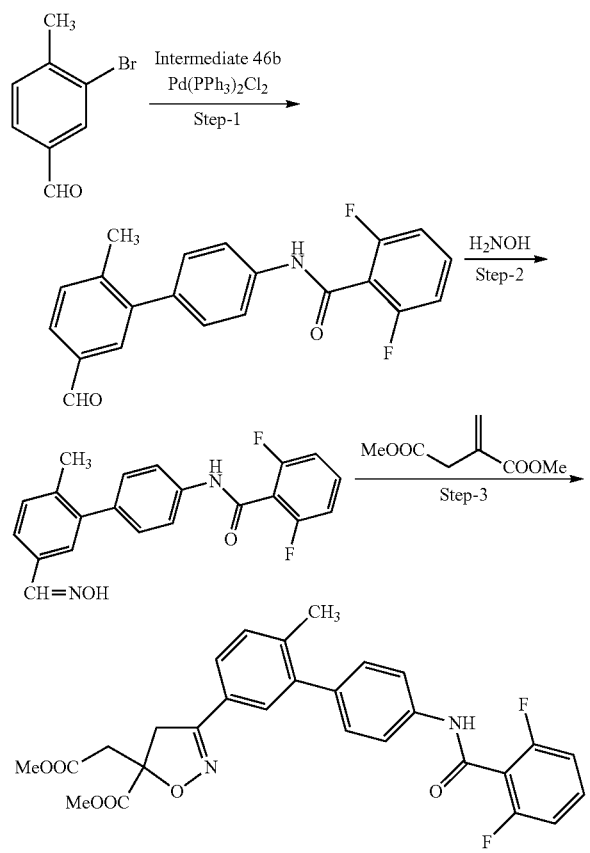

Example 76

Step-1: 2,6-Difluoro-N-(5'-formyl-2'-methyl-[1,1'-biphenyl]-4-yl)benzamide: To a stirred solution of 3-bromo-4-methylbenzaldehyde (1.40 g, 7.0 mmol, 1.0 eq) in dioxane (20 mL), the borate intermediate 46b (2.52 g, 1.27 mmol, 1.0 eq), aq sodium carbonate solution (2N, mL) and Pd(PPh$_3$)$_2$Cl$_2$ (246 mg, 0.35 mmol, 0.05 eq) were sequentially added. The resulting mixture was thoroughly deoxygenated by subjecting to vacuum/nitrogen cycle three times and then heated at 100° C. for 24 h under nitrogen atmosphere. The reaction mixture was cooled to room temperature and filtered through celite. The filtrate was concentrated under vacuum and the crude product was purified by flash column chromatography (silica gel, ethyl acetate in hexane system as eluent) to afford 1.70 g of the desired product as a white solid. $^1$HNMR (400 MHz, DMSO-d$_6$) δ 9.98 (s, 1H), 7.86 (s, 1H, D$_2$O exchangeable), 7.77-7.71 (m, 4H), 7.46-7.39 (m, 2H), 7.34 (d, J=8.5 Hz, 1H), 7.00 (t, J=8.0 Hz, 2H), 2.36 (s, 3H); ESI-MS (m/z) 352 (MH)$^+$.

Step-2: 2,6-Difluoro-N-(5'-((hydroxyimino)methyl)-2'-methyl-[1,1'-biphenyl]-4-yl)benzamide: To a 0° C. cooled solution of 2,6-difluoro-N-(5'-formyl-2'-methyl-[1,1'-biphenyl]-4-yl)benzamide (683 mg, 1 mmol, 1.0 eq) in methanol (30 mL) and hydroxylamine hydrochloride (168 mg, 2.4 mmol, 2.5 eq) in water (1 mL) was added drop wise a solution of sodium carbonate (123 mg, 1.14 mmol, 1.1 eq) in water (1.0 mL). The resulting mixture was stirred at room temperature for 1 h. The solvent was evaporated under vacuum and the residue was diluted with water (10 mL) and extracted with ethyl acetate (3×20 mL). The combined organic layers were dried (Na$_2$SO$_4$) and filtered. The filtrate was rotary evaporated to afford 650 mg of the title compound as a white solid. $^1$HNMR (400 MHz, DMSO-d$_6$) δ 8.13 (s, 1H), 7.71-7.68 (m, 3H), 7.48-7.43 (m, 3H), 7.35-7.28 (m, 3H), 7.03 (t, J=8.0 Hz, 2H), 2.29 (s, 3H); ESI-MS (m/z) 367 (MH)$^+$.

Step-3: Methyl-3-(4'-(2,6-difluorobenzmido)-6-methyl-[1,1'-biphenyl]-3-yl)-5-(2-methoxy-2-oxoethyl)-4,5-dihydroisoxazole-5-carboxylate: To a solution of 2,6-difluoro-N-(5'-((hydroxyimino)methyl)-2'-methyl-[1,1'-biphenyl]-4-yl)benzamide (400 mg, 1.0 mmol, 1.0 eq) in THF (15 mL) was added NCS (173 mg, 1.3 mmol, 1.3 eq) followed by pyridine (60 µL, 0.6 mmol, 0.6 eq). The resulting mixture was heated to 70° C. for 1h. The reaction was then cooled down to room temperature and dimethyl 2-methylenesuccinate (0.14 mL, 1.0 mmol, 1.0 eq) was added to the above mixture followed by triethyl amine (0.27 mL, 1.7 mmol, 1.7 eq). The resulting mixture was then further heated to 70° C. for 2 h. The reaction was cooled back down to room temperature and water (30 mL) was then added followed by ethyl acetate (20 mL). The layers were separated and the aqueous layer was extracted with ethyl acetate (2×10 mL). The combined organic layers were washed with brine (10 mL), dried (Na$_2$SO$_4$) and filtered. The filtrate was concentrated under vacuum and the crude product was purified by flash column chromatography (silica gel, ethyl acetate and hexane system as eluent) to afford 510 mg of the desired product as a white solid. $^1$HNMR (400 MHz, CDCl$_3$) δ 7.76 (s, 1H, D$_2$O exchangeable), 7.70 (d, J=8.5 Hz, 2H), 7.58 (d, J=8.0 Hz, 1H), 7.49 (s, 1H), 7.45-7.41 (m, 1H), 7.33-7.30 (m, 3H), 7.02 (t, J=8.0 Hz, 2H), 4.02 (d, J=17.0 Hz, 1H), 3.81 (s, 3H), 3.70 (s, 3H), 3.49 (d, J=17.0 Hz, 1H), 3.26 (d, J=17.5 Hz, 1H), 2.98 (d, J=17.5 Hz, 1H), 2.30 (s, 3H); ESI-MS (m/z) 523 (MH)$^+$.

Example 77

Methyl 3-(3-(5-(2,6-difluorobenzamido)pyrazin-2-yl)-4-methylphenyl)-5-(2-methoxy-2-oxoethyl)-4,5-dihydroisoxazole-5-carboxylate

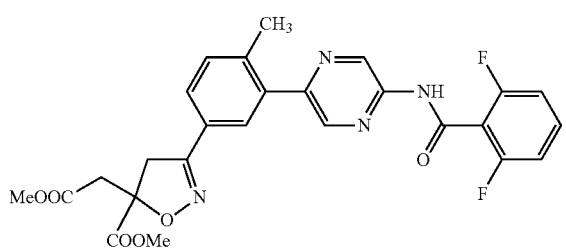 [SMILES: COC(=O)CC1(C(=O)OC)CC(c2ccc(C)c(-c3cnc(NC(=O)c4c(F)cccc4F)cn3)c2)=NO1]

The title compound was prepared by following the procedure similar to that described in Example 76. ¹HNMR (400 MHz, DMSO-d6) δ 11.82 (s, 1H, D₂O exchangeable), 9.51 (s, 1H), 8.71 (s, 1H), 7.75 (d, J=1.5 Hz, 1H), 7.71 (dd, J=8.0, 1.5 Hz, 1H), 7.65-7.60 (m, 1H), 7.46 (d, J=8.0 Hz, 1H), 7.27 (t, J=8.0 Hz, 2H), 3.96 (d, J=17.0 Hz, 1H), 3.71 (d, J=17.0 Hz, 1H), 3.71 (s, 3H), 3.61 (s, 3H), 3.20 (d, J=17.0 Hz, 1H), 3.13 (d, J=17.0 Hz, 1H), 2.42 (s, 3H); ESI-MS (m/z) 525 (MH)⁺.

Example 77A 2,6-Difluoro-N-(5-(2-methyl-5-(4-oxo-3a,4,5,6,7,7a-hexahydrobenzo[d]isoxazol-3-yl)phenyl)pyrazin-2-yl)benzamide

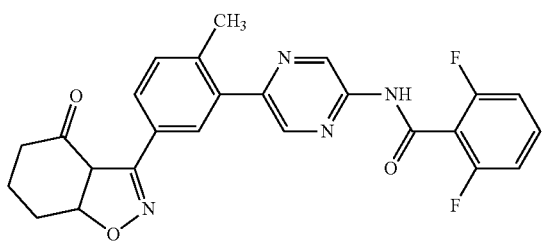 [SMILES: Cc1ccc(C2=NOC3CCCC(=O)C23)cc1-c1cnc(NC(=O)c2c(F)cccc2F)cn1]

The title compound was prepared by following the procedure similar to that described in Example 76 by using cyclohex-2-en-1-one in place of dimethyl 2-methylenesuccinate in step-3. ¹HNMR (400 MHz, CDC₃) δ 9.76 (s, 1H), 8.56 (s, 1H, D₂O exchangeable), 8.40 (s, 1H), 7.83 (d, J=2.0 Hz, 1H), 7.43 (dd, J=8.0, 2.0 Hz, 1H), 7.52-7.49 (m, 1H), 7.36 (d, J=8.0 Hz, 1H), 7.07 (t, J=7.5 Hz, 2H), 5.14-5.13 (m, 1H), 4.29 (d, J=9.5 Hz, 1H), 2.50-2.39 (m, 2H), 2.47 (s, 3H), 2.30-2.26 (m, 1H), 2.17-2.12 (m, 1H), 2.00-1.93 (m, 2H); ESI-MS (m/z) 463 (MH)⁺.

Example 78

2-Chloro-N-(5-(5-(5,5-dimethyl-4-oxo-4,5-dihydroisoxazol-3-yl)-2-methylphenyl)pyrazin-2-yl)benzamide

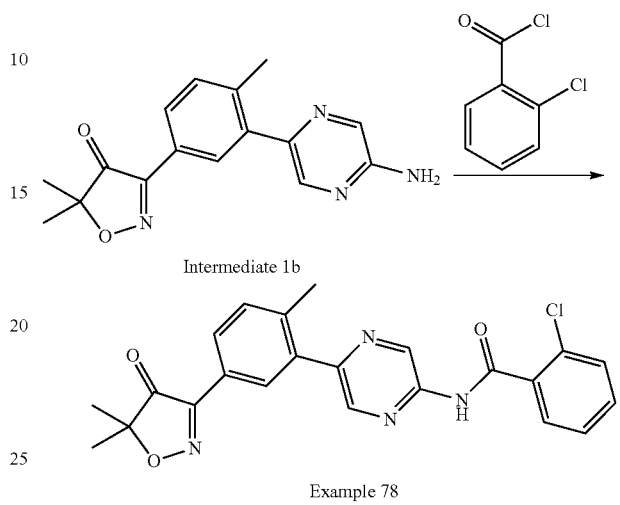

To a 0° C. cooled and stirred, solution of 2-chlorobenzoyl chloride (43 μL, 0.34 mmol, 1.0 eq) in DCM (2 mL) was added drop wise a solution of Intermediate 1b, (100 mg, 0.34 mmol, 1.0 eq) in DCM (5 mL) followed by pyridine (47 μL, 0.44 mmol, 1.3 eq). The resulting mixture was stirred at room temperature for 15 h. The reaction was diluted with DCM (10 mL), and washed with 10% hydrochloric acid (5 mL), dried (Na₂SO₄) and filtered. The filtrate was concentrated under vacuum and the crude product was purified by flash column chromatography (silica gel, ethyl acetate in hexane as eluent) to afford 50 mg of the title product as a white solid. ¹HNMR (400 MHz, CDCl₃) δ 9.78 (s, 1H), 8.80 (s, 1H, D₂O exchangeable), 8.39 (s, 1H), 8.19 (d, J=2.0 Hz, 1H), 8.09 (dd, J=8.0, 2.0 Hz, 1H), 7.84 (dd, J=7.0, 1.5 Hz, 1H), 7.52-7.40 (m, 4H), 2.47 (s, 3H), 1.48 (s, 6H); ESI-MS (m/z) 435, 437 [(MH)⁺, Cl³⁵,³⁷].

The below Examples 79 to 83 were prepared by following a procedure similar to that described in Example 78:

| Example No: IUPAC name | Structure | ¹H NMR/ESI-MS (MH)⁺ |
|---|---|---|
| Example 79: N-(5-(5-(5,5-dimethyl-4-oxo-4,5-dihydroisoxazol-3-yl)-2-methylphenyl)pyrazin-2-yl)-2-fluoro-6-(trifluoromethyl)benzamide | 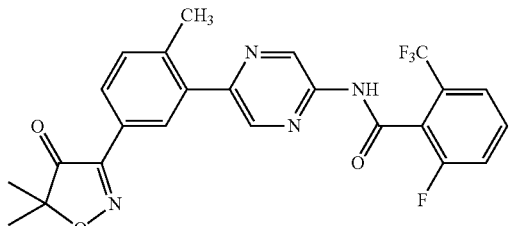 | ¹HNMR (400 MHz, CDCl₃) δ 9.74 (s, 1H), 8.40 (s, 1H, D₂O exchangeable), 8.37 (s, 1H), 8.17 (d, J = 1.5 Hz, 1H), 8.09 (dd, J = 8.0, 2.0 Hz, 1H), 7.64-7.59 (m, 2H), 7.46-7.42 (m, 2H), 2.47 (s, 3H), 1.48 (s, 6H); ESI-MS (m/z) 487 (MH)⁺ |
| Example 80: 2-Chloro-N-(5-(5-(5,5-dimethyl-4-oxo-4,5-dihydroisoxazol-3-yl)-2-methylphenyl)pyrazin-2-yl)-6-fluorobenzamide | 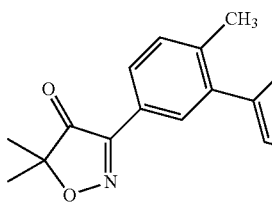 | ¹HNMR (400 MHz, CDCl₃) δ 9.79 (s, 1H), 8.56 (s, 1H, D₂O exchangeable), 8.32 (s, 1H), 8.16 (d, J = 1.5 Hz, 1H), 8.10 (dd, J = 8.0, 2.0 Hz, 1H), 7.43 (d, J = 8.0 Hz, 1H), 7.41-7.38 (m, 1H), 7.31 (d, J = 8.0 Hz, 1H), 7.14 (t, J = 8.0 Hz, 1H), 2.46 (s, 3H), 1.48 (s, 6H); ESI-MS (m/z) 453, 455 [(MH)⁺, (Cl³⁵,³⁷)] |

| Example No: IUPAC name | Structure | ¹H NMR/ESI-MS (MH)⁺ |
|---|---|---|
| Example 81: N-(5-(5-(5,5-dimethyl-4-oxo-4,5-dihydroisoxazol-3-yl)-2-methylphenyl)pyrazin-2-yl)-2-methoxybenzamide | 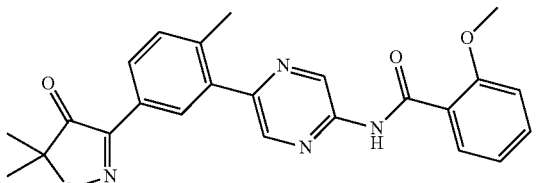 | ¹HNMR (400 MHz, CDCl₃) δ 10.48 (s, 1H, D₂O exchangeable), 9.83 (s, 1H), 8.46 (s, 1H), 8.32 (dd, J = 1.5, 7.5 Hz, 1H), 8.20 (d, J = 2.0 Hz, 1H), 8.08 (dd, J = 8.0, 2.0 Hz, 1H), 7.57 (ddd, J = 1.5, 7.5, 9.0 Hz, 1H), 7.42 (d, J = 8.0 Hz, 1H), 7.17 (dt, J = 8.0, 1.0 Hz, 1H), 7.09 (d, J = 8.5 Hz, 1H), 4.13 (s, 3H), 2.47 (s, 3H), 1.48 (s, 6H); ESI-MS (m/z) 431 (MH)⁺ |
| Example 82: N-(5-(5-(5,5-dimethyl-4-oxo-4,5-dihydroisoxazol-3-yl)-2-methylphenyl)pyrazin-2-yl)cyclohexanecarboxamide | 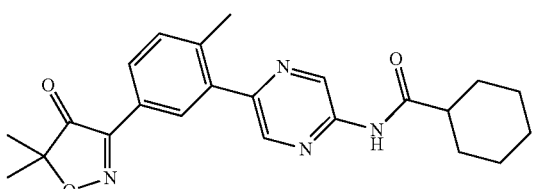 | ¹HNMR (400 MHz, DMSO-d6) δ 10.81 (s, 1H, D₂O exchangeable), 9.44 (s, 1H), 8.59 (s, 1H), 8.06 (d, J = 2.0 Hz, 1H), 7.96 (dd, J = 8.0, 2.0 Hz, 1H), 7.51 (d, J = 8.0 Hz, 1H), 2.59-2.55 (m, 1H), 2.41 (s, 3H), 1.85-1.64 (m, 5H), 1.46-1.37 (m, 2H), 1.42 (s, 6H), 1.39-1.18 (m, 3H); ESI-MS (m/z) 407 (MH)⁺ |
| Example 83: N-(5-(5-(5,5-dimethyl-4-oxo-4,5-dihydroisoxazol-3-yl)-2-methylphenyl)pyrazin-2-yl)cyclopentanecarboxamide | 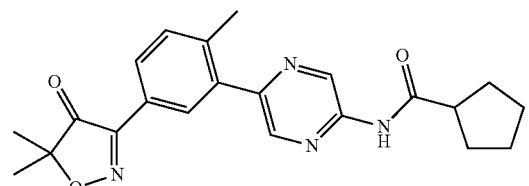 | ¹HNMR (400 MHz, CDCl₃) δ 9.62 (s, 1H), 8.38 (s, 1H), 8.16 (d, J = 2.0 Hz, 1H), 8.07 (dd, J = 8.0, 2.0 Hz, 1H), 7.91 (brs, 1H, D₂O exchangeable), 7.40 (d, J = 8.0 Hz, 1H), 2.83-2.79 (m, 1H), 2.43 (s, 3H), 2.04-1.93 (m, 4H), 1.84-1.79 (m, 2H), 1.68-1.64 (m, 2H), 1.47 (s, 6H); ESI-MS (m/z) 393 (MH)⁺ |

Example 84

N-(5-(2-(tert-butyl)-5-(5,5-dimethyl-4-oxo-4,5-dihydroisoxazol-3-yl)phenyl)pyrazin-2-yl)-2,6-difluorobenzamide

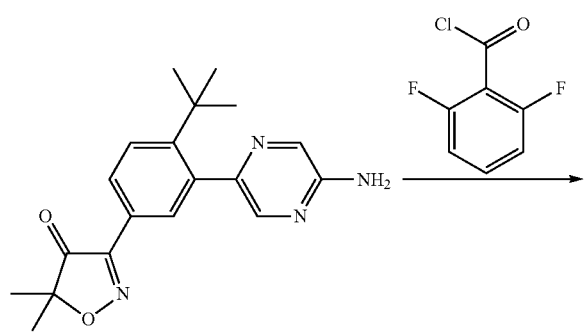

Intermediate 4b

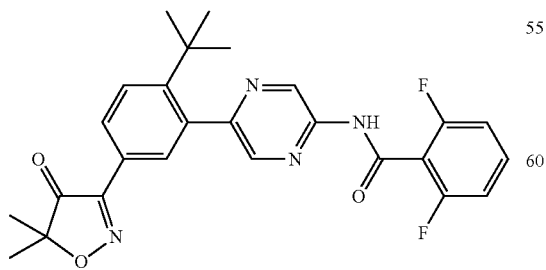

Example 84

To a 0° C. cooled and stirred, solution of 2,6-difluorobenzoyl chloride (0.083 mL, 0.66 mmol, 1.5 eq) in DCM (200 mL) was added drop wise a solution of 3-(3-(5-aminopyrazin-2-yl)-4-(tert-butyl)phenyl)-5,5-dimethylisoxazol-4(5H)-one, Intermediate 4b, (150 mg, 0.44 mmol, 1.0 eq) in DCM (50 mL) followed by pyridine (0.053 mL, 0.66 mmol, 1.5 eq). The resulting mixture was stirred at room temperature for 2 h. The reaction was diluted with DCM (100 mL), and washed with 10% hydrochloric acid (100 mL), dried (Na₂SO₄) and filtered. The filtrate was concentrated under vacuum and the crude product was purified by flash column chromatography (silica gel, 10% ethyl acetate in hexane) to afford 40 mg of the title product as a white solid. ¹HNMR (400 MHz, CDCl₃) δ 9.72 (s, 1H), 8.55 (s, 1H, D₂O exchangeable), 8.28 (s, 1H), 8.14 (dd, J=9.0, 2.5 Hz, 1H), 7.86 (s, 1H), 7.70 (d, J=8.5 Hz, 1H), 7.52-7.45 (m, 1H), 7.07 (t, J=8.5 Hz, 2H), 1.43 (s, 6H), 1.23 (s, 9H); ESI-MS (m/z) 479 (MH)⁺.

Example 85

N-(5-(3-(5,5-Dimethyl-4-oxo-4,5-dihydroisoxazol-3-yl)-2-methoxyphenyl)pyrazin-2-yl)-2,6-difluorobenzamide

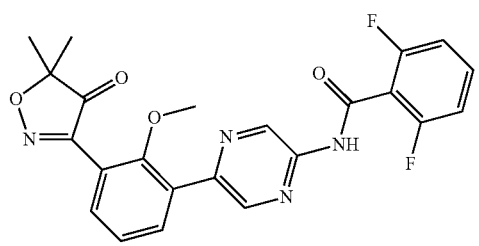 [SMILES: COc1c(C2=NOC(C)(C)C2=O)cccc1-c1cnc(NC(=O)c2c(F)cccc2F)cn1]

The title compound was prepared by following a procedure similar to that described in Example 84 by using intermediate 12b and 2,6-difluorobenzoyl chloride. ¹HNMR (400 MHz, CDCl₃) δ 9.81 (s, 1H), 8.89 (s, 1H), 8.55 (s, 1H, D₂O exchangeable), 7.98 (dd, J=7.5, 1.5 Hz, 1H), 7.72 (dd, J=7.5, 1.5 Hz, 1H), 7.54-7.47 (m, 1H), 7.39 (t, J=7.5 Hz, 1H), 7.07 (t, J=8.0 Hz, 2H), 3.57 (s, 3H), 1.54 (s, 6H); ESI-MS (m/z) 453 (MH)⁺.

The title compound was prepared by following a procedure similar to that described in Example 84 by using intermediate 5 and 2,6-difluorobenzoyl chloride. ¹HNMR (400 MHz, CDCl₃) δ 9.78 (s, 1H), 8.68 (s, 1H), 8.58 (s, 1H, D₂O exchangeable), 8.29 (d, J=1.5 Hz, 1H), 8.15 (dd, J=8.0, 1.5 Hz, 1H), 7.76 (d, J=8.0 Hz, 1H), 7.51-7.43 (m, 1H), 7.04 (t, J=8.5 Hz, 2H) 1.49 (s, 6H); ESI-MS (m/z) 457, 459 (MH)⁺, Cl³⁵,³⁷]

Example 86

N-(5-(2-chloro-5-(5,5-dimethyl-4-oxo-4,5-dihydroisoxazol-3-yl)phenyl)pyrazin-2-yl)-2,6-difluorobenzamide

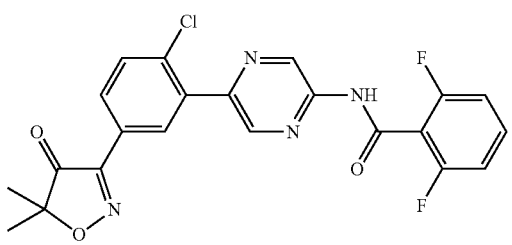 [SMILES: CC1(C)ON=C(c2ccc(Cl)c(-c3cnc(NC(=O)c4c(F)cccc4F)cn3)c2)C1=O]

Example 87-96

The below Examples 87 to 96 were prepared by following a procedure similar to that described in Example 84 by taking the corresponding intermediate and suitably substituted benzoyl chloride as given in the Scheme below.

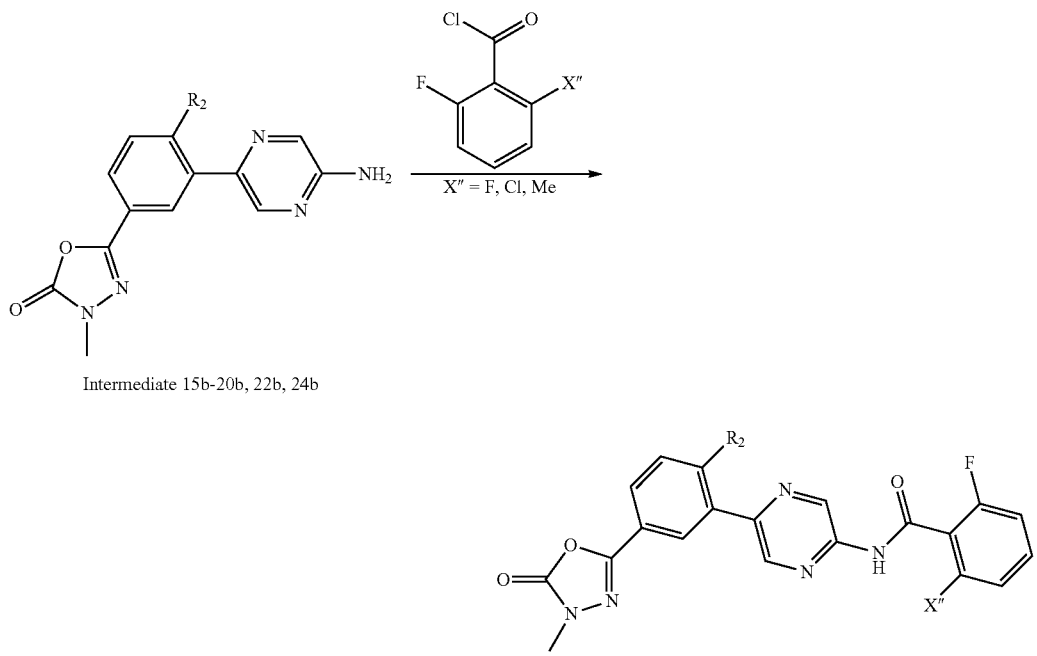

| Example: IUPAC name | Structure | ¹HNMR/ESI-MS (MH)⁺ |
|---|---|---|
| Example 87: 2,6-Difluoro-N-(5-(2-methyl-5-(4-methyl-5-oxo-4,5-dihydro-1,3,4-oxadiazol-2-yl)phenyl)pyrazin-2-yl)benzamide | 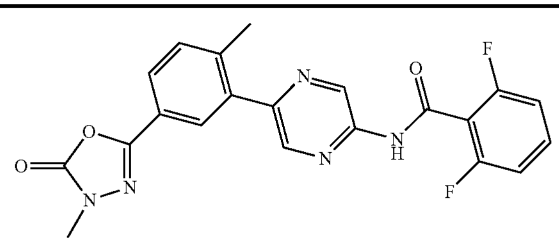 | ¹HNMR (400 MHz, DMSO-d6) δ 11.84 (s, 1H, D₂O exchangeable), 9.53 (s, 1H), 8.73 (s, 1H), 7.89 (s, 1H), 7.80 (d, J = 8.0 Hz, 1H), 7.65-7.59 (m, 1H), 7.56 (d, J = 8.0 Hz, 1H), 7.27 (t, J = 8.5 Hz, 2H), 3.42 (s, 3H), 2.46 (s, 3H); ESI-MS (m/z) 424 (MH)⁺. |

-continued

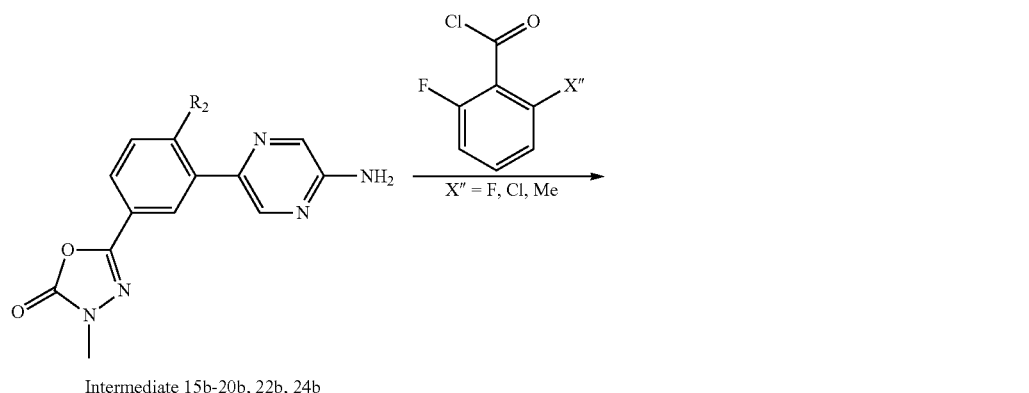

Intermediate 15b-20b, 22b, 24b

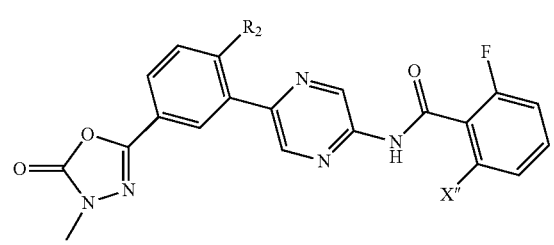

Examples 87-96

| Example: IUPAC name | Structure | ¹HNMR/ESI-MS (MH)⁺ |
|---|---|---|
| Example 88: N-(5-(5-(4-Ethyl-5-oxo-4,5-dihydro-1,3,4-oxadiazol-2-yl)-2-methylphenyl)pyrazin-2-yl)-2,6-difluorobenzamide | 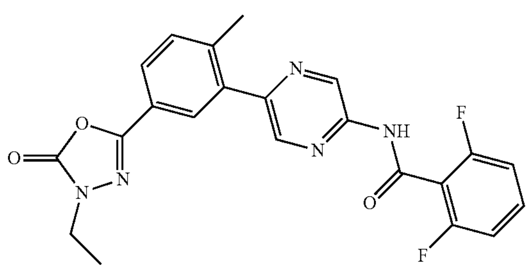 [SMILES: CCn1nc(-c2ccc(C)c(-c3cnc(NC(=O)c4c(F)cccc4F)cn3)c2)oc1=O] | ¹HNMR (400 MHz, DMSO-d6) δ 11.84 (s, 1H, $D_2O$ exchangeable), 9.53 (s, 1H), 8.73 (s, 1H), 7.89 (s, 1H), 7.80 (d, J = 8.0 Hz, 1H), 7.65-7.59 (m, 1H), 7.56 (d, J = 8.0 Hz, 1H), 7.27 (t, J = 8.5 Hz, 2H), 3.78 (q, J = 7.0 Hz, 2H), 2.45 (s, 3H), 1.30 (t, J = 7.0 Hz, 3H); ESI-MS (m/z) 438 (MH)⁺. |
| Example 89: 2,6-Difluoro-N-(5-(2-methyl-5-(5-oxo-4-propyl-4,5-dihydro-1,3,4-oxadiazol-2-yl)phenyl)pyrazin-2-yl)benzamide | 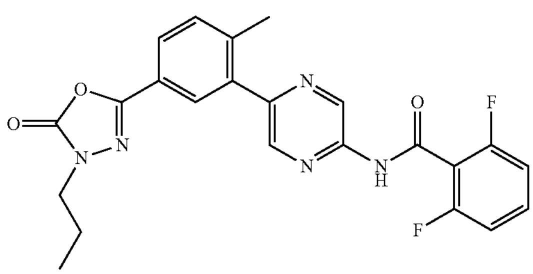 [SMILES: CCCn1nc(-c2ccc(C)c(-c3cnc(NC(=O)c4c(F)cccc4F)cn3)c2)oc1=O] | ¹HNMR (400 MHz, DMSO-d6) δ 11.84 (s, 1H, $D_2O$ exchangeable, 9.53 (s, 1H), 8.73 (s, 1H), 7.90 (d, J = 2.0 Hz, 1H), 7.80 (dd, J = 8.0, 2.0 Hz, 1H), 7.66-7.59 (m, 1H), 7.56 (d, J = 8.0 Hz, 1H), 7.27 (t, J = 8.5 Hz, 2H), 3.71 (t, J = 7.0 Hz, 2H), 2.46 (s, 3H), 1.74 (q, J = 7.0 Hz, 2H), 0.91 (t, J = 7.0 Hz, 3H); ESI-MS (m/z) 452 (MH)⁺. |
| Example 90: N-(5-(2-Ethyl-5-(4-methyl-5-oxo-4,5-dihydro-1,3,4-oxadiazol-2-yl)phenyl)pyrazin-2-yl)-2,6-difluorobenzamide | 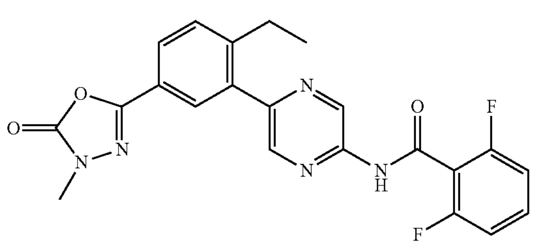 [SMILES: CCc1ccc(-c2nn(C)c(=O)o2)cc1-c1cnc(NC(=O)c2c(F)cccc2F)cn1] | ¹HNMR (400 MHz, CDCl₃) δ 9.78 (s, 1H), 8.62 (s, 1H, $D_2O$ exchangeable), 8.39 (s, 1H), 7.86-7.83 (m, 2H), 7.53-7.46 (m, 2H), 7.07 (t, J = 8.5 Hz, 2H), 3.51 (s, 3H), 2.80 (q, J = 7.0 Hz, 2H), 1.18 (t, J = 7.5 Hz, 3H); ESI-MS (m/z) 438 (MH)⁺ |

-continued

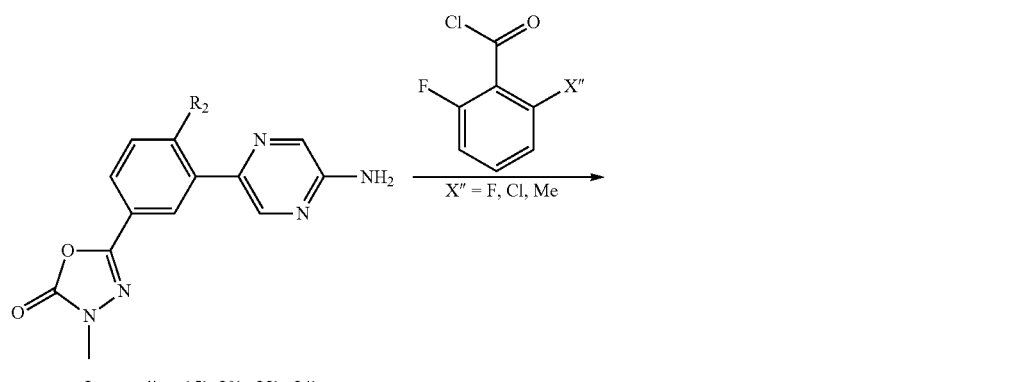

Intermediate 15b-20b, 22b, 24b

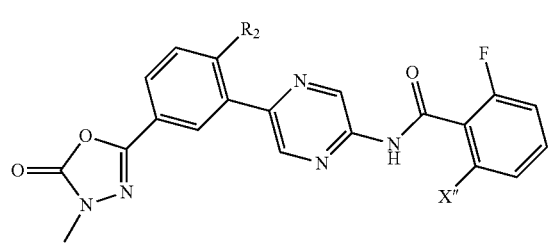

Examples 87-96

| Example: IUPAC name | Structure | $^1$HNMR/ESI-MS (MH)+ |
|---|---|---|
| Example 91: 2-Chloro-N-(5-(2-ethyl-5-(4-methyl-5-oxo-4,5-dihydro-1,3,4-oxadiazol-2-yl)phenyl)pyrazin-2-yl)-6-fluorobenzamide | 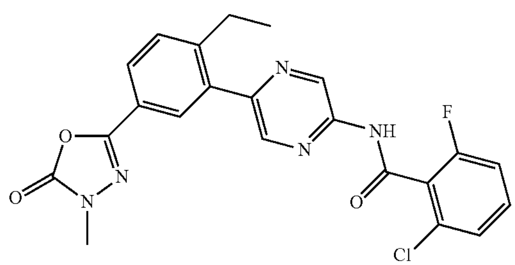 [SMILES: CCc1ccc(-c2nn(C)c(=O)o2)cc1-c1cnc(NC(=O)c2c(F)cccc2Cl)cn1] | $^1$HNMR (400 MHz, CdCl$_3$) δ 9.78 (s, 1H)), 8.38 (s, 1H, D$_2$O exchangeable), 8.37 (s, 1H), 7.86 (d, J = 1.5 Hz, 1H), 7.84 (s, 1H), 7.48 (d, J = 8.5 Hz, 1H), 7.47-7.41 (m, 1H), 7.32 (d, J = 8.5 Hz, 1H), 7.18-7.14 (td, J = 8.5, 1.0 Hz, 1H), 3.51 (s, 3H), 2.82-2.78 (q, J = 7.5 Hz, 2H), 1.18 (t, J = 7.5 Hz, 3H); ESI-MS (m/z) 454, 456 [(MH)+, Cl$^{35,37}$] |
| Example 92: N-(5-(2-Ethyl-5-(4-methyl-5-oxo-4,5-dihydro-1,3,4-oxadiazol-2-yl)phenyl)pyrazin-2-yl)-2-fluoro-6-methylbenzamide | 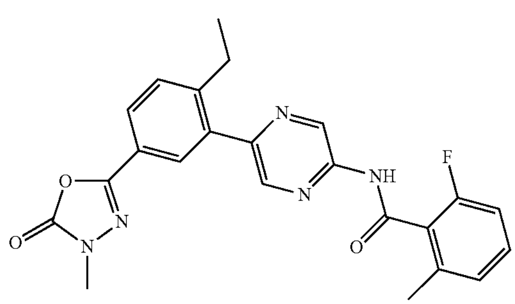 [SMILES: CCc1ccc(-c2nn(C)c(=O)o2)cc1-c1cnc(NC(=O)c2c(C)cccc2F)cn1] | $^1$HNMR (400 MHz, CDCl$_3$) δ 9.78 (s, 1H), 8.45 (s, 1H, D$_2$O exchangeable),8.31 (s, 1H), 7.85-7.82 (m, 2H), 7.47 (d, J = 8.5 Hz, 1H), 7.38-7.32 (m, 1H), 7.10 (d, J = 7.5 Hz, 1H), 7.02 (t, J = 8.5 Hz, 1H), 3.50 (s, 3H), 2.80 (q, J = 7.5 Hz, 2H), 2.52 (s, 3H), 1.17 (t, J = 7.5 Hz, 3H); ESI- MS (m/z) 434 (MH)+ |
| Example 93: 2,6-Difluoro-N-(5-(2-methoxy-5-(4-methyl-5-oxo-4,5-dihydro-1,3,4-oxadiazol-2-yl)phenyl)pyrazin-2-yl)benzamide | 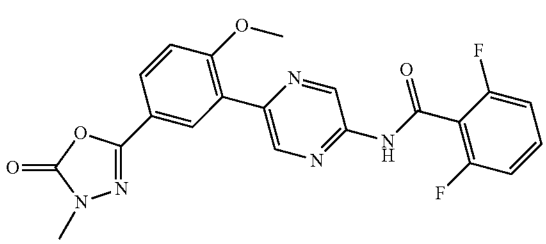 [SMILES: COc1ccc(-c2nn(C)c(=O)o2)cc1-c1cnc(NC(=O)c2c(F)cccc2F)cn1] | $^1$HNMR (400 MHz, DMSO-d6) δ 11.78 (s, 1H, D$_2$O exchangeable), 9.53 (s, 1H), 9.01 (s, 1H), 8.28 (d, J = 2.0 Hz, 1H), 7.88 (dd, J = 8.0, 2.0 Hz, 1H), 7.66-7.59 (m, 1H), 7.39 (d, J = 8.0 Hz, 1H), 7.27 (t, J = 8.5 Hz, 2H), 3.99 (s, 3H), 3.41 (s, 3H); ESI-MS (m/z) 440 (MH)+. |

-continued

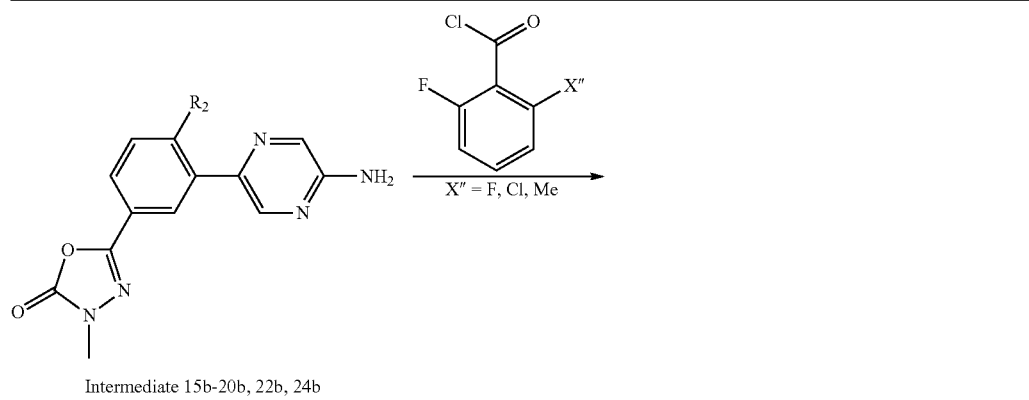

Intermediate 15b-20b, 22b, 24b

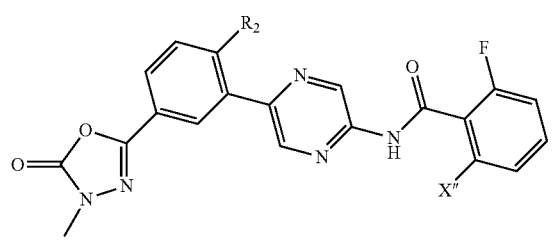

Examples 87-96

| Example: IUPAC name | Structure | $^1$HNMR/ESI-MS (MH)$^+$ |
|---|---|---|
| Example 94: 2,6-Difluoro-N-(5-(2-fluoro-5-(4-methyl-5-oxo-4,5-dihydro-1,3,4-oxadiazol-2-yl)phenyl)pyrazin-2-yl)benzamide | 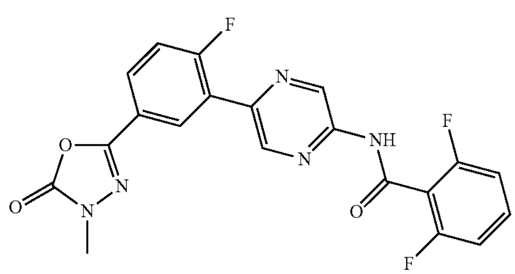 [SMILES: Cn1nc(-c2ccc(F)c(-c3cnc(NC(=O)c4c(F)cccc4F)cn3)c2)oc1=O] | $^1$HNMR (400 MHz, CDCl$_3$) δ 9.80 (s, 1H), 8.83 (t, J = 1.5 Hz, 1H), 8.62 (dd, J = 7.0, 2.0 Hz, 1H), 8.49 (s, 1H, D$_2$O exchangeable), 7.90-7.86 (m, 1H), 7.54-7.47 (m, 1H), 7.31 (dd, J = 11.0, 9.0 Hz, 1H), 7.07 (t, J = 8.5 Hz, 2H), 3.52 (s, 3H); ESI-MS (m/z) 428 (MH)$^+$. |
| Example 95: N-(5-(2-(difluoromethoxy)-5-(4-methyl-5-oxo-4,5-dihydro-1,3,4-oxadiazol-2-yl)phenyl)pyrazin-2-yl)-2,6-difluorobenzamide | 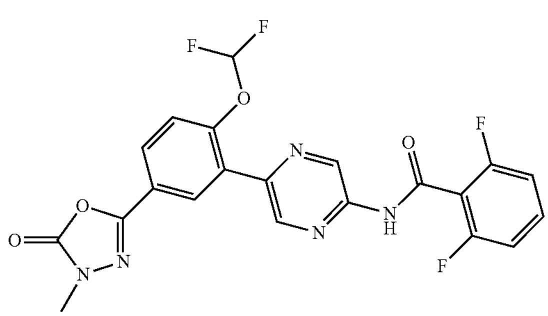 [SMILES: Cn1nc(-c2ccc(OC(F)F)c(-c3cnc(NC(=O)c4c(F)cccc4F)cn3)c2)oc1=O] | $^1$HNMR (400 MHz, CDCl$_3$) δ 9.82 (s, 1H), 8.78 (s, 1H), 8.48 (s, 1H, D$_2$O exchangeable), 8.43 (d, J = 2.5 Hz, 1H), 7.91 (dd, J = 8.5, 2.5 Hz, 1H), 7.54-7.50 (m, 1H), 7.38 (d, J = 8.0 Hz, 1H), 7.08 (t, J = 8.5 Hz, 2H), 6.64 (t, J = 73 Hz, 1H), 3.52 (s, 3H); ESI-MS (m/z) 476 (MH)$^+$. |
| Example 96: N-(5-(2-ethyl-3-(4-methyl-5-oxo-4,5-dihydro-1,3,4-oxadiazol-2-yl)phenyl)pyrazin-2-yl)-2,6-difluorobenzamide | 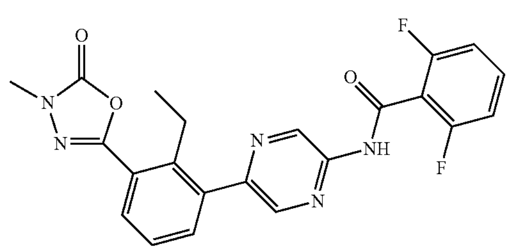 [SMILES: CCc1c(-c2cnc(NC(=O)c3c(F)cccc3F)cn2)cccc1-c1nn(C)c(=O)o1] | $^1$HNMR (400 MHz, CDCl$_3$) δ 9.78 (s,1H), 8.44 (s, 1H), 8.38 (d, J = 1.5 Hz, 1H), 7.89 (dd, J = 7.5, 1.5 Hz, 1H), 7.54-7.41 (m, 3H), 7.08 (t, J = 8.5 Hz, 2H), 3.55 (s, 3H), 3.03 (q, J = 7.5 Hz, 2H), 1.10 (t, J = 7.5 Hz, 3H); ESI-MS (m/z) 438 (MH)$^+$ |

Examples 97-118

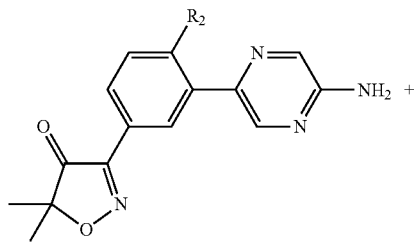

Intermediate 1b, 7b

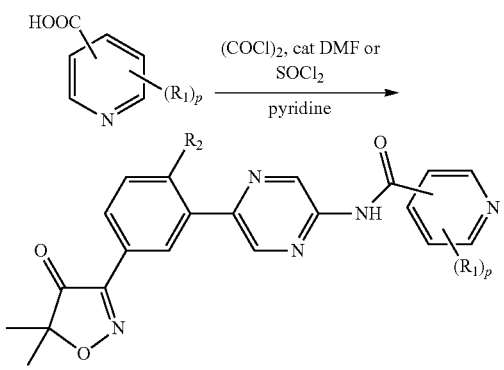

Examples (97-116)

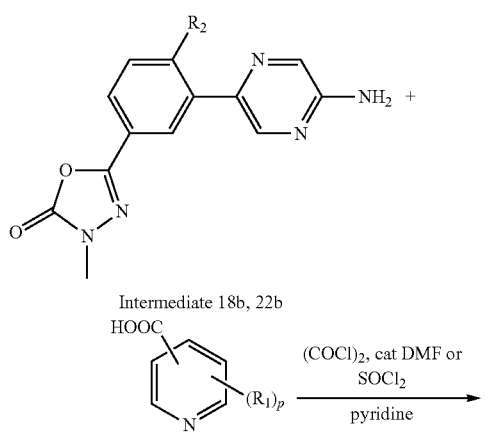

Intermediate 18b, 22b

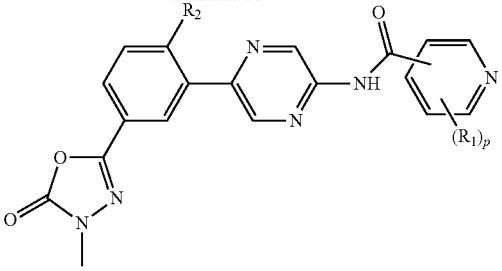

Examples (117-118)

Method A: To a stirred and cooled (0° C.) solution of a corresponding substituted pyridine carboxylic acid (0.44 mmol, 1.3 eq) in DCM (5 mL) was added oxalyl chloride (1.5 eq) followed by a catalytic amount of DMF. The resulting mixture was stirred at the same temperature for 2 h. The solvent and the excess of oxalyl chloride were removed under vacuum and the residue was dissolved in DCM. The resulting acid chloride solution was cooled to 0° C., and a solution of aminopyrazine intermediate (1.0 eq) in DCM was added followed by pyridine (1.5 eq). The reaction mixture was stirred at room temperature for 15 h. The reaction was diluted with DCM (10 mL) and the organic layer was washed with water (5 mL), brine (5 mL), dried ($Na_2SO_4$) and filtered. The filtrate was concentrated under reduced pressure and the crude product was purified by flash column chromatography (silica gel, ethyl acetate in hexane) to afford the desired product as a solid.

Method B: A mixture of a corresponding substituted pyridine carboxylic acid (0.37 mmol, 1.3 eq) and thionyl chloride (2 mL) was refluxed for 2 h. The excess of thionyl chloride was removed by evaporation under reduced pressure. The resulting acid chloride in DCM (3 mL) was added drop wise to a stirred and cooled (0° C.) solution of aminopyrazine intermediate (1.0 eq) and pyridine (1.5 eq) in DCM (5 mL). The resulting mixture was stirred at room temperature for 15 h. Work up and isolation as described in method A afforded the desired product as a white solid.

The below Examples-97 to 118 were prepared by following a procedure similar to that described in method A or method B by using corresponding intermediates 1b, 7b, 18b or 22b.

| Example No: IUPAC name | Structure | $^1$HNMR ESI-MS (MH)$^+$ |
|---|---|---|
| Example 97: N-(5-(5-(5,5-Dimethyl-4-oxo-4,5-dihydroisoxazol-3-yl)-2-methylphenyl)pyrazin-2-yl)picolinamide | 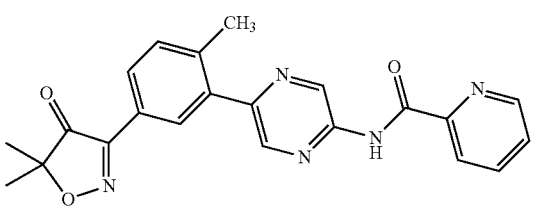 [SMILES: Cc1ccc(C2=NOC(C)(C)C2=O)cc1-c1cnc(NC(=O)c2ccccn2)cn1] | $^1$HNMR (400 MHz, DMSO-d6) δ 10.75 (s, 1H, $D_2O$ exchangeable), 9.61 (s, 1H), 8.80 (d, J = 4.5 Hz, 1H), 8.72 (s, 1H), 8.26 (d, J = 8.0 Hz, 1H), 8.15 (t, J = 8.0 Hz, 1H), 8.12 (s, 1H), 7.99 (d, J = 8.0 Hz, 1H), 7.77 (t, J = 5.0 Hz, 1H), 7.54 (d, J = 8.0 Hz, 1H), 2.45 (s, 3H), 1.43 (s, 6H); ESI-MS (m/z) 402 (MH)$^+$. |

| Example No: IUPAC name | Structure | ¹HNMR ESI-MS (MH)⁺ |
|---|---|---|
| Example 98: N-(5-(5-(5,5-Dimethyl-4-oxo-4,5-dihydroisoxazol-3-yl)-2-methylphenyl)pyrazin-2-yl)nicotinamide | 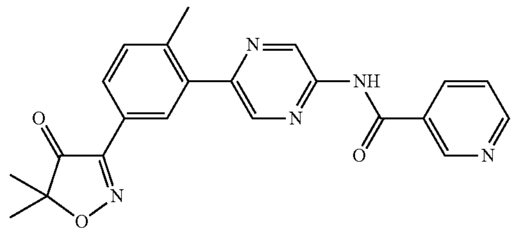 [SMILES: Cc1ccc(C2=NOC(C)(C)C2=O)cc1-c1cnc(NC(=O)c2cccnc2)cn1] | ¹HNMR (400 MHz, CDCl$_3$) δ 9.76 (s, 1H), 9.22 (d, J = 1.5, Hz, 1H), 8.86 (dd, J = 4.5, 1.5 Hz, 1H), 8.61 (s, 1H, D$_2$O exchangeable), 8.49 (s, 1H), 8.31 (td, J = 8.0, 2.0 Hz, 1H), 8.21 (d, J = 2.0 Hz, 1H), 8.10 (dd, J = 8.0, 2.0 Hz, 1H), 7.53 (ddd, J = 8.0, 4.5, 1.0 Hz, 1H), 7.42 (d, J = 8.0 Hz, 1H), 2.46 (s, 3H), 1.47 (s, 6H); ESI-MS (m/z) 402 (MH)⁺ |
| Example 99: N-(5-(5-(5,5-Dimethyl-4-oxo-4,5-dihydroisoxazol-3-yl)-2-methylphenyl)pyrazin-2-yl)isonicotinamide | 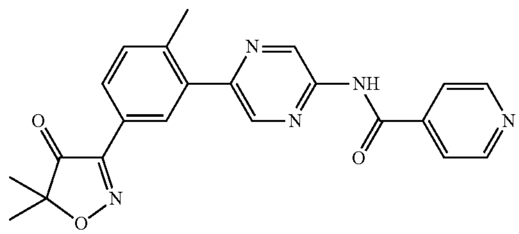 [SMILES: Cc1ccc(C2=NOC(C)(C)C2=O)cc1-c1cnc(NC(=O)c2ccncc2)cn1] | ¹HNMR (400 MHz, CDCl$_3$) δ 9.76 (s, 1H), 8.87 (dd, J = 1.5, 4.5 Hz, 2H), 8.63 (s, 1H, D$_2$O exchangeable), 8.47 (s, 1H), 8.19 (s, 1H), 8.08 (dd, J = 8.0, 2.0 Hz, 1H), 7.80 (dd, J = 1.5, 4.5 Hz, 2H), 7.42 (d, J = 8.0 Hz, 1H), 2.46 (s, 3H), 1.47 (s, 6H); ESI-MS (m/z) 402 (MH)⁺ |
| Example 100: N-(5-(5-(5,5-Dimethyl-4-oxo-4,5-dihydroisoxazol-3-yl)-2-methylphenyl)pyrazin-2-yl)-2-methylnicotinamide | 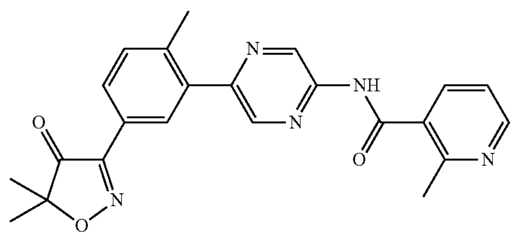 [SMILES: Cc1ccc(C2=NOC(C)(C)C2=O)cc1-c1cnc(NC(=O)c2cccnc2C)cn1] | ¹HNMR (400 MHz, CDCl$_3$) δ 9.76 (s, 1H), 8.65 (dd, J = 5.0, 1.5 Hz, 1H), 8.40 (s, 1H), 8.39 (s, 1H, D$_2$O exchangeable), 8.19 (d, J = 1.5 Hz, 1H), 8.09 (d, J = 8.0, 1.5 Hz, 1H), 7.90 (dd, J = 7.5, 1.5 Hz, 1H), 7.43 (d, J = 8.0 Hz, 1H), 7.18-7.15 (m, 1H), 2.80 (s, 3H), 2.47 (s, 3H), 1.48 (s, 6H); ESI-MS (m/z) 416 (MH)⁺. |
| Example 101: 6-Chloro-N-(5-(5-(5,5-dimethyl-4-oxo-4,5-dihydroisoxazol-3-yl)-2-methylphenyl)pyrazin-2-yl)nicotinamide | 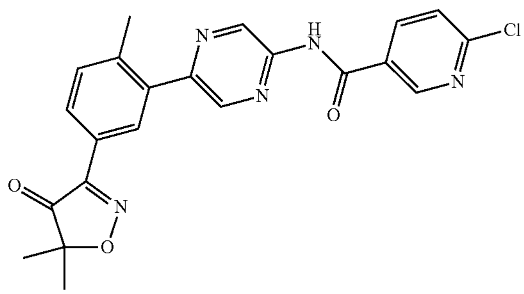 [SMILES: Cc1ccc(C2=NOC(C)(C)C2=O)cc1-c1cnc(NC(=O)c2ccc(Cl)nc2)cn1] | ¹HNMR (400 MHz, CDCl$_3$) δ 9.75 (s, 1H), 8.98 (d, J = 2.5 Hz, 1H), 8.53 (s, 1H, D$_2$O exchangeable), 8.48 (s, 1H), 8.26 (dd, J = 8.0, 2.5 Hz, 1H), 8.20 (d, J = 2.0 Hz, 1H), 8.10 (dd, J = 8.0, 2.0 Hz, 1H), 7.53 (d, J = 8.0 Hz, 1H), 7.44 (d, J = 8.0 Hz, 1H), 2.47 (s, 3H), 1.48 (s, 6H); ESI-MS (m/z) 436, 438 [(MH)⁺, Cl³⁵,³⁷] |
| Example 102: 6-Chloro-N-(5-(5-(5,5-dimethyl-4-oxo-4,5-dihydroisoxazol-3-yl)-2-methylphenyl)pyrazin-2-yl)isonicotinamide | 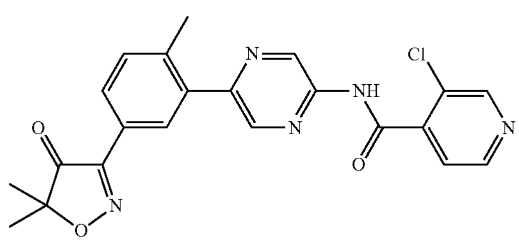 [SMILES: Cc1ccc(C2=NOC(C)(C)C2=O)cc1-c1cnc(NC(=O)c2ccncc2Cl)cn1] | ¹HNMR (400 MHz, CDCl$_3$) δ 9.75 (s, 1H), 8.78 (s, 1H), 8.75 (s, 1H, D$_2$O exchangeable), 8.70 (d, J = 4.5 Hz, 1H), 8.47 (s, 1H), 8.19 (d, J = 2.0 Hz, 1H), 8.10 (dd, J = 8.0, 2.0 Hz, 1H), 7.74 (d, J = 4.5 Hz, 1H), 7.43 (d, J = 8.0 Hz, 1H), 2.47 (s, 3H), 1.47 (s, 6H); ESI-MS (m/z) 436, 438 [(MH)⁺, Cl³⁵,³⁷] |
| Example 103: 3,5-Dichloro-N-(5-(5-(5,5-dimethyl-4-oxo-4,5-dihydroisoxazol-3-yl)-2-methylphenyl)pyrazin-2-yl)isonicotinamide | 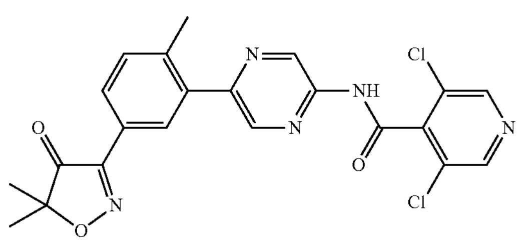 [SMILES: Cc1ccc(C2=NOC(C)(C)C2=O)cc1-c1cnc(NC(=O)c2c(Cl)cncc2Cl)cn1] | ¹HNMR (400 MHz, CDCl$_3$) δ 9.74 (s, 1H), 8.63 (s, 2H), 8.46 (s, 1H), 8.19 (s, 1H + 1H, D$_2$O exchangeable), 8.10 (d, J = 8.0, 1.5 Hz, 1H), 7.43 (d, J = 8.0 Hz, 1H), 2.47 (s, 3H), 1.47 (s, 6H); ESI-MS (m/z) 470, 472, 474 [(MH)⁺, Cl³⁵,³⁷] |

| Example No: IUPAC name | Structure | ¹HNMR ESI-MS (MH)⁺ |
| --- | --- | --- |
| Example 104: 4-Chloro-N-(5-(5-(5,5-dimethyl-4-oxo-4,5-dihydroisoxazol-3-yl)-2-methylphenyl)pyrazin-2-yl)nicotinamide | 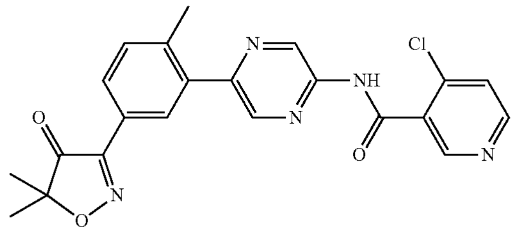 [SMILES: Cc1ccc(C2=NOC(C)(C)C2=O)cc1-c1cnc(NC(=O)c2cnccc2Cl)cn1] | ¹HNMR (400 MHz, CDCl₃) δ 9.76 (s, 1H), 9.05 (s, 1H), 8.67 (d, J = 5.5 Hz, 2H), 8.47 (s, 1H), 8.20 (s, 1H), 8.10 (dd, J = 8.0, 2.0 Hz, 1H), 7.48 (d, J = 5.5 Hz, 1H), 7.43 (d, J = 8.0 Hz, 1H), 2.47 (s, 3H), 1.46 (s, 6H); ESI-MS (m/z) 436, 438 [(MH)⁺, Cl³⁵,³⁷] |
| Example 105: N-(5-(5-(5,5-dimethyl-4-oxo-4,5-dihydroisoxazol-3-yl)-2-methylphenyl)pyrazin-2-yl)-6-methylnicotinamide | 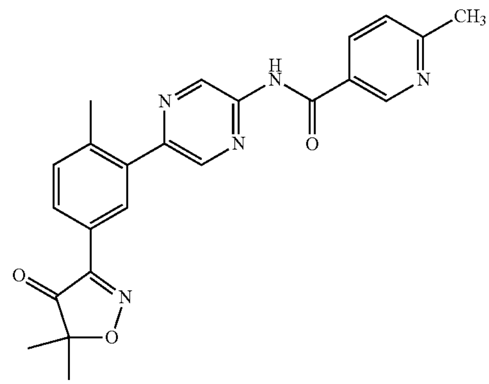 [SMILES: Cc1ccc(C(=O)Nc2cnc(-c3cc(C4=NOC(C)(C)C4=O)ccc3C)cn2)cn1] | ¹HNMR (400 MHz, CDCl₃) δ 9.77 (s, 1H), 9.09 (d, J = 2.0 Hz, 1H), 8.56 (s, 1H, D₂O exchangeable), 8.47 (s, 1H), 8.20 (d, J = 2.0 Hz, 1H), 8.18 (dd, J = 8.0, 2.0 Hz, 1H), 8.09 (dd, J = 8.0, 2.0 Hz, 1H), 7.43 (d, J = 8.0 Hz, 1H), 7.35 (d, J = 8.0 Hz, 1H), 2.68 (s, 3H), 2.47 (s, 3H), 1.47 (s, 6H); ESI-MS (m/z) 416 (MH)⁺ |
| Example 106: 5-Chloro-N-(5-(5-(5,5-dimethyl-4-oxo-4,5-dihydroisoxazol-3-yl)-2-methylphenyl)pyrazin-2-yl)nicotinamide | 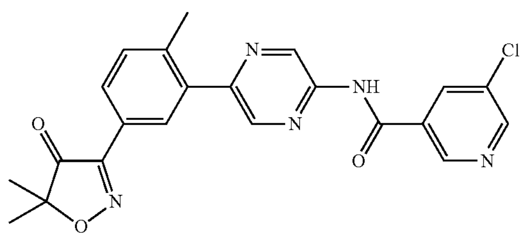 [SMILES: Cc1ccc(C2=NOC(C)(C)C2=O)cc1-c1cnc(NC(=O)c2cncc(Cl)c2)cn1] | ¹HNMR (400 MHz, CDCl₃) δ 9.77 (s, 1H), 9.09 (s, 1H), 8.83 (d, J = 2.5 Hz, 1H), 8.68 (s, 1H, D₂O exchangeable), 8.52 (d, J = 1.5 Hz, 1H), 8.33 (t, J = 2.0 Hz, 1H), 8.23 (d, J = 1.5 Hz, 1H), 8.12 (dd, J = 8.0, 1.5 Hz, 1H), 7.46 (d, J = 8.0 Hz, 1H), 2.50 (s, 3H), 1.49 (s, 6H); ESI-MS (m/z) 436, 438 [(MH)⁺, Cl³⁵,³⁷] |
| Example 107: N-(5-(5-(5,5-dimethyl-4-oxo-4,5-dihydroisoxazol-3-yl)-2-methylphenyl)pyrazin-2-yl)-3-fluoroisonicotinamide | 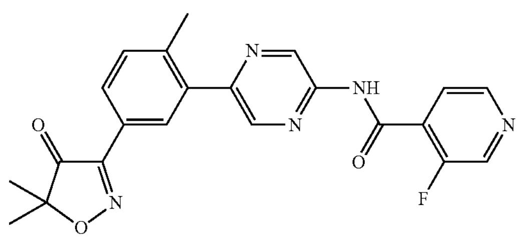 [SMILES: Cc1ccc(C2=NOC(C)(C)C2=O)cc1-c1cnc(NC(=O)c2ccncc2F)cn1] | ¹HNMR (400 MHz, CDCl₃) δ 9.76 (s, 1H), 9.07 (d, J = 12.5 Hz, 1H), 8.73 (d, J = 2.0 Hz, 1H), 8.69 (dd, J = 5.0, 1.0 Hz, 1H), 8.49 (s, 1H), 8.20 (d, J = 2.0 Hz, 1H), 8.09 (dd, J = 8.0, 2.0 Hz, 1H), 8.05 (dd, J = 6.5, 5.0 Hz, 1H), 7.43 (d, J = 8.0 Hz, 1H), 2.46 (s, 3H), 1.47 (s, 6H); ESI-MS (m/z) 420 (MH)⁺ |
| Example 108: N-(5-(5-(5,5-dimethyl-4-oxo-4,5-dihydroisoxazol-3-yl)-2-methylphenyl)pyrazin-2-yl)-5-fluoronicotinamide | 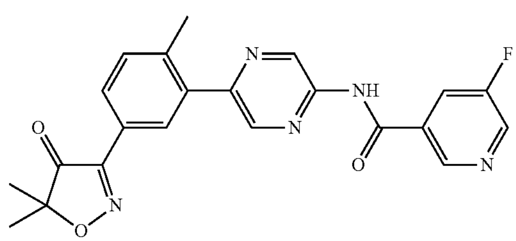 [SMILES: Cc1ccc(C2=NOC(C)(C)C2=O)cc1-c1cnc(NC(=O)c2cncc(F)c2)cn1] | ¹HNMR (400 MHz, CDCl₃) δ 9.77 (s, 1H), 9.19 (d, J = 13.5 Hz, D₂O exchangeable, 1H), 8.71 (dt, J = 7.5, 2.0 Hz, 1H), 8.51 (s, 1H), 8.47-8.45 (m, 1H), 8.21 (d, J = 2.0 Hz, 1H), 8.10 (dd, J = 8.0, 2.0 Hz, 1H), 7.50-7.47 (m, 1H), 7.43 (d, J = 8.0 Hz, 1H), 2.47 (s, 3H), 1.48 (s, 6H); ESI-MS (m/z) 420 (MH)⁺. |
| Example 109: N-(5-(5-(5,5-dimethyl-4-oxo-4,5-dihydroisoxazol-3-yl)-2-methylphenyl)pyrazin-2-yl)-2-fluoronicotinamide | 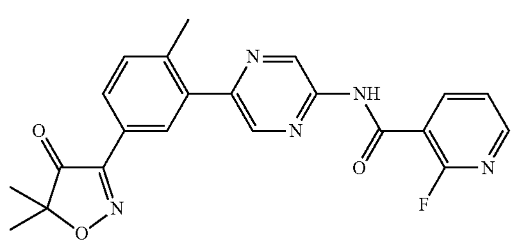 | ¹HNMR (400 MHz, CDCl₃) δ 9.79 (s, 1H), 9.23 (d, J = 14 Hz, D₂O exchangeable, 1H), 8.72 (dt, J = 8.0, 2.0 Hz, 1H), 8.53 (s, 1H), 8.48 (d, J = 4.5 Hz, 1H), 8.23 (s, 1H), 8.11 (dd, J = 8.0, 2.0 Hz, 1H), 7.52-7.48 (m, 1H), 7.45 (d, J = 8.0 Hz, 1H), 2.49 (s, 3H), 1.50 (s, 6H); ESI-MS (m/z) 420 (MH)⁺ |

| Example No: IUPAC name | Structure | ¹HNMR ESI-MS (MH)⁺ |
|---|---|---|
| Example 110: 2-Chloro-N-(5-(5-(5,5-dimethyl-4-oxo-4,5-2-methylphenyl) pyrazin-2-yl)isonicotinamide | 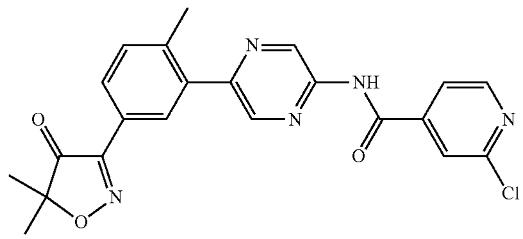 [SMILES: Cc1ccc(C2=NOC(C)(C)C2=O)cc1-c1cnc(NC(=O)c2ccnc(Cl)c2)cn1] | 436 ¹HNMR (400 MHz, CDCl₃) δ 9.77 (s, 1H), 8.67 (dd, J = 1.0, 5.0 Hz, 1H), 8.63 (s, 1H, D₂O exchangeable), 8.52 (s, 1H), 8.23 (d, J = 2.0 Hz, 1H), 8.13 (dd, J = 8.0, 2.0 Hz, 1H), 7.90 (dd, J = 1.5, 1.0 Hz, 1H), 7.75 (dd, J = 5.0, 1.0 Hz, 1H), 7.46 (d, J = 8.0 Hz, 1H), 2.46 (s, 3H), 1.47 (s, 6H); ESI-MS (m/z) 436, 438 [(MH)⁺, Cl³⁵,³⁷] |
| Example 111: 2-Chloro-N-(5-(5-(5,5-dimethyl-4-oxo-4,5-dihydroisoxazol-3-yl)-2-methylphenyl) pyrazin-2-yl)-6-methylisonicotinamide | 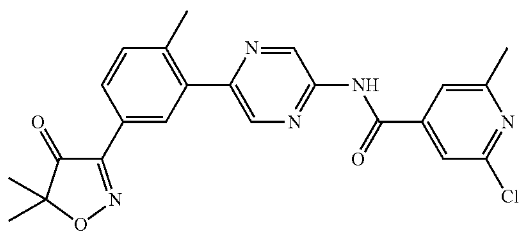 | ¹HNMR (400 MHz, CDCl₃) δ 9.74 (s, 1H), 8.56 (s, 1H, D₂O exchangeable), 8.49 (s, 1H), 8.20 (d, J = 2.0 Hz, 1H), 8.10 (dd, J = 8.0, 2.0 Hz, 1H), 7.64 (s, 1H), 7.58 (s, 1H), 7.44 (d, J = 8.0 Hz, 1H), 2.67 (s, 3H), 2.47 (s, 3H), 1.46 (s, 6H); ESI-MS (m/z) 450, 452 [(MH)⁺, Cl³⁵,³⁷] |
| Example 112: N-(5-(5-(5,5-dimethyl-4-oxo-4,5-dihydroisoxazol-3-yl)-2-methylphenyl) pyrazin-2-yl)-2-fluoroisonicotinamide | 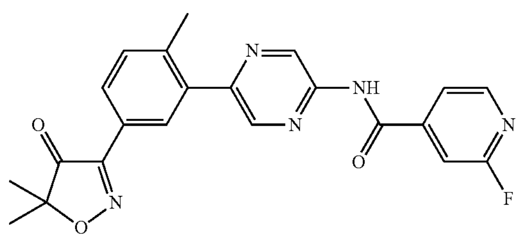 [SMILES: Cc1ccc(C2=NOC(C)(C)C2=O)cc1-c1cnc(NC(=O)c2ccnc(F)c2)cn1] | ¹HNMR (400 MHz, CDCl₃) δ 9.75 (s, 1H), 8.66 (s, 1H, D₂O exchangeable), 8.48 (s, 1H), 8.47 (d, J = 5.0 Hz, 1H), 8.20 (s, 1H), 8.10 (d, J = 8.0 Hz, 1H), 7.69 (d, J = 5.0 Hz, 1H), 7.48 (s, 1H), 7.43 (d, J = 8.0 Hz, 1H), 2.47 (s, 3H), 1.47 (s, 6H); ESI-MS (m/z) 420 (MH)⁺ |
| Example 113: N-(5-(5-(5,5-dimethyl-4-oxo-4,5-dihydroisoxazol-3-yl)-2-methylphenyl) pyrazin-2-yl)-2-methylnicotinamide | 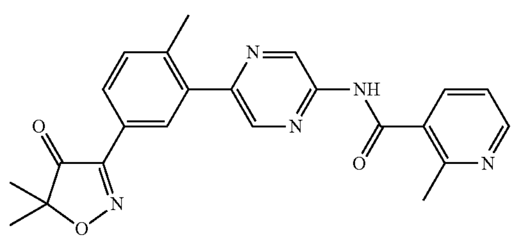 [SMILES: Cc1ccc(C2=NOC(C)(C)C2=O)cc1-c1cnc(NC(=O)c2cccnc2C)cn1] | ¹HNMR (400 MHz, CDCl₃) δ 9.76 (s, 1H), 8.66 (dd, J = 1.5, 5.0 Hz, 1H), 8.40 (s, 1H), 8.39 (s, 1H, D₂O exchangeable), 8.19 (d, J = 2.0 Hz, 1H), 8.09 (dd, J = 8.0, 2.0 Hz, 1H), 7.90 (dd, J = 1.5, 7.5 Hz, 1H), 7.43 (d, J = 8.0 Hz, 1H), 7.29-7.23 (m, 1H), 2.80 (s, 3H), 2.47 (s, 3H), 1.48 (s, 6H); ESI-MS (m/z) 416 (MH)⁺ |
| Example 114: N-(5-(5-(5,5-dimethyl-4-oxo-4,5-dihydroisoxazol-3-yl)-2-methylphenyl) pyrazin-2-yl)-3,5-difluoroisonicotinamide | 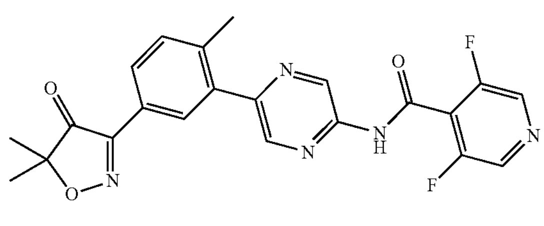 [SMILES: Cc1ccc(C2=NOC(C)(C)C2=O)cc1-c1cnc(NC(=O)c2c(F)cncc2F)cn1] | ¹HNMR (400 MHz, CDCl₃) δ 9.75 (s, 1H), 8.57 (s, 2H + 1H, D₂O exchangeable), 8.49 (s, 1H), 8.21 (d, J = 2.0 Hz, 1H), 8.12 (dd, J = 8.0, 2.0 Hz, 1H), 7.45 (d, J = 8.0 Hz, 1H), 2.48 (s, 3H), 1.49 (s, 6H); ESI-MS (m/z) 438 (MH)⁺ |
| Example 115: N-(5-(5-(5,5-dimethyl-4-oxo-4,5-dihydroisoxazol-3-yl)-2-methylphenyl) pyrazin-2-yl)-3-methylisonicotinamide | 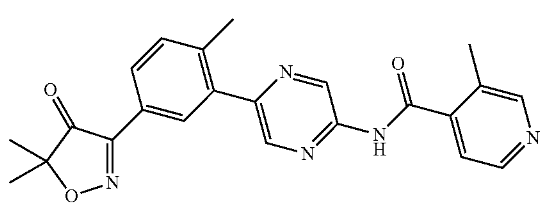 [SMILES: Cc1cnccc1C(=O)Nc1cnc(-c2cc(C3=NOC(C)(C)C3=O)ccc2C)cn1] | ¹HNMR (400 MHz, CDCl₃) δ 9.77 (s, 1H), 8.65 (s, 1H), 8.65 (d, J = 5.0 Hz, 1H), 8.47 (s, 1H), 8.29 (s, 1H, D₂O exchangeable), 8.21 (d, J = 2.0 Hz, 1H), 8.12 (dd, J = 8.0, 2.0 Hz, 1H), 7.47-7.44 (m, 2H), 2.58 (s, 3H), 2.49 (s, 3H), 1.49 (s, 6H); ESI-MS (m/z) 416 (MH)⁺ |

| Example No: IUPAC name | Structure | $^1$HNMR ESI-MS (MH)$^+$ |
|---|---|---|
| Example 116: N-(5-(5-(5,5-dimethyl-4-oxo-4,5-dihydroisoxazol-3-yl)-2-methoxyphenyl)pyrazin-2-yl)-3,5-difluoroisonicotinamide | 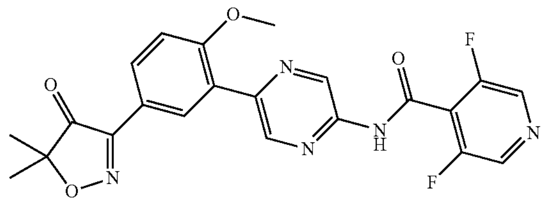 [SMILES: COc1ccc(C2=NOC(C)(C)C2=O)cc1-c1cnc(NC(=O)c2c(F)cncc2F)cn1] | $^1$HNMR (400 MHz, CDCl$_3$) δ 9.71 (s, 1H), 8.87 (s, 1H), 8.63 (d, J = 2.5 Hz, 1H), 8.54 (s, 2H), 8.41 (s, 1H, D$_2$O exchangeable), 8.17 (dd, J = 8.5, 2.5 Hz, 1H), 7.10 (d, J = 8.5 Hz, 1H), 3.95 (s, 3H), 2.03 (s, 3H); ESI-MS (m/z) 454 (MH)$^+$ |
| Example 117: N-(5-(2-ethyl-5-(4-methyl-5-oxo-4,5-dihydro-1,3,4-oxadiazol-2-yl)phenyl)pyrazin-2-yl)-3,5-difluoroisonicotinamide | 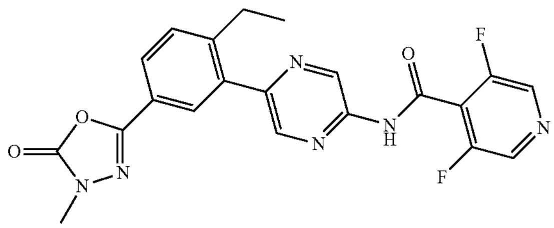 [SMILES: CCc1ccc(-c2nn(C)c(=O)o2)cc1-c1cnc(NC(=O)c2c(F)cncc2F)cn1] | $^1$HNMR (400 MHz, CDCl$_3$) δ 9.73 (s, 1H), 8.57 (s, 2H), 8.45 (d, J = 1.0 Hz, 1H + 1H, D$_2$O exchangeable), 7.87-7.84 (m, 2H), 7.49 (d, J = 8.5 Hz, 1H), 3.51 (s, 3H), 2.80 (q, J = 7.5 Hz, 2H), 1.18 (t, J = 7.5 Hz, 3H); ESI-MS (m/z) 439 (MH)$^+$ |
| Example 118: 3,5-Difluoro-N-(5-(2-fluoro-5-(4-methyl-5-oxo-4,5-dihydro-1,3,4-oxadiazol-2-yl)phenyl)pyrazin-2-yl)isonicotinamide | 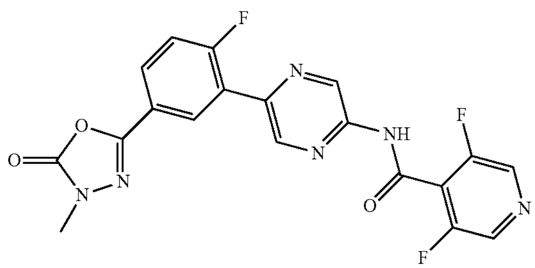 [SMILES: Cn1nc(-c2ccc(F)c(-c3cnc(NC(=O)c4c(F)cncc4F)cn3)c2)oc1=O] | $^1$HNMR (400 MHz, CDCl$_3$) δ 9.77 (s, 1H), 8.87 (t, J = 1.5 Hz, 1H), 8.62 (dd, J = 7.0, 2.0 Hz, 1H), 8.57 (s, 2H), 8.48 (s, 1H, D$_2$O exchangeable), 7.91-7.87 (m, 1H), 7.32 (dd, J = 11.0, 9.0 Hz, 1H), 3.53 (s, 3H); ESI-MS (m/z) 429 (MH)$^+$. |

Example 119

N-(5-(5-(5,5-dimethyl-4-oxo-4,5-dihydroisoxazol-3-yl)-2-methylphenyl)pyrazin-2-yl)benzofuran-2-carboxamide

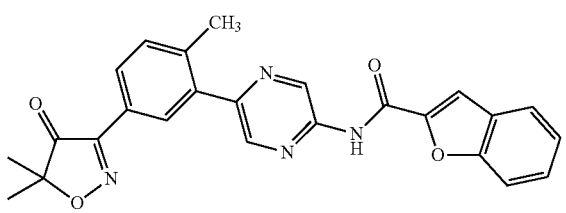 [SMILES: Cc1ccc(C2=NOC(C)(C)C2=O)cc1-c1cnc(NC(=O)c2cc3ccccc3o2)cn1]

The title compound was prepared by following a procedure similar to that described in method B of Examples 97 to 118 by using Intermediate 1b and benzofuran-2-carboxylic acid.
$^1$HNMR (400 MHz, CDCl$_3$) δ 9.79 (s, 1H), 9.04 (s, 1H, D$_2$O exchangeable), 8.50 (s, 1H), 8.21 (d, J=2.0 Hz, 1H), 8.09 (dd, J=8.0, 2.0 Hz, 1H), 7.74 (d, J=7.5 Hz, 1H), 7.70 (s, 1H), 7.59 (dd, J=8.5, 1.0 Hz, 1H), 7.51 (dt, J=7.5, 1.0 Hz, 1H), 7.43 (d, J=8.0 Hz, 1H), 7.36 (dt, J=8.0, 1.0 Hz, 1H), 2.48 (s, 3H), 1.47 (s, 6H); ESI-MS (m/z) 441 (MH)$^+$.

Example 120

2,6-Difluoro-N-(5-(2-methyl-5-(4-oxo-1-oxa-2-aza-spiro[4.5]dec-2-en-3-yl)phenyl)pyrazin-2-yl)benzamide

Intermediate 30

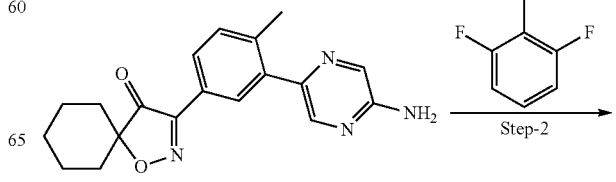

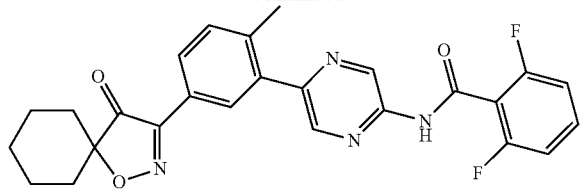

Example 120

Step-1: 3-(3-(5-Aminopyrazin-2-yl)-4-methylphenyl)-1-oxa-2-azaspiro[4.5]dec-2-en-4-one: To a solution of intermediate 30 (100 mg, 0.311 mmol, 1.0 eq) and 5-(trimethyl stannyl)-pyrazine-2-amine (prepared from 2-amino-5-bromopyrazine by following the procedure described in *Chem. Eur. J.* 2000, 6, 4132) (241 mg, 0.93 mmol, 3 eq) in dioxane (5 mL) was added Pd(PPh$_3$)$_4$ (18 mg, 0.015 mmol, 0.05 eq). The resulting mixture was thoroughly deoxygenated by subjecting to a vacuum/nitrogen cycle three times and the reaction mixture was heated at 75° C. for 15 h under nitrogen atmosphere. The resulting mixture was cooled to room temperature and filtered through celite. The filtrate was concentrated under vacuum and the crude product was purified by flash column chromatography (silica gel using ethyl acetate-hexane mixture as eluent) to afford 44 mg of the title compound as a white solid. $^1$HNMR (400 MHz, CDCl$_3$) δ 9.72 (s, 1H), 8.55 (s, 1H, D$_2$O exchangeable), 8.16 (s, 1H), 8.13 (s, 1H), 8.08 (d, J=2.0 Hz, 1H), 8.01 (dd, J=8.0, 2.0 Hz, 1H), 7.36 (d, J=8.0 Hz, 1H), 4.64 (s, 2H, D$_2$O exchangeable), 2.42 (s, 3H), 1.86-1.65 (m, 10H); ESI-MS (m/z) 337 (MH)$^+$.

Step-2: 2,6-Difluoro-N-(5-(2-methyl-5-(4-oxo-1-oxa-2-azaspiro[4.5]dec-2-en-3-yl)phenyl) pyrazin-2-yl)benzamide: To a 0° C. cooled and stirred, solution of 2,6-difluorobenzoyl chloride (0.013 mL, 0.11 mmol, 1.0 eq) in DCM (3 mL) was added drop wise a solution of 3-(3-(5-aminopyrazin-2-yl)-4-methylphenyl)-1-oxa-2-azaspiro[4.5]dec-2-en-4-one (40 mg, 0.11 mmol, 1.0 eq) in DCM (2 mL) followed by pyridine (0.01 mL, 0.11 mmol, 1.0 eq). The resulting mixture was stirred at room temperature overnight. The reaction was diluted with DCM (5 mL), and washed with 10% hydrochloric acid (5 mL), dried (Na$_2$SO$_4$) and filtered. The filtrate was concentrated under vacuum and the crude product was purified by flash column chromatography (silica gel, ethyl acetate in hexane) to afford 8 mg of the title product as a white solid. $^1$HNMR (400 MHz, CDCl$_3$) δ 9.76 (s, 1H), 8.51 (s, 1H, D$_2$O exchangeable), 8.41 (s, 1H), 8.18 (s, 1H), 8.08 (d, J=7.5 Hz, 1H), 7.51-7.47 (m, 1H) 7.42 (d, J=7.5 Hz, 1H), 7.06 (t, J=8.0 Hz, 2H), 2.48 (s, 3H), 1.82-0.87 (m, 10H); ESI-MS (m/z) 477 (MH)$^+$.

Example 121

N-(2,6-Difluorophenyl)-5-(5-(5,5-dimethyl-4-oxo-4,5-dihydroisoxazol-3-yl)-2-methylphenyl)pyrazine-2-carboxamide

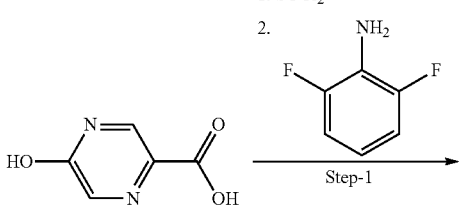

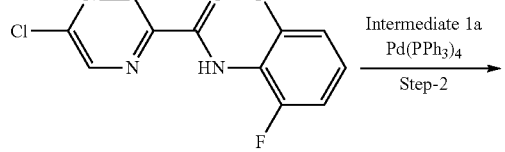

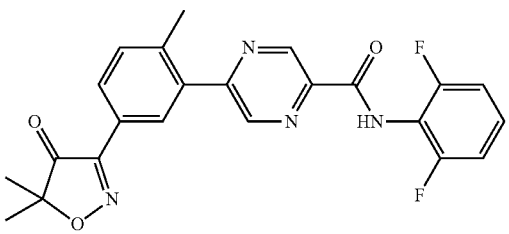

Example 121

Step-1: 5-Chloro-N-(2,6-difluorophenyl)pyrazine-2-carboxamide: A mixture of 5-hydroxypyrazine-2-carboxylic acid (500 mg, 3.57 mmol, 1.0 eq), thionyl chloride (5 mL) and DMF (0.3 mL) was refluxed for 15 h. The excess of thionyl chloride was removed under vacuum and the residue was taken in THF (5 mL). The resulting mixture was cooled to 0° C. and a solution of 2,6-difluoroaniline (0.58 mL, 5.35 mmol, 1.5 eq) was added to the above mixture followed by triethyl amine (0.75 mL, 5.35 mmol, 1.5 eq). After stirring for 3 h at room temperature, the reaction was diluted with ethyl acetate (15 mL). The organic layer was washed with water (10 mL), 2N HCl (10 mL), dried (Na$_2$SO$_4$) and filtered. The filtrate was concentrated under vacuum. The crude product was purified with flash column chromatography (silica gel, ethyl acetate and hexane system as eluent) to afford 500 mg of the title product as a white solid. $^1$HNMR (400 MHz, DMSO-d6) δ 10.67 (s, 1H, D$_2$O exchangeable), 9.11 (s, 1H), 9.98 (s, 1H), 7.47-7.41 (m, 1H), 7.26-7.21 (m, 2H); ESI-MS (m/z) 270, 272 [(MH)$^+$, Cl$^{35,37}$]

Step-2: N-(2,6-Difluorophenyl)-5-(5-(5,5-dimethyl-4-oxo-4,5-dihydroisoxazol-3-yl)-2-methyl phenyl)pyrazine-2-carboxamide: To a solution of intermediate 1a (100 mg, 0.30 mmol, 1.0 eq) and 5-chloro-N-(2,6-difluorophenyl)pyrazine-2-carboxamide (61 mg, 0.30 mmol, 1.0 eq), in THF:H$_2$O (4:1, 5 mL) was added sodium bicarbonate (38 mg, 0.45 mmol, 1.5 eq) followed by Pd(PPh$_3$)$_4$ (17 mg, 0.015 mmol, 0.05 eq). The resulting mixture was thoroughly deoxygenated by subjecting to a vacuum/nitrogen cycle three times and the reaction mixture was heated at 75° C. for 15 h under nitrogen atmosphere. The resulting mixture was cooled to room temperature and filtered through celite. The filtrate was concentrated under vacuum and the crude product was purified by flash column chromatography (silica gel, ethyl acetate in hexane) to afford 50 mg of the title product as a white solid. $^1$HNMR (400 MHz, CDCl$_3$) δ 9.59 (s, 1H), 9.26 (s, 1H, D$_2$O exchangeable), 8.82 (s, 1H), 8.29 (d, J=2.0 Hz, 1H), 8.18 (dd, J=8.0, 2.0 Hz, 1H), 7.50 (d, J=8.0 Hz, 1H), 7.31-7.28 (m, 1H), 7.07 (t, J=8.0 Hz, 2H), 2.53 (s, 3H), 1.51 (s, 6H); ESI-MS (m/z) 437 (MH)$^+$.

Example 122

4-(2,6-Difluorobenzamido)-3'-(5,5-dimethyl-4-oxo-4,5-dihydroisoxazol-3-yl)-[1,1'-biphenyl]-2-carboxylic acid

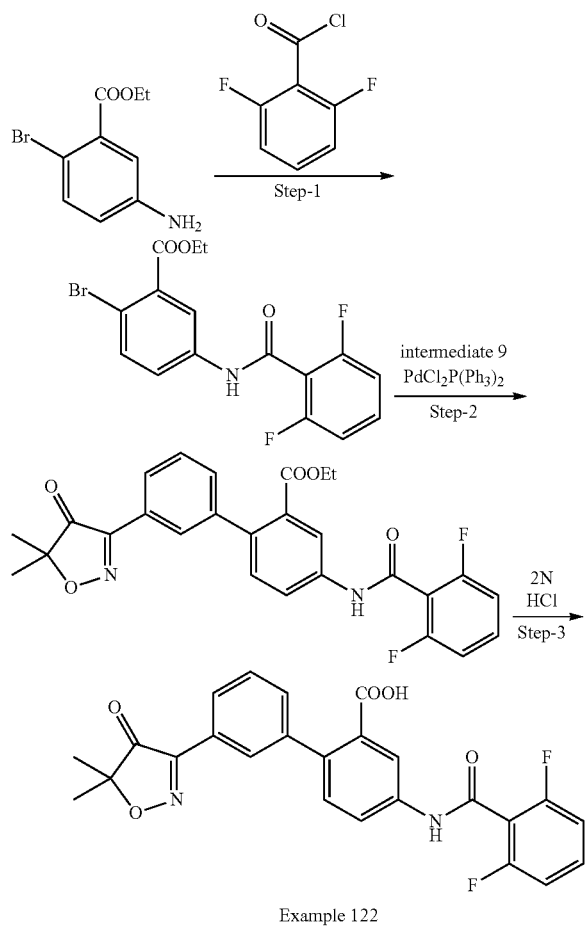

Example 122

Step-1: Ethyl-2-bromo-5-(2,6-difluorobenzamido)benzoate: To a 0° C. cooled and stirred, solution of 2,6-difluorobenzoyl chloride (0.5 mL, 4.11 mmol, 1.0 eq) in DCM (5 mL) was added drop wise a solution of ethyl-2-bromo-5-aminobenzoate (1.0 g, 4.11 mmol, 1.0 eq) in DCM (5 mL) followed by pyridine (0.43 mL, 4.93 mmol, 1.2 eq). The resulting mixture was stirred at room temperature for 15 h. The reaction was diluted with DCM (15 mL), and washed with 10% hydrochloric acid (10 mL), dried (Na$_2$SO$_4$) and filtered. The filtrate was concentrated under vacuum and the crude product was purified by flash column chromatography (silica gel, ethyl acetate in hexane as eluent) to afford 500 mg of the title product as a white solid. $^1$HNMR (400 MHz, CDCl$_3$) δ 8.23 (s, 1H, D$_2$O exchangeable), 7.97 (d, J=2.5 Hz, 1H), 7.73 (dd, J=8.5, 2.5 Hz, 1H), 7.60 (d, J=8.5 Hz, 1H), 7.41-7.34 (m, 1H), 6.92 (t, J=8.0 Hz, 2H); ESI-MS (m/z) 384, 386 [(MH)$^+$ Br$^{79,81}$].

Step-2: Ethyl 4-(2,6-difluorobenzamido)-3'-(5,5-dimethyl-4-oxo-4,5-dihydroisoxazol-3-yl)-[1,1'-biphenyl]-2-carboxylate: To a solution of ethyl-2-bromo-5-(2,6-difluorobenzamido)benzoate (180 mg, 0.47 mmol, 1.0 eq), in dioxane (5 mL), successively intermediate 9 (150 mg, 0.47 mmol, 1.0 eq) sodium carbonate (100 mg, 0.95 mmol, 2 eq) and Pd(PPh$_3$)$_2$Cl$_2$ (33 mg, 0.047 mmol, 0.1 eq) were added. The resulting solution was thoroughly deoxygenated by subjecting to vacuum/nitrogen cycle three times and the reaction mixture was then heated at 120° C. in microwave (Biotage) for 30 min. The resulting mixture was cooled to room temperature, diluted with ethyl acetate (10 mL) and filtered through celite. The filtrate was concentrated under vacuum and the crude product was purified by flash column chromatography (silica gel, ethyl acetate in hexane system as eluent) to afford 90 mg of the title compound as a white solid. $^1$HNMR (400 MHz, CDCl$_3$) δ 8.13-8.09 (m, 2H), 8.05-8.01 (m, 2H), 7.88 (s, 1H, D$_2$O exchangeable), 7.52-7.42 (m, 4H), 7.04 (t, J=8.0 Hz, 2H), 4.14 (q, J=7.0 Hz, 2H), 1.49 (s, 6H), 1.09 (t, J=7.0 Hz, 3H); ESI-MS (m/z) 493 (MH)$^+$.

Step-3: 4-(2,6-Difluorobenzamido)-3'-(5,5-dimethyl-4-oxo-4,5-dihydroisoxazol-3-yl)-[1,1'-biphenyl]-2-carboxylic acid: A solution of ethyl 4-(2,6-difluorobenzamido)-3'-(5,5-dimethyl-4-oxo-4,5-dihydroisoxazol-3-yl)-[1,1'-biphenyl]-2-carboxylate (80 mg, 0.16 mmol) in a mixture of dioxane and 2N HCl (5 mL, 1:1 (v/v)) was refluxed for 15 h. The solvent was removed under vacuum and the residue was purified by column chromatography (silica gel, DCM: MeOH as eluent) to afford 30 mg of the desired product as a white solid. $^1$HNMR (400 MHz, CDCl$_3$) δ 8.12-8.09 (m, 3H), 8.06 (d, J=2.0 Hz, 1H), 7.96 (s, 1H, D$_2$O exchangeable), 7.51-7.41 (m, 4H), 7.03 (t, J=8.0 Hz, 2H), 1.46 (s, 6H); ESI-MS (m/z) 465 (MH)$^+$.

Example 123

N-(5'-(5,5-Dimethyl-4-oxo-4,5-dihydroisoxazol-3-yl)-2'-hydroxy-[1,1'-biphenyl]-4-yl)-2,6-difluorobenzamide

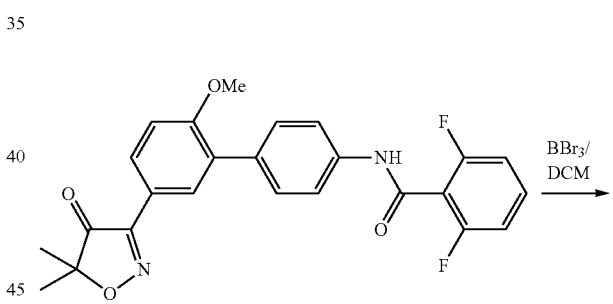

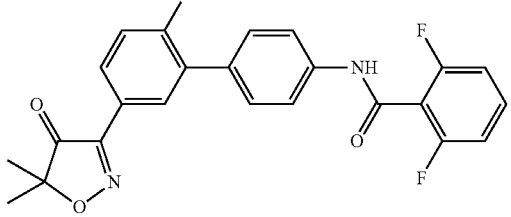

Example 123

To a 0° C. cooled and stirred solution of Example 15 (60 mg, 0.13 mmol, 1.0 eq) in DCM (2 mL) was added drop wise boron tribromide (1M in DCM, 0.20 mL, 1.5 eq) and then allowed to warm to 10° C. After stirring for 1 h, boron tribromide (1M in DCM, 0.20 mL, 1.5 eq) was again added to the reaction and then continued to stir at 10° C. for another 2 h. The reaction was quenched with methanol (1 mL) at 0° C. and the solvent was removed under vacuum. The residue was dissolved in ethyl acetate (5 mL) and washed with water (3 mL), brine (3 mL), dried (Na$_2$SO$_4$) and filtered. The filtrate was evaporated under vacuum and the crude product was purified by column chromatography (silica gel, ethyl acetate and hexane as eluent) to afford 45 mg of the desired product as a white solid. $^1$HNMR (400 MHz, DMSO-d6) δ 10.89 (s, 1H, D$_2$O exchangeable), 10.29 (s, 1H, D$_2$O exchangeable), 7.93 (d, J=2.0 Hz, 1H), 7.83 (dd, J=8.0, 2.0 Hz, 1H), 7.75 (d, J=8.5 Hz, 2H), 7.65-7.59 (m, 1H), 7.57 (d, J=8.5 Hz, 2H), 7.27 (t, J=8.0 Hz, 2H), 7.09 (d, J=8.0 Hz, 1H), 1.40 (s, 6H); ESI-MS (m/z) 437 (MH)$^+$.

Example 124

N-(5-(5-(5,5-Dimethyl-4-oxo-4,5-dihydroisoxazol-3-yl)-2-hydroxyphenyl)pyrazin-2-yl)-2,6-difluorobenzamide

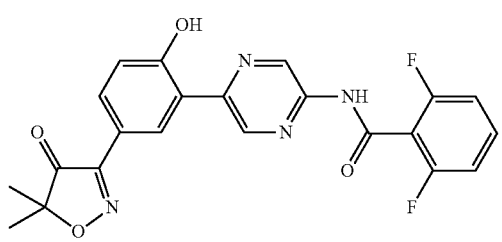 [SMILES: CC1(C)ON=C(c2ccc(O)c(-c3cnc(NC(=O)c4c(F)cccc4F)cn3)c2)C1=O]

The title compound was prepared by following a procedure similar to that described in Example 123 by using Example 14. $^1$HNMR (400 MHz, CDCl$_3$) δ 13.13 (s, 1H, D$_2$O exchangeable), 9.60 (s, 1H), 9.00 (s, 1H), 8.68 (s, 1H), 8.61 (s, 1H, D$_2$O exchangeable), 8.11 (dd, J=8.5, 2.0 Hz, 1H), 7.58-7.43 (m, 1H), 7.14 (d, J=8.5 Hz, 1H), 7.06 (t, J=8.0 Hz, 2H), 1.49 (s, 6H); ESI-MS (m/z) 439 (MH)$^+$.

Examples 125 to 133

General procedure for the O-alkylation of the compounds of examples 123 and 124:

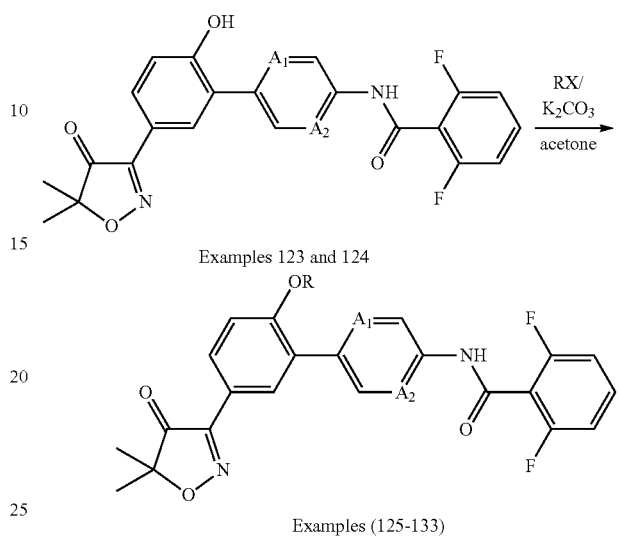

To a stirred solution of hydroxyl compound of Example 123 or Example 124 (1.0 eq) in acetone (5 mL) was added potassium carbonate (1.0 eq) and the corresponding alkyl halide (1.0-3.0 eq) and the resulting mixture was refluxed overnight. The reaction was cooled to room temperature and then filtered. The solid residue was washed with acetone and the combined filtrates were evaporated under vacuum. The crude residue was purified with flash column chromatography (silica gel, ethyl acetate:hexane as eluent) to afford the desired product as white solid.

| Example No: IUPAC name | Structure | $^1$HNMR/ESI-MS (MH)$^+$ |
|---|---|---|
| Example 125: N-(5'-(5,5-dimethyl-4-oxo-4,5-dihydroisoxazol-3-yl)-2'-isopropoxy-[1,1'-biphenyl]-4-yl)-2,6-difluorobenzamide | 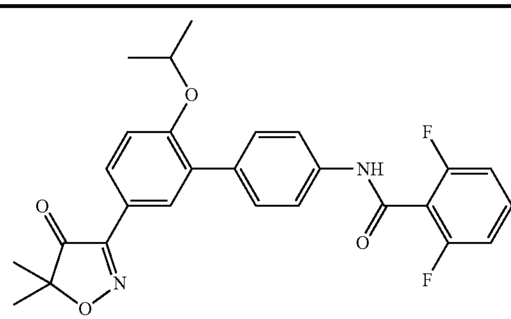 | $^1$HNMR (400 MHz, CDCl$_3$) δ 8.12 (d, J = 2.0 Hz, 1H), 8.07 (dd, J = 8.5, 2.0 Hz, 1H), 7.71-7.68 (m, 2H + 1H, D$_2$O exchangeable), 7.61 (d, J = 8.5 Hz, 2H), 7.47-7.42 (m, 1H), 7.06 (d, J = 8.5 Hz, 1H), 7.03 (t, J = 8.0 Hz, 2H), 4.65-4.61 (m, 1H), 1.48 (s, 6H), 1.33 (d, J = 6.0 Hz, 6H); ESI-MS (m/z) 479 (MH)$^+$. |
| Example 126: N-(5-(5-(5,5-dimethyl-4-oxo-4,5-dihydroisoxazol-3-yl)-2-isopropoxyphenyl)pyrazin-2-yl)-2,6-difluorobenzamide | 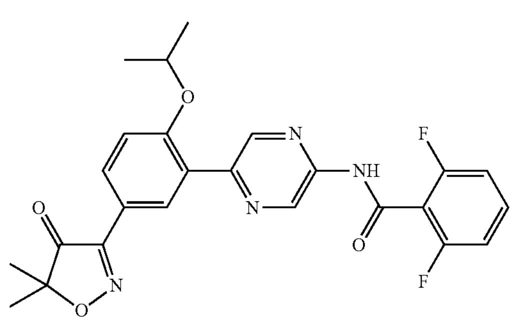 [SMILES: CC(C)Oc1ccc(C2=NOC(C)(C)C2=O)cc1-c1cnc(NC(=O)c2c(F)cccc2F)cn1] | $^1$HNMR (400 MHz, CDCl$_3$) δ 9.76 (s, 1H), 8.90 (s, 1H), 8.66 (d, J = 2.0 Hz, 1H), 8.49 (s, 1H, D$_2$O exchangeable), 8.13 (dd, J = 8.5, 2.0 Hz, 1H), 7.50-7.44 (m, 1H), 7.10 (d, J = 8.5 Hz, 1H), 7.05 (t, J = 8.0 Hz, 2H), 4.78-4.72 (m, 1H), 1.48 (s, 6H), 1.40 (d, J = 6.0 Hz, 6H); ESI-MS (m/z) 481 (MH)$^+$. |

| Example No: IUPAC name | Structure | ¹HNMR/ESI-MS (MH)⁺ |
|---|---|---|
| Example 127: N-(5'-(5,5-dimethyl-4-oxo-4,5-dihydroisoxazol-3-yl)-2'-isobutoxy-[1,1'-biphenyl]-4-yl)-2,6-difluorobenzamide | 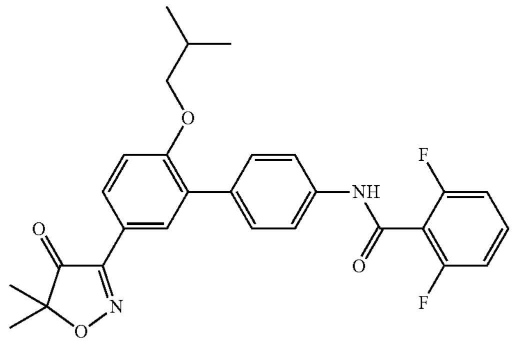 [SMILES: CC(C)COc1ccc(C2=NOC(C)(C)C2=O)cc1-c1ccc(NC(=O)c2c(F)cccc2F)cc1] | ¹HNMR (400 MHz, CDCl₃) δ 8.09 (d, J = 2.0 Hz, 1H), 8.06 (dd, J = 8.5, 2.0 Hz, 1H), 7.70-7.66 (m, 2H + 1H, D₂O exchangeable), 7.59 (d, J = 8.5 Hz, 2H), 7.43-7.40 (m, 1H), 7.02 (d, J = 8.5 Hz, 1H), 7.00 (t, J = 8.0 Hz, 2H), 3.79 (d, J = 6.5 Hz, 2H), 2.09-2.02 (m, 1H), 1.46 (s, 6H), 0.98 (d, J = 6.5 Hz, 6H); ESI-MS (m/z) 493 (MH)⁺. |
| Example 128: N-(5-(5-(5,5-dimethyl-4-oxo-4,5-dihydroisoxazol-3-yl)-2-isobutoxyphenyl)pyrazin-2-yl)-2,6-difluorobenzamide | 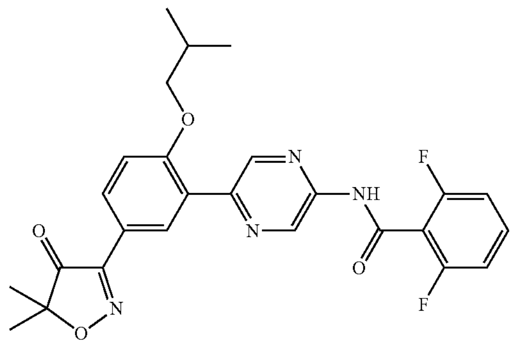 [SMILES: CC(C)COc1ccc(C2=NOC(C)(C)C2=O)cc1-c1cnc(NC(=O)c2c(F)cccc2F)cn1] | ¹HNMR (400 MHz, CDCl₃) δ 9.75 (s, 1H), 8.87 (s, 1H), 8.63 (d, J = 2.0 Hz, 1H), 8.47 (s, 1H, D₂O exchangeable), 8.12 (dd, J = 8.5, 2.0 Hz, 1H), 7.50-7.42 (m, 1H), 7.07 (d, J = 8.5 Hz, 1H), 7.00 (t, J = 8.0 Hz, 2H), 3.88 (d, J = 6.5 Hz, 2H), 2.16-2.09 (m, 1H), 1.46 (s, 6H), 1.01 (d, J = 6.5 Hz, 6H); ESI-MS (m/z) 495 (MH)⁺. |
| Example 129: N-(5'-(5,5-dimethyl-4-oxo-4,5-dihydroisoxazol-3-yl)-2'-ethoxy-[1,1'-biphenyl]-4-yl)-2,6-difluorobenzamide | 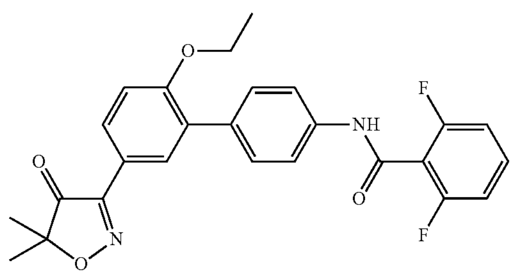 [SMILES: CCOc1ccc(C2=NOC(C)(C)C2=O)cc1-c1ccc(NC(=O)c2c(F)cccc2F)cc1] | ¹HNMR (400 MHz, CDCl₃) δ 8.11 (d, J = 2.0 Hz, 1H), 8.07 (dd, J = 8.5, 2.0 Hz, 1H), 7.71-7.68 (m, 2H + 1H, D₂O exchangeable), 7.61 (d, J = 8.5 Hz, 2H), 7.47-7.42 (m, 1H), 7.03 (d, J = 8.5 Hz, 1H), 7.02 (t, J = 8.0 Hz, 2H), 4.12 (q, J = 7.0 Hz, 2H), 1.47 (s, 6H), 1.40 (t, J = 7.0 Hz, 3H); ESI-MS (m/z) 465 (MH)⁺. |
| Example 130: N-(5-(5-(5,5-dimethyl-4-oxo-4,5-dihydroisoxazol-3-yl)-2-ethoxyphenyl)pyrazin-2-yl)-2,6-difluorobenzamide | 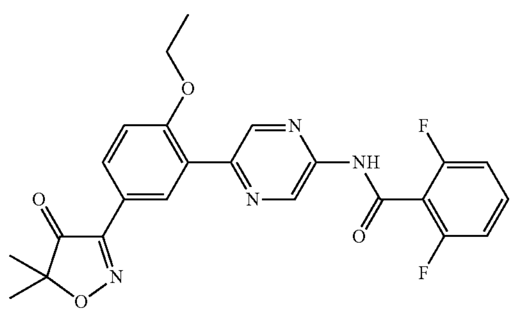 [SMILES: CCOc1ccc(C2=NOC(C)(C)C2=O)cc1-c1cnc(NC(=O)c2c(F)cccc2F)cn1] | ¹HNMR (400 MHz, CDCl₃) δ 9.76 (s, 1H), 8.91 (s, 1H), 8.67 (d, J = 2.0 Hz, 1H), 8.44 (s, 1H, D₂O exchangeable), 8.14 (dd, J = 8.5, 2.0 Hz, 1H), 7.50-7.46 (m, 1H), 7.09 (d, J = 8.5 Hz, 1H), 7.05 (t, J = 8.0 Hz, 2H), 4.21 (q, J = 6.5 Hz, 2H), 1.48 (t, J = 6.5 Hz, 3H), 1.48 (s, 6H); ESI-MS (m/z) 467 (MH)⁺. |
| Example 131: N-(5'-(5,5-dimethyl-4-oxo-4,5-dihydroisoxazol-3-yl)-2'-propoxy-[1,1'-biphenyl]-4-yl)-2,6-difluorobenzamide | 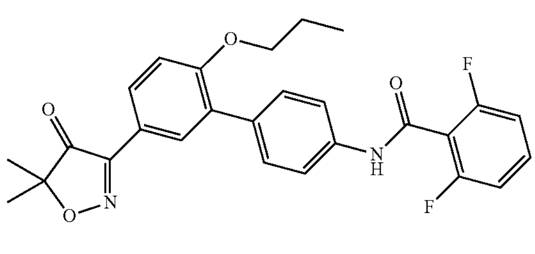 [SMILES: CCCOc1ccc(C2=NOC(C)(C)C2=O)cc1-c1ccc(NC(=O)c2c(F)cccc2F)cc1] | ¹HNMR (400 MHz, CdCl₃) δ 8.12 (d, J = 2.5 Hz, 1H), 8.09 (dd, J = 8.5, 2.5 Hz, 1H), 7.72-7.69 (m, 3H), 7.62 (d, J = 8.5 Hz, 2H), 7.48-7.41 (m, 1H), 7.05-7.01 (m, 3H), 4.02 (q, J = 6.5 Hz, 2H), 1.83-1.78 (m, 2H), 1.48 (s, 6H), 1.02 (t, J = 6.5 Hz, 3H); ESI-MS (m/z) 479 (MH)⁺ |

| Example No: IUPAC name | Structure | $^1$HNMR/ESI-MS (MH)$^+$ |
|---|---|---|
| Example 132: N-(2'-(allyloxy)-5'-(5,5-dimethyl-4-oxo-4,5-dihydroisoxazol-3-yl)-[1,1'-biphenyl]-4-yl)-2,6-difluorobenzamide | 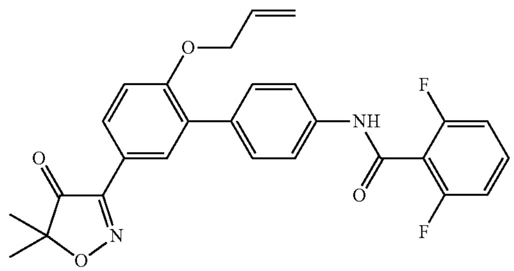 [SMILES: C=CCOc1ccc(C2=NOC(C)(C)C2=O)cc1-c1ccc(NC(=O)c2c(F)cccc2F)cc1] | $^1$H NMR (400 MHz, CDCl$_3$) δ 8.11 (d, J = 2.5 Hz, 1H), 8.07 (dd, J = 8.5, 2.5 Hz, 1H), 7.71-7.68 (m, 3H), 7.61 (d, J = 8.0 Hz, 2H), 7.48-7.39 (m, 1H), 7.05-6.99 (m, 3H), 6.05-5.95 (m, 1H), 5.39-5.24 (m, 2H), 4.63-4.61 (m, 2H), 1.46 (s, 6H); ESI-MS (m/z) 477 (MH)$^+$ |
| Example 133: N-(2'-(cyclopentyloxy)-5'-(5,5-dimethyl-4-oxo-4,5-dihydroisoxazol-3-yl)-[1,1'-biphenyl]-4-yl)-2,6-difluorobenzamide | 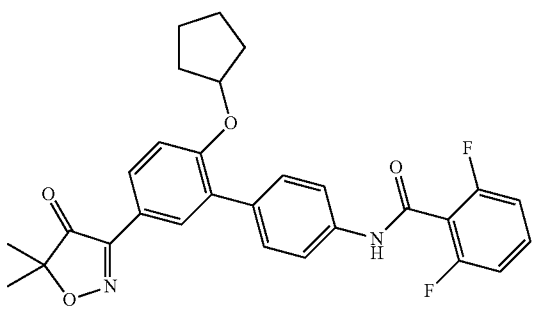 [SMILES: CC1(C)ON=C(c2ccc(OC3CCCC3)c(-c3ccc(NC(=O)c4c(F)cccc4F)cc3)c2)C1=O] | $^1$HNMR (400 MHz, CDCl$_3$) δ 8.10 (d, J = 2.5 Hz, 1H), 8.06 (dd, J = 8.5, 2.5 Hz, 1H), 7.68 (d, J = 8.5 Hz, 2H), 7.58 (d, J = 8.5 Hz, 2H), 7.48-7.41 (m, 1H), 7.05-7.02 (m, 3H), 4.87-4.85 (m, 1H), 1.92-1.82 (m, 4H), 1.79-1.70 (m, 2H), 1.59-1.64 (m, 2H), 1.47 (s, 6H); ESI-MS (m/z) 505 (MH)$^+$ |

Example 134

N-(2'-Amino-5'-(5,5-dimethyl-4-oxo-4,5-dihydroisoxazol-3-yl)-[1,1'-biphenyl]-4-yl)-2,6-difluorobenzamide

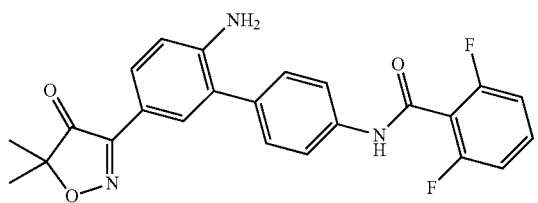 [SMILES: CC1(C)ON=C(c2ccc(N)c(-c3ccc(NC(=O)c4c(F)cccc4F)cc3)c2)C1=O]

A solution of Example 19 (50 mg, 0.10 mmol) in a mixture of dioxane and methanol (5 mL, 1:1 (v/v)) was heated to 70° C. for 12 h. The solvent was removed under vacuum and the residue was taken in water (5 mL) and ethyl acetate (5 mL). The mixture was basified with saturated aqueous solution of sodium bicarbonate (5 mL). The layers were separated and the aqueous layer was extracted with ethyl acetate (10 mL). The combined organic layers were washed with brine (5 mL), dried (Na$_2$SO$_4$) and filtered. The filtrate was rotary evaporated and the crude product was purified with column chromatography (silica gel, DCM:MeOH as eluent) to afford 20 mg of the desired product as a white solid. $^1$HNMR (400 MHz, DMSO-d6) δ 10.92 (s, 1H, D$_2$O exchangeable), 7.80 (d, J=8.5 Hz, 2H), 7.71 (dd, J=8.5, 2.0 Hz, 1H), 7.64-7.56 (m, 1H), 7.41 (d, J=8.5 Hz, 2H), 7.26 (t, J=8.0 Hz, 2H), 6.84 (d, J=8.5 Hz, 1H), 5.48 (s, 2H, D$_2$O exchangeable), 1.35 (s, 6H); ESI-MS (m/z) 436 (MH)$^+$.

Example 135

N-(5'-(5,5-Dimethyl-4-oxo-4,5-dihydroisoxazol-3-yl)-2'-(methylamino)-[1,1'-biphenyl]-4-yl)-2,6-difluorobenzamide

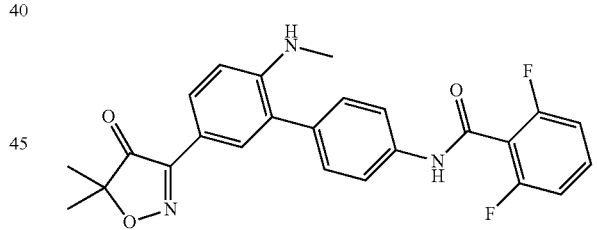

To a 0° C. solution of Example 134 (50 mg, 0.11 mmol, 1.0 eq) in methanol (5 mL) was added formaldehyde (37% aqueous solution) (10 μL, 0.12 mmol, 1.1 eq). After stirring for 30 min at room temperature, sodium cyanoborohydride (8 mg, 0.14 mmol, 1.2 eq) was added to the above reaction mixture followed by a catalytic amount of acetic acid. The resulting mixture was stirred at room temperature for 12 h. The solvent was removed under vacuum and the residue was dissolved in ethyl acetate (10 mL) and washed with water (5 mL), brine (5 mL), dried (Na$_2$SO$_4$) and filtered. The filtrate was evaporated under vacuum and the crude product was purified by column chromatography (silica gel, DCM:MeOH as eluent) to afford 8 mg of title compound $^1$HNMR (400 MHz, CDCl$_3$) δ 8.07 (dd, J=8.5, 2.0 Hz, 1H), 7.87 (d, J=2.0 Hz, 1H), 7.45-7.09 (m, 3H), 7.46-7.43 (m, 3H), 7.04 (t, J=8.0 Hz, 2H), 6.72 (d, J=8.5 Hz, 1H), 4.33 (s, 1H, D$_2$O exchangeable), 2.86 (s, 3H), 1.45 (s, 6H); ESI-MS (m/z) 450 (MH)$^+$.

Example 136

N-(5'-(5,5-Dimethyl-4-oxo-4,5-dihydroisoxazol-3-yl)-2'-(dimethylamino)-[1,1'-biphenyl]-4-yl)-2,6-difluorobenzamide

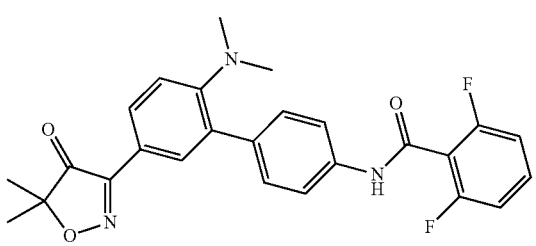 [SMILES: CN(C)c1ccc(C2=NOC(C)(C)C2=O)cc1-c1ccc(NC(=O)c2c(F)cccc2F)cc1]

The title compound was prepared by following a procedure similar to that described in Example 135 by using Example 134 (yield: 10 mg) $^1$HNMR (400 MHz, CDCl$_3$) δ 8.01 (dd, J=8.5, 2.0 Hz, 1H), 7.97 (d, J=2.0 Hz, 1H), 7.69 (d, J=8.5 Hz, 2H), 7.65 (s, 1H, D$_2$O exchangeable), 7.61 (d, J=8.5 Hz, 2H), 7.48-7.41 (m, 1H), 7.06-7.00 (m, 3H), 2.64 (s, 6H), 1.45 (s, 6H); ESI-MS (m/z) 464 (MH)$^+$.

Example 137

(R/S)—N-(5-(5-(5,5-Dimethyl-4-hydroxy-4,5-dihydroisoxazol-3-yl)-2-methylphenyl)pyrazine-2-yl)-2,6-difluorobenzamide

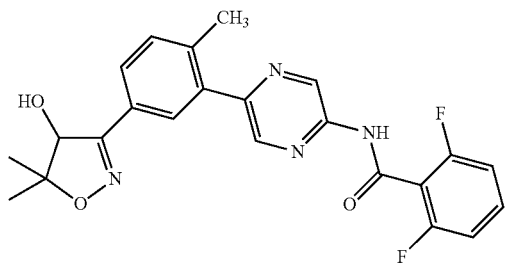 [SMILES: Cc1ccc(C2=NOC(C)(C)C2O)cc1-c1cnc(NC(=O)c2c(F)cccc2F)cn1]

To a solution of Example 1 (100 mg, 0.23 mmol, 1.0 eq) in methanol (5 mL) at room temperature was added sodium borohydride (13 mg, 0.34 mmol, 1.5 eq) portion wise. After stirring for 10 min at the same temperature, the solvent was removed under vacuum. Water (3 mL) was added to the above obtained residue followed by ethyl acetate. The layers were separated and the aqueous layer was extracted with ethyl acetate (2×10 mL). The combined organic layers were washed with brine (10 mL), dried (Na$_2$SO$_4$) and filtered. The filtrate was concentrated under vacuum. The crude product was triturated with hexane and dried to afford 90 mg of the desired product as a white solid. $^1$HNMR (400 MHz, DMSO-d$_6$) δ 11.81 (s, 1H, D$_2$O exchangeable), 9.51 (s, 1H), 8.69 (s, 1H), 7.86 (d, J=1.5 Hz, 1H), 7.77 (dd, J=8.0, 1.5 Hz, 1H), 7.64-7.60 (m, 1H), 7.44 (d, J=8.0 Hz, 1H), 7.27 (t, J=8.0 Hz, 2H), 5.95 (d, J=8.0 Hz, 1H, D$_2$O exchangeable), 4.92 (d, J=8.0 Hz, 1H), 2.42 (s, 3H), 1.18 (s, 6H); ESI-MS (m/z) 439 (MH)$^+$.

Example 138

(R/S)—N-(5-(2-Methyl-3-(4-methyl-5-oxo-4,5-dihydro-1,3,4-oxadiazol-2-yl)phenyl)pyrazin-2-yl)-1,2,3,4-tetrahydronaphthalene-2-carboxamide

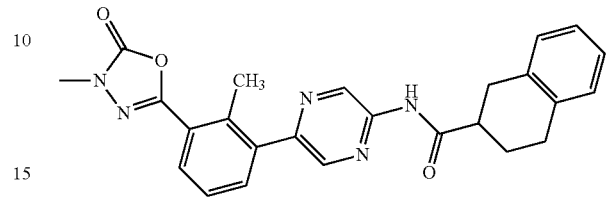

The title compound was prepared by following a procedure similar to that described in method B of Examples 97 to 118 by using intermediate 23b and 1,2,3,4-tetrahydronaphthalene-2-carboxylic acid. $^1$HNMR (400 MHz, CDCl$_3$) δ 9.71 (s, 1H), 8.35 (s, 1H), 8.08 (s, 1H, D$_2$O exchangeable), 7.87 (dd, J=8.0, 1.5 Hz, 1H), 7.54 (dd, J=8.0, 1.5 Hz, 1H), 7.43 (t, J=8.0 Hz, 1H), 7.19-7.14 (m, 4H), 3.55 (s, 3H), 3.24-2.81 (m, 5H), 2.56 (s, 3H), 2.33-2.28 (m, 1H), 2.10-2.03 (m, 1H); ESI-MS (m/z) 442 (MH)$^+$

Example 139

3-(4'-(2,6-Difluorobenzamido)-6-methyl-[1',1'-biphenyl]-3-yl)-5-methyl-4,5-dihydroisoxazole-5-carboxylic acid

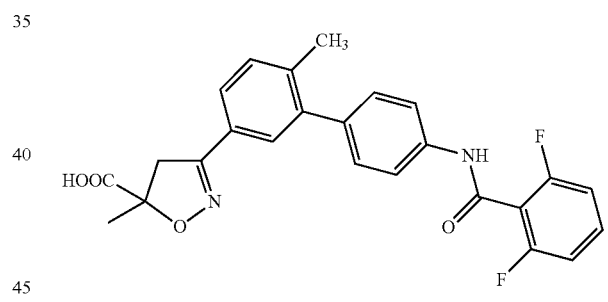

To a solution of Example 55 (50 mg, 0.1 mmol, 1.0 eq) in THF (2 mL) was added a solution of lithium hydroxide (13 mg, 0.32 mmol, 3.0 eq) in water (1 mL) at room temperature. The resulting solution was then stirred at the same temperature for 4 h. The solvent was removed under vacuum and the residue was taken in water (3 mL) and acidified with 10% aqueous hydrochloric acid to p$^H$=2.0, and then extracted with ethyl acetate (2×10 mL). The combined organic layers were washed with brine (10 mL), dried (Na$_2$SO$_4$) and filtered. The filtrate was concentrated under vacuum to afford 35 mg of the desired product as a white solid. $^1$HNMR (400 MHz, CDCl$_3$) δ 7.74 (s, 1H, D$_2$O exchangeable), 7.71 (d, J=8.5 Hz, 2H), 7.55 (d, J=8.0 Hz, 1H), 7.46 (s, 1H), 7.46-7.41 (m, 1H), 7.32 (d, J=8.5 Hz, 3H), 7.02 (t, J=8.0 Hz, 2H), 3.87 (d, J=17.5 Hz, 1H), 3.31 (d, J=17.5 Hz, 1H), 2.30 (s, 3H), 1.77 (s, 3H); ESI-MS (m/z) 451 (MH)$^+$.

Examples 140-142

The below examples were prepared by following a procedure similar to that described in Example 139 by using Example 54 to prepare Example 140, Example 76 to prepare Example 141 Example 77 to prepare Example 142.

| Example No:<br>IUPAC name | Structure | ¹HNMR/ESI-MS (MH)⁺ |
|---|---|---|
| Example 140: 3-(3-(5-(2,6-difluorobenzamido)pyrazin-2-yl)-4-methylphenyl)-5-methyl-4,5-dihydroisoxazole-5-carboxylic acid | 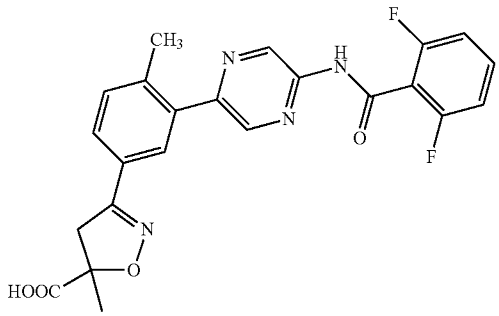 [SMILES: Cc1ccc(C2=NOC(C)(C(=O)O)C2)cc1-c1cnc(NC(=O)c2c(F)cccc2F)cn1] | ¹HNMR (400 MHz, CDCl₃) δ 9.79 (s, 1H), 9.09 (s, 1H, D₂O exchangeable), 8.37 (s, 1H), 7.66 (s, 1H), 7.62 (d, J = 8.0 Hz, 1H), 7.52-7.44 (m, 1H), 7.35 (d, J = 8.0 Hz, 1H), 7.04 (t, J = 8.0 Hz, 2H), 3.88 (d, J = 17.0 Hz, 1H), 3.29 (d, J = 17.0 Hz, 1H), 2.43 (s, 3H), 1.74 (s, 3H); ESI-MS (m/z) 453 (MH)⁺. |
| Example 141: 5-Carboxymethyl-3-(4'-(2,6-difluorobenzmido)-6-methyl-[1,1'-biphenyl]-3-yl)-4,5-dihydroisoxazole-5-carboxylic acid | 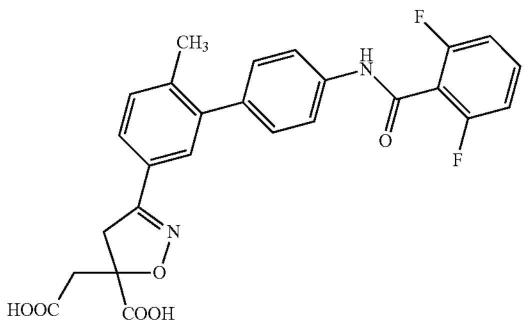 [SMILES: Cc1ccc(C2=NOC(CC(=O)O)(C(=O)O)C2)cc1-c1ccc(NC(=O)c2c(F)cccc2F)cc1] | ¹HNMR (400 MHz, DMSO-d6) δ 13.22 (s, 1H, D₂O exchangeable), 12.56 (s, 1H, D₂O exchangeable), 10.91 (s, 1H, D₂O exchangeable), 7.77 (d, J = 8.5 Hz, 2H), 7.60-7.56 (m, 2H), 7.49 (s, 1H), 7.45 (d, J = 1.5 Hz, 1H), 7.40-7.37 (m, 3H), 7.26 (t, J = 8.0 Hz, 2H), 3.87 (d, J = 17.5 Hz, 1H), 3.58 (d, J = 17.5 Hz, 1H), 2.98 (s, 2H), 2.28 (s, 3H); ESI-MS (m/z) 495 (MH)⁺. |
| Example 142: 5-(Carboxymethyl)-3-(3-(5-(2,6-difluorobenzamido)pyrazin-2-yl)-4-methylphenyl)-4,5-dihydroisoxazole-5-carboxylic acid | 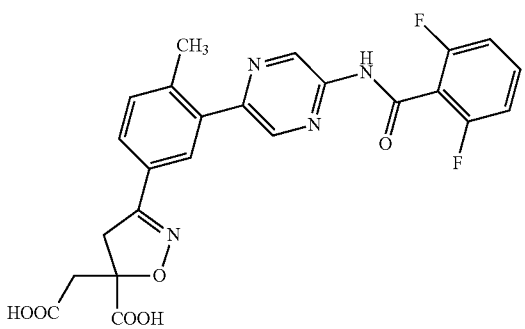 [SMILES: Cc1ccc(C2=NOC(CC(=O)O)(C(=O)O)C2)cc1-c1cnc(NC(=O)c2c(F)cccc2F)cn1] | ¹HNMR (400 MHz, DMSO-d6) δ 13.29 (s, 1H, D₂O exchangeable), 12.58 (s, 1H, D₂O exchangeable), 11.82 (s, 1H, D₂O exchangeable), 9.51 (s, 1H), 8.71 (s, 1H), 7.76 (s, 1H), 7.71 (dd, J = 8.0, 1.5 Hz, 1H), 7.65-7.60 (m, 1H), 7.45 (d, J = 8.0 Hz, 1H), 7.27 (t, J = 8.0 Hz, 2H), 3.92 (d, J = 17.0 Hz, 1H), 3.61 (d, J = 17.0 Hz, 1H), 3.00 (s, 2H), 2.42 (s, 3H); ESI-MS (m/z) 495 (M − H). |

Example 143

2,6-Difluoro-N-(5'-(5-(hydroxymethyl)-5-methyl-4,5-dihydroisoxazol-3-yl)-2'-methyl-[1,1'-biphenyl]-4-yl)benzamide

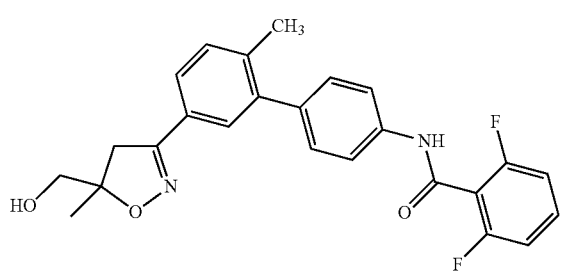 [SMILES: Cc1ccc(C2=NOC(C)(CO)C2)cc1-c1ccc(NC(=O)c2c(F)cccc2F)cc1]

To a solution of Example 55 (50 mg, 0.10 mmol, 1.0 eq) in methanol (5 mL), was added sodium borohydride (11 mg, 0.3 mmol, 3 eq) portion wise. The resulting solution was stirred at room temperature for 1 h. The solvent was removed under vacuum and the residue was taken in ethyl acetate (10 mL) and water (5 mL). The layers were separated and the aqueous layer was extracted with ethyl acetate (2×10 mL). The combined organic layers were washed with brine (10 mL), dried (Na₂SO₄) and filtered. The filtrate was concentrated under vacuum to afford 40 mg of the desired product as a white solid. ¹HNMR (400 MHz, CDCl₃) δ 7.74 (s, 1H, D₂O exchangeable), 7.70 (d, J=8.5 Hz, 2H), 7.57 (d, J=8.0 Hz, 1H), 7.47 (s, 1H), 7.46-7.43 (m, 1H), 7.32 (d, J=8.5 Hz, 2H), 7.30 (d, J=8.0 Hz, 1H), 7.02 (t, J=8.0 Hz, 2H), 3.72 (d, J=12 Hz, 1H), 3.57 (d, J=12 Hz, 1H), 3.48 (d, J=17.0 Hz, 1H), 3.02 (d, J=17.0 Hz, 1H), 2.29 (s, 3H), 1.23 (s, 3H); ESI-MS (m/z) 437 (MH)⁺.

Examples 144-146

The below examples were prepared by following a procedure similar to that described in Example 143 by using Example 54 to prepare Example 144, Example 76 to prepare Example 145 Example 77 to prepare Example 146.

| Example No: IUPAC name | Structure | $^1$HNMR/ESI-MS (MH)$^+$ |
|---|---|---|
| Example 144: 2,6-Difluoro-N-(5-(5-(5-(hydroxymethyl)-5-methyl-4,5-dihydroisoxazol-3-yl)-2-methylphenyl)pyrazin-2-yl)benzamide | 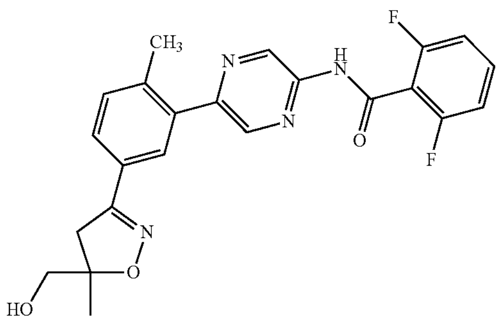 [SMILES: Cc1ccc(C2=NOC(C)(CO)C2)cc1-c1cnc(NC(=O)c2c(F)cccc2F)cn1] | $^1$HNMR (400 MHz, CDCl$_3$) δ 9.75 (s, 1H), 8.70 (s, 1H, D$_2$O exchangeable), 8.35 (s, 1H), 7.67 (s, 1H), 7.63 (d, J = 8.0 Hz, 1H), 7.52-7.45 (m, 1H), 7.34 (d, J = 8.0 Hz, 1H), 7.05 (t, J = 8.0 Hz, 2H), 3.75-3.71 (m, 1H), 3.61-3.50 (m, 1H), 3.50 (d, J = 17.0 Hz, 1H), 3.04 (d, J = 17.0 Hz, 1H), 2.42 (s, 3H), 1.43 (s, 3H); ESI-MS (m/z) 439 (MH)$^+$. |
| Example 145: 2,6-Difluoro-N-(5'-(5-(2-hydroxyethyl)-5-(hydroxymethyl)-4,5-dihydroisoxazol-3-yl)-2'-methyl-[1,1'-biphenyl]-4-yl)benzamide | 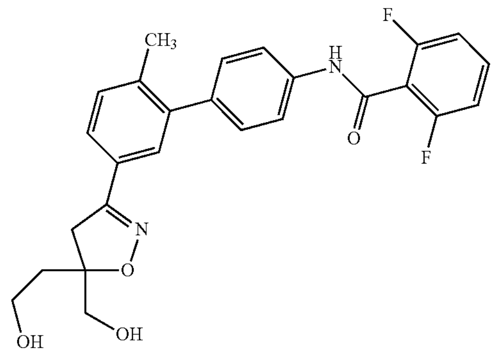 [SMILES: Cc1ccc(C2=NOC(CO)(CCO)C2)cc1-c1ccc(NC(=O)c2c(F)cccc2F)cc1] | $^1$HNMR (400 MHz, DMSO-d6) δ 10.92 (s, 1H, D$_2$O exchangeable), 7.78 (d, J = 8.5 Hz, 2H), 7.65-7.53 (m, 2H), 7.43-7.35 (m, 4H), 7.27 (d, J = 8.0 Hz, 2H), 5.04 (t, J = 6.0 Hz, 1H), 4.51 (t, J = 5.0 Hz, 1H), 3.52 (dd, J = 6.5, 5.0 Hz, 2H), 3.42 (d, J = 6.0 Hz, 2H), 3.28 (s, 2H), 2.27 (s, 3H), 1.90-1.82 (m, 2H); ESI-MS (m/z) 467 (MH)$^+$. |
| Example 146: N-(5-(5-(5,5-bis(hydroxymethyl)-4,5-dihydroisoxazol-3-yl)-2-methylphenyl)pyrazin-2-yl)-2,6-difluorobenzamide | 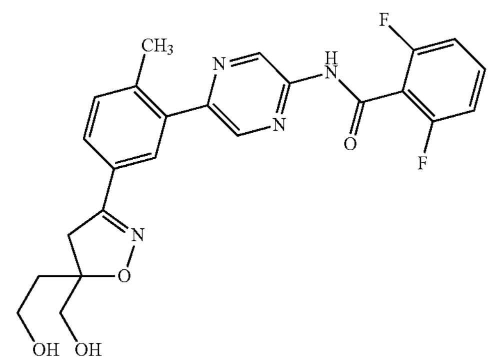 [SMILES: Cc1ccc(C2=NOC(CO)(CCO)C2)cc1-c1cnc(NC(=O)c2c(F)cccc2F)cn1] | $^1$HNMR (400 MHz, DMSO-d6) δ 11.80 (s, 1H, D$_2$O exchangeable), 9.51 (s, 1H), 8.69 (s, 1H), 7.73 (d, J = 1.5 Hz, 1H), 7.67 (dd, J = 8.0, 1.5 Hz, 1H), 7.64-7.58 (m, 1H), 7.43 (d, J = 8.0 Hz, 1H), 7.27 (d, J = 8.0 Hz, 2H), 5.01 (t, J = 6.0 Hz, 1H), 3.49 (dd, J = 6.0, 1.0 Hz, 4H), 3.48 (s, 4H), 3.27 (s, 2H), 2.41 (s, 3H); ESI-MS (m/z) 469 (MH)$^+$. |

Example 147

N-Cyclopropyl-3-(4'-(2,6-difluorobenzamido)-6-methyl-[1,1'-biphenyl]-3-yl)-5-methyl-4,5-dihydroisoxazole-5-carboxamide

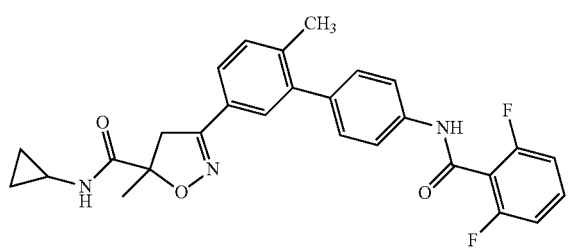 [SMILES: Cc1ccc(C2=NOC(C)(C(=O)NC3CC3)C2)cc1-c1ccc(NC(=O)c2c(F)cccc2F)cc1]

To a solution of Example 139 (200 mg, 0.44 mmol, 1.0 eq), in acetonitrile (10 mL) was added thionyl chloride (0.3 mL, 4.4 mmol, 10 eq) and the resulting solution was refluxed for 2 h. The solvent and the excess of thionyl chloride was removed under vacuum and dried. The residue was dissolved in DCM (10 mL) cooled to 0° C. and cyclopropyl amine (30 μL, 0.44 mmol, 1.0 eq) and triethyl amine (0.6 mL, 3.52 mmol, 8 eq) were added sequentially. The resulting solution was stirred at room temperature for 1 h. The reaction mixture was concentrated and the crude product was purified by flash column chromatography (silica gel, 40% ethyl acetate in hexane) to afford 90 mg of the desired product as a white solid. $^1$HNMR (400 MHz, CDCl$_3$) δ 7.78 (s, 1H, D$_2$O exchangeable), 7.71 (d, J=8.5 Hz, 2H), 7.52 (dd, J=8.0, 1.5 Hz, 1H), 7.48 (d, J=1.5 Hz, 1H), 7.46-7.41 (m, 1H), 7.33-7.29 (m, 3H), 7.02 (t, J=8.0 Hz, 2H), 6.91 (d, J=3.0 Hz, 1H, D$_2$O exchangeable), 3.82 (d, J=17.5 Hz, 1H), 3.22 (d, J=17.5 Hz, 1H), 2.74-2.69 (m, 1H), 2.30 (s, 3H), 1.69 (s, 3H), 0.89-0.74 (m, 2H), 0.54-0.50 (m, 2H); ESI-MS (m/z) 490 (MH)$^+$.

Examples 148-153

The below Examples 148 to 153 were prepared by following a procedure similar to that described in Example 147 by using Example 139 or Example 140 and appropriate amine.

| Example No: IUPAC name | Structure | ¹HNMR/ESI-MS (MH)⁺ |
|---|---|---|
| Example 148: 3-(4'-(2,6-difluorobenzamido)-6-methyl-[1,1'-biphenyl]-3-yl)-5-methyl-4,5-dihydroisoxazole-5-carboxamide | 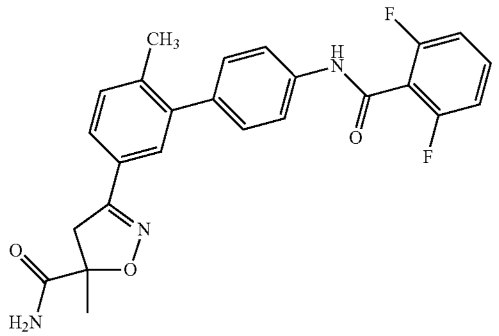 [SMILES: Cc1ccc(C2=NOC(C)(C(N)=O)C2)cc1-c1ccc(NC(=O)c2c(F)cccc2F)cc1] | ¹HNMR (400 MHz, CDCl₃) δ 7.76 (s, 1H, D₂O exchangeable), 7.71 (d, J = 8.5 Hz, 2H), 7.53 (dd, J = 8.0, 1.5 Hz, 1H), 7.48 (d, J = 1.5 Hz, 1H), 7.46-7.41 (m, 1H), 7.33-7.30 (m, 3H), 7.02 (t, J = 8.0 Hz, 2H), 6.82 (s, 1H, D₂O exchangeable), 5.52 (s, 1H, D₂O exchangeable), 3.84 (d, J = 17.0 Hz, 1H), 3.24 (d, J = 17.0 Hz, 1H), 2.30 (s, 3H), 1.74 (s, 3H); ESI-MS (m/z) 450 (MH)⁺. |
| Example 149: 3-(3-(5-(2,6-Difluorobenzamido)pyrazin-2-yl)-4-methylphenyl)-N,5-dimethyl-4,5-dihydroisoxazole-5-carboxamide | 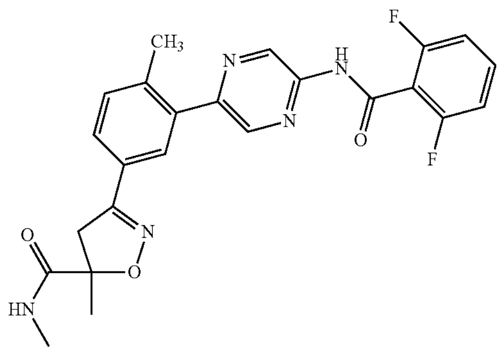 [SMILES: CNC(=O)C1(C)CC(c2ccc(C)c(-c3cnc(NC(=O)c4c(F)cccc4F)cn3)c2)=NO1] | ¹HNMR (400 MHz, CDCl₃) δ 9.76 (s, 1H), 8.46 (s, 1H, D₂O exchangeable), 8.39 (s, 1H), 7.70 (d, J = 1.5 Hz, 1H), 7.60 (dd, J = 8.0, 1.5 Hz, 1H), 7.54-7.46 (m, 1H), 7.36 (d, J = 8.0 Hz, 1H), 7.06 (t, J = 8.0 Hz, 2H), 6.91-6.89 (m, 1H, D₂O exchangeable), 3.85 (d, J = 17.0 Hz, 1H), 3.25 (d, J = 17.0 Hz, 1H), 2.82 (d, J = 5.0 Hz, 3H), 2.43 (s, 3H), 1.72 (s, 3H); ESI-MS (m/z) 466 (MH)⁺. |
| Example 150: 3-(4'-(2,6-Difluorobenzamido)-6-methyl-[1,1'-biphenyl]-3-yl)-N,N,5-trimethyl-4,5-dihydroisoxazole-5-carboxamide | 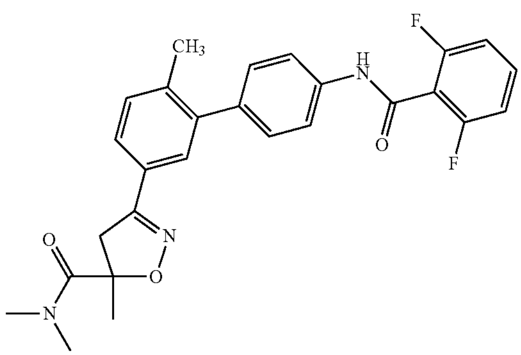 [SMILES: Cc1ccc(C2=NOC(C)(C(=O)N(C)C)C2)cc1-c1ccc(NC(=O)c2c(F)cccc2F)cc1] | ¹HNMR (400 MHz, CDCl₃) δ 7.76 (s, 1H, D₂O exchangeable), 7.70 (d, J = 8.5 Hz, 2H), 7.57 (dd, J = 8.0, 1.5 Hz, 1H), 7.51 (d, J = 1.5 Hz, 1H), 7.46-7.41 (m, 1H), 7.33-7.29 (m, 3H), 7.02 (t, J = 8.0 Hz, 2H), 4.34 (d, J = 17.0 Hz, 1H), 3.29 (s, 3H), 3.14 (d, J = 17.0 Hz, 1H), 2.97 (s, 3H), 2.30 (s, 3H), 1.69 (s, 3H); ESI-MS (m/z) 478 (MH)⁺. |
| Example 151: N-Cyclopropyl-3-(3-(5-(2,6-difluorobenzamido)pyrazin-2-yl)-4-methylphenyl)-5-methyl-4,5-dihydroisoxazole-5-carboxamide | 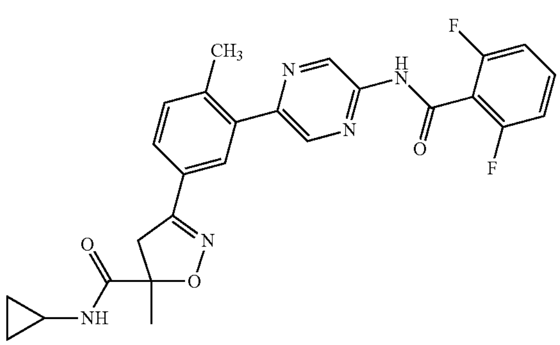 [SMILES: Cc1ccc(C2=NOC(C)(C(=O)NC3CC3)C2)cc1-c1cnc(NC(=O)c2c(F)cccc2F)cn1] | ¹HNMR (400 MHz, CDCl₃) δ 9.76 (s, 1H), 8.52 (s, 1H, D₂O exchangeable), 8.38 (s, 1H), 7.69 (d, J = 1.5 Hz, 1H), 7.60 (dd, J = 8.0, 1.5 Hz, 1H), 7.54-7.46 (m, 1H), 7.36 (d, J = 8.0 Hz, 1H), 7.06 (t, J = 8.0 Hz, 2H), 6.91-6.89 (m, 1H, D₂O exchangeable), 3.85 (d, J = 17.0 Hz, 1H), 3.24 (d, J = 17.0 Hz, 1H), 2.74-2.70 (m, 1H), 2.43 (s, 3H), 1.70 (s, 3H), 0.81-0.75 (m, 2H), 0.55-0.52 (m, 2H); ESI-MS (m/z) 492 (MH)⁺. |

| Example No:<br>IUPAC name | Structure | ¹HNMR/ESI-MS (MH)⁺ |
|---|---|---|
| Example 152: 2,6-Difluoro-N-(2'-methyl-5'-(5-methyl-5-(4-methylpiperazine-1-carbonyl)-4,5-dihydroisoxazol-3-yl)-[1,1'-biphenyl]-4-yl)benzamide | 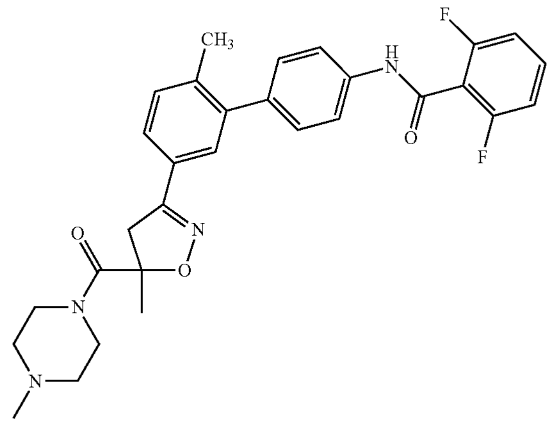 [SMILES: Cc1ccc(C2=NOC(C)(C(=O)N3CCN(C)CC3)C2)cc1-c1ccc(NC(=O)c2c(F)cccc2F)cc1] | ¹HNMR (400 MHz, CDCl₃) δ 7.91 (s, 1H, D₂O exchangeable), 7.71 (d, J = 8.5 Hz, 2H), 7.55 (dd, J = 8.0, 1.5 Hz, 1H), 7.51 (d, J = 1.5 Hz, 1H), 7.46-7.41 (m, 1H), 7.33-7.29 (m, 3H), 7.02 (t, J = 8.0 Hz, 2H), 4.42-4.35 (m, 2H), 4.20-4.17 (m, 1H), 3.83-3.78 (m, 1H), 3.53-3.48 (m, 1H), 3.17-3.08 (m, 3H), 2.85-2.80 (m, 1H), 2.67-2.63 (m, 1H), 2.57 (s, 3H), 2.31 (s, 3H), 1.69 (s, 3H); ESI-MS (m/z) 533 (MH)⁺. |
| Example 153: 2,6-Difluoro-N-(5-(2-methyl-5-(5-methyl-5-(4-methylpiperazine-1-carbonyl)-4,5-dihydroisoxazol-3-yl)phenyl)pyrazin-2-yl)benzamide | 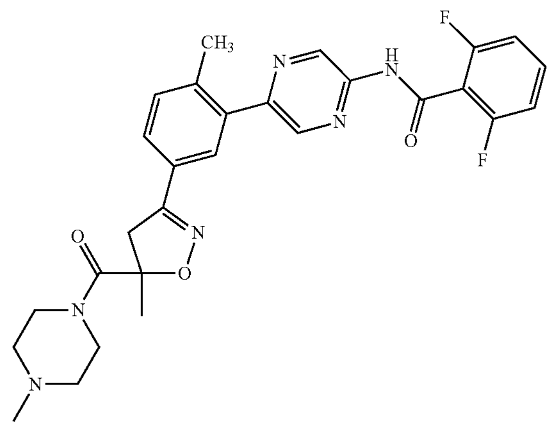 [SMILES: Cc1ccc(C2=NOC(C)(C(=O)N3CCN(C)CC3)C2)cc1-c1cnc(NC(=O)c2c(F)cccc2F)cn1] | ¹HNMR (400 MHz, CDCl₃) δ 9.76 (s, 1H), 8.55 (s, 1H, D₂O exchangeable), 8.38 (s, 1H), 7.72 (d, J = 1.5 Hz, 1H), 7.65 (dd, J = 8.0, 1.5 Hz, 1H), 7.52-7.47 (m, 1H), 7.36 (d, J = 8.0 Hz, 1H), 7.06 (t, J = 8.0 Hz, 2H), 4.41 (d, J = 17.0 Hz, 1H), 4.08-4.04 (m, 1H), 3.77-3.73 (m, 2H), 3.60-3.55 (m, 1H), 3.15 (d, J = 17.0 Hz, 1H), 2.49-2.43 (m, 4H), 2.43 (s, 3H), 2.31 (s, 3H), 1.69 (s, 3H); ESI-MS (m/z) 535 (MH)⁺. |

Example 154

5-(2-Amino-2-oxoethyl)-3-(4'-(2,6-difluorobenzamido)-6-methyl-[1,1'-biphenyl]-3-yl)-4,5-dihydroisoxazole-5-carboxamide

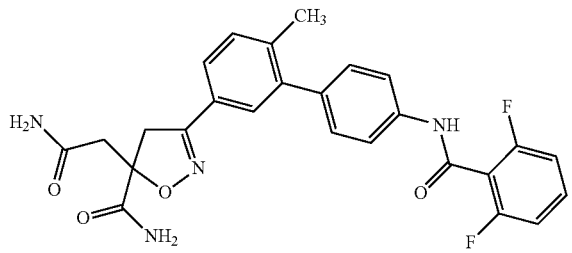 [SMILES: Cc1ccc(C2=NOC(CC(N)=O)(C(N)=O)C2)cc1-c1ccc(NC(=O)c2c(F)cccc2F)cc1]

A solution of Example 76 (200 mg, 0.4 mmol, 1.0 eq), and aqueous ammonia (33%, 5 mL) in THF (5 mL) was stirred at room temperature for 12 h. The solvent was removed under vacuum and the crude residue was purified by preparative HPLC to afford 30 mg of the desired product as a white solid. ¹HNMR (400 MHz, DMSO-d6) δ 13.22 (s, 1H, D₂O exchangeable), 12.56 (s, 1H, D₂O exchangeable), 10.92 (s, 1H, D₂O exchangeable), 7.70 (d, J=8.5 Hz, 2H), 7.54-7.50 (m, 2H), 7.42-7.33 (m, 2H), 7.19-7.14 (m, 2H), 3.70 (d, J=17.5 Hz, 1H), 3.57 (d, J=17.5 Hz, 1H), 2.86 (d, J=15.0 Hz, 1H), 2.67 (d, J=15.0 Hz, 1H), 2.23 (s, 3H); ESI-MS (m/z) 493 (MH)⁺.

Example 155

3-(4'-(2,6-Difluorobenzamido)-6-methyl-[1,1'-biphenyl]-3-yl)-N-methyl-5-(2-(methylamino)-2-oxoethyl)-4,5-dihydroisoxazole-5-carboxamide The title compound was prepared by following a procedure similar to that described in Example 154 by using Example 76 and methylamine. ¹HNMR (400 MHz, DMSO-d6) δ 10.92 (s, 1H, D₂O exchangeable), 7.98 (q, J=4.5 Hz, 1H, D₂O exchangeable), 7.84 (q, J=4.5 Hz, 1H, D₂O exchangeable), 7.78 (d, J=8.5 Hz, 2H), 7.63-7.58 (m, 1H), 7.57 (dd, J=8.0, 1.5 Hz, 1H), 7.46 (s, 1H), 7.39 (d, J=8.5 Hz, 2H), 7.27 (t, J=8.0 Hz, 2H), 3.84 (d, J=17.5 Hz, 1H), 3.61 (d, J=17.5 Hz, 1H), 2.75 (d, J=15.0 Hz, 1H), 2.69 (d, J=15.0 Hz, 1H), 2.59 (d, J=4.5 Hz, 3H), 2.52 (d, J=4.5 Hz, 3H), 2.28 (s, 3H); ESI-MS (m/z) 521 (MH)$^+$.

Examples 156-169

General procedure for the synthesis of compounds of the present invention:

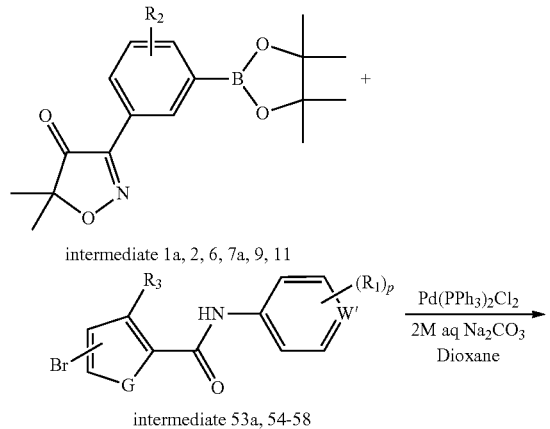

intermediate 1a, 2, 6, 7a, 9, 11 intermediate 53a, 54-58

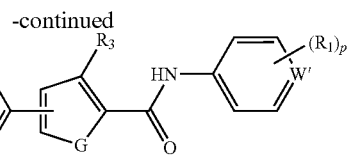

Examples 156-169

W' = C or N

To a stirred solution of any one of boronate derivatives of intermediates 1a, 2, 6, 7a, 9 or 11 (1.0 eq) in dioxane (10 mL), any one of halo intermediates of 53a, 54, 55, 56, 57 or 58 (1.0 eq), aq sodium carbonate solution (2M, 4 mL) and Pd(PPh$_3$)$_2$Cl$_2$ (0.05 eq) were sequentially added. The resulting mixture was thoroughly deoxygenated by subjecting to vacuum/nitrogen cycle three times and then heated at 130° C. for 30 min in microwave (Biotage). The reaction mixture was cooled to room temperature and filtered through celite. The filtrate was concentrated under vacuum and the crude product was purified by flash column chromatography (silica gel, ethyl acetate in hexane) to afford the desired product as a solid.

The below examples were prepared by following a procedure similar to that described in above mentioned general procedure.

| Example No: IUPAC Name | Structure | $^1$HNMR/ESI-MS (MH)$^+$ |
|---|---|---|
| Example 156: N-(2,6-Difluorophenyl)-5-(5-(5,5-dimethyl-4-oxo-4,5-dihydroisoxazol-3-yl)-2-methylphenyl)thiophene-2-carboxamide | 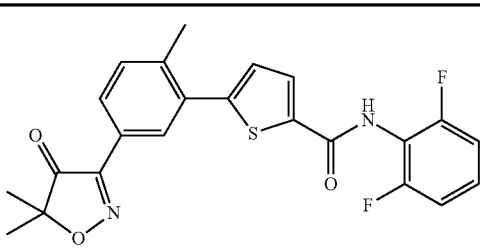 | $^1$HNMR (400 MHz, CDCl$_3$) δ 8.20 (d, J = 1.5 Hz, 1H), 8.05 (dd, J = 8.0, 1.5 Hz, 1H), 7.72 (d, J = 4.0 Hz, 1H), 7.42 (d, J = 8.0 Hz, 1H), 7.33 (s, 1H, D$_2$O exchangeable), 7.28-7.22 (m, 1H), 7.16 (d, J = 4.0 Hz, 1H), 7.00 (t, J = 8.0 Hz, 2H), 2.51 (s, 3H), 1.50 (s, 6H); ESI-MS (m/z) 441 (MH)$^+$ |
| Example 157: N-(2,6-Difluorophenyl)-5-(5-(5,5-dimethyl-4-oxo-4,5-dihydroisoxazol-3-yl)-2-ethylphenyl)thiophene-2-carboxamide | 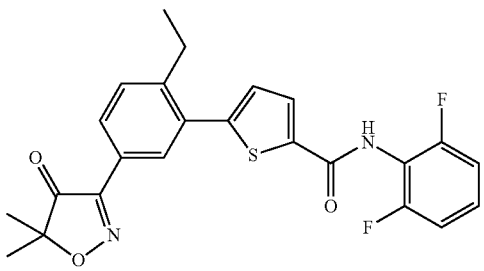 [SMILES: CCc1ccc(C2=NOC(C)(C)C2=O)cc1-c1ccc(C(=O)Nc2c(F)cccc2F)s1] | $^1$HNMR (400 MHz, CDCl$_3$) δ 8.13 (d, J = 1.5 Hz, 1H), 8.09 (dd, J = 8.0, 1.5 Hz, 1H), 7.70 (d, J = 3.5 Hz, 1H), 7.43 (d, J = 8.0 Hz, 1H), 7.32 (s, 1H, D$_2$O exchangeable), 7.27-7.22 (m, 1H), 7.10 (d, J = 3.5 Hz, 1H), 7.00 (t, J = 8.0 Hz, 2H), 2.80 (q, J = 7.5 Hz, 2H), 1.47 (s, 6H), 1.21 (t, J = 7.5 Hz, 3H); ESI-MS (m/z) 455 (MH)$^+$ |
| Example 158: 5-(5-(5,5-Dimethyl-4-oxo-4,5-dihydroisoxazol-3-yl)-2-ethylphenyl)-N-(3-methylpyridin-4-yl)thiophene-2-carboxamide | 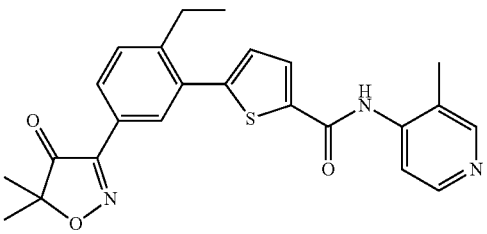 [SMILES: CCc1ccc(C2=NOC(C)(C)C2=O)cc1-c1ccc(C(=O)Nc2ccncc2C)s1] | $^1$HNMR (400 MHz, CDCl$_3$) δ 8.48 (d, J = 5.5 Hz, 1H), 8.43 (s, 1H), 8.25 (d, J = 5.5 Hz, 1H), 8.15 (d, J = 1.5 Hz, 1H), 8.12 (dd, J = 8.0, 1.5 Hz, 1H), 7.71 (s, 1H, D$_2$O exchangeable), 7.68 (d, J = 4.0 Hz, 1H), 7.46 (d, J = 8.0 Hz, 1H), 7.14 (t, J = 4.0 Hz, 1H), 2.82 (q, J = 7.5 Hz, 2H), 2.37 (s, 3H), 1.49 (s, 6H), 1.23 (t, J = 7.5 Hz, 3H); ESI-MS (m/z) 434 (MH)$^+$ |

| Example No: IUPAC Name | Structure | $^1$HNMR/ESI-MS (MH)$^+$ |
| --- | --- | --- |
| Example 159: N-(2,6-Difluorophenyl)-5-(5-(5,5-dimethyl-4-oxo-4,5-dihydroisoxazol-3-yl)-2-fluorophenyl)thiophene-2-carboxamide | 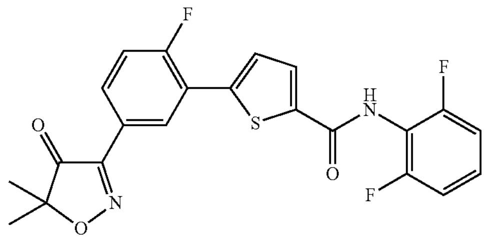 [SMILES: CC1(C)ON=C(c2ccc(F)c(-c3ccc(C(=O)Nc4c(F)cccc4F)s3)c2)C1=O] | $^1$HNMR (400 MHz, CDCl$_3$) δ 8.51 (dd, J = 7.5, 5.0 Hz, 1H), 8.15-8.11 (m, 1H), 7.74 (d, J = 4.0 Hz, 1H), 7.58 (d, J = 4.0 Hz, 1H), 7.33 (s, 1H, D$_2$O exchangeable), 7.31-7.25 (m, 2H), 7.03 (t, J = 7.5 Hz, 2H), 1.52 (s, 6H); ESI-MS (m/z) 445 (MH)$^+$ |
| Example 160: N-(2,6-Difluorophenyl)-5-(5-(5,5-dimethyl-4-oxo-4,5-dihydroisoxazol-3-yl)-2-methoxyphenyl)thiophene-2-carboxamide | 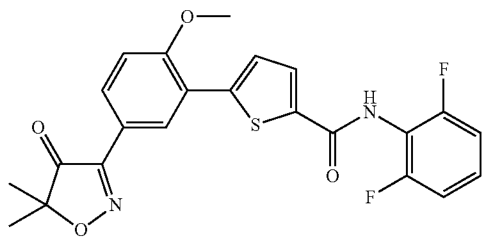 [SMILES: COc1ccc(C2=NOC(C)(C)C2=O)cc1-c1ccc(C(=O)Nc2c(F)cccc2F)s1] | $^1$HNMR (400 MHz, CDCl$_3$) δ 8.53 (s, 1H), 8.13 (dd, J = 9.0, 2.0 Hz, 1H), 7.72 (d, J = 4.0 Hz, 1H), 7.60 (d, J = 4.0 Hz, 1H), 7.36 (s, 1H, D$_2$O exchangeable), 7.28-7.21 (m, 1H), 7.11 (d, J = 9.0 Hz, 1H), 7.03 (t, J = 7.5 Hz, 2H), 4.05 (s, 3H), 1.50 (s, 6H); ESI-MS (m/z) 457 (MH)$^+$ |
| Example 161: N-(2,6-Difluorophenyl)-5-(3-(5,5-dimethyl-4-oxo-4,5-dihydroisoxazol-3-yl)-2-methylphenyl)thiophene-2-carboxamide | 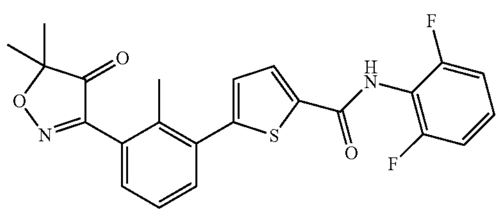 [SMILES: Cc1c(C2=NOC(C)(C)C2=O)cccc1-c1ccc(C(=O)Nc2c(F)cccc2F)s1] | $^1$HNMR (400 MHz, CDCl$_3$) δ 7.70 (d, J = 3.5 Hz, 1H), 7.52 (t, J = 7.5 Hz, 2H), 7.36 (t, J = 7.5 Hz, 1H), 7.32 (s, 1H, D$_2$O exchangeable) 7.28-7.22 (m, 1H), 7.08 (d, J = 4.0 Hz, 1H), 7.03 (t, J = 8.0 Hz, 2H), 2.39 (s, 3H), 1.51 (s, 6H); ESI-MS (m/z) 441 (MH)$^+$ |
| Example 162: N-(2,6-Difluorophenyl)-5-(5-(5,5-dimethyl-4-oxo-4,5-dihydroisoxazol-3-yl)-2-methylphenyl)-3-methylthiophene-2-carboxamide | 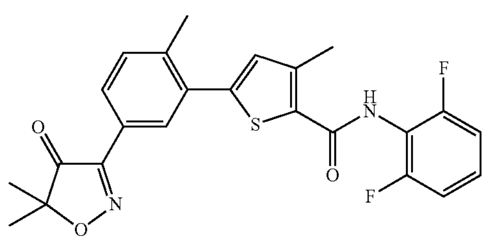 [SMILES: Cc1ccc(C2=NOC(C)(C)C2=O)cc1-c1cc(C)c(C(=O)Nc2c(F)cccc2F)s1] | $^1$HNMR (400 MHz, CDCl$_3$) δ 8.18 (d, J = 1.5 Hz, 1H), 8.03 (dd, J = 8.0, 1.5 Hz, 1H), 7.39 (d, J = 8.0 Hz, 1H), 7.26-7.21 (m, 1H), 7.13 (s, 1H, D$_2$O exchangeable), 7.03-6.98 (m, 3H), 2.63 (s, 3H), 2.51 (s, 3H), 1.48 (s, 6H); ESI-MS (m/z) 455 (MH)$^+$ |
| Example 163: N-(2,6-Difluorophenyl)-5-(3-(5,5-dimethyl-4-oxo-4,5-dihydroisoxazol-3-yl)phenyl)-3-methylthiophene-2-carboxamide | 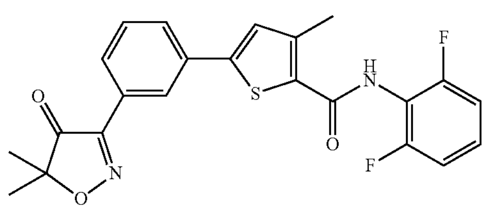 [SMILES: Cc1cc(-c2cccc(C3=NOC(C)(C)C3=O)c2)sc1C(=O)Nc1c(F)cccc1F] | $^1$HNMR (400 MHz, CDCl$_3$) δ 8.40 (t, J = 1.5 Hz, 1H), 8.09 (d, J = 7.5 Hz, 1H), 7.73 (d, J = 7.5 Hz, 1H), 7.52 (t, J = 7.5 Hz, 1H), 7.26-7.20 (m, 2H), 7.13 (s, 1H, D$_2$O exchangeable), 7.00 (t, J = 8.0 Hz, 2H), 2.62 (s, 3H), 1.50 (s, 6H); ESI-MS (m/z) 441 (MH)$^+$ |
| Example 164: N-(2,6-Difluorophenyl)-4-(5-(5,5-dimethyl-4-oxo-4,5-dihydroisoxazol-3-yl)-2-methoxyphenyl)thiophene-2-carboxamide | 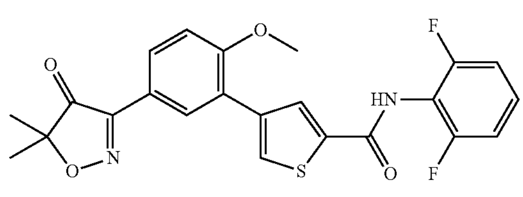 [SMILES: COc1ccc(C2=NOC(C)(C)C2=O)cc1-c1csc(C(=O)Nc2c(F)cccc2F)c1] | $^1$HNMR (400 MHz, CDCl$_3$) δ 8.27 (d, J = 2.0 Hz, 1H), 8.10 (dd, J = 9.0, 2.0 Hz, 1H), 8.04 (d, J = 1.0 Hz, 1H), 7.88 (d, J = 1.0 Hz, 1H), 7.41 (s, 1H, D$_2$O exchangeable), 7.26-7.21 (m, 1H), 7.08 (d, J = 9.0 Hz, 1H), 7.02 (t, J = 7.5 Hz, 2H), 3.96 (s, 3H), 1.48 (s, 6H); ESI-MS (m/z) 457 (MH)$^+$ |
| Example 165: N-(2,6-Difluorophenyl)-4-(5-(5,5-dimethyl-4-oxo-4,5-dihydroisoxazol-3-yl)-2-methylphenyl)-3-methylthiophene-2-carboxamide | 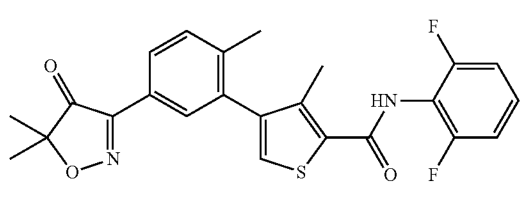 [SMILES: Cc1ccc(C2=NOC(C)(C)C2=O)cc1-c1csc(C(=O)Nc2c(F)cccc2F)c1C] | $^1$HNMR (400 MHz, CDCl$_3$) δ 8.05 (dd, J = 7.5, 1.5 Hz, 1H), 7.90 (d, J = 1.5 Hz, 1H), 7.39 (d, J = 8.0 Hz, 1H), 7.26-7.20 (m, 2H), 7.19 (s, 1H, D$_2$O exchangeable), 7.01 (t, J = 8.0 Hz, 2H), 2.32 (s, 3H), 2.18 (s, 3H), 1.47 (s, 6H); ESI-MS (m/z) 455 (MH)$^+$ |

| Example No: IUPAC Name | Structure | $^1$HNMR/ESI-MS (MH)$^+$ |
|---|---|---|
| Example 166: N-(2,6-Difluorophenyl)-4-(3-(5,5-dimethyl-4-oxo-4,5-dihydroisoxazol-3-yl)phenyl)-3-methylthiophene-2-carboxamide | 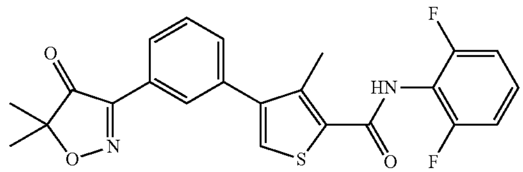 [SMILES: Cc1c(-c2cccc(C3=NOC(C)(C)C3=O)c2)csc1C(=O)Nc1c(F)cccc1F] | $^1$HNMR (400 MHz, CDCl$_3$) δ 8.16-8.13 (m, 2H), 7.56 (td, J = 7.5, 1.0 Hz, 1H), 7.49 (dt, J = 7.5, 1.0 Hz, 1H), 7.41 (s, 1H), 7.27-7.22 (m, 1H), 7.21 (s, 1H, D$_2$O exchangeable), 7.03 (t, J = 8.0 Hz, 2H), 2.57 (s, 3H), 1.51 (s, 6H); ESI-MS (m/z) 441 (MH)$^+$ |
| Example 167: N-(2,6-difluorophenyl)-5-(5-(5,5-dimethyl-4-oxo-4,5-dihydroisoxazol-3-yl)-2-methylphenyl)-1-methyl-1H-pyrrole-2-carboxamide | 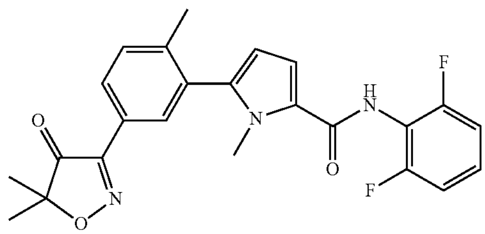 [SMILES: Cc1ccc(C2=NOC(C)(C)C2=O)cc1-c1ccc(C(=O)Nc2c(F)cccc2F)n1C] | $^1$HNMR (400 MHz, CDCl$_3$) δ 8.09 (dd, J = 8.5, 2.0 Hz, 1H), 8.01 (d, J = 2.0 Hz, 1H), 7.42 (d, J = 8.5 Hz, 1H), 7.26-7.19 (m, 2H), 7.02 (t, J = 7.5 Hz, 2H), 6.92 (d, J = 4.0 Hz, 1H), 6.18 (d, J = 4.0 Hz, 1H), 3.72 (s, 3H), 2.25 (s, 3H), 1.47 (s, 6H); ESI-MS (m/z) 438 (MH)$^+$ |
| Example 168: N-(2,6-difluorophenyl)-5-(5-(5,5-dimethyl-4-oxo-4,5-dihydroisoxazol-3-yl)-2-methoxyphenyl)-1-methyl-1H-pyrrole-2-carboxamide | 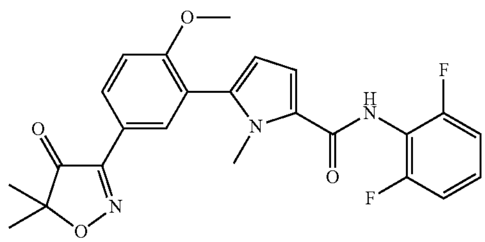 [SMILES: COc1ccc(C2=NOC(C)(C)C2=O)cc1-c1ccc(C(=O)Nc2c(F)cccc2F)n1C] | $^1$HNMR (400 MHz, CDCl$_3$) δ 8.21 (dd, J = 8.5, 2.0 Hz, 1H), 8.08 (d, J = 2.0 Hz, 1H), 7.27-7.18 (m, 2H), 7.08 (d, J = 8.5 Hz, 1H), 7.03 (t, J = 7.5 Hz, 2H), 6.92 (d, J = 4.0 Hz, 1H), 6.25 (d, J = 4.0 Hz, 1H), 3.91 (s, 3H), 3.77 (s, 3H), 1.49 (s, 6H); ESI-MS (m/z) 453 (MH)$^+$ |
| Example 169: N-(2,6-difluorophenyl)-5-(5-(5,5-dimethyl-4-oxo-4,5-dihydroisoxazol-3-yl)-2-ethylphenyl)-1-methyl-1H-pyrrole-2-carboxamide | 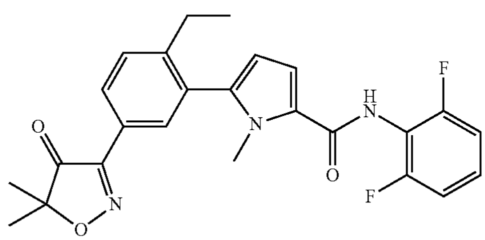 [SMILES: CCc1ccc(C2=NOC(C)(C)C2=O)cc1-c1ccc(C(=O)Nc2c(F)cccc2F)n1C] | $^1$HNMR (400 MHz, CDCl$_3$) δ 8.13 (dd, J = 8.5, 2.0 Hz, 1H), 7.99 (d, J = 2.0 Hz, 1H), 8.04 (d, J = 8.5 Hz, 1H), 7.88 (d, J = 1.0 Hz, 1H), 7.30-7.19 (m, 2H), 7.03 (t, J = 7.5 Hz, 2H), 6.92 (d, J = 4.0 Hz, 1H), 6.18 (d, J = 4.0 Hz, 1H), 3.70 (s, 3H), 2.56 (q, J = 7.5 Hz, 2), 1.48 (s, 6H), 1.42 (t, J = 7.5 Hz, 3H); ESI-MS (m/z) 452 (MH)$^+$ |

Examples 170-177

General procedure for the synthesis of compounds of the present invention:

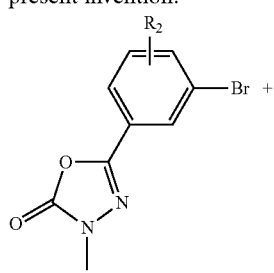

intermediate 15a, 18a-24a

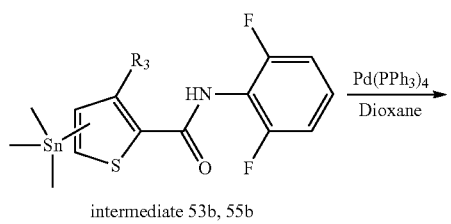

intermediate 53b, 55b

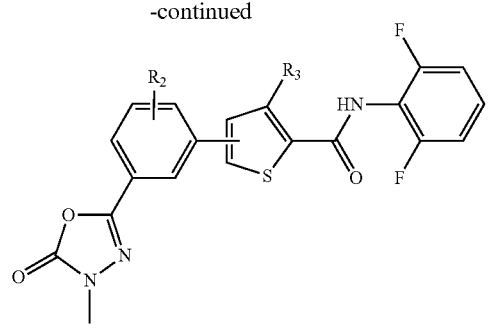

Examples 170-177

To a stirred solution of any one of bromo intermediate of 15a or 18a to 24a (1.0 eq) in dioxane (10 mL), any one of stananne derivative of intermediate 53b or 55b (1.0 eq) and Pd(PPh$_3$)$_4$ (0.05 eq) were sequentially added. The resulting mixture was thoroughly deoxygenated by subjecting to vacuum/nitrogen cycle three times and then heated at 130° C. for 30 min in microwave (Biotage). The reaction mixture was cooled to room temperature and filtered through celite. The filtrate was concentrated under vacuum and the crude product was purified by flash column chromatography (silica gel, ethyl acetate & hexane) to afford the desired product as a solid.

The below examples were prepared by following a procedure similar to that described in above mentioned general procedure.

| Example No/ IUPAC name | Structure | ¹HNMR/ESI-MS (MH)⁺ |
|---|---|---|
| Example 170: N-(2,6-Difluorophenyl)-5-(2-methyl-5-(4-methyl-5-oxo-4,5-dihydro-1,3,4-oxadiazol-2-yl)phenyl)thiophene-2-carboxamide | 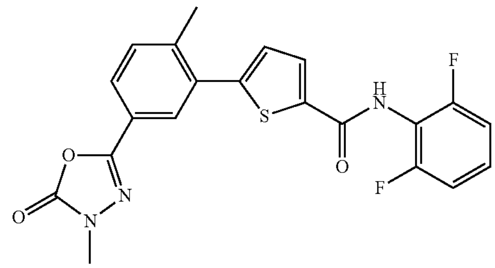 [SMILES: Cc1ccc(-c2nn(C)c(=O)o2)cc1-c1ccc(C(=O)Nc2c(F)cccc2F)s1] | ¹HNMR (400 MHz, CDCl₃) δ 7.88 (d, J = 2.0 Hz, 1H), 7.73 (dd, J = 8.0, 2.0 Hz, 1H), 7.70 (d, J = 4.0 Hz, 1H), 7.40 (d, J = 8.0 Hz, 1H), 7.33 (s, 1H, D₂O exchangeable) 7.27-7.21 (m, 1H), 7.13 (d, J = 4.0 Hz, 1H), 7.00 (t, J = 8.5 Hz, 2H), 3.49 (s, 3H), 2.50 (s, 3H); ESI-MS (m/z) 428 (MH)⁺ |
| Example 171: N-(2,6-Difluorophenyl)-5-(2-ethyl-5-(4-methyl-5-oxo-4,5-dihydro-1,3,4-oxadiazol-2-yl)phenyl)thiophene-2-carboxamide | 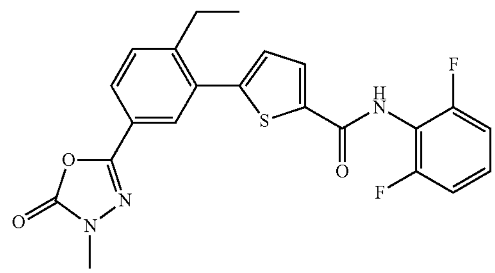 [SMILES: CCc1ccc(-c2nn(C)c(=O)o2)cc1-c1ccc(C(=O)Nc2c(F)cccc2F)s1] | ¹HNMR (400 MHz, CDCl₃) δ 7.84 (d, J = 2.0 Hz, 1H), 7.79 (dd, J = 8.0, 2.0 Hz, 1H), 7.70 (d, J = 4.0 Hz, 1H), 7.44 (d, J = 8.0 Hz, 1H), 7.34 (s, 1H, D₂O exchangeable) 7.27-7.23 (m, 1H), 7.10 (d, J = 4.0 Hz, 1H), 7.00 (t, J = 8.5 Hz, 2H), 3.50 (s, 3H), 2.81 (q, J = 7.5 Hz, 2H), 1.22 (t, J = 7.5 Hz, 3H); ESI-MS (m/z) 442 (MH)⁺ |
| Example 172: N-(2,6-Difluorophenyl)-5-(2-fluoro-5-(4-methyl-5-oxo-4,5-dihydro-1,3,4-oxadiazol-2-yl)phenyl)thiophene-2-carboxamide | 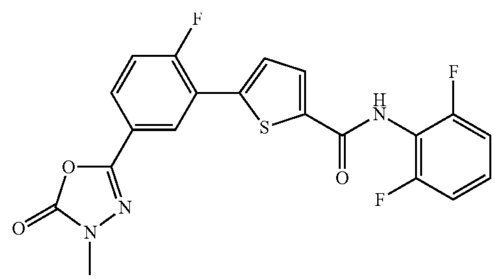 [SMILES: Cn1nc(-c2ccc(F)c(-c3ccc(C(=O)Nc4c(F)cccc4F)s3)c2)oc1=O] | ¹HNMR (400 MHz, DMSO-d6) δ 10.34 (s, 1H, D₂O exchangeable), 8.18 (dd, J = 7.5, 2.0 Hz, 1H), 8.08 (d, J = 4.0, Hz, 1H), 7.87-7.83 (m, 2H), 7.60 (dd, J = 11.0, 8.5 Hz, 1H), 7.46-7.40 (m, 1H), 7.24 (t, J = 8.5 Hz, 2H), 3.43 (s, 3H); ESI-MS (m/z) 432 (MH)⁺ |
| Example 173: 5-(2-(Difluoromethoxy)-5-(4-methyl-5-oxo-4,5-dihydro-1,3,4-oxadiazol-2-yl)phenyl)-N-(2,6-difluorophenyl)thiophene-2-carboxamide | 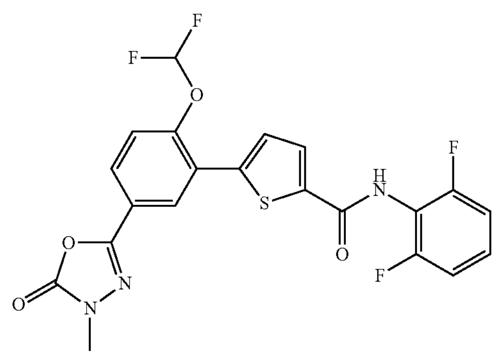 [SMILES: Cn1nc(-c2ccc(OC(F)F)c(-c3ccc(C(=O)Nc4c(F)cccc4F)s3)c2)oc1=O] | ¹HNMR (400 MHz, CDCl₃) δ 8.18 (d, J = 2.0 Hz, 1H), 7.82 (dd, J = 8.5, 2.0 Hz, 1H), 7.71 (d, J = 4.0 Hz, 1H), 7.54 (d, J = 4.0 Hz, 1H), 7.38 (d, J = 8.5 Hz, 1H), 7.33 (s, 1H, D₂O exchangeable) 7.31-7.23 (m, 1H), 7.02 (t, J = 8.5 Hz, 2H), 6.66 (t, J = 73 Hz, 1H), 3.53 (s, 3H); ESI-MS (m/z) 480 (MH)⁺ |
| Example 174: N-(2,6-Difluorophenyl)-5-(2-methoxy-5-(4-methyl-5-oxo-4,5-dihydro-1,3,4-oxadiazol-2-yl)phenyl)-3-methylthiophene-2-carboxamide | 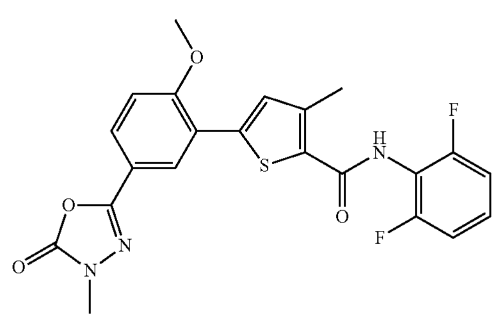 [SMILES: COc1ccc(-c2nn(C)c(=O)o2)cc1-c1cc(C)c(C(=O)Nc2c(F)cccc2F)s1] | ¹HNMR (400 MHz, CDCl₃) δ 8.17 (d, J = 2.5 Hz, 1H), 7.80 (dd, J = 8.5, 2.5 Hz, 1H), 7.44 (s, 1H), 7.25-7.22 (m, 1H), 7.18 (s, 1H, D₂O exchangeable), 7.10 (d, J = 8.5 Hz, 1H), 7.03 (t, J = 8.5 Hz, 2H), 4.06 (s, 3H), 3.53 (s, 3H), 2.64 (s, 3H); ESI-MS (m/z) 458 (MH)⁺ |

-continued

| Example No/IUPAC name | Structure | ¹HNMR/ESI-MS (MH)⁺ |
|---|---|---|
| Example 175: 5-(2-Chloro-5-(4-methyl-5-oxo-4,5-dihydro-1,3,4-oxadiazol-2-yl)phenyl)-N-(2,6-difluorophenyl)thiophene-2-carboxamide | 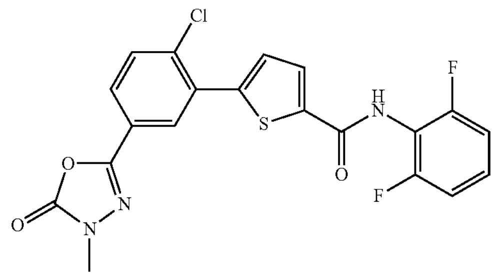 | ¹HNMR (400 MHz, CDCl$_3$) δ 8.04 (d, J = 2.0 Hz, 1H), 7.77 (dd, J = 8.5, 2.0 Hz, 1H), 7.73 (d, J = 3.5 Hz, 1H), 7.63 (d, J = 8.5 Hz, 1H), 7.45 (d, J = 3.5 Hz, 1H), 7.34 (s, 1H, D$_2$O exchangeable) 7.29-7.24 (m, 1H), 7.03 (t, J = 8.5 Hz, 2H), 3.53 (s, 3H); ESI-MS (m/z) 448 (MH)⁺ |
| Example 176: N-(2,6-Difluorophenyl)-5-(2-methyl-3-(4-methyl-5-oxo-4,5-dihydro-1,3,4-oxadiazol-2-yl)phenyl)thiophene-2-carboxamide | 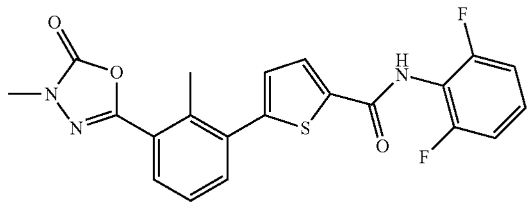 [SMILES: Cc1c(-c2nn(C)c(=O)o2)cccc1-c1ccc(C(=O)Nc2c(F)cccc2F)s1] | ¹HNMR (400 MHz, CDCl$_3$) δ 7.84 (d, J = 7.5 Hz, 1H), 7.72 (d, J = 4.0 Hz, 1H), 7.53 (d, J = 7.5 Hz, 1H), 7.38 (t, J = 7.5 Hz, 1H), 7.32 (s, 1H, D$_2$O exchangeable) 7.28-7.23 (m, 1H), 7.08 (d, J = 4.0 Hz, 1H), 7.03 (t, J = 8.5 Hz, 2H), 3.56 (s, 3H), 2.62 (s, 3H); ESI-MS (m/z) 428 (MH)⁺ |
| Example 177: N-(2,6-difluorophenyl)-5-(2-ethyl-3-(4-methyl-5-oxo-4,5-dihydro-1,3,4-oxadiazol-2-yl)phenyl)thiophene-2-carboxamide | 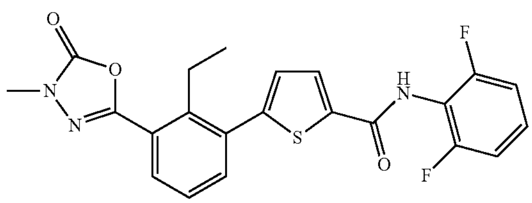 [SMILES: CCc1c(-c2nn(C)c(=O)o2)cccc1-c1ccc(C(=O)Nc2c(F)cccc2F)s1] | ¹HNMR (400 MHz, CDCl$_3$) δ 7.85 (dd, J = 8.0, 1.0 Hz, 1H), 7.71 (d, J = 3.5 Hz, 1H), 7.50 (dd, J = 8.0, 1.0 Hz, 1H), 7.37 (d, J = 8.0 Hz, 1H), 7.35 (s, 1H, D$_2$O exchangeable), 7.31-7.25 (m, 1H), 7.08 (d, J = 3.5 Hz, 1H), 7.03 (t, J = 8.0 Hz, 2H), 3.54 (s, 3H), 3.06 (q, J = 7.0 Hz, 2H), 1.16 (t, J = 7.0 Hz, 3H); ESI-MS (m/z) 442 (MH)⁺ |

Biological Assays and Utility:

The CRAC channel modulatory activity of the compounds were thus evaluated by measuring the secretion of IL-2 by antigen stimulated T-cells in vitro. Alternatively, such activity can also be evaluated by assay methods known to one skilled in the art.

In Vitro Assay

Example-178

Inhibition of IL-2 secretion: Jurkat T cells were seeded at a density of 0.5 to 1 million cells per well in RPMI medium. Test compounds from this invention were added to the cells at different concentrations. This was followed by the addition of PHA, a T cell mitogen after 10 minutes. The cells were then incubated for 20 to 24 hours in a CO$_2$ incubator at 37° C. After incubation with the compounds, cells were centrifuged, collected the supernatant and processed for ELISA to quantitate the amount of IL-2 secreted. A commercial ELISA kit (R&D Systems, Inc. Minneapolis, Minn., USA) was used to estimate the IL-2 concentrations. Amount of IL-2 secreted by cells stimulated with PHA was considered as a 100% maximal signal and the decrease in amount of IL-2 secreted by cells treated with the test compounds was expressed as percent inhibition of the maximal signal. The dose response data was analyzed using 4-parametric sigmoidal dose response (variable slope) curve—fit.

In the above IL-2 assay, compounds of the invention were found to have IC$_{50}$ (nM) values as shown below:

| IC$_{50}$ (nM) | Examples |
|---|---|
| <100 nM | 3, 16, 19, 29, 33, 34, 40, 46, 80, 87, 93, 114, 135, 157, 158, 160, 171, 173, 176 |
| 100 nM-1000 nM | 4, 7, 8, 11, 18, 23, 24, 31, 113, 53, 58, 61, 67, 78, 103, 107, 121, 126, 132, 136, 138, |
| >1000 nM | 10, 17, 69, 145 |

Thus, compounds of the invention are shown to inhibit IL-2 secretion.

Example-179

SOCE inhibition: Jurkat E6.1 cells were seeded at a density of 1-2×10$^5$ cells per well in calcium-4 dye prepared in calcium free HBSS (Sigma, USA). Test compounds from this invention were added to the cells at different concentrations. This was followed by the addition of thapsigargin (TG), a SERCA inhibitor, to empty the stores of calcium. Calcium chloride was added to the cells after 10-30 min to induce calcium influx and the fluorescence was measured for 10 min using the FLIPR-Tetra detection system. Fluorescence was also measured using a plate reader at 485 nm excitation and 520 nm emission (Synergy2, Biotek, USA) after 30-90 minutes of calcium addition. Fluorescence observed in cells treated with Thapsigargin and calcium chloride solution was considered 100% maximal signal and the reduced fluorescent signal observed in the presence of test compounds was expressed as percent inhibition of the maximal signal. The dose response data was analyzed using 4-parametric sigmoidal dose response (variable slope) curve—fit.

In the above SOCE inhibition assay, compounds of the present invention showed activity against SOCE as given below:

| IC$_{50}$ (nM) | Examples |
|---|---|
| <1000 nM | 15, 41, 135, 160, 176 |

Thus, compounds of the invention are shown to have CRAC channel modulation activity by inhibition of SOCE.

Example-180

NFAT Transcriptional Activity: HEK 293 cells were stably transfected with a NFAT-Luc reporter gene. 30,000-80,000 cells were seeded per well. Test compounds from this invention were added to the cells at different concentrations. Thapsigargin (TG) was added after 10 mins and the cells were incubated for 4-8 h. NFAT transcriptional activity was measured using BrightGlo reagent (Promega USA). Luminescence observed in cells treated with thapsigargin was considered 100% maximal signal and the reduced fluorescent signal observed in the presence of test compounds was expressed as percent inhibition of the maximal signal. The data was analyzed using 4-parametric sigmoidal dose response (variable slope) curve—fit.

In the above NFAT transcriptional activity assay, compounds of the present invention showed activity as given below:

| IC$_{50}$ (nM) | Examples |
|---|---|
| <500 nM | 29, 50, 135, 176 |

Thus, compounds of the invention are shown to inhibit NFAT transcription activity.

Thus, the in vitro screening assays showed that the compounds of invention inhibit CRAC channel activity.

Example-181

Effect of Compounds of the Present Invention on Ovalbumin Induced (Delayed Type Hypersensitivity) DTH Model Intradermal injections of emulsions containing Freund's complete adjuvant (FCA), heat killed *Mycobacterium tuberculosis* (4 mg/ml) in complete Freund's adjuvant and Ovalbumin (10 mg/ml) were given to female Lewis rats (n=6 each group) on day 0 at the base of the tail. On day 7, Ovalbumin (20 mg/ml) was injected into the right ear of the animals. 24 h post injection of Ovalbumin, ear swelling induced due to antigenic challenge was assessed using Vernier calipers. Animals were treated with either vehicle or test compounds orally once a day from day 0 till day 8.

Compounds of the present invention showed efficacy in suppressing ear swelling in the animals on antigenic challenge.

Example-182

Effect of Compounds of the Present Invention on Collagen Induced Arthritis (CIA)

Female Lewis rats (n=6 each group) were given intradermal injections (at the base of the tail) of emulsions containing porcine Collagen-II (2 mg/ml) and incomplete Freund's adjuvant on day 0 and day 7. Animals were observed for disease progression from day 10 onwards till day 35. Disease was scored as: 0—Normal, 1—Swelling and erythema limited to one or two digits only, 2—Swelling and erythema in more than two digits or erythema and mild swelling extending from ankle to the tarsals, 3—Erythema and moderate swelling extending from ankles to the metatarsals, 4—Erythema and severe swelling encompassing the ankles foot and digits and or ankylosis of the limb. Animals were dosed with either vehicle or test compounds orally once a day from day 0 till day 35.

Compounds of the present invention were found to reduce arthritis in these animals.

As mentioned hereinbefore, the CRAC channel is involved with numerous biological responses through various Ca$^{2+}$ signaling pathways. The compounds of the present invention are therefore useful for the treatment and/or prophylaxis of, although not limited to, inflammatory conditions, cancer, rheumatoid arthritis, allergic disorders, immune disorders, cardiovascular diseases, thrombocytopathies and all related conditions which can be benefitted by the CRAC channel modulatory properties of the compounds described herein.

The compounds of the present invention can be administered to a warm-blooded animal, including human being, for the treatment and/or prophylaxis of one or many diseases or disorders mentioned hereinabove which can be benefitted by the CRAC channel modulatory properties of the compounds described herein. The compounds may be formulated according to the methods known in the art as well as by new methods and may be administered to the body system via gastro-intestinal tract as well as via other routes known to a person skilled in the art. Thus, administration of the compounds of the present invention via oral route, parenteral route, inhalation and/or topical applications are within the scope of this application. Any combination of a compound of the present invention with excipients and/or other therapeutic agents known in the art for the said conditions, diseases and/or disorders are also encompassed by the present invention.

All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

The invention claimed is:

1. A compound of the structure of Formula(I):

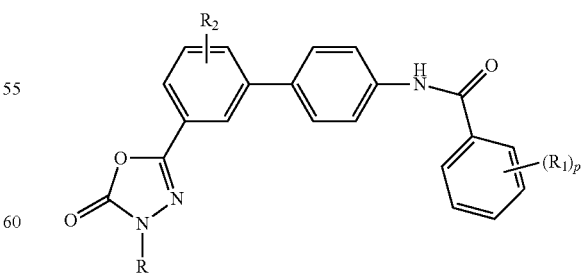

wherein,

R$_1$, which may be same or different at each occurrence, is independently selected from halo, alkyl, haloalkyl, alkoxy and cycloalkyl;

R₂ is selected from hydrogen, halo, hydroxyl, alkyl, haloalkyl, alkoxy, haloalkoxy, and cycloalkyl;

R is alkyl; and p is an integer ranging from 0 to 2, both inclusive;

or a pharmaceutically acceptable salt thereof or stereoisomers thereof.

2. The compound of claim 1, which is selected from:

2,6-Difluoro-N-(2'-methyl-5'-(4-methyl-5-oxo-4,5-dihydro-1,3,4-oxadiazol-2-yl)-[1,1'-biphenyl]-4-yl)benzamide, N-(5'-(4-Ethyl-5-oxo-4,5-dihydro-1,3,4-oxadiazol-2-yl)-2'-methyl-[1,1'-biphenyl]-4-yl)-2,6-difluorobenzamide, 2,6-Difluoro-N-(2'-methyl-5'-(5-oxo-4-propyl-4,5-dihydro-1,3,4-oxadiazol-2-yl)-[1,1'-biphenyl]-4-yl)benzamide, N-(2'-Ethyl-5'-(4-methyl-5-oxo-4,5-dihydro-1,3,4-oxadiazol-2-yl)-[1,1'-biphenyl]-4-yl)-2,6-difluorobenzamide, 2-Chloro-N-(2'-ethyl-5'-(4-methyl-5-oxo-4,5-dihydro-1,3,4-oxadiazol-2-yl)-[1,1'-biphenyl]-4-yl)-6-fluorobenzamide, N-(2'-Ethyl-5'-(4-methyl-5-oxo-4,5-dihydro-1,3,4-oxadiazol-2-yl)-[1,1'-biphenyl]-4-yl)-2-fluoro-6-methylbenzamide, 2,6-Difluoro-N-(2'-methoxy-5'-(4-methyl-5-oxo-4,5-dihydro-1,3,4-oxadiazol-2-yl)-[1,1'-biphenyl]-4-yl)benzamide, 2-Chloro-6-fluoro-N-(2'-methoxy-5'-(4-methyl-5-oxo-4,5-dihydro-1,3,4-oxadiazol-2-yl)-[1,1'-biphenyl]-4-yl)benzamide, 2-Fluoro-N-(2'-methoxy-5'-(4-methyl-5-oxo-4,5-dihydro-1,3,4-oxadiazol-2-yl)41,1'-biphenyl]-4-yl)-6-methylbenzamide, 4-Ethyl-N-(2'-methoxy-5'-(4-methyl-5-oxo-4,5dihydro-1,3,4-oxadiazol-2-yl)-[1,1'-biphenyl]-4-yl)benzamide, N-(2'-(Difluoromethoxy)-5'-(4-methyl-5-oxo-4,5-dihydro-1,3,4-oxadiazol-2-yl)-[1,1'-biphenyl]-4-yl)-2,6-difluorobenzamide, N-(2'-Chloro-5'-(4-methyl-5-oxo-4,5-dihydro-1,3,4-oxadiazol-2-yl)-[1,1'-biphenyl]-4-yl)-2,6-difluorobenzamide, 2,6-Difluoro-N-(2'-methyl-3'-(4-methyl-5-oxo-4,5-dihydro-1,3,4-oxadiazol-2-yl)1,1'-biphenyl]-4-yl)benzamide, 2-Chloro-6-fluoro-N-(2'-methyl-3'-(4-methyl-5-oxo-4,5-dihydro-1,3,4-oxadiazol-2-yl)-[1,1'-biphenyl]-4-yl)benzamide, and N-(2'-ethyl-3'-(4-methyl-5-oxo-4,5-dihydro-1,3,4-oxadiazol-2-yl)-[1,1'-biphenyl]-4-yl)-2,6-difluorobenzamide, or a pharmaceutically acceptable salt thereof.

3. A pharmaceutical composition comprising one or more compounds of Formula (I) according to claim 1 and one or more pharmaceutically acceptable excipients.

4. A pharmaceutical composition comprising one or more compounds according to claim 2 and one or more pharmaceutically acceptable excipients.

* * * * *